US012408673B2

(12) United States Patent
Beau et al.

(10) Patent No.: US 12,408,673 B2

(45) Date of Patent: Sep. 9, 2025

(54) PAENIBACILLUS STRAINS AND METHODS FOR THEIR USE

(71) Applicant: Bayer CropScience LP, St. Louis, MO (US)

(72) Inventors: Jeremy Beau, Woodland, CA (US); Andreas Goertz, Dormagen (DE); Adam Newman, Sacramento, CA (US); Patrick Schwientek, Davis, CA (US); Colleen S. Taylor, Folsom, CA (US); Donglan Tian, Davis, CA (US); Bjorn A. Traag, Walnut Creek, CA (US)

(73) Assignee: Bayer CropScience LP, St. Louis, MO (US)

( * ) Notice: Subject to any disclaimer, the term of this patent is extended or adjusted under 35 U.S.C. 154(b) by 820 days.

(21) Appl. No.: 17/435,848

(22) PCT Filed: Mar. 5, 2020

(86) PCT No.: PCT/US2020/021125

§ 371 (c)(1),
(2) Date: Sep. 2, 2021

(87) PCT Pub. No.: WO2020/181053

PCT Pub. Date: Sep. 10, 2020

(65) Prior Publication Data

US 2022/0151242 A1 May 19, 2022

Related U.S. Application Data

(60) Provisional application No. 62/815,069, filed on Mar. 7, 2019.

(51) Int. Cl.

*A01N 63/25* (2020.01)
*C12N 1/20* (2006.01)
*C12R 1/07* (2006.01)

(52) U.S. Cl.

CPC ............ *A01N 63/25* (2020.01); *C12N 1/205* (2021.05); *C12R 2001/07* (2021.05)

(58) Field of Classification Search

CPC ..... A01N 63/25; C12R 2001/12; C12N 1/205
See application file for complete search history.

(56) References Cited

U.S. PATENT DOCUMENTS

| | | | |
|---|---|---|---|
| 9,883,676 B2 | 2/2018 | Beau et al. | |
| 10,159,257 B2 | 12/2018 | Beau et al. | |
| 10,499,656 B2 | 12/2019 | Beau et al. | |
| 10,703,775 B2 | 7/2020 | Kimmelshue et al. | |
| 11,479,516 B2 * | 10/2022 | Voigt | C05F 11/08 |
| 2018/0146682 A1 | 5/2018 | Beau et al. | |
| 2020/0054023 A1 | 2/2020 | Beau et al. | |
| 2021/0127684 A1 | 5/2021 | Singh et al. | |
| 2021/0204550 A1 | 7/2021 | Görtz et al. | |
| 2021/0244031 A1 | 8/2021 | Collins et al. | |
| 2022/0235315 A1 | 7/2022 | Curtis | |

FOREIGN PATENT DOCUMENTS

| | | |
|---|---|---|
| KR | 20140008903 A | 1/2014 |
| WO | 2016187703 A1 | 12/2016 |

OTHER PUBLICATIONS

Aleti, G., et al., "The Draft Genome Sequence of Paenibacillus polymyxa Strain CCI-25 Encompasses High Potential for Secondary Metabolite Production," Genome Announcements, May 19, 2016, vol. 4, No. 3, pp. 1-2.
Cochrane, S.A., et al., "Antimicrobial Lipopeptide Tridecaptin A1 Selectively Binds to Gram-Negative Lipid II," 2016, PNAS, Oct. 11, 2016, vol. 113, No. 41, pp. 11561-11566.
Lee, S.H., et al., "An Antibiotic Fusaricidin: A Cyclic Depsipeptide from Paenibacillus polymyxa E681 Induces Systemic Resistance Against Phytophthora Blight of Red-Pepper," Phytoparasitica, 2013, vol. 41, pp. 49-58.
Li, J. et al., "Use of PCR-Targeted Mutagenesis to Disrupt Production of Fusaricidin-Type Antifungal Antibiotics in Paenibacillus polymyxa," Applied and Environmental Microbiology, Jun. 2007, vol. 72, No. 11, pp. 3480-3489.
Li, J., et al., "Nonribosomal Biosynthesis of Fusaricidins by Paenibacillus polymyxa PKV1 Involves Direct Activation of the D-Amino Acid," Chemistry & Biology, Feb. 2008, vol. 15, pp. 118-127.
Lohans, C.T., et al., "Biochemical, Structural, and Genetic Characterization of Tridecaptin A1, an Antagonist of Campylobacter jejuni," ChemBioChem, 2014, vol. 15, pp. 243-249.
Lohans, C.T., et al., "Structural Characterization of Bacterial Antimicrobial Peptides," Doctoral Thesis, Department of Chemistry, University of Alberta, 2014, 270 pages.
Wang, L. et al., "A Minimal Nitrogen Fixation Gene Cluster from *Paenibacillus* sp. WLY78 Enables Expression of Active Nitrogenase in *Escherichia coli*," PLOS Genetics, Oct. 2013, vol. 9, No. 10, pp. 1-11.
International Search Report and Written Opinion of the International Searching Authority for PCT International Patent Application No. PCT/US2020/021125, dated Aug. 3, 2020, 14 pages.
Olishevska, S. et al., "Bacillus and Paenibacillus secreted polyketides and peptides involved in controlling human and plant pathogens" Appl Microbiol Biotechnol 103, 1189-1215 (2019).
Li, Y. et al., "Draft Genome Sequence of Paenibacillus polymyxa KF-1, an Excellent Producer of Microbicides" Genome Announcements, vol. 4, issue 4, (2016).
Van Belkum, M.J. et al., "Draft Genome Sequences of *Paenibacillus polymyxa* NRRL B-30509 and *Paenibacillus terrae* NRRL B-30644, Strains from a Poultry Environment That Produce Tridecaptin A and Paenicidins", Genome Announc, 3(2), pp. e00372-15, Apr. 23, 2015.

* cited by examiner

*Primary Examiner* — Johann R Richter
*Assistant Examiner* — Danielle Johnson

(57) ABSTRACT

The present invention provides a composition comprising a biologically pure culture of a *Paenibacillus* sp. strain or a cell-free preparation thereof comprising a fusaricidin and a tridecaptin; wherein the fusaricidin is produced with a fusaricidin synthetase gene of fusA encoded by a DNA sequence exhibiting at least 90.5% sequence identity to SEQ ID NO: 3; and the tridecaptin is produced with a nonribosomal peptide synthetase (NRPS) gene of triE encoded by a DNA sequence exhibiting at least 90.0% sequence identity to SEQ ID NO: 7. Also provided are methods of treating an agricultural plant to control a disease and methods of increasing the vigor and/or crop yield of an agricultural plant with the disclosed compositions.

18 Claims, 2 Drawing Sheets

Specification includes a Sequence Listing.

PAENIBACILLUS STRAINS AND METHODS FOR THEIR USE

CROSS-REFERENCE TO RELATED APPLICATIONS

The present application is a 35 U.S.C. § 371 national phase entry of International Application No. PCT/US2020/021125, filed on Mar. 5, 2020, which claims the benefit under 35 U.S.C. § 119 of U.S. Provisional Patent Application No. 62/815,069, filed Mar. 7, 2019, the entire contents of each of which are hereby incorporated by reference in their entirety.

TECHNICAL FIELD

The present invention relates to the field of bacterial strains and their ability to control plant diseases and to increase plant vigor and crop yield. In particular, the present invention is directed to *Paenibacillus* sp. strains producing fusaricidins and tridecaptins and their use to maintain plant health and improve plant growth.

REFERENCE TO SEQUENCE LISTING SUBMITTED ELECTRONICALLY

The official copy of the sequence listing is submitted electronically via EFS-Web as an ASCII-formatted sequence listing with a file named "BCS189006WO_ST25.txt" created on Feb. 25, 2020, and having a size of 185 kilobytes, and is filed concurrently with the specification. The sequence listing contained in this ASCII-formatted document is part of the specification and is herein incorporated by reference in its entirety.

BACKGROUND

Fungicides have myriad uses, including for crop protection; as food, feed, and cosmetics preservatives; and as therapeutic agents for both human and veterinary applications. Crop yield reduction, foodborne diseases and fungal infections of both humans and animals are a problem in both developed and developing countries.

Synthetic insecticides or fungicides often are non-specific and therefore can act on organisms other than the target ones, including other naturally occurring beneficial organisms. Because of their chemical nature, they may also be toxic and non-biodegradable. Consumers worldwide are increasingly conscious of the potential environmental and health problems associated with the residuals of chemicals, particularly in food products. This has resulted in growing consumer pressure to reduce the use or at least the quantity of chemical (i.e., synthetic) pesticides. Thus, there is a need to manage food chain requirements while still allowing effective pest control.

A further problem arising with the use of synthetic insecticides or fungicides is that the repeated and exclusive application of an insecticide or fungicides often leads to selection of resistant pathogenic microorganisms. Normally, such strains are also cross-resistant against other active ingredients having the same mode of action. An effective control of the pathogens with said active compounds is then not possible any longer. However, active ingredients having new mechanisms of action are difficult and expensive to develop.

The risk of resistance development in pathogen populations as well as environmental and human health concerns have fostered interest in identifying alternatives to synthetic insecticides and fungicides for managing plant diseases. The use of biological control agents is one alternative.

*Paenibacillus* is a genus of low GC-content, endospore-forming, Gram-positive bacteria (Firmicutes). Bacteria belonging to this genus are prolific producers of industrially-relevant extracellular enzymes and antimicrobial substances, including non-ribosomal peptide classes. There is considerable variability between species and strains within the *Paenibacillus* genus with only certain strains showing efficacy in controlling plant pathogens and in promoting plant growth.

There is a need for *Paenibacillus* sp. strains with enhanced fungicidal activity and the ability to improve plant growth and vigor. Improvements to the efficacy of existing fungicides and the development of alternatives that are not susceptible to development of fungal resistance are highly desirable.

SUMMARY

The present invention is directed to a composition comprising a biologically pure culture of a *Paenibacillus* sp. strain or a cell-free preparation thereof comprising a fusaricidin and a tridecaptin; wherein the *Paenibacillus* sp. strain comprises a fusaricidin synthetase gene of fusA encoded by a DNA sequence exhibiting at least 90.5% sequence identity to SEQ ID NO: 3; and the *Paenibacillus* sp. strain comprises a nonribosomal peptide synthetase (NRPS) gene of triE encoded by a DNA sequence exhibiting at least 90.0% sequence identity to SEQ ID NO: 7.

In certain aspects, the fusaricidin synthetase gene of fusA is encoded by a DNA sequence comprising SEQ ID NO: 3 or a degenerate nucleotide sequence thereof encoding the same amino acid sequence. In other aspects, the NRPS gene of triE is encoded by a DNA sequence comprising SEQ ID NO: 7 or a degenerate nucleotide sequence thereof encoding the same amino acid sequence.

In some embodiments, the composition comprises Fusaricidin A, Fusaricidin B, Fusaricidin C, Fusaricidin D, LiF05a, LiF05b, LiF06a, LiF06b, LiF07a, and/or LiF07b.

In other embodiments, the composition effectively controls a plant disease caused by a fungus selected from the group consisting of *Botrytis cinerea, Sphaerotheca fuliginea*, and *Puccinia triticina.*

In certain aspects, the *Paenibacillus* sp. strain is *Paenibacillus* sp. strain NRRL B-50374, *Paenibacillus* sp. strain NRRL B-67721, *Paenibacillus* sp. strain NRRL B-67723, *Paenibacillus* sp. strain NRRL B-67724, or a fungicidal mutant strain thereof.

In other aspects, the composition comprises a fermentation product of *Paenibacillus* sp. strain NRRL B-50374, *Paenibacillus* sp. strain NRRL B-67721, *Paenibacillus* sp. strain NRRL B-67723, *Paenibacillus* sp. strain NRRL B-67724, or a fungicidal mutant strain thereof.

In one aspect, the fungicidal mutant strain has a genomic sequence with greater than about 90% sequence identity to *Paenibacillus* sp. strain NRRL B-50374, *Paenibacillus* sp. strain NRRL B-67721, *Paenibacillus* sp. strain NRRL B-67723, or *Paenibacillus* sp. strain NRRL B-67724 and/or the fungicidal mutant strain has fungicidal activity and/or levels of a fusaricidin that are comparable to or better than that of *Paenibacillus* sp. strain NRRL B-50374, *Paenibacillus* sp. strain NRRL B-67721, *Paenibacillus* sp. strain NRRL B-67723, or *Paenibacillus* sp. strain NRRL B-67724.

In some embodiments, the *Paenibacillus* sp. strain further comprises a nitrogen fixation gene cluster; and the nitrogen fixation gene cluster comprises a nitrogen fixation gene of nifB encoded by a DNA sequence exhibiting at least 96.9% sequence identity to SEQ ID NO: 10.

In one embodiment, the nitrogen fixation gene cluster comprises a nitrogen fixation gene of nifB encoded by a DNA sequence comprising SEQ ID NO: 10 or a degenerate nucleotide sequence thereof encoding the same amino acid sequence.

In other embodiments, the expression of the nitrogen fixation gene cluster contributes to enhanced plant growth, plant vigor, and/or crop yield. In yet other embodiments, the *Paenibacillus* sp. strain comprises a fusaricidin synthetase gene of fusA encoded by a DNA sequence exhibiting at least 97.3% sequence identity to SEQ ID NO: 1 and the *Paenibacillus* sp. strain comprises a NRPS gene of triE encoded by a DNA sequence exhibiting at least 97.5% sequence identity to SEQ ID NO: 5.

In one aspect, the fusaricidin synthetase gene of fusA is encoded by a DNA sequence comprising SEQ ID NO: 1 or a degenerate nucleotide sequence thereof encoding the same amino acid sequence. In another aspect, the NRPS gene of triE is encoded by a DNA sequence comprising SEQ ID NO: 5 or a degenerate nucleotide sequence thereof encoding the same amino acid sequence.

In certain aspects, the *Paenibacillus* sp. strain is *Paenibacillus* sp. strain NRRL B-50374, *Paenibacillus* sp. strain NRRL B-67721, *Paenibacillus* sp. strain NRRL B-67724, or a fungicidal mutant strain thereof.

In other aspects, the composition comprises a fermentation product of *Paenibacillus* sp. strain NRRL B-50374, *Paenibacillus* sp. strain NRRL B-67721, *Paenibacillus* sp. strain NRRL B-67724, or a fungicidal mutant strain thereof.

In some embodiments, the fungicidal mutant strain has a genomic sequence with greater than about 90% sequence identity to *Paenibacillus* sp. strain NRRL B-50374, *Paenibacillus* sp. strain NRRL B-67721, or *Paenibacillus* sp. strain NRRL B-67724 and/or the fungicidal mutant strain has fungicidal activity and/or levels of a fusaricidin that are comparable to or better than that of *Paenibacillus* sp. strain NRRL B-50374, *Paenibacillus* sp. strain NRRL B-67721, or *Paenibacillus* sp. strain NRRL B-67724.

In certain aspects, the present invention provides a method of treating an agricultural plant to control a disease, wherein the method comprises applying an effective amount of a composition disclosed herein to the plant, to a part of the plant and/or to a locus of the plant.

In one aspect, the method comprises applying the composition to foliar plant parts. In another aspect, the composition is applied at about $1\times10^{10}$ to about $1\times10^{12}$ colony forming units (CFU) of the *Paenibacillus* sp. strain per hectare or at about 0.5 kg to about 5 kg fermentation solids per hectare. In yet another aspect, the disease is a fungal disease or a bacterial disease.

In other embodiments, the present invention provides a method for increasing the vigor and/or crop yield of an agricultural plant, wherein the plant, the plant propagule, the seed of the plant and/or a locus where the plant is growing or is intended to grow is treated with an effective amount of a composition disclosed herein.

In one embodiment, the treatment is carried out as an in-furrow treatment, seed treatment, and/or foliar treatment.

In another embodiment, the agricultural plant is selected from the group consisting of soybean, corn, wheat, triticale, barley, oat, rye, rape, millet, rice, sunflower, cotton, sugar beet, pome fruit, stone fruit, citrus, banana, strawberry, blueberry, almond, grape, mango, papaya, peanut, potato, tomato, pepper, cucurbit, cucumber, melon, watermelon, garlic, onion, broccoli, carrot, cabbage, bean, dry bean, canola, pea, lentil, alfalfa, trefoil, clover, flax, elephant grass, grass, lettuce, sugarcane, tea, tobacco and coffee; each in its natural or genetically modified form.

In yet another embodiment, the present invention relates to a seed treated with a composition disclosed herein.

DETAILED DESCRIPTION

Figure 1:
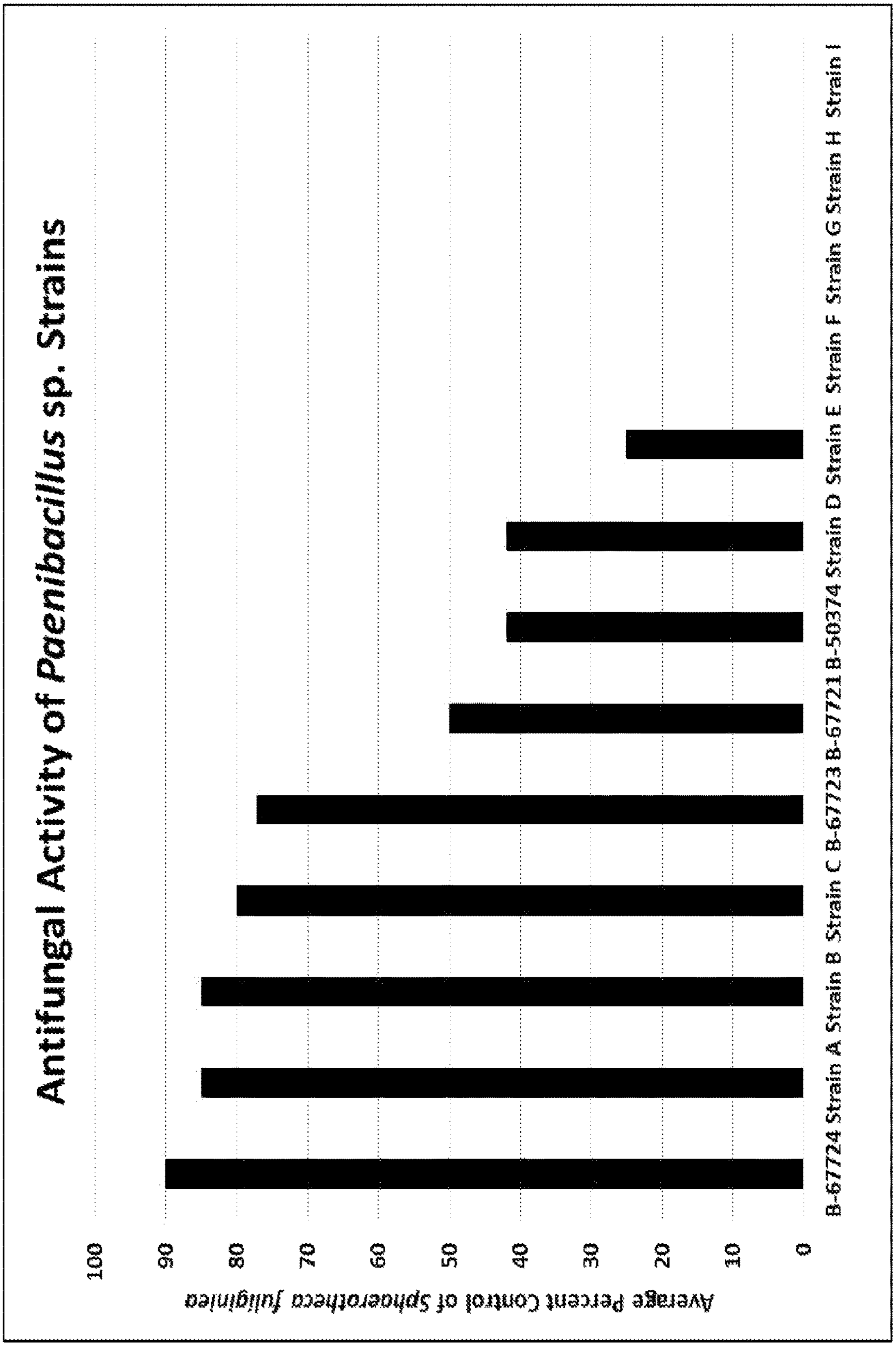
FIG. 1 depicts the control of *Sphaerotheca fuliginea* (PODOXA) achieved with *Paenibacillus* sp. strain NRRL B-50374, *Paenibacillus* sp. strain NRRL B-67721, *Paenibacillus* sp. strain NRRL B-67723, and *Paenibacillus* sp. strain NRRL B-67724 compared to several other *Paenibacillus* sp. strains.

The microorganisms and particular strains described herein, unless specifically noted otherwise, are all separated from nature and grown under artificial conditions such as in shake flask cultures or through scaled-up manufacturing processes, such as in bioreactors to maximize bioactive metabolite production, for example. Growth under such conditions leads to strain "domestication." Generally, such a "domesticated" strain differs from its counterparts found in nature in that it is cultured as a homogenous population that is not subject to the selection pressures found in the natural environment but rather to artificial selection pressures.

As used herein, the verb "comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one".

In certain aspects, the *Paenibacillus* sp. strain of the present invention is selected from any one of the following: *P. terrae, P. brasilensis, P. polymyxa*, or *P. peoriae*. In one aspect, the *Paenibacillus* sp. strain of the present invention is *P. terrae*. In another aspect, the *Paenibacillus* sp. strain of the present invention is *P. brasilensis*. In another aspect, the *Paenibacillus* sp. strain of the present invention is *P. peoriae*. In another aspect, the *Paenibacillus* sp. strain of the present invention is *P. polymyxa.*

In one embodiment, a mutant strain of the *Paenibacillus* sp. strain is *Paenibacillus* sp. strain NRRL B-50374, *Paenibacillus* sp. strain NRRL B-67721, *Paenibacillus* sp. strain NRRL B-67723, or *Paenibacillus* sp. strain NRRL B-67724 is provided. The term "mutant" refers to a genetic variant derived from *Paenibacillus* sp. strain NRRL B-50374, *Paenibacillus* sp. strain NRRL B-67721, *Paenibacillus* sp. strain NRRL B-67723, or *Paenibacillus* sp. strain NRRL B-67724. In one embodiment, the mutant has one or more or all the identifying (functional) characteristics of *Paenibacillus* sp. strain NRRL B-50374, *Paenibacillus* sp. strain NRRL B-67721, *Paenibacillus* sp. strain NRRL B-67723, or *Paenibacillus* sp. strain NRRL B-67724. In a particular instance, the mutant or a fermentation product thereof controls (as an identifying functional characteristic) fungi, oomycetes and/or bacteria at least as well as the parent *Paenibacillus* sp. strain NRRL B-50374, *Paenibacillus* sp. strain NRRL B-67721, *Paenibacillus* sp. strain NRRL B-67723, or *Paenibacillus* sp. strain NRRL B-67724. Such mutants may be genetic variants having a genomic sequence that has greater than about 85%, greater than about 90%, greater than about 95%, greater than about 98%, or greater than about 99% sequence identity to *Paenibacillus* sp. strain NRRL B-50374, *Paenibacillus* sp. strain NRRL B-67721, *Paenibacillus* sp. strain NRRL B-67723, or *Paenibacillus* sp. strain NRRL B-67724. Mutants may be obtained by treating cells of *Paenibacillus* sp. strain NRRL B-50374, *Paenibacillus* sp. strain NRRL B-67721, *Paenibacillus* sp. strain NRRL B-67723, or *Paenibacillus* sp. strain NRRL B-67724 with chemicals or irradiation or by selecting spontaneous mutants from a population of *Paenibacillus* sp. strain NRRL B-50374, *Paenibacillus* sp. strain NRRL B-67721, *Paenibacillus* sp. strain NRRL B-67723, or *Paenibacillus* sp. strain NRRL B-67724 cells (such as phage resistant or antibiotic resistant mutants), by genome shuffling, as described below, or by other means well known to those practiced in the art.

Genome shuffling among *Paenibacillus* strains can be facilitated through the use of a process called protoplast fusion. The process begins with the formation of protoplasts from vegetative bacillary cells. The removal of peptidoglycan cell wall, typically using lysozyme and an osmotic stabilizer, results in the formation of a protoplast. This process is visible under a light microscope with the appearance of spherical cells. Addition of PEG, polyethylene glycol, then induces fusion among protoplasts, allowing genetic contents of two or more cells to come in contact facilitating recombination and genome shuffling. Fused cells then repartition and are recovered on a solid growth medium. During recovery, protoplasts rebuild peptidoglycan cell walls, transitioning back to bacillary shape. See Schaeffer, et. al., (1976) PNAS USA, vol. 73, 6:2151-2155).

In certain aspects, the present invention is directed to *Paenibacillus* sp. strains producing fusaricidins. The fusaricidins are a family of depsipeptides with a 15-guanidino-3-hydroxypentadecanoic acid (GHPD) tail, as well as their linear counterparts. The specific conserved characteristics of fusaricidins are this GHPD tail, as well as three of the six amino acids in the sequence: (1) Threonine, (4) Threonine, and (6) Alanine.

Originally discovered but not characterized by Nakajima et al. (*J. Antibiot.* 1972, 25, 243-247) in the mid-70's, fusaricidins were described by Kurusu et al. (*J. Antibiot.,* 1987, 40, 1506-1514) in the late 1980's. They were further studied by Kajimura et al. (*J. Antibiot.,* 1996, 49, 129-135; *J. Antibiot.,* 1997 50, 220-228), Kuroda et al. (*Heterocycles,* 2000, 53, 1533-1549; *J. Mass Spectrom.,* 2001, 36, 30-37), and Beatty et al. (*Can. J. Microbiol.,* 2002, 48, 159-169) throughout the mid-1990's to the early 2000's. During this period of heavy investigation these compounds were renamed several times depending on the author (Fusaricidin A is also known as LiF04a, Gatavalin, or even KT-6291A). Though there are many publications on the topic, select compounds from the same group of 24 known fusaricidins is described each time.

After a somewhat quiet period on the topic, Vater et al. (*J. Am. Soc. Mass Spectrom.,* 2015, 26, 1130-1141) described the structural elucidation of fusaricidins by mass spectrometry and described several analogs of the family. Vater et al. identified a new class of fusaricidin-like compounds with seven amino acids (i.e., an extra alanine connected to the (4) threonine residue in the peptide sequence). As used herein, the term "acyclic analog" refers to the compound that corresponds to the fusaricidin or fusaricidin-like compound but lacks the ester bond, resulting in a linear structure.

The amino acid chains of fusaricidins are linked together and modified by a non-ribosomal peptide synthetase (NRPS). The multi-domain NRPS consists of up to 15,000 amino acids and is therefore considered among the longest proteins in nature (Schwarzer et al., (2003) Nonribosomal Peptides: From Genes to Products. *Nat. Prod. Rep.* 20, 275-287). NRPS incorporation is not limited to the 21 standard amino acids translated by the ribosome, and this promiscuity contributes to the great structural diversity and biological activity of non-ribosomal peptides (Li and Jensen, (2008). Nonribosomal biosynthesis of fusaricidins by *Paenibacillus polymyxa* PKB1 involves direct activation of a d-amino acid. *Chem. Biol.* 15, 118-127).

In *P. polymyxa* E68, the fusaricidin biosynthetic gene cluster (fusGFEDCBA) has been characterized, and the NRPS coding sequence, the largest coding DNA sequence (CDS) in the cluster, was observed to encode a six-module peptide (Choi et al., Identification and Functional Analysis of the Fusaricidin Biosynthetic Gene of *Paenibacillus polymyxa* E681. Biochem. Biophys. Res. Commun. 365, 89-95; Li and Jensen, Identification and Functional Analysis of the Fusaricidin Biosynthetic Gene of *Paenibacillus polymyxa* E681. Biochem. Biophys. Res. Commun. 365, 89-95; Li et al., (2013). Promoter Analysis and Transcription Regulation of fus Gene Cluster Responsible for Fusaricidin Synthesis of *Paenibacillus polymyxa* SQR-21. Appl. Microbiol. Biotechnol. 97, 9479-9489). The biosynthetic cluster includes other CDS responsible for biosynthesis of the lipid moiety but does not contain transporter genes (Li and Jensen, (2008). Nonribosomal biosynthesis of fusaricidins by *Paenibacillus polymyxa* PKB1 involves direct activation of a d-amino acid. *Chem. Biol.* 15, 118-127). In *P. polymyxa*, a promoter for the fus operon was identified and shown to be bound by a transcriptional repressor (AbrB) which previous studies implicated as a regulator of sporulation; this is of interest since fusaricidin was observed to be synthesized during sporulation, thus coordinating the microbe's secondary metabolism with its life cycle (Li et al., (2013). Promoter Analysis and Transcription Regulation of fus Gene Cluster Responsible for Fusaricidin Synthesis of *Paenibacillus polymyxa* SQR-21. Appl. Microbiol. Biotechnol. 97, 9479-9489).

In other aspects, the present invention is directed to *Paenibacillus* sp. strains producing tridecaptins. The tridecaptins are a group of linear cationic lipopeptides analogous to the polymyxins. The acyl tridecapeptides were first isolated in 1978 and display antimicrobial activity against Gram-positive and Gram-negative bacteria. Shoji, Junichi et al., Journal of Antibiotics (1978), 31 (7), 646-51. More recently, tridecaptin $A_1$ has been characterized in a strain of *Paenibacillus terrae.* Lohans, Christopher T. et al., ChemBioChem (2014), 15 (2), 243-249.

Allelic diversity is typically thought to be responsible for producing chemical diversity. However, an interesting feature of the fus cluster is that a diversity of fusaricidins, differing in their incorporated amino acids (Tyr, Val, Be, allo-Ile, Phe), can be produced by a single allele of fusA; the underlying mechanism is that the NRPS A-domain, responsible for recognition of amino acids, has relaxed substrate specificity (Han et al., (2012). Site-Directed Modification of the Adenylation Domain of the Fusaricidin Nonribosomal Peptide Synthetase for Enhanced Production of Fusaricidin Analogs. Biotechnol. Lett.34, 1327-1334; Mousa et al., (2015) Biodiversity of Genes Encoding Anti-Microbial Traits within Plant Associated Microbes, Front Plant Sci. 2015; 6: 231).

In certain embodiments, the composition comprises a biologically pure culture of a *Paenibacillus* sp. strain comprising a fusaricidin synthetase gene of fusA encoded by a DNA sequence exhibiting at least 90.5% sequence identity to SEQ ID NO: 3 or SEQ ID NO: 1, a nonribosomal peptide synthetase (NRPS) gene of triE encoded by a DNA sequence exhibiting at least 90.0% sequence identity to SEQ ID NO: 7 or SEQ ID NO: 5, and/or a nitrogen fixation gene of nifB encoded by a DNA sequence exhibiting at least 96.9% sequence identity to SEQ ID NO: 10. In some aspects the sequence identity between the fusA, triE, or nifB of the *Paenibacillus* sp. strain and the respective sequence (i.e., SEQ ID NOs: 1 or 3 for fusA; SEQ ID NOs: 5 or 7 for triE; SEQ ID NO: 10 for nifB) is at least 91%, at least 92%, at least 93%, at least 94%, at least 95%, at least 96%, at least 97%, at least 98%, or at least 99%. In other aspects, the sequence identity between the fusA, triE, or nifB of the *Paenibacillus* sp. strain and the respective sequence (i.e., SEQ ID NOs: 1 or 3 for fusA; SEQ ID NOs: 5 or 7 for triE; SEQ ID NO: 10 for nifB) is between about 80% and 100%, between about 85% and 100%, between about 90% and 100%, or between about 95% and 100%.

Due to the degeneracy of the genetic code, different nucleotide codons may be used to code for a particular amino acid. A host cell often displays a preferred pattern of codon usage. Structural nucleic acid sequences are preferably constructed to utilize the codon usage pattern of the particular host cell. This generally enhances the expression of the structural nucleic acid sequence in a transformed host cell. Any of the nucleic acid sequences disclosed herein may be modified to reflect the preferred codon usage of a host cell or organism in which they are contained.

Additional variations in the nucleic acid sequences described herein may encode proteins having equivalent or superior characteristics when compared to the proteins from which they are engineered. Mutations may include deletions, insertions, truncations, substitutions, fusions, shuffling of motif sequences, and the like.

Mutations to a nucleic acid sequence may be introduced in either a specific or random manner, both of which are well known to those of skill in the art of molecular biology. A myriad of site-directed mutagenesis techniques exist, typically using oligonucleotides to introduce mutations at specific locations in a nucleic acid sequence. Examples include single strand rescue (Kunkel et al., Proc. Natl. Acad. Sci. U.S.A., 82: 488-492, 1985), unique site elimination (Deng and Nickloff, Anal. Biochem. 200:81, 1992), nick protection (Vandeyar, et al. Gene 65: 129-133, 1988), and PCR (Costa et al., Methods Mol. Biol. 57: 31-44, 1996). Random or non-specific mutations may be generated by chemical agents (for a general review, see Singer and Kusmierek, Ann. Rev. Biochem. 52: 655-693, 1982) such as nitrosoguanidine (Cerda-Olmedo et al., J. Mol. Biol. 33: 705-719, 1968; Guerola, et al. Nature New Biol. 230: 122-125, 1971) and 2-aminopurine (Rogan and Bessman, J. Bacteriol. 103: 622-633, 1970); or by biological methods such as passage through mutator strains (Greener, et al. Mol. Biotechnol. 7: 189-195, 1997).

The modifications may result in either conservative or non-conservative changes in the amino acid sequence. Conservative changes result from additions, deletions, substitutions, etc. in the structural nucleic acid sequence which do not alter the final amino acid sequence of the protein. In a preferred embodiment, the encoded protein has between 20 and 500 conservative changes, more preferably between 15 and 300 conservative changes, even more preferably between 10 and 150 conservative changes, and most preferably between 5 and 75 conservative changes.

Non-conservative changes include additions, deletions, and substitutions which result in an altered amino acid sequence. In a preferred embodiment, the encoded protein has between 10 and 250 non-conservative amino acid changes, more preferably between 5 and 100 non-conservative amino acid changes, even more preferably between 2 and 50 non-conservative amino acid changes, and most preferably between 1 and 30 non-conservative amino acid changes.

Additional methods of making the alterations described above are described by Ausubel et al., Current Protocols in Molecular Biology, John Wiley and Sons, Inc., 1995, Bauer et al., Gene, 37:73, 1985; Craik, BioTechniques, 3: 12-19, 1985; Frits Eckstein et al., Nucleic Acids Research, 10: 6487-6497, 1982; Sambrook, et al., Molecular Cloning: A Laboratory Manual, Second Edition, Cold Spring Harbor Laboratory Press, Cold Spring Harbor, N.Y., 1989, Smith, et al, In: Genetic Engineering: Principles and Methods, Setlow et al., Eds., Plenum Press, N.Y., 1-32, 1981, and Osuna, et al., Critical Reviews In Microbiology, 20: 107-116, 1994.

Modifications may be made to the protein sequences of the present invention and the nucleic acid segments which encode them that maintain the desired properties of the molecule. The following is a discussion based upon changing the amino acid sequence of a protein to create an equivalent, or possibly an improved molecule.

Certain amino acids may be substituted for other amino acids in a protein sequence without appreciable loss of the desired activity.

It is thus contemplated that various changes may be made in the peptide sequences of the disclosed protein sequences, or their corresponding nucleic acid sequences without appreciable loss of the biological activity.

In making such changes, the hydropathic index of amino acids may be considered. The importance of the hydropathic amino acid index in conferring interactive biological function on a protein is generally understood in the art (Kyte and Doolittle, *J. Mol. Biol.*, 157: 105-132, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics. These are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate/glutamine/aspartate/asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biologically functional protein. In making such changes, the substitution of amino acids whose hydropathic indices are within ±2 is preferred, those within ±1 are more preferred, and those within ±0.5 are most preferred.

It is also understood in the art that the substitution of like amino acids may be made effectively on the basis of hydrophilicity. U.S. Pat. No. 4,554,101 (Hopp) states that the greatest local average hydrophilicity of a protein, as governed by the hydrophilicity of its adjacent amino acids, correlates with a biological property of the protein. The following hydrophilicity values have been assigned to amino acids: arginine/lysine (+3.0); aspartate/glutamate (+3.0±1); serine (+0.3); asparagine/glutamine (+0.2); glycine (0); threonine (−0.4); proline (−0.5±1); alanine/histidine (−0.5); cysteine (−1.0); methionine (−1.3); valine (−1.5); leucine/isoleucine (−1.8); tyrosine (−2.3); phenyl alanine (−2.5); and tryptophan (−3.4).

It is understood that an amino acid may be substituted by another amino acid having a similar hydrophilicity score and still result in a protein with similar biological activity, i.e., still obtain a biologically functional protein. In making such changes, the substitution of amino acids whose hydropathic indices are within ±2 is preferred, those within ±1 are more preferred, and those within ±0.5 are most preferred.

As outlined above, amino acid substitutions are therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine, and isoleucine.

The present invention also encompasses methods of treating a plant to control plant diseases by administering to a plant or a plant part, such as a leaf, stem, flowers, fruit, root, or seed or by applying to a locus on which plant or plant parts grow, such as soil, the disclosed *Paenibacillus* sp. strains or mutants thereof, or cell-free preparations thereof or metabolites thereof.

In a method according to the invention a composition containing a disclosed *Paenibacillus* sp. strain or a fungicidal mutant thereof can be applied to any plant or any part of any plant grown in any type of media used to grow plants (e.g., soil, vermiculite, shredded cardboard, and water) or applied to plants or the parts of plants grown aerially, such as orchids or staghorn ferns. The composition may for instance be applied by spraying, atomizing, vaporizing, scattering, dusting, watering, squirting, sprinkling, pouring or fumigating. As already indicated above, application may be carried out at any desired location where the plant of interest is positioned, such as agricultural, horticultural, forest, plantation, orchard, nursery, organically grown crops, turfgrass and urban environments.

Compositions of the present invention can be obtained by culturing the disclosed *Paenibacillus* sp. strains or a fungicidal mutant (strain) derived therefrom according to methods well known in the art, including by using the media and other methods described in the examples below. Conventional large-scale microbial culture processes include submerged fermentation, solid state fermentation, or liquid surface culture. Towards the end of fermentation, as nutrients are depleted, cells begin the transition from growth phase to sporulation phase, such that the final product of fermentation is largely spores, metabolites and residual fermentation medium. Sporulation is part of the natural life cycle of *Paenibacillus* and is generally initiated by the cell in response to nutrient limitation. Fermentation is configured to obtain high levels of colony forming units of and to promote sporulation. The bacterial cells, spores and metabolites in culture media resulting from fermentation may be used directly or concentrated by conventional industrial methods, such as centrifugation, tangential-flow filtration, depth filtration, and evaporation.

Compositions of the present invention include fermentation products. In some embodiments, the concentrated fermentation broth is washed, for example, via a diafiltration process, to remove residual fermentation broth and metabolites. The term "broth concentrate," as used herein, refers to whole broth (fermentation broth) that has been concentrated by conventional industrial methods, as described above, but remains in liquid form. The term "fermentation solid," as used herein, refers to the solid material that remains after the fermentation broth is dried. The term "fermentation product," as used herein, refers to whole broth, broth concentrate and/or fermentation solids. Compositions of the present invention include fermentation products.

The fermentation broth or broth concentrate can be dried with or without the addition of carriers using conventional drying processes or methods such as spray drying, freeze drying, tray drying, fluidized-bed drying, drum drying, or evaporation.

The resulting dry products may be further processed, such as by milling or granulation, to achieve a specific particle size or physical format. Carriers, described below, may also be added post-drying.

Cell-free preparations of fermentation broth of the strains of the present invention can be obtained by any means known in the art, such as extraction, centrifugation and/or filtration of fermentation broth. Those of skill in the art will appreciate that so-called cell-free preparations may not be devoid of cells but rather are largely cell-free or essentially cell-free, depending on the technique used (e.g., speed of centrifugation) to remove the cells. The resulting cell-free preparation may be dried and/or formulated with components that aid in its application to plants or to plant growth media. Concentration methods and drying techniques described above for fermentation broth are also applicable to cell-free preparations.

In one embodiment, the fermentation product comprises at least about $1\times10^4$ colony forming units (CFU) of the microorganism (e.g., *Paenibacillus* sp. strain NRRL B-50374, *Paenibacillus* sp. strain NRRL B-67721, *Paenibacillus* sp. strain NRRL B-67723, or *Paenibacillus* sp. strain NRRL B-67724 or a fungicidal mutant strain thereof)/mL broth. In another embodiment, the fermentation product comprises at least about $1\times10^5$ colony forming units (CFU) of the microorganism/mL broth. In another embodiment, the fermentation product comprises at least about $1\times10^6$ CFU of the microorganism/mL broth. In yet another embodiment, the fermentation product comprises at least about $1\times10^7$ CFU of the microorganism/mL broth. In another embodiment, the fermentation product comprises at least about $1\times10^8$ CFU of the microorganism/mL broth. In another embodiment, the fermentation product comprises at least about $1\times10^9$ CFU of the microorganism/mL broth. In another embodiment, the fermentation product comprises at least about $1\times10^{10}$ CFU of the microorganism/mL broth. In another embodiment, the fermentation product comprises at least about $1\times10^{11}$ CFU of the microorganism/mL broth.

The inventive compositions can be used as such or, depending on their particular physical and/or chemical properties, in the form of their formulations or the use forms prepared therefrom, such as aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, gas (under pressure), gas generating product, foams, pastes, pesticide coated seed, suspension concentrates, oil dispersion, suspo-emulsion concentrates, soluble concentrates, suspensions, wettable powders, soluble powders, dusts and granules, water-soluble and water-dispersible granules or tablets, water-soluble and water-dispersible powders for the treatment of seed, wettable powders, natural products and synthetic substances impregnated with active ingredient, and also microencapsulations in polymeric substances and in coating materials for seed, and also ULV cold-fogging and warm-fogging formulations.

In some embodiments, the inventive compositions are liquid formulations. Non-limiting examples of liquid formulations include suspension concentrations and oil dispersions. In other embodiments, the inventive compositions are solid formulations. Non-limiting examples of liquid formulations include freeze-dried powders and spray-dried powders.

All plants and plant parts can be treated in accordance with the invention. In the present context, plants are understood as meaning all plants and plant populations, such as desired and undesired wild plants or crop plants (including naturally occurring crop plants). Crop plants can be plants which can be obtained by traditional breeding and optimization methods or by biotechnological and recombinant methods, or combinations of these methods, including the transgenic plants and including the plant varieties capable or not of being protected by Plant Breeders' Rights. Plant parts are understood as meaning all aerial and subterranean parts and organs of the plants, such as shoot, leaf, flower and root, examples which may be mentioned being leaves, needles, stalks, stems, flowers, fruiting bodies, fruits and seeds, and also roots, tubers and rhizomes. The plant parts also include crop material and vegetative and generative propagation material, for example cuttings, tubers, rhizomes, slips and seeds.

As has already been mentioned above, all plants and their parts may be treated in accordance with the invention. In a preferred embodiment, plant species and plant varieties, and their parts, which grow wild or which are obtained by traditional biological breeding methods such as hybridization or protoplast fusion are treated. In a further preferred embodiment, transgenic plants and plant varieties which have been obtained by recombinant methods, if appropriate in combination with traditional methods (genetically modified organisms), and their parts are treated. The term "parts" or "parts of plants" or "plant parts" has been explained hereinabove. Plants of the plant varieties which are in each case commercially available or in use are especially preferably treated in accordance with the invention. Plant varieties are understood as meaning plants with novel traits which have been bred both by traditional breeding, by mutagenesis or by recombinant DNA techniques. They may take the form of varieties, races, biotypes and genotypes.

The treatment of the plants and plant parts with the compositions according to the invention is carried out directly or by acting on the environment, habitat or storage space using customary treatment methods, for example by dipping, spraying, atomizing, misting, evaporating, dusting, fogging, scattering, foaming, painting on, spreading, injecting, drenching, trickle irrigation and, in the case of propagation material, in particular in the case of seed, furthermore by the dry seed treatment method, the wet seed treatment method, the slurry treatment method, by encrusting, by coating with one or more coats and the like. It is furthermore possible to apply the active substances by the ultra-low volume method or to inject the active substance preparation or the active substance itself into the soil.

A preferred direct treatment of the plants is the leaf application treatment, i.e., compositions according to the invention are applied to the foliage, it being possible for the treatment frequency and the application rate to be matched to the infection pressure of the pathogen in question.

Preferred plants are those from the group of the useful plants, ornamentals, turfs, generally used trees which are employed as ornamentals in the public and domestic sectors, and forestry trees. Forestry trees comprise trees for the production of timber, cellulose, paper and products made from parts of the trees.

The term "agricultural plants" as used in the present context refers to crop plants which are employed as plants for obtaining foodstuffs, feedstuffs, fuels or for industrial purposes.

The terms "plant propagation material" and "plant propagule" are to be understood to denote all the generative parts of the plant such as seeds and vegetative plant material such as cuttings and tubers (e.g., potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be mentioned. These young plants may also be treated totally or partially by immersion or pouring before transplantation.

The term "locus" is to be understood as any type of environment, soil, area or material where the plant is growing or intended to grow as well as the environmental conditions (such as temperature, water availability, radiation) that have an influence on the growth and development of the plant and/or its propagules. In addition, the term "locus" is to be understood as a plant, seed, soil, area, material or environment in which a pest is growing or may grow.

"Crop yield" is an indicator for the condition of the plant, whereas "crop" is to be understood as any plant or plant product which is further utilized after harvesting, e.g., fruits in the proper sense, vegetables, nuts, grains, seeds, wood (e.g., in the case of silviculture plants), flowers (e.g., in the case of gardening plants, ornamentals) etc., that is anything of economic value that is produced by the plant.

According to the present invention, "increased yield" of a plant, in particular of an agricultural, silvicultural and/or ornamental plant means that the yield of a product of the respective plant is increased by a measurable amount over the yield of the same product of the plant produced under the same conditions, but without the application of the composition of the invention.

The term "seed" embraces seeds and plant propagules of all kinds including but not limited to true seeds, seed pieces, suckers, corms, bulbs, fruit, tubers, grains, cuttings, cut shoots and the like and means in a preferred embodiment true seeds.

The term "seed treatment" comprises all suitable seed treatment techniques known in the art, such as seed dressing, seed coating, seed dusting, seed soaking, seed impregnation and seed pelleting.

The agricultural plants which can be treated and/or improved with the compositions and methods of the present invention include for example the following types of plants: turf, vines, cereals, for example wheat, barley, rye, oats, rice, maize and millet/sorghum; beet, for example sugar beet and fodder beet; fruits, for example pome fruit, stone fruit and soft fruit, for example apples, pears, plums, peaches, almonds, cherries and berries, for example strawberries, raspberries, blackberries; legumes, for example beans, lentils, peas and soybeans; oil crops, for example oilseed rape, mustard, poppies, olives, sunflowers, coconuts, castor oil plants, cacao and peanuts; cucurbits, for example pumpkin/squash, cucumbers and melons; fibre plants, for example cotton, flax, hemp and jute; citrus fruit, for example oranges, lemons, grapefruit and tangerines; vegetables, for example spinach, lettuce, asparagus, cabbage species, carrots, onions, tomatoes, potatoes and bell peppers; *Lauraceae*, for example avocado, *Cinnamomum*, camphor, or else plants such as tobacco, nuts, coffee, aubergine, sugar cane, tea, pepper, grapevines, hops, bananas, latex plants and ornamentals, for example flowers, shrubs, deciduous trees and coniferous trees. This enumeration is no limitation.

The following plants are considered to be particularly suitable target crops for applying compositions and methods of the present invention: cotton, aubergine, turf, pome fruit, stone fruit, soft fruit, maize, wheat, barley, cucumber, tobacco, vines, rice, cereals, pear, beans, soybeans, oilseed rape, tomato, bell pepper, melons, cabbage, potato and apple.

Additional agricultural plants of particular interest include for example, cereals, for example wheat, rye, barley, triticale, oats or rice; beet, for example sugar beet or fodder beet; fruits, such as pomes, stone fruits or soft fruits, for example apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as broccoli, spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; natural rubber plants or ornamental and forestry plants, such as flowers, shrubs, broad-leaved trees or evergreens, for example conifers; and on the plant propagation material, such as seeds, and the crop material of these plants.

Examples of trees which can be improved in accordance with the method according to the invention are: *Abies* sp., *Eucalyptus* sp., *Picea* sp., *Pinus* sp., *Aesculus* sp., *Platanus* sp., *Tilia* sp., Acer sp., *Tsuga* sp., *Fraxinus* sp., *Sorbus* sp., *Betula* sp., *Crataegus* sp., *Ulmus* sp., *Quercus* sp., *Fagus* sp., Salix sp., *Populus* sp.

Preferred trees which can be improved in accordance with the method according to the invention are: from the tree species *Aesculus: A. hippocastanum, A. pariflora, A. carnea*; from the tree species *Platanus: P. aceriflora, P. occidentalis, P. racemosa*; from the tree species *Picea: P. abies*; from the tree species *Pinus: P. radiata, P. ponderosa, P. contorta, P. sylvestre, P. elliottii, P. montecola, P. albicaulis, P. resinosa, P. palustris, P. taeda, P. flexilis, P. jeffregi, P. baksiana, P. strobus*; from the tree species *Eucalyptus: E. grandis, E. globulus, E. camadentis, E. nitens, E. obliqua, E. regnans, E. pilularus.*

Especially preferred trees which can be improved in accordance with the method according to the invention are: from the tree species *Pinus: P. radiata, P. ponderosa, P. contorta, P. sylvestre, P. strobus*; from the tree species *Eucalyptus: E. grandis, E. globulus, E. camadentis.*

Very particularly preferred trees which can be improved in accordance with the method according to the invention are: horse chestnut, Platanaceae, linden tree, maple tree.

The present invention can also be applied to any turf grasses, including cool-season turf grasses and warm-season turf grasses. Examples of cold-season turf grasses are bluegrasses (*Poa* spp.), such as Kentucky bluegrass (*Poa pratensis* L.), rough bluegrass (*Poa trivialis* L.), Canada bluegrass (*Poa compressa* L.), annual bluegrass (*Poa annua* L.), upland bluegrass (*Poa glaucantha* Gaudin), wood bluegrass (*Poa nemoralis* L.) and bulbous bluegrass (*Poa bulbosa* L.); bentgrasses (*Agrostis* spp.) such as creeping bentgrass (*Agrostis palustris* Huds.), colonial bentgrass (*Agrostis tenuis* Sibth.), velvet bentgrass (*Agrostis canina* L.), South German mixed bentgrass (*Agrostis* spp. including *Agrostis tenuis* Sibth., *Agrostis canina* L., and *Agrostis palustris* Huds.), and redtop (*Agrostis alba* L.);

fescues (*Festuca* spp.), such as red fescue (*Festuca rubra* L. spp. *rubra*), creeping fescue (*Festuca rubra* L.), chewings fescue (*Festuca rubra commutata* Gaud.), sheep fescue (*Festuca ovina* L.), hard fescue (*Festuca longifolia* Thuill.), hair fescue (*Festucu capillata* Lam.), tall fescue (*Festuca arundinacea* Schreb.) and meadow fescue (*Festuca* elanor L.);

ryegrasses (*Lolium* spp.), such as annual ryegrass (*Lolium multiflorum* Lam.), perennial ryegrass (*Lolium perenne* L.) and Italian ryegrass (*Lolium multiflorum* Lam.);

and wheatgrasses (*Agropyron* spp.), such as fairway wheatgrass (*Agropyron cristatum* (L.) Gaertn.), crested wheatgrass (*Agropyron desertorum* (Fisch.) Schult.) and western wheatgrass (*Agropyron smithii* Rydb.)

Examples of further cool-season turf grasses are beachgrass (*Ammophila breviligulata* Fern.), smooth bromegrass (*Bromus inermis* Leyss.), cattails such as timothy (*Phleum pratense* L.), sand cattail (*Phleum subulatum* L.), orchardgrass (*Dactylis glomerata* L.), weeping alkaligrass (*Puccinellia distans* (L.) Parl.) and crested dog's-tail (*Cynosurus cristatus* L.)

Examples of warm-season turf grasses are Bermuda grass (*Cynodon* spp. L. C. Rich), *zoysia* grass (*Zoysia* spp. Willd.), St. Augustine grass (*Stenotaphrum secundatum* Walt Kuntze), centipede grass (*Eremochloa ophiuroides* Munro Hack.), carpetgrass (*Axonopus affinis* Chase), Bahia grass (*Paspalum notatum* Flugge), Kikuyu grass (*Pennisetum clandestinum* Hochst. ex Chiov.), buffalo grass (*Buchloe dactyloids* (Nutt.) Engelm.), blue grama (*Bouteloua gracilis* (H.B.K.) Lag. ex Griffiths), seashore *paspalum* (*Paspalum vaginatum* Swartz) and sideoats grama (*Bouteloua curtipendula* (Michx. Torr.) Cool-season turf grasses are generally preferred for the use according to the invention. Especially preferred are bluegrass, benchgrass and redtop, fescues and ryegrasses. Bentgrass is especially preferred.

The inventive compositions have potent microbicidal activity and can be used for control of unwanted microorganisms, such as fungi and bacteria, in crop protection and in the protection of materials.

The invention also relates to a method for controlling unwanted microorganisms, characterized in that the inventive compositions are applied to the phytopathogenic fungi, phytopathogenic bacteria and/or their habitat.

Fungicides can be used in crop protection for control of phytopathogenic fungi. They are characterized by an outstanding efficacy against a broad spectrum of phytopathogenic fungi, including soilborne pathogens, which are in particular members of the classes Plasmodiophoromycetes, Peronosporomycetes (Syn. Oomycetes), Chytridiomycetes, Zygomycetes, Ascomycetes, Basidiomycetes and Deuteromycetes (Syn. Fungi imperfecti). Some fungicides are systemically active and can be used in plant protection as foliar, seed dressing or soil fungicide. Furthermore, they are suitable for combating fungi, which inter alia infest wood or roots of plant.

Bactericides can be used in crop protection for control of Pseudomonadaceae, Rhizobiaceae, Enterobacteriaceae, Corynebacteriaceae and Streptomycetaceae.

Non-limiting examples of pathogens of fungal diseases which can be treated in accordance with the invention include:

- diseases caused by powdery mildew pathogens, for example *Blumeria* species, for example *Blumeria graminis; Podosphaera* species, for example *Podosphaera leucotricha; Sphaerotheca* species, for example *Sphaerotheca fuliginea; Uncinula* species, for example *Uncinula necator;*
- diseases caused by rust disease pathogens, for example *Gymnosporangium* species, for example *Gymnosporangium sabinae; Hemileia* species, for example *Hemileia vastatrix; Phakopsora* species, for example *Phakopsora pachyrhizi* and *Phakopsora meibomiae; Puccinia* species, for example *Puccinia recondite, P. triticina, P. graminis* or *P. striiformis; Uromyces* species, for example *Uromyces appendiculatus;*
- diseases caused by pathogens from the group of the Oomycetes, for example *Albugo* species, for example *Albugo candida; Bremia* species, for example *Bremia lactucae; Peronospora* species, for example *Peronospora pisi* or *P. brassicae; Phytophthora* species, for example *Phytophthora infestans; Plasmopara species*, for example *Plasmopara viticola; Pseudoperonospora* species, for example *Pseudoperonospora humuli* or *Pseudoperonospora cubensis; Pythium* species, for example *Pythium ultimum;*
- leaf blotch diseases and leaf wilt diseases caused, for example, by *Alternaria* species, for example *Alternaria solani; Cercospora* species, for example *Cercospora beticola; Cladiosporium* species, for example *Cladiosporium cucumerinum; Cochliobolus* species, for example *Cochliobolus sativus* (conidia form: *Drechslera*, Syn: *Helminthosporium*), *Cochliobolus miyabeanus; Colletotrichum* species, for example *Colletotrichum lindemuthanium; Cycloconium* species, for example *Cycloconium oleaginum; Diaporthe* species, for example *Diaporthe citri; Elsinoe* species, for example *Elsinoe fawcettii; Gloeosporium* species, for example *Gloeosporium laeticolor; Glomerella* species, for example *Glomerella cingulata; Guignardia* species, for example *Guignardia bidwelli; Leptosphaeria* species, for example *Leptosphaeria maculans, Leptosphaeria nodorum; Magnaporthe* species, for example *Magnaporthe grisea; Marssonia* species, for example *Marssonia coronaria; Microdochium* species, for example *Microdochium nivale; Mycosphaerella* species, for example *Mycosphaerella graminicola, M. arachidicola* and *M. fijiensis; Phaeosphaeria* species, for example *Phaeosphaeria nodorum; Pyrenophora* species, for example *Pyrenophora teres, Pyrenophora tritici repentis; Ramularia* species, for example *Ramularia collo-cygni, Ramularia areola; Rhynchosporium* species, for example *Rhynchosporium secalis; Septoria* species, for example *Septoria apii, Septoria lycopersii; Typhula* species, for example *Typhula incarnata; Venturia* species, for example *Venturia inaequalis;*
- root and stem diseases caused, for example, by *Corticium* species, for example *Corticium graminearum; Fusarium* species, for example *Fusarium oxysporum; Gaeumannomyces* species, for example *Gaeumannomyces graminis; Rhizoctonia* species, such as, for example *Rhizoctonia solani; Sarocladium* diseases caused for example by *Sarocladium oryzae; Sclerotium* diseases caused for example by *Sclerotium oryzae; Tapesia* species, for example *Tapesia acuformis; Thielaviopsis* species, for example *Thielaviopsis basicola;*
- ear and panicle diseases (including corn cobs) caused, for example, by *Alternaria* species, for example *Alternaria* spp.; *Aspergillus* species, for example *Aspergillus flavus; Cladosporium* species, for example *Cladosporium cladosporioides; Claviceps* species, for example *Claviceps purpurea; Fusarium* species, for example *Fusarium culmorum; Gibberella* species, for example *Gibberella zeae; Monographella* species, for example *Monographella nivalis; Septoria* species, for example *Septoria nodorum;*
- diseases caused by smut fungi, for example *Sphacelotheca* species, for example *Sphacelotheca reiliana; Tilletia* species, for example *Tilletia caries, T. controversa; Urocystis* species, for example *Urocystis occulta; Ustilago* species, for example *Ustilago nuda, U. nuda tritici;*
- fruit rot caused, for example, by *Aspergillus* species, for example *Aspergillus flavus; Botrytis* species, for example *Botrytis cinerea; Penicillium* species, for example *Penicillium expansum* and *P. purpurogenum; Sclerotinia* species, for example *Sclerotinia sclerotiorum; Verticilium* species, for example *Verticilium alboatrum;*
- seed and soilborne decay, mould, wilt, rot and damping-off diseases caused, for example, by *Alternaria* species, caused for example by *Alternaria brassicicola; Aphanomyces* species, caused for example by *Aphanomyces euteiches; Ascochyta* species, caused for example by *Ascochyta lentis; Aspergillus* species, caused for example by *Aspergillus flavus; Cladosporium* species, caused for example by *Cladosporium herbarum; Cochliobolus* species, caused for example by *Cochliobolus sativus*; (conidia form: *Drechslera, Bipolaris* Syn: *Helminthosporium*); *Colletotrichum* species, caused for example by *Colletotrichum coccodes; Fusarium* species, caused for example by *Fusarium culmorum; Gibberella* species, caused for example by *Gibberella zeae; Macrophomina* species, caused for example by *Macrophomina phaseolina; Monographella* species, caused for example by *Monographella nivalis; Penicillium* species, caused for example by *Penicillium expansum; Phoma* species, caused for example by *Phoma lingam; Phomopsis* species, caused for example by *Phomopsis sojae; Phytophthora* species, caused for example by *Phytophthora cactorum; Pyrenophora* species, caused for example by *Pyrenophora graminea; Pyricularia* species, caused for example by *Pyricularia oryzae; Pythium* species, caused for example by *Pythium ultimum; Rhizoctonia* species, caused for example by *Rhizoctonia solani; Rhizopus* species, caused for example by *Rhizopus oryzae; Sclerotium* species, caused for example by *Sclerotium rolfsii; Septoria* species, caused for example by *Septoria nodorum; Typhula* species, caused for example by *Typhula incarnata; Verticillium* species, caused for example by *Verticillium dahliae;*
- cancers, galls and witches' broom caused, for example, by *Nectria* species, for example *Nectria galligena;* wilt diseases caused, for example, by *Monilinia* species, for example *Monilinia laxa;* leaf blister or leaf curl diseases caused, for example, by *Exobasidium* species, for example *Exobasidium vexans;*

*Taphrina* species, for example *Taphrina deformans;* decline diseases of wooden plants caused, for example, by Esca disease, caused for example by *Phaemoniella clamydospora, Phaeoacremonium aleophilum* and *Fomitiporia mediterranea; Eutypa dyeback*, caused for example by *Eutypa lata; Ganoderma* diseases caused for example by *Ganoderma boninense; Rigidoporus* diseases caused for example by *Rigidoporus lignosus;* diseases of flowers and seeds caused, for example, by *Botrytis* species, for example *Botrytis cinerea;* diseases of plant tubers caused, for example, by *Rhizoctonia* species, for example *Rhizoctonia solani; Helminthosporium* species, for example *Helminthosporium solani;*

Club root caused, for example, by *Plasmodiophora* species, for example *Plamodiophora brassicae;* diseases caused by bacterial pathogens, for example *Xanthomonas* species, for example *Xanthomonas campestris* pv. *oryzae; Pseudomonas* species, for example *Pseudomonas syringae* pv. *lachrymans; Erwinia* species, for example *Erwinia amylovora.*

The following diseases of soya beans can be controlled with preference:

Fungal diseases on leaves, stems, pods and seeds caused, for example, by *Alternaria* leaf spot (*Alternaria* spec. *atrans tenuissima*), Anthracnose (*Colletotrichum gloeosporoides dematium* var. *truncatum*), brown spot (*Septoria glycines*), *cercospora* leaf spot and blight (*Cercospora kikuchii*), *choanephora* leaf blight (*Choanephora infundibulifera trispora* (Syn.)), *dactuliophora* leaf spot (*Dactuliophora glycines*), downy mildew (*Peronospora manshurica*), *drechslera* blight (*Drechslera glycini*), frogeye leaf spot (*Cercospora sojina*), *leptosphaerulina* leaf spot (*Leptosphaerulina trifolii*), *phyllostica* leaf spot (*Phyllosticta sojaecola*), pod and stem blight (*Phomopsis sojae*), powdery mildew (*Microsphaera diffusa*), *pyrenochaeta* leaf spot (*Pyrenochaeta glycines*), *rhizoctonia* aerial, foliage, and web blight (*Rhizoctonia solani*), rust (*Phakopsora pachyrhizi, Phakopsora meibomiae*), scab (*Sphaceloma glycines*), *stemphylium* leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), *fusarium* blight or wilt, root rot, and pod and collar rot (*Fusarium oxysporum, Fusarium orthoceras, Fusarium semitectum, Fusarium equiseti*), *mycoleptodiscus* root rot (*Mycoleptodiscus terrestris*), *neocosmospora* (*Neocosmospora vasinfecta*), pod and stem blight (*Diaporthe phaseolorum*), stem canker (*Diaporthe phaseolorum* var. *caulivora*), *phytophthora* rot (*Phytophthora megasperma*), brown stem rot (*Phialophora gregata*), *pythium* rot (*Pythium aphanidermatum, Pythium irregulare, Pythium debaryanum, Pythium myriotylum, Pythium ultimum*), *rhizoctonia* root rot, stem decay, and damping-off (*Rhizoctonia solani*), *sclerotinia* stem decay (*Sclerotinia sclerotiorum*), *sclerotinia* southern blight (*Sclerotinia rolfsii*), *thielaviopsis* root rot (*Thielaviopsis basicola*).

The inventive fungicidal compositions can be used for curative or protective/preventive control of phytopathogenic fungi. The invention therefore also relates to curative and protective methods for controlling phytopathogenic fungi by the use of the inventive compositions, which are applied to the seed, the plant or plant parts, the fruit or the soil in which the plants grow.

The fact that the compositions are well tolerated by plants at the concentrations required for controlling plant diseases allows the treatment of above-ground parts of plants, of propagation stock and seeds, and of the soil.

According to the invention all plants and plant parts can be treated including cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods.

In some embodiments, the compositions disclosed herein are used to enhance plant growth, plant vigor, and/or crop yield. "Yield" is to be understood as any plant product of economic value that is produced by the plant such as grains, fruits in the proper sense, vegetables, nuts, grains, seeds, wood (e.g., in the case of silviculture plants) or even flowers (e.g., in the case of gardening plants, ornamentals). The plant products may in addition be further utilized and/or processed after harvesting.

According to the present invention, "increased yield" of a plant, in particular of an agricultural, silvicultural and/or ornamental plant means that the yield of a product of the respective plant is increased by a measurable amount over the yield of the same product of the plant produced under the same conditions, but without the application of the composition of the invention. Increased yield can be characterized, among others, by following improved properties of the plant:

increased plant weight,
increased plant height,
increased biomass such as higher fresh and/or dry weight,
higher grain yield,
more tillers,
larger leaves,
increased shoot growth,
increased protein content,
increased oil content,
increased starch content.
increased pigment content According to one embodiment of the present invention, the yield is increased by at least 5%. According to another embodiment of the present invention, the yield is increased by least 10%. According to another embodiment of the present invention, the yield is increased by least 15%. According to another embodiment of the present invention, the yield is increased by least 30%. According to another embodiment of the present invention, the yield is increased by least 40%.

Another indicator for the condition of the plant is the "plant vigor". The plant vigor becomes manifest in several aspects such as the general visual appearance. Improved plant vigor can be characterized, among others, by following improved properties of the plant:

improved vitality of the plant,
improved plant growth,
improved plant development,
improved visual appearance,
improved plant stand (less plant verse/lodging),
improved emergence,
enhanced root growth and/or more developed root system, enhanced nodulation, in particular rhizobial nodulation,
bigger leaf blade,
increased plant size,
increased plant weight,
increased plant height,
increased tiller number,
increased shoot growth,
increased root growth (extensive root system),
increased size of root mass (extensive root system),
increased yield when grown on poor soils or unfavorable climate,
enhanced photosynthetic activity,
change of color (e.g., enhanced pigment content (e.g., Chlorophyll content),
earlier flowering,
earlier fruiting,
earlier and improved germination,
earlier (advanced) grain maturity,
improved self-defence mechanisms,
less non-productive tillers,
less dead basal leaves,
less input needed (such as fertilizers or water),
greener leaves and increased green leaf area,
complete maturation under shortened vegetation periods,
less fertilizers needed,
less seeds needed,
easier harvesting,
faster and more uniform ripening,
longer shelf-life,
longer panicles,
delay of senescence,
stronger and/or more productive tillers,
better extractability of ingredients,
improved quality of seeds (for being seeded in the following seasons for seed production),
reduced production of ethylene and/or the inhibition of its reception by the plant,
spindliness of leaves,
increased number of ears/$m^2$.

The improvement of the plant vigor according to the present invention particularly means that the improvement of any one or several or all of the above mentioned plant characteristics are improved independently of the pesticidal action of the composition or active ingredients. An increased vigor may for example result in a higher percentage of plants that can be transplanted to the field or an increased number of marketable plants (such as tomatoes).

In certain aspects, the compositions of the present invention are applied at about $1\times10^4$ to about $1\times10^{14}$ colony forming units (CFU) per hectare, at about $1\times10^4$ to about $1\times10^{12}$ colony forming units (CFU) per hectare, at about $1\times10^4$ to about $1\times10^{10}$ colony forming units (CFU) per hectare, at about $1\times10^4$ to about $1\times10^8$ colony forming units (CFU) per hectare, at about $1\times10^6$ to about $1\times10^{14}$ colony forming units (CFU) per hectare, at about $1\times10^6$ to about $1\times10^{12}$ colony forming units (CFU) per hectare, at about $1\times10^6$ to about $1\times10^{10}$ colony forming units (CFU) per hectare, at about $1\times10^6$ to about $1\times10^8$ colony forming units (CFU) per hectare, at about $1\times10^8$ to about $1\times10^{14}$ colony forming units (CFU) per hectare, at about $1\times10^8$ to about $1\times10^{12}$ colony forming units (CFU) per hectare, or at about $1\times10^8$ to about $1\times10^{10}$ colony forming units (CFU) per hectare.

In other aspects, the compositions of the present invention are applied at about $1\times10^6$ to about $1\times10^{14}$ colony forming units (CFU) per hectare, at about $1\times10^6$ to about $1\times10^{12}$ colony forming units (CFU) per hectare, at about $1\times10^6$ to about $1\times10^{10}$ colony forming units (CFU) per hectare, at about $1\times10^6$ to about $1\times10^8$ colony forming units (CFU) per hectare. In yet other aspects, the compositions of the present invention are applied at about $1\times10^9$ to about $1\times10^{13}$ colony forming units (CFU) per hectare. In one aspect, the compositions of the present invention are applied at about $1\times10^{10}$ to about $1\times10^{12}$ colony forming units (CFU) per hectare.

In certain embodiments, the compositions of the present invention are applied at about 0.1 kg to about 20 kg fermentation solids per hectare. In some embodiments, the compositions of the present invention are applied at about 0.1 kg to about 10 kg fermentation solids per hectare. In other embodiments, the compositions of the present invention are applied at about 0.25 kg to about 7.5 kg fermentation solids per hectare. In yet other embodiments, the compositions of the present invention are applied at about 0.5 kg to about 5 kg fermentation solids per hectare. The compositions of the present invention may also be applied at about 1 kg or about 2 kg fermentation solids per hectare.

The inventive compositions, when they are well tolerated by plants, have favorable homeotherm toxicity and are well tolerated by the environment, are suitable for protecting plants and plant organs, for enhancing harvest yields, for improving the quality of the harvested material. They can preferably be used as crop protection compositions. They are active against normally sensitive and resistant species and against all or some stages of development.

Plants which can be treated in accordance with the invention include the following main crop plants: maize, soya bean, alfalfa, cotton, sunflower, *Brassica* oil seeds such as *Brassica napus* (e.g., canola, rapeseed), *Brassica rapa, B. juncea* (e.g., (field) mustard) and *Brassica carinata, Arecaceae* sp. (e.g., oilpalm, coconut), rice, wheat, sugar beet, sugar cane, oats, rye, barley, millet and sorghum, triticale, flax, nuts, grapes and vine and various fruit and vegetables from various botanic taxa, e.g., *Rosaceae* sp. (e.g., pome fruits such as apples and pears, but also stone fruits such as apricots, cherries, almonds, plums and peaches, and berry fruits such as strawberries, raspberries, red and black currant and gooseberry), *Ribesioidae* sp., *Juglandaceae* sp., *Betulaceae* sp., *Anacardiaceae* sp., *Fagaceae* sp., *Moraceae* sp., *Oleaceae* sp. (e.g. olive tree), *Actinidaceae* sp., *Lauraceae* sp. (e.g., avocado, cinnamon, camphor), *Musaceae* sp. (e.g., banana trees and plantations), *Rubiaceae* sp. (e.g., coffee), *Theaceae* sp. (e.g., tea), *Sterculiceae* sp., *Rutaceae* sp. (e.g., lemons, oranges, mandarins and grapefruit); *Solanaceae* sp. (e.g., tomatoes, potatoes, peppers, capsicum, aubergines, tobacco), *Llliaceae* sp., *Compositae* sp. (e.g., lettuce, artichokes and chicory—including root chicory, endive or common chicory), *Umbelliferae* sp. (e.g., carrots, parsley, celery and celeriac), *Cucurbitaceae* sp. (e.g., cucumbers—including gherkins, pumpkins, watermelons, calabashes and melons), *Alliaceae* sp. (e.g., leeks and onions), *Cruciferae* sp. (e.g., white cabbage, red cabbage, broccoli, cauliflower, Brussels sprouts, pak choi, kohlrabi, radishes, horseradish, cress and chinese cabbage), *Leguminosae* sp. (e.g., peanuts, peas, lentils and beans—e.g., common beans and broad beans), *Chenopodiaceae* sp. (e.g. Swiss chard, fodder beet, spinach, beetroot), *Linaceae* sp. (e.g., hemp), *Cannabeacea* sp. (e.g., cannabis), *Malvaceae* sp. (e.g., okra, cocoa), *Papaveraceae* (e.g., poppy), *Asparagaceae* (e.g., asparagus); useful plants and ornamental plants in the garden and woods including turf, lawn, grass and *Stevia rebaudiana*; and in each case genetically modified types of these plants.

In certain aspects, the fermentation product further comprises a formulation ingredient. The formulation ingredient may be a wetting agent, extender, solvent, spontaneity promoter, emulsifier, dispersant, frost protectant, thickener, and/or an adjuvant. In one embodiment, the formulation ingredient is a wetting agent. In other aspects, the fermentation product is a freeze-dried powder or a spray-dried powder.

Compositions of the present invention may include formulation ingredients added to compositions of the present invention to improve recovery, efficacy, or physical properties and/or to aid in processing, packaging and administration. Such formulation ingredients may be added individually or in combination.

The formulation ingredients may be added to compositions comprising cells, cell-free preparations, isolated compounds, and/or metabolites to improve efficacy, stability, and physical properties, usability and/or to facilitate processing, packaging and end-use application. Such formulation ingredients may include agriculturally acceptable carriers, inerts, stabilization agents, preservatives, nutrients, or physical property modifying agents, which may be added individually or in combination. In some embodiments, the carriers may include liquid materials such as water, oil, and other organic or inorganic solvents and solid materials such as minerals, polymers, or polymer complexes derived biologically or by chemical synthesis. In some embodiments, the formulation ingredient is a binder, adjuvant, or adhesive that facilitates adherence of the composition to a plant part, such as leaves, seeds, or roots. See, for example, Taylor, A. G., et al., "Concepts and Technologies of Selected Seed Treatments," Annu. Rev. Phytopathol., 28: 321-339 (1990). The stabilization agents may include anti-caking agents, anti-oxidation agents, anti-settling agents, antifoaming agents, desiccants, protectants or preservatives. The nutrients may include carbon, nitrogen, and phosphorus sources such as sugars, polysaccharides, oil, proteins, amino acids, fatty acids and phosphates. The physical property modifiers may include bulking agents, wetting agents, thickeners, pH modifiers, rheology modifiers, dispersants, adjuvants, surfactants, film-formers, hydrotropes, builders, antifreeze agents or colorants. In some embodiments, the composition comprising cells, cell-free preparation and/or metabolites produced by fermentation can be used directly with or without water as the diluent without any other formulation preparation. In a particular embodiment, a wetting agent, or a dispersant, is added to a fermentation solid, such as a freeze-dried or spray-dried powder. In some embodiments, the formulation inerts are added after concentrating fermentation broth and/or during and/or after drying. A wetting agent increases the spreading and penetrating properties, or a dispersant increases the dispersability and solubility of the active ingredient (once diluted) when it is applied to surfaces. Exemplary wetting agents are known to those of skill in the art and include sulfosuccinates and derivatives, such as MULTIWET™ MO-70R (Croda Inc., Edison, NJ); siloxanes such as BREAK-THRU® (Evonik, Germany); nonionic compounds, such as ATLOX™ 4894 (Croda Inc., Edison, NJ); alkyl polyglucosides, such as TERWET® 3001 (Huntsman International LLC, The Woodlands, Texas); C12-C14 alcohol ethoxylate, such as TERGITOL® 15-S-15 (The Dow Chemical Company, Midland, Michigan); phosphate esters, such as RHODAFAC® BG-510 (Rhodia, Inc.); and alkyl ether carboxylates, such as EMULSOGEN™ LS (Clariant Corporation, North Carolina).

Deposit Information

Samples of the *Paenibacillus* sp. strains of the invention have been deposited with the Agricultural Research Service Culture Collection located at the National Center for Agricultural Utilization Research, Agricultural Research Service, U.S. Department of Agriculture (NRRL), 1815 North University Street, Peoria, IL 61604, U.S.A., under the Budapest Treaty. *Paenibacillus* sp. NRRL B-67721, *Paenibacillus* sp. NRRL B-67723, and *Paenibacillus* sp. NRRL B-67724 were each deposited on Dec. 4, 2018. *Paenibacillus* sp. NRRL B-50374 was deposited on May 18, 2010.

The *Paenibacillus* sp. strains have been deposited under conditions that assure that access to the culture will be available during the pendency of this patent application to one determined by the Commissioner of Patents and Trademarks to be entitled thereto under 37 C.F.R. § 1.14 and 35 U.S.C. § 122. However, it should be understood that the availability of a deposit does not constitute a license to practice the subject invention in derogation of patent rights granted by governmental action.

The following examples are given for purely illustrative and non-limiting purposes of the present invention.

EXAMPLES

Example 1. Antifungal Activity Against *Sphaerotheca fuliginea* of *Paenibacillus* sp. Strains NRRL B-50374, NRRL B-67721, NRRL B-67723, and NRRL B-67724

*Paenibacillus* sp. strain NRRL B-50374, *Paenibacillus* sp. strain NRRL B-67721, *Paenibacillus* sp. strain NRRL B-67723, and *Paenibacillus* sp. strain NRRL B-67724 were cultured in a soy-based medium to produce whole broths along with several other *Paenibacillus* sp. strains. The whole broths were diluted in a mixture of water and organic solvent to a concentration of 20%. The diluted whole broths were applied to young plants which were subsequently exposed to an inoculum of *Sphaerotheca fuliginea* (PODOXA) also known as Cucumber Powdery Mildew.

Several days after exposure to the inoculum of plant pathogen, each plant was scored for percent control of the pathogen relative to the untreated control plants. Each treatment was evaluated with three replicates and the average percent control was reported.

All of the strains had previously been evaluated for antifungal activity in several initial rounds of screening and outperformed other *Paenibacillus* sp. strains. The present analysis represented a subsequent round of screening to further narrow the list of candidate strains with superior antifungal activity. *Paenibacillus* sp. strain NRRL B-50374, *Paenibacillus* sp. strain NRRL B-67721, *Paenibacillus* sp. strain NRRL B-67723, and *Paenibacillus* sp. strain NRRL B-67724 were among the *Paenibacillus* strains with the greatest antifungal activity in this subsequent analysis (see FIG. 1).

Example 2. Antifungal Activity Against *Botrytis cinerea* of *Paenibacillus* sp. Strains NRRL B-50374, NRRL B-67721, NRRL B-67723, and NRRL B-67724

*Paenibacillus* sp. strain NRRL B-50374, *Paenibacillus* sp. strain NRRL B-67721, *Paenibacillus* sp. strain NRRL B-67723, and *Paenibacillus* sp. strain NRRL B-67724 were cultured in a soy-based medium to produce whole broths that were diluted in a mixture of water and organic solvent to concentrations of 20% and 5%. The diluted whole broths were applied to young plants which were subsequently exposed to an inoculum of *Botrytis cinerea* (BOTRCI) also known as Gray Mold.

Several days after exposure to the inoculum of plant pathogen, each plant was scored for percent control of the pathogen relative to the untreated control plants. Each treatment was evaluated with three replicates and the average percent control was reported. This assay was repeated several times and representative results are shown in Table 1. *Paenibacillus* sp. strain NRRL B-50374, *Paenibacillus* sp. strain NRRL B-67721, *Paenibacillus* sp. strain NRRL B-67723, and *Paenibacillus* sp. strain NRRL B-67724 demonstrated consistently high antifungal activity against *Botrytis cinerea* (BOTRCI).

TABLE 1

Control of *Botrytis cinerea* (BOTRCI) achieved with *Paenibacillus* sp. strain NRRL B-50374, *Paenibacillus* sp. strain NRRL B-67721, *Paenibacillus* sp. strain NRRL B-67723, and *Paenibacillus* sp. strain NRRL B-67724 at dilution rates of 20% and 5%.

| Treatment | Application Rate | Average Percent Control |
|---|---|---|
| *Paenibacillus* sp. strain NRRL B-50374 | 20% | 98 |
| | 5% | 85 |
| *Paenibacillus* sp. strain NRRL B-67721 | 20% | 88 |
| | 5% | 0 |
| *Paenibacillus* sp. strain NRRL B-67723 | 20% | 98 |
| | 5% | 68 |
| *Paenibacillus* sp. strain NRRL B-67724 | 20% | 60 |
| | 5% | 50 |

Example 3. Antifungal Activity Against *Puccinia triticina* of *Paenibacillus* sp. Strains NRRL B-50374, NRRL B-67721, NRRL B-67723, and NRRL B-67724

*Paenibacillus* sp. strain NRRL B-50374, *Paenibacillus* sp. strain NRRL B-67721, *Paenibacillus* sp. strain NRRL B-67723, and *Paenibacillus* sp. strain NRRL B-67724 were cultured in a soy-based medium to produce whole broths that were diluted in a mixture of water and organic solvent to concentrations of 20% and 5%. The diluted whole broths were applied to young plants which were subsequently exposed to an inoculum of *Puccinia triticina* (PUCCRT) also known as Wheat Leaf Rust.

Several days after exposure to the inoculum of plant pathogen, each plant was scored for percent control of the pathogen relative to the untreated control plants. Each treatment was evaluated with three replicates and the average percent control was reported. This assay was repeated several times and representative results are shown in Table 2. *Paenibacillus* sp. strain NRRL B-50374, *Paenibacillus* sp. strain NRRL B-67721, *Paenibacillus* sp. strain NRRL B-67723, and *Paenibacillus* sp. strain NRRL B-67724 demonstrated consistently high antifungal activity against *Botrytis cinerea* (BOTRCI).

TABLE 2

Control of *Puccinia triticina* (PUCCRT) achieved with *Paenibacillus* sp. strain NRRL B-50374, *Paenibacillus* sp. strain NRRL B-67721, *Paenibacillus* sp. strain NRRL B-67723, and *Paenibacillus* sp. strain NRRL B-67724 at dilution rates of 20% and 5%.

| Treatment | Application Rate | Average Percent Control |
|---|---|---|
| *Paenibacillus* sp. strain NRRL B-50374 | 20% | 77 |
| | 5% | 17 |
| *Paenibacillus* sp. strain NRRL B-67721 | 20% | 80 |
| | 5% | 17 |
| *Paenibacillus* sp. strain NRRL B-67723 | 20% | 65 |
| | 5% | 25 |
| *Paenibacillus* sp. strain NRRL B-67724 | 20% | 80 |
| | 5% | 50 |

Example 4. Analysis of Fusaricidin and Tridecaptin Biosynthetic Gene Clusters in *Paenibacillus* sp. Strains NRRL B-50374, NRRL B-67721, NRRL B-67723, and NRRL B-67724

The genomes of *Paenibacillus* sp. strains NRRL B-50374, NRRL B-67721, NRRL B-67723, and NRRL B-67724 were sequenced and analyzed for the presence of known gene clusters encoding proteins responsible for the biosynthesis of antimicrobial compounds. This analysis revealed that each of the four strains has a fusaricidin synthetase (fusA) with at least 90.5% sequence identity to that found in the other strains (see Table 3). In addition, all four strains possess a tridecaptin gene cluster. Identification of a tridecaptin gene cluster in a laboratory strain of *Paenibacillus terrae* had previously been reported. Lohans C T, van Belkum M J, Cochrane S A, Huang Z, Sit C S, McMullen L M, and Vederas J C. (2014) Biochemical, Structural, and Genetic Characterization of Tridecaptin A1, an Antagonist of *Campylobacter jejuni. ChemBioChem* 15:243-249. The tridecaptin biosynthetic gene cluster contains triA, triB, triC, triD, and triE. In each of the four strains, the gene encoding the nonribosomal peptide synthetase (NRPS) TriE exhibited at least 90.0% sequence identity to that found in the other strains (see Table 4). The nucleotide sequences for the fusA and the triE genes from the four strains are presented in Table 5 and Table 6, respectively. Without wishing to be bound to any theory, the expression of fusaricidins and tridecaptin in these strains may contribute to their capacity to effectively colonize plants and prevent plant disease.

TABLE 3

Percent identity matrix created with Multiple Alignment using Fast Fourier Transform (MAFFT) for the fusA genes from *Paenibacillus* sp. strains NRRL B-50374, NRRL B-67721, NRRL B-67723, and NRRL B-67724.

| | Percent Sequence Identity | | | |
|---|---|---|---|---|
| Strain | NRRL B-67724 | NRRL B-50374 | NRRL B-67721 | NRRL B-67723 |
| NRRL B-67724 | 100.00 | 97.34 | 97.80 | 90.51 |
| NRRL B-50374 | 97.34 | 100.00 | 98.18 | 90.71 |
| NRRL B-67721 | 97.80 | 98.18 | 100.00 | 90.67 |
| NRRL B-67723 | 90.51 | 90.71 | 90.67 | 100.00 |

TABLE 4

Percent identity matrix created with MAFFT for the triE genes from *Paenibacillus* sp. strains NRRL B-50374, NRRL B-67721, NRRL B-67723, and NRRL B-67724.

| | Percent Sequence Identity | | | |
|---|---|---|---|---|
| Strain | NRRL B-67724 | NRRL B-50374 | NRRL B-67721 | NRRL B-67723 |
| NRRL B-67724 | 100.00 | 97.58 | 97.65 | 90.06 |
| NRRL B-50374 | 97.58 | 100.00 | 98.48 | 90.28 |
| NRRL B-67721 | 97.65 | 98.48 | 100.00 | 90.09 |
| NRRL B-67723 | 90.06 | 90.28 | 90.09 | 100.00 |

TABLE 5

Nucleotide sequences of genes encoding the fusaricidin synthetase (fusA) in *Paenibacillus* sp. strains NRRL B-50374, NRRL B-67721, NRRL B-67723, and NRRL B-67724.

| Strain | SEQ ID NO: | Sequence |
|---|---|---|
| NRRL B-50374 | 1 | ATGAATGACATGCAGTTATATGATTTAACAAATGCGCAGAAGCGTATATGGTATACCGAATTACTCTACCCAGATACG<br>TCAGTGTCACAGCTTTCCGGTACAGCTAAGATGAAGGGGCATATCAATATTGCTGCCTTTATGCAGTCCATTAATTTG<br>ATTATCAAACAGTATGATGCGTTCCGCATCCGTATTACCTCAGTGGATGGAGTGCCTCAGCAGTACGTCGTTCCTTAT<br>GAAGAGAGACAGCTGGAGTGCCTGGATCTTAGCCACTATGAAAGTGTATCTGAGGTGGAAGCCTTACTTGAGCAACA<br>CAAAAGCAAACCTTTGCCCCTGCTGGATTCTGAGCTCTTCCAGTTTTTAATTGTGAAGATTAGCGAGGAAGAGTATTG<br>GATTAATATCAAGATGCACCATATTATTTCTGACGGAATATCAATGGTGGTCTATGGCAATCAGCTGACAACATTTTA<br>CATGGAGTTAATTCAAGGAAATGAACCGAAGCTGGGCGACGATTGCTCGTATATTCAATATATTGCAGATGAGAATG<br>CATACGAACTTTCTGACAGATACCAAAAGGATAAGGCTTACTGGCTGGATAAATTTTCTGATTTGCCTGAGCTTACGG<br>GTTGGAAGTCATATAATCCGTTATCTTTAAGCACCCACGCCGTTCGGGAGCATTTTACCGTACCAGAAGTGCTATATC<br>ACGAGCTGCAAGCATTTTGCCAACAGAACAGGATTTCTTTGTTCCAGTTCTTCATGGGTGCGATGTATATCTACATAC<br>ACAAAATGACGAATCAGCCGGATGTGGTGATTGGCACTTCGTTCGCTAACCGGGGGAACAAAAAAGAGAAGCAAAA<br>GATAGGTATGTTTGTCAGCACCGCTGCTGCCAGAACATACGTCAAAAAGGATATGGATGTGTTGAGCTTCCTGCAGG<br>ATGTAGCCAGAGATCAGATGTCAGTCCTGCGGCATCAGAAGTATCCGTACAATCAGTTAATTCAGGATCTTAGAGAA<br>ATGCATGGTAACAAGGATATTCAGCGGCTTTTTGGCGTTTCAATGGAATATCGTCTTATCAATTGGGTTGATTTGGAT<br>GATGTGCGCATTTTGACGGATTATGATTTCTGCGGGGACGAAGTGAACGATTTCGTGCTTCATATCGTGGAGATCCTG<br>GATGAAGGCGAACTGGTACTGGATGTCGATTATCGGACGGAGCTGTTTGAACGCAGTGAAGTTAAGGACATGGTTTC<br>CCAGTTGCTTACGATCGCCGAGCAGATCATTCATTCACCTCAGCTTTCTATCGCAGAGGTAAACTTATTGGGTGAACC<br>AGAAGAGCAGTCCATTTTGGCTCTTTCGGAAGGCGCTGCAGTCGATTATCCACGTGAGAAGACCATCCATGGCTTATT<br>CGAGGAACAAGCCGAGCGCACGCCAGATCACGTAGCCGTTCAGATGGACGAACAGAGCATTACATACCTAGCTCTAA<br>ACGAGCAGGCTAACCAGCTTGCGAGATATTTGCGCTCCGAGGGAGTAGTTGCAGATACGCTCGTAGGGATTATGGCT<br>GACCGTTCCTTGGAGATGGTCATTGGGATGTTGGCCATTTTGAAAGCAGGTGGTGCCTATGTACCGATTGACCCCGAT<br>TATCCCGAGGAACGTATCCATTATATGCTGGAGGATTCAGGGGTCCGTCTGTTGCTCACCCAAAGTCATCTATGGGAG<br>AGCACCACTTTTGACGGAAAGCTTGTGAGTTTGGACGAAGCTACAACGTATACAGGAGATGCTTCCAATCTGGAGAG<br>TATTTCGGGACCAAGCCATCTAGCCTATGTTATCTACACGTCGGGTACGACCGGCAAGCCGAAGGGCACGCTGATTG<br>AACACAAAAATGTGGTTCGACTGCTCTTTAACGATAAAAATCTATTTGATTTCAGCTCTCAGGATACGTGGACGCTAT<br>TCCATTCGTTCTGCTTCGATTTCTCCGTTTGGGAGATGTACGGAGCGCTTCTTTACGGAGGGAAATTGGTGATTGTTCC<br>ATCTCTCACAGCCAAGAGCCCAGCAGCTTTCCTGGAGTTGTTGAAAGACAACCAAGTCACCATTTTAAATCAGACGCC<br>GACGTATTTTTATCAGGTGCTACAGGAAGAGTTAACGCACTCTTCGACAGAGCTTGGCCTTAGAAAAATCATTTTTGG<br>TGGAGAGGCCTTAAGTCCATCTCTTCTGAGAAACTGGCGGGTCAAGTATCCTGATGTGCAGCTGATTAATATGTACGG<br>AATTACGGAAACAACGGTCCATGTCACCTACAAGGAAATCACGGAACATGAGATTGAAGCGGGGAAAAGCAATATT<br>GGCAGAACGATCCCCACACTTAGCGCTTATATTCTCGATGAGCAAAGACGGCTGCAGCCTGTTGGGGTTCCGGGAGA<br>GCTATACATTGCAGGGGACGGTCTTGCCCGTGGGTATTTGAATCGGCCGGATTTGACGTCTGAGAAATTCGTTGAGCA<br>TCCGTATCGGGCGGGAGAGCGGCTGTACCGAACTGGGGATCTTGCTCGTTGGTTGCCTGATGGCAATATTGAATATTT<br>GGGACGGATCGACCATCAGGTCAAAATTCGCGGCTACCGAATTGAGCTTGGCGAGGTAGAAGCCCAAATTCTCAAGG<br>CTCCGAACGTACGAGAAACGATTGTCCTCGCACGGGATGACGAACAGGGCCAAAAATTGCTGTGCGCCTACTATGTA<br>GCCTCCAGTGATCTTTCGCCGGGGGAATTGCGGTCTCAGCTGGCAGCGGAACTCCCCGCTTACATGATTCCTTCTTATT<br>TTGTCCGGCTGGAGCAAATGCCGCTTACGCCAAATGGCAAACTGGATCGCCGTGCGTTGCCGGCTCCTGAAAGCAGC<br>GTACAATCCGGCGAGGCTTATTTGGCTCCGAGAACTGCTGTGGAAGCTCAGATGGTACTCATCTGGCAAGATATCTTG<br>GGAGTTGCCCGCGTCGGTGTCAGAGATAATTTCTTTGAAATTGGTGGTCACTCTTTGCGGGCAACAGTGCTCGTTTCA<br>CGGATTCACAAAGAATTGGGATGTAGCATTTCGCTGCGTGAGGTGTTTCAGTCACCTACGGTCGAATCCTTGGCGCAA<br>CTTGTGAAAAAACACATTCCGACCCTGTACGAATCCATCCCACAGGCAACGGAAAGCGAAGCTTACCCAGTGTCCTC<br>AGCGCAAAAGCGGTTATACGTGCTGAGACAGATGGATGGGGAGAGCTTAGCTACAATATGCCAGGGGCCTTCACA<br>GTGGATGGACCGTTGGATCGCACGCGGCTGGAGTCCGCGTTCCAGGGACTGATCCAGCGTCATGAATCCCTAAGAAC<br>CGGCTTTTATATGCAGGATGGAGAGCTTGTTCAGCGTGTGCATAGGAATGTGCCGTTCGCGTTGAACTATACAGAGGC<br>TTCGGTGGAGGAGACGGATACGCTCATTCACAACTTTATTCGTGCCTTTGATCTGAGCCAGGCTCCATTACTGCGTGTT<br>AGCTTGGTGAAGCTCCAGGAGGAGCGTCATCTGTTGCTGTTTGATATGCATCACATCATTTCAGATGGGGTTTCTATTC<br>AAATATTGATACAGGAACTTACTCATTTGTATCAAGGAGAACAGCTACCAGAACTGCACATCCAATACAAGGATTAT<br>GCCGTATGGCAACGAGAACAGTCAGAGAACCAATGGCAAGATCTTGAGAAATATTGGCTGCAATCCTTTGAAGGAGA<br>GTTGCCGGTATTGGATTTGCCTACAGACTTCCAACGACCTTCAGTTCGGAGCTTCGAGGGTAGCCGAATTGATTTTAC<br>ATTGGATGAGTCTGGAAATAAGGCGATACAAGAGCTTGCATCCCGTACAGGTACTACACTGTATATGGTATTGCTGGC<br>CGCTTATTCGGTACTACTGCACAAATATACAGGACAGGAGGACATCGTCGTAGGTTCTCCAGTAGCCGGAAGACCGC<br>AGGCTGAGCTTGAGGGCATCATCGGAATGTTTGTCAACACACTGGCCTTGCGCAGCTACCCGGCAGGAGATAAAACC<br>TTTCAGGATTATCTTCTGGAAATCAAGGAAACGGCGCTCAAGGCGTTTGAGCATCAGGATTACCCTTTTGAAAAATTG<br>GTCGAAAAGCTGGGCGTAGGACGTGATGTCAGCCGCAATCCGCTCTTTGACACCTTATTGGTATTACAAAATACCGAG |

TABLE 5-continued

Nucleotide sequences of genes encoding the fusaricidin synthetase (fusA) in *Paenibacillus* sp. strains NRRL B-50374, NRRL B-67721, NRRL B-67723, and NRRL B-67724.

| Strain | SEQ ID NO: | Sequence |
|---|---|---|
| | | CAGGAAGAGCAGGATATGGACGGAGTGCACTTTACTCCTTACTTGATGGACACCGTCACAGCCAAATTTGACCTGTCC |
| | | CTCAATGTAGAGGAGAAGGGATCAAAATTAGCCTTTGGCCTCGAGTATAGTACGGCTTTATATCGGCGTGAAAGTGT |
| | | AGAGCGACTTGCAACGCACTTGCTCCGGGTTCTGCATGCAGTCTCGGCCAATCCTCAGTTGCAACTGGCCGAGATTGA |
| | | AATGATCACACCGGAGGAGAAAGTACAGATCGTTGAAGTATTTAACGCGACATCGGCCCCTTATCCAAGGGACAAGA |
| | | CCATTCATGATCTGTTCGCGGAACAAGTCAAGCGTACACCGGAGCAGACGGCGCTTGTATTCGGCGATGTCCAGCTA |
| | | ACGTACCTTGAATTGGAAGACAAGGCGAGCCGACTGGCCCAAACACTGCGTCGTTTGGGAACGTTGAGGGAGCAGCC |
| | | TGTGGCCGTGATGGGCGGACGAAGCATTGAGATGGTCATTGGTATGCTCGCGGTGCTTCAGGCAGGTGGAGCCTATG |
| | | TGCCGATTGATCCTGATTACCCGGAAGATCGGGTTCGTTATATGCTTGATGATTCCGACGCCAAGCTATTATTGGTGC |
| | | AAAAGGGCGAGCTTATAAGTGTAGACTACGGTATACCGATTGTCGATCTTAGCAGTGAAGAGGCTTATGCTGCTGAG |
| | | CCTGCCCAGCCGGAGACGGCTCAGGGATCGCAGGGGCTTGCTTATGTCATCTATACATCGGGTACGACGGGTAGACC |
| | | GAAGGGCGTTATGGTTGAACACCGGAACGTGGTCCGTCTGGTCAAAGAGACCAACTATGTGGAGCTGAATGAATCCA |
| | | CACGAATTTTGCAAACAGGAGCCGTGGCCTTTGATGCTTCTACATTTGAGATATGGGGAGCGTTGCTTAACGGTGGGC |
| | | AGCTCTATTTTGTAGAGAATGACGACATTCTGATTGCTGATAGGCTCAAAGCGGCTATTGCCAAGTACGGGATTACAA |
| | | CATTGTGGCTTACTTCACCCCTTTTCAATCAGCTTTCTCTGCAGGATGAGTACCTGTTCAGAGGGCTAAAAGCATTGTT |
| | | AGTCGGCGGTGACGTACTGTCTCTATCTCATATGAATCGTGTAATCGAGGCTAATCCTGATCTTGTCCCTATCAATTGC |
| | | TATGGTCCGACAGAGAATACGACCTTCTCCACCACCTACAAGATTCCAGGTTGTGCCGAAGGGGGTGTGCCGATTGGT |
| | | CGCCCAATTAGTAATTCGACCGCTTATGTGGTCAATGGATCGCTGCAATTACAGCCTATTGGTGCTTGGGGTGAACTC |
| | | ATTGTCGGCGGTGAAGGTGTAGCACGCGGATATCTCAATCGTCCTGATCTCACAGCAGAGAAATTTGTTCCTAGTCCT |
| | | GTGAAGGACGGAGAACCCTGCTACCGAACTGGGGATTTGGTACGCTGGCTTCCAGATGGGAATTTGGAGTTTAAAGG |
| | | AAGAATTGATGAGCAGGTCAAAATACGTGGTTACCGCATCGAACTCCCTGAAATCGAGGCCCAACTGGCCAAGGTGG |
| | | AGTCGGTAATCGACGCCGTAGTGGTCGTTCGCGCGGACGAGCTTGGCGAGAAGCAGCTTTGCGCTTATTATGTGGCG |
| | | GATCGTACGCTCACGGCAGGCGAAGTACGTCTTTCCCTATCGCAGGTACTTCCAGGCTATATGATTCCATCCTACTTTA |
| | | TCCAGATGGATCGTATGCCATTAACATCAAACGGAAAGGTGGACCGCAGGTCTCTGCCGGCTCCTCAAGTAGGCGCG |
| | | CATACAGGACGGAAGTATACAGCTCCTCGTACACCGGCTGAGGAAGCTTTGGCATCTGTCTGGCAAGGGGTGCTGGG |
| | | TGCCGAACAGGTGGGTATCCATGATAATTTCTTTGAATTGGGTGGAGACTCCATAAAAGCTATCCAGGTGTCGTCACG |
| | | GTTACTACAGGCCGGCTATCGGTTAGAGATGAAGCAGCTGTTCAAATCGCCAACCATTGCCGAGCTAGGAGCGGAAA |
| | | TACAAACGGCTGTGCATATGGCTGAACAGGGAGTTGTGCGTGGAGCGACTCGCTTGACTCCAGTCCAACAGTGGTTCT |
| | | TTGGACGGAAGCAGGCAGAGCCTCATCACTTCAATCAAGCGGTTATGCTGTATCGTGAACAGGGATTTGAGGAAAAG |
| | | GCCTTGCATCAGGTGCTAAGAAAACTCGCTGAGCATCATGACGCCCTTCGCATGGTTTTCCGTCAGACAGAGCATGGT |
| | | TACGAAGCTTGGAATCGTGATCTTGAAGAAGGAGAGCTTTATAGCCTGTTCACCGCTGATTTACGGAATGAATCCGAT |
| | | CCGGCTGCAGCCATTACATCGCTGTCGGATGACATTCAGCGCAGTATCAATCTGGCAGAAGGCCCGCTGCTGAAGTTA |
| | | GGACTTTTCCATTGTCAGGATGGAGACCACCTTCTGATCGTGATCCACCATTTGGTGGTGGACGGAGTATCCTGGCGG |
| | | ATTTTGTTCGAGGATATTGCAGCAGGCTATGAGCAGGTGATTCAAGGACAAGCGCTGACATTCCCGCAGAAGACGAA |
| | | TTCCTTCCGTGACTGGGGAGACGCCCTTGCTCGTTATTCGGAAGGTCCTGAAATGGAGACTCATCGGGCGTATTGGAG |
| | | GGAGCTGGAGAATCAGCCACTCGAACAGTTGCCGAAGGATGAGGCTGTGGAAAGCCTTCTTTTACAGGATAGCAAAG |
| | | TAATAACAGCACAATGGACTATAGAAGAAACCGACCAATTGTTGAGAAAAGCCCATCGTGCTTATCAAACAGAGACG |
| | | AATGATCTGCTATTGACTGCTCTGGGCATGGCGGTATCCAAATGGTCTGGCATCGGAAAGGTTGCTGTGAATCTGGAA |
| | | GGACACGGTCGTGAGCCGATTATACCGAATATCGACATCACCCGTACCGTCGGCTGGTTTACAAGTCAATACCCGGTG |
| | | ATTTTAGACTTGGGGGATGACCCAGAAGTGGCCTCCTTGATCAAGTCTGTGAAAGAAGGGCTGCGCCGAATTCCGAA |
| | | CAAAGGTATTGGCTACGGGTTGCTTAAAACGATGGCAAGTCAGTTGGATGAAGACAGCTTCAGCTTGCAGCCTGAGA |
| | | TTTCTTTTAACTATTTGGGGCAATTTGATCAGGATTTGCAAGGCAGCTCGTTGCAGATTTCTCCTTATCCGACCGGAAG |
| | | CGCCCAAAGCTTGTTGGAGGAACCAGCCTATACGCTAGATATCAATGGCATGGTGACGGACGGAGCCCTGACTCTGA |
| | | CGATTACTTATAACGGAAAACAGTATAAGTTATCTACGATGGAACAGCTCGCTGGATATATTGAAGAAAGCCTGCGA |
| | | GAGCTTCTCCAGCATTGCGTAACCCAAGAAAAAACCGTATTGACACCAAGCGACGTGCTTGCGAAGGGTCTAAGCAT |
| | | TGCCGATCTGGAGGAGCTTTCTAAGCAGATCAGCCACATAGGCGATATTGAGAATGTATATAGTCTGACGCCGATGC |
| | | AGAAGGGCATGCTGTTCCATGATATGTTTGAGCCGCATACAGGTGCTTATTTTGAGCAGGCTGCCTTTGACTTTAAGG |
| | | GTAGCTTTGATCCGACTGCATTCGGACACAGTCTGGATGCCGTGGTGGAGCGTCATGCCATCCTGCGCACGAACTTTT |
| | | ACAGCGGATGGGGCAGCGAGCCTTTGCAGGTTGTATTTCGACACAGAGGCGCTAAATTGGTGTACGAAGACCTGCGT |
| | | GAGATGAATGCATCGCAGCGCGAAGCTTACCTGAAGACATTTGGTGCTAAGGACAAAGCACAGGGCTTCAACCTAGC |
| | | TGAAGACGAGCTTCTCCGTGTATCAATTTTACAAACAGATGAAGAGAGCTTCCGACTCTTATGGAGCTTTCACCACAT |
| | | CGTCATGGATGGCTGGTGTGTTCCGTTAATTACGCAGGAGGTATTTGAACACTATTTTGCCCTCCTGGAAGGAAGAGA |
| | | GCCGCAGCTGGCAGAGGTCCATCCGTACAGTCGATATATCGAATGGCTGGAACAGCAGGATGAAGCAGTTGCGTCCA |
| | | ACTATTGGAGCCGATATCTGGCCGGTTACGAGCAGCAGACGCTTTTACCTCAAGTCGGTGGAGCAAGTAAGGGAGAA |
| | | GGCTATGTAGCAGAAAAGCTGAATTATCCTCTCAGCAGGGAATTGACTGAGCGCCTTGAAAAGGTGGCCAGGGATGC |
| | | TCATGTCACGATGAATATATTGCTGCAGTCCCTCTGGGGCATTGCGCTTCAACGCTACAACGGTAGCCGGGATGTCGT |
| | | GTACGGAAGTGTAGTATCAGGCCGACCAGCAGAAATTCCGGGCATTGACCGGATGATCGGTTTGTTCATCAATACGA |
| | | TTCCCGTTCGTGTGAAGACAGAGGAGAATCTCCCCTTCACCGTTCTGATGAAGCAGCAGCAGGAACAATATATGGCTT |
| | | CTCATATGTATGACACCTACCCGTTGTTTGAGATTCAGGCTCAGACGGATCAGAAGCAGGATCTAATCTCCCATATTA |
| | | TGGTGTTTGAGAACTATCCTGTGGAGGAGGAGGTAGAGCGTCTGGGTGGTGGCGAGGCTGCCTTTGAGATTGAGGAA |
| | | GCGGAGCTTCTTGAGCAAACGAATTATGATTTTAATTTAATTGTCCTCCCTGGCGAAGAGATGAGATTGCTGTTCCAG |
| | | TACAATGCACTTGTTTATGACCAAGTGACAATTGGGCAAATCAAGGGCCATCTGGTTCACCTTATGGAACAAATTGTA |
| | | GAGAACCCTGCTATTTCCGTGGATGCTCTAGAATTAGTCACGCCGCAGGAGAGAGAACAGATTCTGAACGTATGGGG |
| | | AAATATGAAAGGCATTTACGAGCACTGTAACACGTTCCACGGGCTATTGGAGGAACAGGCGGGACGAACGCCGGAT |
| | | GCGACTGCCATTTGGTTCGAGGACGAGAGTCTGACCTATGCCGAGCTTAATGCAAAAGCCAATGGACTGGCCAGAAG |
| | | GCTCCGTACTCAGGGAATCAAGACGGGAGATCTGGTGGGACTGATTGCTGAACGGTCGCTCGAAATGATCGTTGGGA |
| | | TCTACGGCATTATGAAAGCCGGGGGTGCCTATGTTCCAATCGACCCAGAGTATCCGAAAGAACGAATCAGTTATATG |
| | | CTTGAAGATTCCGGAGCGAAGCTGATCCTTACACAGGCCCATCTCTTGGAACATCTCGGATGGACGGAAAATGTTTTG |
| | | CTGCTGGATGAATCATCGACCTATGATGCCGACACCTCGAATTTGGAGGATACTGCTGGCCCGGATGATCTGGCTTAC |
| | | GTGATCTATACTTCAGGTACGACCGGTCAGCCTAAGGGCGTATTAGTCGAGCATCGGGGACTACCAAATCTTTCAAAC |
| | | GTATATGGGGCACACTTCGAAGTTACACCGCAGGATCGGATCGTTCAGTTTGCAAGCCTGTCGTTTGATGCATCGGTT |
| | | TCGGAAATTTTAACGGCGCTGAGCCATGGGGGTGTTCTGTGCATCCCTTCTACAGAAGATATTTTAGATCATGCCCTG |
| | | TTCGAGCAGTTCATGAACGATAAGGGGATTACGGTAGCGACTTTGCCACCCGCTTACGCTATCCACCTTGATCCAGAG |
| | | CGTTTGCCAACACTGCGGTGCCTGCTAACCGCTGGATCGGCCGCATCGGTCGAGTTGATCGAAGAGTGGAGGAAGCA |

TABLE 5-continued

Nucleotide sequences of genes encoding the fusaricidin synthetase (fusA) in *Paenibacillus* sp. strains NRRL B-50374, NRRL B-67721, NRRL B-67723, and NRRL B-67724.

| Strain | SEQ ID NO: | Sequence |
|---|---|---|
| | | TGTACGTTACTCTAATGGCTATGGCCCAACGGAGGACTCCGTATGCACCACAATCTGGTCTGTCCCGGACAGTGAGGA |
| | | AGCAACGGATATTGTATCTATTGGACGACCTATTGCTAACCATAGTGTGTACATCTTGGATGACCATTTTAGATTGCA |
| | | ACCTGTCGGTGTAGCTGGAGAGCTATGCATTTCGAGTATCGGATTAGCACGGGGGTATCATAACCGGCCTGAGTTAAT |
| | | GGATGAGAAGTTCGTGGACAATCCGTTTGCTCCAGGAGAGCGTATGTATCGGACGGGTGACCTGGTTCGCTGGTTACC |
| | | GAATGGAACCATCGAGTACTTAGGCCGAATAGATCATCAAGTCAAAATCCGCGGCTACCGTATCGAGCTAGGCGAGG |
| | | TAGAAGCACAAATGCTCAGAGTGCCGTCCGTTCAGGAAGTCGTAGCCATGGCTGTAGAGGGCGATGACGGCTACAAA |
| | | GATCTAGTCGCTTATTTCGTAGCTGCTCAGAAACTTGAGGTATCCGAGCTTCGGGCCGTCCTGTCGGAGATATTACCT |
| | | GGATATATGATCCCTTCCCGCTTCATACAACTGGAGGATATGCCTCTGACGTCGAACGGAAAAATCGATCGAAAAGC |
| | | GCTGCAGGGCGAGCGTGGATGGGCAGCGGCTTCATCTGAGGCTCCAAGGACACCTGTGGAAATTCAATTAGCCGAAA |
| | | TCTGGCAAGAGGTGCTGGGTGTAGAGAGCGCGGGAGTGAAGGATAATTTCTTCCATTTTGGAGGTCATTCACTGCGTG |
| | | CAGCCCTGCTAGTCTCACGAATTCGCAAGGAAATGAATCGCGAGATTAGTCTGAGAGCAGTGTTCGAGTCTCCTACTA |
| | | TTGAAGGATTGGCTCGTGCCATTGAGGGCTATACACCGCTGAATTTCGAAGAAATTCCTACAGCGGGAGCGAGAGAG |
| | | CATTATCCATTGTCCTCGGCCCAAAAACGACTGTTTATTCTAAGTCAGCTGGAAGGTGGAGAGCTGAGCTACAATATG |
| | | CCGGGTATCCTTACCGTTGAGGGAGCTTTGGATCGGGAACGGCTAGAGCAGGCATTCCGTCGTCTAATTCATCGTCAT |
| | | GGTTCGCTGCGTACTCGTTTTGTGACCGTGAACGGTGAACCTGTACAGCAGCTCCTGACGGATGTTCCGTTTACTGTG |
| | | GAATATGCGGAGTTGAGCGAGGAAGAGGCAGGAGCTACCCTTCAGCAGTTTGTCCGTCCTTTTGATTTAGGTGTAGCT |
| | | CCATTGCTGCGGGTCGGCCTTATTCGAATTGCACATGAGCGCCATTTACTATTGTTTGACATGCATCATATTGTCTCAG |
| | | ATGGGGTTTCTATGAATATTCTCATAGAAGAGTTTCTCCGCTTCTACCAAGAGGAGGACGTATTCCCTGAACTACAGA |
| | | TCCAGTACACAGACTATGCTGTATGGCAGCAAGAGCAGCTCGGAAGCGAGCGTCTTAAGGCCCAGGAAGCTTACTGG |
| | | CTGGATGCTTTCCGCGGAAGCTTGCCAGTGCTGGATTTGCCAGGAGATGAAGTTCGTCCTGCGGTGCGAAGCTTTGCG |
| | | GGCGATCGAATCGACTTCCAAATTGATTCTTCTCTGAGTGCTTCACTTCAGGAGCTGGCTACCCGAACGGGTTCCACT |
| | | CTGTTCATGGTACTGCTGGCAGCCTATACGGCGCTCTTACACAAGTACACAGGTCAGGAAGATGTCATTGTCGGTTCA |
| | | CCTGTGGCAGGAAGATCCCATGCGACACTCGAAGGCCTCATCGGTATGTTCGTCGGCACAGTGGCACTTCGTACTTAT |
| | | CCAGAAGGGGAAAAGCCTTTCGAGGCTTATCTGCAGGAAGTGAAGGAAACAGCGCTGCGGGCCTATGAAAACCAGG |
| | | ATTACCCGTTCGAGGAGCTGGTAGAAAAGCTGGAGCTTCAGCGTGATTTGAGCCGTAACCCGCTATTTGATACCATGT |
| | | TTGTCCTGCAAAATATCGAGCAGGGAGAACAAGAAATAGAAGGATTGCGCTTCACTCCTTACGATAATGTACATCCG |
| | | GCTGCCAAGTTCGATCTCACGCTGACCGTGAGTGAAGCAGACGGGGTATTGAACTGCACGCTTGAGTACGCGACTGC |
| | | GATCTACAAGCAAGAGACTGCCCAGCGGATGGCAGGACACTTTGTACAGCTTATTCGGGAAGCCGTCTCCAATCCGG |
| | | GAATGCCGTTGTCATCCCTTGATATCGTGACACCTCAGGAAAAATCAAGGCTGATGAAAGCGCCGGACGAAGCCAAG |
| | | GCAGATTATCCTCGTGACAAGACGATCCATGCGCTGTTCGAGGAACAGGCTGCACGTACTCCGAATGCGGTGGCAGT |
| | | CGTATGTGAAAATGCAGCCCTGTCCTACAGCGAGCTGAACGAGCGGGCCAATGGACTTGCCAGAACGCTGAGGGAAC |
| | | GTGGTTTGCAACCAGACGGTTTGGCTGGAATCATGGCGGATCGGTCCCTTGAAATGGTGGTTGGAATTTTAGCCATCT |
| | | TGAAGGCAGGCGGGGCCTATGTCCCTGTAGACCCTGAATATCCAGAGGACCGCATTCGCTTTATGCTTGAGGATTCGG |
| | | GAGCCAAGCTACTGCTGACACAAGCGCATCTGGAGCAACGTGTCTCCTTCGCTGGGGACATCGTGAGTCTGGATAAA |
| | | ATGGCTTCCTATAAGGAAGATGTCTCAAACCTGCAGCCTGCAGCCGGACCGGAGCATCTTGCCTACGTCATCTACACA |
| | | TCGGGCACGACAGGCAAGCCAAAGGGAACGCTGATTGAGCATAAAAATGTAGTTCGCTTGCTCTTTAATGATAAAAA |
| | | TATGTTTGACTTTGGTCCTCAGGATACGTGGACACTGTTCCATTCATTCTGTTTTGACTTCTCTGTATGGGAAATGTAC |
| | | GGAGCATTGCTGAACGGAGGACGGTTGGTCATCGTTCCATCGCTTACCGCGAAGAGTCCAGATCGTTTCTTGCAATTG |
| | | CTTAAGGATCAGAAGGTCACCGTTTTGAACCAGACACCGACGTACTTCTATCAGTTGCTACAGGAAGAGCTTGGTCAT |
| | | CAGGCGGCAGAACTGAGCCTCCGTTTGATTATCTTCGGTGGAGAGGCATTAGCCCCGGCCCTGCTCAAGGACTGGAG |
| | | AACGAAGTATCCGCAAGTGCAGCTCATTAACATGTACGGCATTACCGAAACGACCGTGCATGTAACCTACAAGGAAA |
| | | TTACAGAGTTGGAAATTGAACAGGGTCGCAGCAATATCGGCACCACGATTCCGACGCTGCGGGCGTACATTTTGGAT |
| | | GAACAACGTCGTCCACAGCCGATTGGCATTCCGGGTGAACTCTATGTGGCGGGCGTAGGCCTGGCGCGAGGTTATCT |
| | | GAACCGACCGGAATTGACGGAAGAGAAGTTTGTCGCTCATCCGTTTGAAGCGGGCGAGCGTATGTACCGCTCGGGTG |
| | | ACTTGGCACGCTGGTTGCCGGATGGAAGCATGGAGTATTTGGGACGCATTGACCATCAGGTTAAAATCCGTGGTTACC |
| | | GTATCGAGCTGGGCGAAGTGGAAGCGAAGCTGCTCCATGCTCCGTCTGTAAGGGAGGCCGTTGTGCTCGCCCGGGAG |
| | | GATGGAAGTGGACAAAAAGTGCTTGTCGGCTATTTCACTGCCGATCAGATGCTGACGGTAGGCGAGTTGAGAAAAGA |
| | | CTTGGCTGCCGAACTGCCGACTTATATGATTCCATCTTACTTTATGCAATTGGAACAGATGCCTTTGACGCCAAATGG |
| | | CAAGCTGGATCGCAAAGCGCTTCCGGCTCCTGAGGCCAATGTGCAGACTGGGGCGGTTTATGAACCGCCAAGGACGA |
| | | AGGCTGAGGAAGCTTTAGTTTCCGTATGGCAAGGTGTGCTGGGAGCGCAGCAGGTCGGCATCCATGATCATTTCTTCG |
| | | ATCTGGGTGGTGACTCCATCAAGGCGATCCAAGTGTCCTCGAGATTGTTCCAAGCTGGATATAAATTAGAGATGAAG |
| | | GATCTCTTCAAATATCCGACAATTGCCGAGCTAAGCCCGTATCTTCAGGCAGCTGGACGTATAGCGGAACAGGGTGA |
| | | AATTAAAGGTGCAGCAGAGTTAATGCCAATTCAGCGTTGGTTCTTTGAACGCCATACAGCGGAGCCGCACCATTATA |
| | | ATCATGCCGTCATGCTCTATCGGAAAGACGGCTTTGATGAGGCTGCACTCCGGTTGACAATGGACCAAATTGCGATCC |
| | | ATCATGACGCGCTGCGCATGGTTTTCCGGCCTACAGAAGCTGGATACGCAGCTTGGAATCGGGGAACGGACGAAGGC |
| | | GAGCTCTACACATTGGACATTGCCGATATGCGGCAGGCGGAAGACCAGACAGCTGCGGTTCAGGCCCAAGCCGATGC |
| | | CATTCAGGCAAGCTTTGACTTGGAAGGTGGCCCACTGTTCAAGCTAGGCCTGTTCCATTGTGACGATGGCGATCATTT |
| | | GTTGATTGTCATTCATCACCTCTTGGTTGACGGCGTATCCTGGCGCATCCTGTTTGAGGACATTGCAGCGGGGTACGA |
| | | GCAGGCATGGAATGGACAAGCAATCGTCCTTCCACAAAAGACCGATTCGTATCTTGTATGGTCTGAGCAAGCGACGA |
| | | AGTATGCAGCAGGGCCTGCTCTGGACAAGGAGCGTGCATACTGGCAGCTGATCGAGGAGGCGATTTTGGCTCCACTG |
| | | CCGAAGGATGAGGATCAGAAGCCGGGCACCATTCGGGATACTGAATCGGTTACGGTAACGTGGTCTGCGCAGGAAA |
| | | CTGACCTGCTGTTGCGACAAGCGAACCGGGCGTATCATACGGAGACGAATGACTTGCTCTTGACTGCTCTGGGGGCA |
| | | GCCATTCAGCGCTGGACAGGCATGGAGCAGATTTTGGTCAATCTTGAAGGACATGGACGGGAAATAATCGTACCAGA |
| | | CCTGGATATTACCCGTACCGTGGGTTGGTTCACAACCCAGTATCCAGTTCTGCTGAACCTGCAAGGCAGACAGGAAGT |
| | | ATCTGCGCGAATCAAGCGCATCAAGGAGAATTTGCGAGAGGTTCCGCATAAAGGAATCGGCTACGGTCTTCTGAAGT |
| | | ATATGGCACCGGAGAAAAGTGTCGGACTCGGCGTGGAGCCGGAAATTTCCTTCAATTATCTTGGGCAGTTTGATCAG |
| | | GATTTGGAGGGTAATGCCCTTAGCCTATCCACACATTCAGTTGGTAAAGCGCTCAGCGATCTCACACCACAGCAATAT |
| | | GCTCTGGATGTGAATGGCATGATTGCCGAAGGCCAGCTATCACTGACGATTACGTACAGCAGCAGGCAGTATCGTAA |
| | | GGAGACGGTGAGTCATTTTGCTGAATTATTACAGTCAAGCCTTAGTGAGGTCATCCGTCATTGTGTGGCTCAGGAGCG |
| | | TTCACAGCTTACACCAAGTGATGTTCTGTTCCAAGGATTAACATTGGAGCAGCTTGATCGACTCACGGCGCAGACGGC |
| | | TCACATCGGAGAGATTGAGGATGTGTACAAGCTGACGCCGATGCAGAAGGGAATGCTGTTTCACAGCCTACTGGAGC |
| | | CGGGCTCCTCTTCATACTTCGAACAGGCAACGTTTGAGCTGCGTGGCAGCTTCGATGTAGATACCTTCTTCGAGAGCT |
| | | TCCAGGCTCTGGTGCAACGACATGCCATACTACGTACCGGCTTTTACAACAACATTGCTGATGTACCGCTGCAAGTTG |

TABLE 5-continued

Nucleotide sequences of genes encoding the fusaricidin synthetase (fusA) in *Paenibacillus* sp. strains NRRL B-50374, NRRL B-67721, NRRL B-67723, and NRRL B-67724.

| Strain | SEQ ID NO: | Sequence |
|---|---|---|
| | | TCTTTAAGCAACGGTTAATCCCTCTGCACTACGTAGATTTGCGCGACGCATCTACGCAGGAACAAGAAGCCCGAATCA<br>AGGCTTATATTGCTGAAGATATGGTTAAGGGGTTCGGCCTGTCAGAAGATCCGCTGATGCGGGTGACCGTCTTGCAGA<br>AGGATCAAAGCTGTCTTGTATTGTGGAGCTTCCACCATATTGTCATGGATGGCTGGTGTATCCCGATCATTACACAGG<br>AGCTGTTCGATTATTATTCTGCCAAGAAACAGCAAGTACAGCCTGTCCTACCGCCAGCTCAGCCCTATAGTCGTTATA<br>TCGAGTGGCTTGATGCACAGGATGATCAAGAAGCTTCAACGTATTGGAGCCAATATCTCGAAGATTATGACGGGAAT<br>ACTGTATTGCCGGAAGGTAAAACGAAATCTCAAGCCAAAGAGGCGGGCTATGTTCTAAAAGAGCATGTTCTCCATCT<br>GGGTGTATCTTTGACAGGTAAAATGGATGTTGTCGCGAAGCGCAATCACGTGACCGTCAACACACTCATGCAGACAG<br>CTTGGGGACTGATTCTTCAACGTTATAATGCCAGCTCGGATGTCGTTTTCGGCGGCGTTGTGTCGGGTAGACCCGCTG<br>AGATTGCAGGGATCGAAAATATGGTGGGTCTGTTCATTAATACAGTACCTATCCGTGTACAGTCATCCAAAGACGAA<br>GCCTTTGTCGAAGTGATGAAACGTACACAGGCACAGTCATTGGCTGGTCGTGCCTACGACACCTATCCACTGTATGAG<br>ATTCAGGGGAAAACAACCCAAAAGCAGGACCTGATTTCTCATATTATGATCTTTGAAAATTACCCGCTCGACGAACA<br>GGTGGAGCAATCGGGTAATCAAACGGAGGACAATCTCGAAGTTGCCAACTTCACCATGTTTGAACAAACCAACTATG<br>ACTTTAACCTGGTTGTAATTCCAGGCGAAGACATCAAGGTCTGCATTCGCTATAATGCTTCGGTTTACGAGCAAGAAA<br>GCATTGCACGAATCGGAGGACACTTGTTGCAGATGCTCGACCAGGTGGCTGCTCGTCCGCAGGCGACGATACAGGAA<br>CTGGAGATTGTAACATCTGAGGAACGGATGAACCTGCTTGACTGGGGCGGCAAGGCCCATACCTATCCAAGTGATCA<br>GGGGCTGCACACCTTGTTTGAGGAACAGGTGGTCCGTACGCCGGATAAGATTGCGGCAGTAAACGGCGACATCCAGA<br>TCACGTATCGGGAGCTGAACGAGCAGGCGAACAGACTAGCTTCCACCTTGATAGACCAAGGACTACGGAGTGAACA<br>AGTGGTAGGTCTGTTGGCAGATCGGTCTGTAGAGCTGCTTGTCGCCATCATGGGTGTACTCAAAGCGGGTGGAGCCTA<br>TGTACCTATTGATCCTGAATATCCGCAGGAGCGGATTCAGTATATTCTGAAGGATTCTGGCGCTGAAATTCTGCTCAC<br>ACAGAGCCACCTGACTAAGTTGGCCTCTTTTGAGGGAACGGTTATGGAATTGGATTCCCCGCACATCTACGGAACCGA<br>GGTGGATAATCCCAATATTCCTGTTGGAGGAAACGATCTGGTGTACTTAATCTATACCTCGGGTACAACCGGAAATCC<br>GAAGGGAACCATGATTAACCACAAAGGGATCGTGAACTACATCTGGTGGGCCAATAAGGTCTATTGTGCTGGGAAAC<br>CAACGGATTTCCCGTTGTATTCATCCATTTCGTTTGACTTGACGATGACATCAATGTTTACTCCGTTAATAAACGGAGG<br>AATAGTGCGGATTTATGATGGTATAGATAAAGCGGAGGTTGTTCAGCATATTTTGCGCGAAAATGCGGTCGATATTCT<br>CAAGCTGACGCCAACGCATCTCAGTCTGATAAAAGACATGACCATTCCAGCGGAAAGTCGTATTCAGCAACTCATTG<br>TGGGCGGAGAAAATCTGACCACACATTTGTCCAAAACGATTACCGACCTCTTTGGTGGCAACATCAAAATCTACAAT<br>GAATACGGTCCGACCGAAACCGTCGTCGGCTGCATGATTCACCTGTACGATCCTGCGAAGGATACACGGGAATCCGT<br>ACCGATTGGGTTGCCGTCCGACAACATATTCATCCATATTCTGGATGATCAGCTTCGTCTCGTACCGTTAGGCGTGGA<br>GGGCGAAATGTACATCGCCGGGGACGGGGTAGCCCGTGGATATCTGAACCGTCCTGAGCTTACCGCAGATAAATTCA<br>TTAGAAATCCGTTCGCTTCGGAAGGAAATATGTATCGCACTGGGGATTTGGCTCGTCGCCTTCCTAATGGAGACATTG<br>AGTACATTGGACGCATTGACCATCAAGTTAAAATACGGGGCTATCGTATTGAGCTTGGTGAGATTGAGGCCAAGCTG<br>CTGGACATTCCACTTGTCGAGGAAGCTCTCGTTGTTGCGTGGGCAGATGCTCATGGGCAGAAATCGCTGTGTGCTTAC<br>TTCGTAGCTGATCGCGAAATGTCTGTCAGCGAGCTGAGAGACGAACTGTCTGCCGGACTGCCTGCATATATGATTCCG<br>TCTTACTTCGTCCAACTGGACGTGATGCCTCTGACACCGAATGGCAAGCTGGATCGCAAGGCACTGCCTGAACCGAAC<br>TCGGGTATAAAGGCGGGAGCAGACTTTACCGCTCCGCGGACGGATGTGGAGAACATTTTGGCTTCAATCTGGCAAGG<br>TGTACTCGGCGTGCCGCTTGTCGGCATACATGATAATTTCTTTGAGCTTGGAGGTGACTCGATCAAATCCATTCAAGT<br>ATCCTCAAGGCTTCTCCAAGCAGGCTATAAGCTTGAAATGAAGGATTTGTTCGGTTATCCGACAATTGCAGAGTTGGC<br>GCAGCGCGTTAGTGTGGTCAGCCGAATTGCGGATCAAAGCGAGGTACACGGAGCGGTAAGACTGGGGCCTGCCCAG<br>CACAGATTCTTCCATGAACAGTCTATGGATCTGCATCACTTTAATCAGTCGGTCATGTTGTACCGACGGGATGGCTTC<br>AATACCGATGCGCTCGCCGAGGTTGTTCGGAAAATTGCAGAGCATCATGATGCTTTACGACTGGTGCTCCGCCAAGG<br>AGAGCAGGGGTTGGAGGCCTGGAACCGGAGCGTGGGTGAGGGAGAACTCTATAGTCTCCAAATCCATGACCTGCGG<br>GATGAAACAGACCCCGCTTCAGCGATAGAAGCAGGTGCGGAAGCCATTCAGCGTAGCATCTCTCTGGAGGATGGACC<br>TCTCTTTAGACTGGGTCTGTTCCGCTGTGTGGAAGGCGAACATCTGTTGATCGTTATTCATCATCTGGCTGTGGATGGC<br>GTATCCTGGCGTATTCTCTTTGAGGACCTGCAGGAAGGCTACGAGCAGGCAGTACGTGGAGAAGCGGTCAAGCTTCC<br>ACAGAAGACGGATTCGTACCGTGCATGGGTTGAGGGAATCACACAATTTGCAAACAGCCCGGCGGCTGAACAAGAA<br>CTCAGCTATTGGGCAGAGGTAGAGGGAGATGGCTTTGCCCCTCTTCCAAAAGACAAGGTAGACGGCGCTCTTCTCATC<br>AAAGACAGTGAGGCTGTCACGGTGAGATGGTCACCAGAAGAGACAGAGCAGTTCCTGAAAGAAGCGAACCGCACTT<br>ACAATACGGAGGTTAACGATCTGCTCCTGACGGCTCTGGGTATGGCTGTTCACGAGTGGACGGGAATCGAACGTGTA<br>GGCATCCTTCTGGAGGGACATGGGCGGGAGCCTATTGTGCCGGAACTGGATATTACTCGCACAATAGGCTGGTTTAC<br>AAGTCAATACCCTGTCGCCCTTGAGATGGGAGGGGAATTGGAGATCGGCGCCAGAATCAAGCACATTAAGGAAGGCT<br>TGCGTCGTATCCCGAACAAAGGTGTCGGATATGGTATTTTGAAATATTTAAGCGGCGGTTCTGGTGTCTCCTCCTTCTC<br>GGCTGAACCTGAGATTACCTTCAACTACTTGGGACAGTTCGACCAGGATCTTGCAGGAGGGACGATGGAAGTATCGC<br>CTTACTCAGTAGGACCTGAGGTCAGTGAGCAGATGGTGCAGCATCAGACATTGAACATTAATGGACTGATTGCCGAA<br>GGACAGCTTCAACTTTCGGTCAGCTATAACCGTCATCAGTTCCACGGGGAGTCTGTGGCTAAGTTTGTTGACATTCTG<br>AAGAACCGTCTCAGCGAAGTCATTGGACATTGCGTAAGTAAGAAAAGAACAGAACTTACACCAAGCGATGTACTCCT<br>CAAAGATATCAGCTTGGAAAAAATCGAGGAGTTAGAAGAGCAGACACGGCATATCGGCAGTATTGAAAATATGTAT<br>AAACTGACGCCGATGCAAAAAGGAATGTTGTTCCACAGCTTGCTGGAGCCTCATTCGGAAGTCTACTTTGAGCAGGC<br>CAAGTTTGAAATTCAGGGAGCATTCTATCCTGAGGATTTCAAACGCAGCTTAAAATATCTGATGAAACGGCATGCCAT<br>ATTGAGAACCAATTTCCATGCCGGGTGGGGCGATTTCCCTATTCAGATTGTGTTCAAAGAAAGAGCATGTGACTTCGT<br>ATACGAGGATCTGCACGAGCTGGAAGCCGATGAAATTCAAGCGCGTCTTGCAGCTTATACTGCTCAGGACAAAGCAA<br>GAGGCTTTAATCTTGCTGAAGAAGCATTGCTGCGTGTTGCTATTCTACGTACAGCAGAAGAGGCTTACCATTTGCTGT<br>GGAGCTCTCATCACATCATTTTGGATGGCTGGTGTATGCCGCTTGTGCTCCAGGAAGTGTTTGAGACGTATGGGGTTC<br>TGCGTGAGCAAAGGGAACCTGAGCTTCCTGCAGCTGTATCGTACAGCCAGTATATTCAATGGTTGGAGAAGCAAGGC<br>GAGGAAGAGGCATCCTCTTACTGGAGAGGGTACCTGGAAGGCTACGAGCAGCAGACGAAGCTGCCACAAGCCATCA<br>CACAGCCATCGGCAAAAGCAGAAGCCTACGTGTCGGAGAAGCTGGTATTCACGTTGGATGCGGAACTGACCGATCGC<br>CTGGAACAGGTGGCCAAACAGCATCAGGTGACGATGAATACGCTGATGCAAGCAGCCTGGGGAATCGTGTTGCAGC<br>GTTACAATAGAAGCCAGGATATCGTCTTCGGAAGTGTGGTATCGGGAAGACCTGCCGAGATTCCGGGTATCGAAAGC<br>ATGATCGGTCTCTTCATTAATACAGTTCCGGTTCGGGTACAGGCCGAGGGAAGCGATTCGTTCTCCCATGTGATGAAA<br>AGACAGCAGGAATTATATTTGGCAGGACATGCTTATGATTCCTATCCGCTCTATGAGATTCAAGCACAGAGCGAACA<br>AAAGCAAGATTTGATTTCTCATATTATGGTGTTCGAAAATTACCCAGTAGAAGAGCATTTGGAAGAGAAAATTGCCA<br>GTGAAGAGGCTGAATACAAAATTACGGATGTTCAGATGTTTGAACAGACGAATTATGATTTTAACCTCATTGTGCTGC<br>CGGGTCGTAATCTGGAGTTCTTGTACCGTTACAATGCCCGCGTCTATGATCGGGAGAGCGTGGAACGAATTCAAGGA<br>CACTTGACGAGAATTCTGACAAGCGTTGCTGTTCAACCTGCTATCCGTATTGATGAGCTGGAGCTGATCACGCCAGAA |

TABLE 5-continued

| Nucleotide sequences of genes encoding the fusaricidin synthetase (fusA) in *Paenibacillus* sp. strains NRRL B-50374, NRRL B-67721, NRRL B-67723, and NRRL B-67724. | | |
|---|---|---|
| Strain | SEQ ID NO: | Sequence |
| | | GAGAAATCGCAGATTATAGAGGTGTGGGGCGATACAGCAGCTCCTTATCCGCGTGAGCAGACCCTTCACGGTATATT<br>TGAGGAAAAAGCAGCACTCACACCGGATTGTACAGCACTTATTTACGGTGAAACGGAGCTTACCTATGGAGAACTTC<br>ATCAGCAGGCGAACCGCCTTGCACGTACGCTGCGTGCCCAAGGGGTCAGACCGGACCAACCAGTCGGCATCATGGTC<br>GAGCGTTCGCTTGAGATGATCATTGGCATTCATGCCATTCTAAAAGCTGGCGGGGCCTATGTACCGATTGATCCGGAG<br>TTCCCAGAAGATCGTATTCGCCACATGCTGGAGGATTCGGGAGCGAAGCTTCTGCTGACGAAGAACCATCTCAAAGA<br>TCGTTTTCCGTTCACTGGCACGATCCTGGCACTTGATGATCCGCAGGCGTATCATGCGGATAGCTCGAATCTGGAGCC<br>AATTGCGGGGCCGGAGCATCTGGCGTATATCATTTACACGTCAGGTTCAACCGGCAAGCCGAAAGGGGTAATGATTG<br>AACATCGCGCTGCCGTCCATACGCTGAGTCAGTTGGAAGCTGAATATCCGATGTTGGCAGGCGACCGTTTCCTGCTCA<br>AAACGACATTTACCTTTGACTTCTCCGTGCCGGAGCTGTTCTGCTGGTTCTTTGGAGAGGGGACTCTCGTGATCCTGCC<br>ACAAGGCGTGGACAAAGACCCGATGGCACTGCTAGGGGCCGTGGATACGAACCGTATCACGCATCTCAATTTGGTGC<br>CGTCGATGCTCAGTGTGCTCGTTCAATACTTGAAAGAAAGCGGCACCCAAGGATTCCTTACTCTGAAATATCTGTTTG<br>CCTGCGGCGAGACGCTGCCTGCCAAACTTGTGGAAGAGTATTATAAAGTATCTCCTTACGCAGTACTGGAAAACATCT<br>ACGGTCCTACGGAAGCAGCCGTATATGCGACTCGGTATACAACGAGCCTTGAGACTGCGGCTCTAACGCATGTGCCA<br>ATCGGCAAACCGTACGCTAACGTCCAAGTATGGATGATGGACAGCGCTTCTCAGGTATCACCTGTGGGGGTACCGGG<br>AGAACTCTGCATTGCGGGCGAAGGGGTAGCGCGGGGGTATTTCAACCAGCCGGACCTGACGGCAGAGAAGTTCATTC<br>CTCACCCGTACAAACCGGGAGCACGGATTTACCGAACGGGCGATTTAGCCCGATGGCTGCCGGACGGGAATATTGAG<br>TATTTGGGACGGATCGATCACCAGGTAAAAATCCGGGGTTACCGCATTGAGCTGGGAGAAGTGGAAGCACAAATTTT<br>GAAAGTGCCATCTGTGCAGGAAGCGGTTGTTCTTGCACTGGCTGATTCTACTGGAAGTACTCAGCTTTGTGCATACTT<br>TGTGGCCGAAGAGGGGCTTACAGCGGGCATACTACGCGAGGCACTGGCCAGCGAGCTGCCAAGCTACATGATTCCGA<br>CTGCTTTCGTACAGTTGGCACAAATGCCGCTGAATCCGAATGGCAAATTGGATCGCAAAGCGCTACCGGCACCGGAA<br>ACACTTCTGCGGAGCACAGCGGAGTATATCGCGCCGCGTACGCAGACAGAAGTAGAGCTCGCTCAGATTTGGTCCGA<br>GGTGCTCGGCGTACAGGAAATCGGGATCAGGGATCATTTCTTTGAACTTGGGGGCCATTCCCTGAAAGTATTGGGCTT<br>GATCCAAAGGATCTCGTCCGGTATGGGCGTCCAGCTCCCACTCCAAGTCGTGTTTAATCTGCCGACTGTGGAAGAAAT<br>GGCGCATGAAATTTCCAAGCTGCAGGCAACAACTGCTGCTAATGAAGAGGAAATGGAAATTATCCGCTTCCCAGGGA<br>AAGGAACGCTCAAAGTGTTTTGCTTCCCTCCACGGGTGGGCCACTCTCTGGGATACTATGAGATGGCCAAGGAGCTG<br>GAAGGGCTTTGCGAGGTGTACGGGATGGAATTTATCGGCGATCGTTTCCAGGGTCAAGATATGCTGGATCGATACAT<br>CGATGCCATCGTGGATATTCAAGCAGAGGGTCCGTATATATTCCTGGGATACTCACTTGGAGGAAACCTCGCCTTCGA<br>GGTAGCTAAAGCCATGGAAAGCCGAGGTCACCATGTTAGCGACCTTATTATGGTAGATGCTATGAGAAAGATGTCCA<br>AGGATGAATCGACACCGGAGGAGCTTGAAGAGATTGTCGAGATGGTACTGGACAGCATTAGGGACCAGTACAAAGC<br>GTTCCTTGCCGATCCAGTGGACAGGGAGCGAGTCATGGACAAAATGTTGGTTTACTCCGTCTACCGCGATGAGCTTAT<br>TAACTCAGGTGAAGTTCATGCGAATATCCATGCTCTAATTGCAGAGGATGATAGTATTGGTCCGGATACATCATTAGA<br>TAAATTGTTATGGCAACAGGCGACACTTGGTCAATACAAAGAATACGAAGTCATCGGAACGCATGATGTGCTGCTTG<br>ATTCCGGTTTTATTGGGGAAAATGCTAAAGTACTGAGACAGATACTTGGCAAGGTCACAGAGGCCTCATCTAAAAAC<br>AAGCCCATTTTGTCCTAA |
| NRRL B-67721 | 2 | ATGAATGACATGCAGTTATATGATTTAACAAATGCGCAGAAGCGTATATGGTATACCGAATTACTCTACCCAGATAC<br>GTCAGTGTCACAGCTTTCCGGTACAGCTAAGATGAAGGGGCACATCAATATTGCTGCCTTTATGCAGTCCATTAATTT<br>GATTATCAAACAGTATGATGCGTTCCGCATCCGTATTACCTCAGTGGATGGAGTGCCTCAGCAGTACGTCGTCCCTTA<br>TGAAGAGAGACAGCTGGAGTGCCTGGATCTTAGCCACTATGAAAGTGTATCTGAGGTGGAAGCCTTACTTGAGCAAC<br>ACAAAAGCAAGCCCTTGCCCCTGTTGGATTCTGAGCTCTTCCAGTTTTTAATTGTGAAGATTAGCGAGGAAGAGTATT<br>GGATTAATATCAAGATGCACCATATTATTTCTGACGGAATATCAATGGTGGTCTATGGCAATCAGCTGACAGCATTTT<br>ACATGGAGTTAATTCAAGGAAATGAACCGAAGCTGGGCGACGATTGCTCGTATATTCAATATATTGCTGATGAGAAT<br>GCATACGAACTTTCTGACAGATACCAAAAGGATAAGGCTTACTGGCTGGATAAATTTTCTGATTTGCCTGAGCTTACG<br>GGTTGGAAGTCATATAATCCGTTATCTTTAAGCACCCACGCCGTTCGGGAGCATTTTACCGTACCAGAAGTGCTATAT<br>CACGAGCTGCAAGCATTTTGCCAACAGAACAGAATTTCTTTGTTCCAGTTCTTCATGGGTGCGATGTATATCTACATA<br>CACAAAATGACGAATCAGCCGGATGTGGTGATTGGAACTTCGTTCGCTAACCGGGGGAACAAAAAAGAGAAGCAAA<br>AGATAGGTATGTTCGTCAGCACCGCTGCTGCCAGAACATACGTCAAAAAGGATATAGATGTATTGAGCTTCCTGCAG<br>GATGTAGCCAGAGATCAGATGTCAGTCCTGCGGCATCAGAAATATCCATACAATCAGTTAATTCAGGATCTTAGAGA<br>AATGCATGGGAACAAGGATATTCAGCGGCTTTTTGGCGTTTCCATGGAATATCGTCTTATCAATTGGGTTGATTTGGA<br>TGATGTGCGTATTTTGACAGATTATGATTTCTGCGGGGACGAAGTGAACGATTTCGTGCTTCATATCGTGGAGATTCT<br>GGATGAAGGCGAACTGGTACTGGATGTCGATTATCGGACAGAGCTGTTTGAACGCAGTGAAGTTAAGGACATGGTTT<br>CCCAGTTGCTTACGATCGCCGAGCAGATCATTCATTCACCTCAGCTTTCTATTGCAGAGGTAAACTTATTGGGTGAAC<br>CAGAAGAGCAATCCATTTTGGCTCTTTCGGAAGGCGCCGCAGTCGATTATCCACGTGAGAAGACCATTCATGGCTTAT<br>TCGAGGAACAAGCCGAGCGCACACCAGATCACGTAGCCGTTCAGATGGACGAGCAGAGCATTACATACCAAGCTCT<br>AAACGAGCAGGCTAACCAGCTTGCGAGATATTTGCGCTCCGAGGGAGTAGGAGCAGATACGCTCGTAGGGATTATGG<br>CTGACCGTTCCTTGGAGATGGTCATCGGGATGTTGGCCATTTTGAAAGCAGGTGGTGCCTATGTACCGATTGACCCCG<br>ATTATCCCGAAGAACGTATCCATTATATGCTGGAGGATTCAGGTGTCCGTCTGTTGCTCACCCAAAGTCATCTATGGG<br>AGAGCACCACTTTTGACGGAAAGCTTGTGAGTCTGGACGAAGCTACAACGTATACAGGGGATGCTTCCAATCTGGAG<br>AGTATTTCGGGACCAAGCCATCTGGCCTATGTTATCTACACGTCGGGTACGACCGGCAAGCCGAAGGGCACGCTGAT<br>TGAACACAAAAACGTAGTTCGACTGCTCTTTAACGATAAAAATCTATTTGATTTCAGCTCTCAGGATACGTGGACGCT<br>ATTCCATTCGTTCTGCTTCGATTTCTCCGTTTGGGAGATGTACGGAGCGCTTCTTTACGGAGGGAAATTGGTGATTGTT<br>CCATCTCTCACAGCCAAGAGCCCAGCAGCTTTCCTGGAGTTGTTGAAAGACAACCAAGTCACCATTTTAAATCAGACG<br>CCGACGTATTTTTATCAGGTGCTACAGGAAGAGTTAACGCACTCTTCGACAGAGCTTGGCCTTAGAAAAATCATTTTT<br>GGTGGAGAGGCCTTAAGTCCATCTCTTCTGAGAAACTGGCGGGTCAAGTATCCTGATGTGCAGCTGATTAATATGTAC<br>GGAATTACGGAAACAACAGTCCATGTCACCTACAAGGAAATCACGGAACATGAGATTGAAGCGGGGAAAAGCAATA<br>TTGGCAGAACGATCCCCACACTTAGCGCTTATATTCTCGATGAGCAAAGACGGCTGCAGCCTGTTGGGGTTCCGGGA<br>GAGCTATACATTGCAGGGGACGGTCTTGCCCGTGGGTATTTGAATCGGCCGGATTTGACGTCTGAGAAATTCGTTGAG<br>CATCCGTATCGGGCGGGAGAGCGGCTGTACCGAACTGGGGATCTTGCTCGTTGGTTGCCTGATGGCAATATTGAATAT<br>TTGGGACGGATCGACCATCAGGTCAAAATTCGCGGCTACCGAATTGAGCTTGGCGAGGTAGAAGCCCAAATTCTCAA<br>GGCTCCGAACGTACGAGAAACGATTGTCCTCGCACGGGATGACGAACAGGGCCAAAAATTGCTGTGCGCCTACTATG<br>TAGCCTCCAGTGATCTTTCGCCGGGGGAATTGCGGTCTCAGCTGGCAGCGGAACTCCCCGCTTACATGATTCCTTCTT<br>ATTTTGTCCGGCTGGAGCAAATGCCGCTTACGCCAAATGGCAAACTGGATCGCCGTGCGTTGCCGGCTCCTGAAAGC<br>AGCGTACAATCCGGCGAGGCTTATTTGGCTCCGAGAACTGCTGTGGAAGCTCAGATGGTACTCATCTGGCAAGATAT |

TABLE 5-continued

Nucleotide sequences of genes encoding the fusaricidin synthetase (fusA) in *Paenibacillus* sp. strains NRRL B-50374, NRRL B-67721, NRRL B-67723, and NRRL B-67724.

| Strain | SEQ ID NO: | Sequence |
|---|---|---|
| | | CTTGGGAGTTGCCCGCGTCGGTGTCAGAGATAATTTCTTTGAAATTGGTGGTCACTCTTTGCGGGCAACAGTGCTCGT |
| | | TTCACGGATTCACAAAGAATTGGGATGTAGCATTTCGCTGCGTGAGGTGTTTCAGTCACCTACGGTCGAATCCTTGGC |
| | | GCAACTTGTGAAAAAACACATTCCGACCCTGTACGAATCCATCCCGCGGGCAGCGGAAAGCGAAGCTTACCCAGTGT |
| | | CCTCAGCGCAAAAGCGGTTATACGTGCTGAGACAGATGGACGGGGGAGAGCTTAGCTACAATATGCCAGGGGTCTTC |
| | | ACAGTGGATGGACCATTGGATCGCACGCGGCTGGAGTCCGCGTTCCAGGCACTGATCCAGCGTCATGAATCCCTAAG |
| | | AACCGGCTTTTATATGCAGGATGGAGAGCTTGTTCAGCGTGTGCATAGGAATGTGCCGTTCGCGTTGAACTATACAGA |
| | | GGCTTCGGTGGAGGAGACGGATACGCTCATTCACAACTTTATTCGTGCCTTTGATCTGAGCCAGGCTCCATTACTGCG |
| | | TGTTAGCTTGGTGAAGCTCCAGGAGGAGCGTCATCTGTTGCTGTTTGATATGCATCACATCATTTCAGATGGGGTTTCT |
| | | ATTCAAATATTGATACAGGAACTTACTCATTTGTATCAAGGAGAACAGCTACCAGAACTGCACATCCAATACAAGGA |
| | | TTATGCCGTATGGCAACGAGAACAGTCAGAGAATCAATGGCAAGATCTTGAGAAATATTGGCTGCAATCCTTTGAAG |
| | | GAGAGTTGCCGGTATTGGATTTGCCTACAGACTTCCAACGACCTTCGGTTCGGAGCTTCGAGGGTAGCCGAATTGATT |
| | | TTACATTGGATGAGTCTGGAAATAAGGCGATACAAGAGCTTGCATCCCGTACAGGTACTACACTGTATATGGTATTGC |
| | | TGGCCGCTTATTCGGTACTACTGCACAAATATACAGGACAAGAGGACATCGTCGTAGGTTCTCCAGTAGCCGGAAGA |
| | | CCGCAGGCTGAGCTTGAGGGCATCATCGGAATGTTTGTCAACACACTGGCCTTGCGCAGCTACCCGACAGGAGATAA |
| | | AACCTTTCAGGATTACCTTCTTGAAATCAAGGAAACGGCGCTCAAGGCGTTTGAGCATCAGGATTACCCTTTTGAAAA |
| | | ATTGGTAGAAAAGCTGGGCGTAGGACGTGATGTCAGCCGCAATCCGCTCTTTGACACCTTATTGGTATTACAAAATAC |
| | | CGAGCAGGAAGAGCAGGATATGGACGGAGTGCACTTTACTCCTTACTTGATGGACACCGTCACAGCCAAATTTGATC |
| | | TGTCCCTCAATGTAGAGGAGAAGGGGTCAAAATTAGCCTTTGGCCTCGAGTATAGTACGGCTTTATATCGGCGTGAA |
| | | ACCGTAGAGCGACTTGCAACGCACTTGCTCCGGGTTCTGCACGCAGTCTCGGCCAATCCTCAGTTGCAACTGGCCGAG |
| | | ATAGAAATGATCACACCGGAGGAGAAAGTACAGATCGTTGAAGTATTTAACGCGACATCGGCTCCTTATCCAAGGGA |
| | | CAAGACCATTCATGAGCTGTTCGTAGAACAAGTCAAGCGTACACCAGAGCAGACGGCGCTTGTATTCGGCGATGTCC |
| | | AGCTAACGTACCTTGAATTGCAAGACAAGGCGAGCCGACTGGCCCAAACACTGCGTCGTTTGGGAACGTTGAGGGAG |
| | | CAGCCTGTGGCCGTGATGGGCGGACGAAGCATCGAGATGGTCATTGGTATGCTCGCGGTGCTTCAAGCGGGTGGAGC |
| | | CTATGTGCCGATTGATCCTGATTACCCGGAAGATCGGGTTCGTTATATGCTTGATGATTCCGACGCCAAGTTATTATTG |
| | | GTGCAAAAGGGCGAGCTTATAAGTGTAGACTACGGTATACCAATTGTCGATCTTAGCAGTGAAGAGGCTTATGCTGC |
| | | TGAGCCTGCCCAGCCGGAGACGGCTCAGGGATCGCAGGGGCTTGCTTATGTCATCTATACATCGGGTACGACGGGTA |
| | | GACCGAAGGGCGTTATGGTTGAACACCGGAACGTGGTCCGTCTGGTCAAAGAGACCAACTATGTGGAGCTGAATGAA |
| | | TCCACACGAATTTTGCAAACAGGAGCCGTGGCCTTTGATGCTTCTACATTTGAGATATGGGGAGCGTTGCTTAACGGT |
| | | GGGCAGCTCTATTTTGTAGAGAATGACGACATTCTGATTGCTGATAGGCTCAAAGCGGCTATTGCCAAGTACGGGATT |
| | | ACAATATTGTGGCTTACTTCACCCCTTTTCAATCAGCTTTCTCTGCAGGATGAGTACCTGTTCAGAGGGCTAAAAGCA |
| | | TTGTTAGTCGGCGGTGACGTACTGTCCATATCTCATATGAACCGTGTAATGGAGGCTAATCCTGATCTTGTCCCTATCA |
| | | ATGGCTATGGTCCGACAGAGAATACGACCTTCTCCACCACCTACAAGATTCTGGGTCGTGCCGAAGGGGTCGTGCCG |
| | | ATTGGCCGCCCAATTAGTAATTCTACCGCTTATGTGGTCAATGGATCGCTGCAATTACAGCCTATTGGTGCTTGGGGT |
| | | GAACTCATTGTCGGCGGTGAAGGTGTAGCGCGCGGATATCTCAATCGTCCTGATCTCACAGCAGAGAAATTTGTTCCT |
| | | AGTCCTGTTAAGGACGGAGAACCCTGCTACAGAACTGGGGATTTGGTACGCTGGCTTCCAGATGGCAATTTGGAGTTT |
| | | AAAGGAAGAATTGATGAGCAGGTCAAAATACGTGGTTACCGCATCGAACTCCCTGAAATCGAGGCCCAACTGGCCA |
| | | AGGTGGAGTCAGTAATCGACGCCGTAGTGGTCGTTCGCGCGGATGAGCTTGGCGAGAAGCAGCTTTGCGCTTATTAT |
| | | GTGGCGGATCGTACGCTCACGGCAGGCGAAGTACGTCTTTCCCTATCGCAGGTACTTCCAGGCTATATGATTCCATCC |
| | | TACTTTATCCAGATGGATCGTATGCCATTAACGTCAAACGGAAAAGTGGACCGCAGGTCTCTGCCGGCTCCTCAAGTA |
| | | GGCGCGCATACAGGACGGAAGTATACAGCTCCTCGTACACCGGCTGAGGAAGCTTTGGCATCTGTCTGGCAAGGGGT |
| | | GCTGGGTGCCGAACAGGTGGGTATCCATGACAATTTCTTTGAATTGGGTGGAGACTCCATAAAAGCTATTCAAGTGTC |
| | | GTCACGGTTACTGCAGGCCGGCTATCGGTTAGAGATGAAGCAGCTGTTCAAATCGCCAACCATTGCCGAGCTAGGCG |
| | | CGGAAATTCAAACGGCTGTGCATATGGCTGAACAGGGAGTTGTGCGTGGAACGACTCGCTTGACTCCAGTCCAACAG |
| | | TGGTTCTTTGGACGGAAGCAGGCAGAGCCTCATCACTTCAATCAAGCGGTTATGCTGTATCGTGAACAGGGATTTGAG |
| | | GAAAAGGCCTTGCATCAGGTGCTAAGAAAACTCGCTGAGCATCATGACGCCCTTCGCATGGTTTTCCGTCAGACAGA |
| | | GCATGGCTACGAAGCTTGGAATCGTGATCTTGAAGAAGGAGAGTTGTATAGCCTATTCACCGCTGATTTACGGAATG |
| | | AATCCGATCCGGCTGCAGCCATTACATCGCTGTCGGATGACATTCAGCGCAGTATCAATCTGGCAGAAGGTCCGCTGC |
| | | TGAAGTTAGGACTTTTCCATTGTCAGGATGGAGACCACCTTCTAATCGTGATCCACCATTTGGTGGTGGACGGAGTAT |
| | | CCTGGCGGATTTTGTTCGAGGATATTGCAGCAGGCTATGAGCAGGTGATTCAAGGACAAGCGCTGACATTCCCGCAG |
| | | AAGACGGATTCCTTCCGTGACTGGGGAGACGCCCTTGCTCGTTATTCGGAAGGTCCTGAAATGGAGACTCATCGGGC |
| | | GTATTGGAGAGAGCTGGAGGATCAGCCACTCGAACAGTTACCGAAGGATGAGGCTGTGGAAAGCCTTCTTTTACAGG |
| | | ATAGCAAAGTAGTAACAGCACAATGGACTCTAGAAGAAACCGACCAATTGTTGAGAAAAGCCCATCGTGCTTATCAA |
| | | ACAGAGACGAATGATCTGCTATTGACTGCTCTGGGCATGGCGGTATCCAAATGGTCTGGCATCGGAAAGGTTGCTGT |
| | | GAATCTGGAAGGACACGGTCGTGAGCCGATTATACCGAATATCGACATCACCCGTACCGTAGGCTGGTTTACAAGTC |
| | | AATATCCGGTGATTTTAGACTTGGGGGATAACCCGGAAGTGGCCTCCTTGATCAAGTCTGTGAAAGAAGGGCTGCGC |
| | | CGAATTCCGAACAAAGGTATTGGCTACGGGTTGCTTAAAAAGATGGCAAGTCAGTTGGATAAAGACAGCTTCAGCTT |
| | | GCAGCCTGAGATTTCTTTTAACTATTTGGGGCAATTTGATCAGGATTTGCAAGGAAGCTCGTTGCAGATTTCTCCTTAT |
| | | CCGACCGGAAGCGCCCAAAGCTTGTTGGAGGAACCGGCCTATACGCTAGATATCAATGGCATGGTGACGGACGGAG |
| | | CCCTGACTCTGACGATTACTTATAACGGAAAACAGTATAAGTCATCTACGATGGAACAGCTCGCTGGATATATTGAA |
| | | AAAAGCCTGCGGGAGCTTCTCCAGCATTGCGTAACCCAAGAAAAAACCGTATTGACACCAAGCGACGTGCTTGCGAA |
| | | GGGTCTAAGCATTGCCGATCTGGAGGAGCTTTCTAAGCAGACCAGCCACATAGGCGATATTGAGAATGTATATAGTC |
| | | TGACGCCGATGCAGAAGGGCATGCTGTTCCATGATATGTTTGAGCCGCATACAGGTGCTTATTTTGAGCAGGCTGCCT |
| | | TTGACTTTAAGGGTAGCTTTGATCCGACCGCCTTCGGACACAGTCTGGATGCAGTGGTGGAGCGTCATGCCATCCTGC |
| | | GCACGAACTTTTACAGCGGATGGGGCAGCGAGCCTTTGCAGGTTGTATTTCGGCACAGAGGCGCTAAATTGGTGTAC |
| | | GAAGACCTGCGTGAGATGAATGCATCGCAGCGCGAAGCTTACCTGAAGACATTTGGTGCTAAGGACAAAGCACAGG |
| | | GCTTCAACCTAGCTGAAGACGAGCTTCTCCGTGTATCAATTTTACAAACAGATGAAGAGAGCTTCCGCCTCTTATGGA |
| | | GCTTTCACCACATCGTCATGGATGGCTGGTGTGTTCCGTTAATTACGCAGGAGGTATTTGAACACTATTTGCCCTCCT |
| | | GGAAGGAAGAGAGCCGCAGCTGGCAGAGGTTCATCCGTACAGTCGATATATCGAATGGCTGGAACAGCAGGATGAA |
| | | GCAGTTGCGTCCAACTATTGGAGCCGATATCTGGCCGGTTACGAGCAGCAGACGCTTTTACCTCAAGTCGGTGGAGC |
| | | AAGTAAGGGAGAAGGCTATGTAGCAGAAAAGCTGAATTATCCTCTCAGCAGGGAATTGACTGAGCGCCTTGAAAAG |
| | | GTGGCCAGGGATGCTCATGTCACGATGAATATATTGCTGCAGTCCCTCTGGGGCATTGCGCTTCAACGCTACAACGGT |
| | | AGCCGGGATGTCGTGTACGGAAGTGTAGTATCAGGCCGACCAGCAGAAATTCCGGGCATTGACCGGATGATCGGTTT |
| | | GTTCATCAATACGATTCCCGTTCGTGTGAAGACAGAGGAGAATCTCCCCTTCACAGTTCTGATGAAGCAGCAGCAGG |

TABLE 5-continued

Nucleotide sequences of genes encoding the fusaricidin synthetase (fusA) in *Paenibacillus* sp. strains NRRL B-50374, NRRL B-67721, NRRL B-67723, and NRRL B-67724.

| Strain | SEQ ID NO: | Sequence |
|---|---|---|
| | | AACAATATATGGCTTCTCATATGTATGACACCTACCCGCTGTTTGAGATTCAGGCTCAGACGGATCAGAAGCAGGATC<br>TAATCTCCCATATTATGGTGTTTGAAAACTATCCTGTGGAAGAGGAGGTAGAGCGTCTGGGTGGTGGCGAGGCTGCCT<br>TTGAGATTGAGGAAGCGGAGCTTCTTGAGCAAACGAATTATGATTTTAATTTAATTGTCCTCCCTGGCGAAGAAATGA<br>GATTGCTGTTCCAGTACAATGCACTTGTTTATGACCCAGTGACAATTGAGCAAATCAAGGGCCATCTGGTTCACCTCA<br>TGGAACAAATTGTAGAGAACCCTGCCATTTCCGTGGATGCACTAGAATTAGTCACGCCGCAGGAGAGAGAACAGATT<br>CTGAACGTATGGGGAAATACAAAAGGCATTTACGAGCACTGTAACACGTTCCACGGGCTGTTGGAGGAACAGGCGG<br>GACGAACGCCGGATGCGACTGCCATTTGGTTCGAGGACGAGAGTCTGACCTATGCCGAGCTCAATGCAAAAGCCAAT<br>GGACTGGCGAGAAGGCTCCGTACTCAGGGAATCAAGACGGGAGATCTGGTGGGACTGATTGCTGAACGGTCGCTCG<br>AAATGATCGTTGGGATCTACGGCATTATGAAAGCCGGGGGTGCCTATGTTCCAATCGATCCAGAGTATCCGAAAGAA<br>CGAATCAGTTACATGCTTGAAGATTCCGGGGCGAAGCTAATCCTTACACAGGCCCATTTCTTGGAGCATCTCGGATGG<br>ACGGAAAATGTTTTGCTGCTGGATGAATCATCGACCTATGATGCCGACACCTCGAATTTGGAGGATACTGCTGGCCCG<br>GATGATCTGGCTTACGTGATCTATACTTCAGGTACGACCGGTCAGCCTAAGGGCGTATTAGTCGAGCATCGGGGACTA<br>CCAAATCTTTCAGACGTATATGGGGCACACTTCGAAGTTACACCGCAGGATCGGATCGTTCAGTTTGCAAGCCTGTCG<br>TTTGATGCATCGGTTTCGGAAATTTTAACGGCGCTGAGCCATGGGGGTGTTCTGTGCATCCCTTCTACAGAAGATATT<br>TTAGATCATGCCCTGTTCGAGCAGTTCATGAACGATAAGGGGGTTACGGTAGCGACTTTGCCACCCGCTTACGCTATC<br>CACCTTGATCCAGAGCGTTTGCCAACACTGCGGTGCCTGCTAACCGCTGGATCGGCCGCATCGGTCGAGTTGATCGAA<br>GAGTGGAGGAAGCATGTACGTTACTCTAATGGCTATGGCCCAACGGAGGACTCCGTATGCACCACAATCTGGTCTGT<br>CCCGGACAGTGAGGAAGCAACGGATATTGTATCTATTGGACGTCCTATTGCTAACCATAGTGTGTACATCTTGGATGA<br>CCATTTTAGATTGCAACCTGTCGGTGTAGCTGGAGAGCTATGCATTTCGAGTATCGGATTAGCACGGGGGTATCATAA<br>CCAGCCTGAGTTAATGGATGAGAAATTCGTAGACAATCCGTTTGCTCCAGGAGAGCGTATGTATCGGACGGGTGACC<br>TGGTTCGCTGGTTACCGAATGGAACCATCGAGTACTTAGGCAGAATAGATCACCAAGTCAAAATCCGCGGCTACCGT<br>ATCGAGCTAGGCGAGGTAGAAGCACAAATGCTCAGAGTGCCGTCCGTTCAGGAAGTCGTAGCCATGGCTGCAGAGG<br>GCGAAGACGGCTACAAAGATCTAGTCGCTTATTTCGTAGCTGCTCAGAAACTTGAGGTATCCGAGCTTCGGGCCGTCC<br>TGTCGGAGATGTTACCTGGATATATGATCCCTTCCCGCTTCATACAACTGGAGGATATGCCTCTGACGTCGAACGGAA<br>AAATCGATCGAAAAGCGCTGCAGGGCGAGCGTGGATGGGCAGCGGCTTCATCGGAGGCTCCAAGGACACCTGTGGA<br>AATCCAATTAGCCGAAATCTGGCAAGAGGTGCTGGGTGTAGAGAGCGCGGGAGTGAAGGATGATTTCTTCCATTTTG<br>GAGGTCATTCCCTGCGTGCAGCCCTGCTAGTCTCACGAATTCGCAAGGAAATGAATCGCGAGATTAGTCTGAGAGCA<br>GTGTTCGAGTCTCCTACTATTGAAGGATTGGCTCGTGCCATTGAGGGCTATACACCGCTGAATTTCGAAGAAATTCCT<br>ACAGCGGGAGCGAGAGAGCATTATCCATTGTCCTCGGCCCAAAAACGACTGTTTATTCTAAGTCAGCTGGAAGGTGG<br>AGAGCTGAGCTACAATATGCCGGGTATCCTTACCGTTGAGGGAGCTTTGGATCGGGAACGGCTAGAGCAGGCATTCC<br>GTCGTCTAATTCATCGTCATGGTTCGCTGCGTACTCGTTTTGTGACCGTGAACGGTGAACCTGTACAGCAGCTCCTGA<br>CGGATGTTCCGTTTACTGTGGAATATGCGGAGTTGAGCGAGGAAGAGGCAGGAGCTACCCTTCAGCAGTTTGTCCGT<br>CCTTTTGATTTAGGTGTAGCTCCATTGCTGCGGGTCGGCCTTATTCGAATTGCACATGAGCGCCATTTACTATTGTTTG<br>ACATGCATCATATTGTCTCAGATGGGGTTTCTATGAATATTCTCATAGAAGAGTTTCTCCGCTTCTACCAAGAGGAGG<br>ACGTATTCCCTGAACTACAGATCCAGTACACAGACTATGCTGTATGGCAGCAAGAGCAGCTCGGAAGCGAGCGTCTT<br>AAGGCCCAGGAAGCTTACTGGCTGGATGCTTTCCGCGGAAGCTTGCCAGTGCTGGATTTGCCAGGAGATGAAGTTCG<br>TCCTGCGGTGCGAAGCTTTGCGGGCGATCGAATCGACTTCCAAATTGATTCTTCTCTGAGTGCTTCACTTCAGGAGCT<br>GGCTACCCGAACGGGTTCCACTCTGTTCATGGTACTGCTGGCAGCCTATACGGCGCTCTTACACAAGTACACAGGTCA<br>GGAAGATGTCATTGTCGGTTCACCTGTGGCAGGAAGATCCCATGCGACACTCGAAGGCCTCATCGGTATGTTCGTCGG<br>CACAGTGGCACTTCGTACTTATCCAGAAGGAGAGAAGCCTTTCGAGGCTTATCTGCAGGAAGTGAAGGAAACAGCGC<br>TGCGGGCCTATGAAAACCAGGATTACCCGTTCGAGGAGCTGGTAGACAAGCTGGAGCTTCAGCGTGATTTGAGCCGT<br>AACCCGCTATTTGATACCATGTTTGTCCTGCAAAATATTGAGCAGGGAGAACAAGAAATAGAAGGATTGCGCTTCAC<br>TCCTTACGATAATGTACATCCGGCTGCCAAGTTCGATCTCACGCTGACCGTGAGTGAAGCAGACGGGGTATTGAACTG<br>CACGCTTGAGTACGCGACTGCGATCTACAAACAAGAGACTGCCCAGCGGATGGCAGGCCACTTTGTACAGCTTATTC<br>GGGAAGCCGTCTCCAATCCGGGAATGCCGTTGTCATCCCTTGATATCGTGACACCTCAGGAAAAATCAAGGCTGATG<br>AAAGCGCCGGACGAAGCCAAGGCAGATTATCCTCGTGACAAGACGATCCATGCGCTGTTCGAGGAACAGGCTGCAC<br>GTACTCCGAATGCAGTGGCAGTCGTATGTGAAAATGCAGCCCTGTCCTACAGCGAGCTGAACGAGCGGGCCAATGGA<br>CTTGCCAGAACGCTAAGGGAACGTGGTTTGCAACCAGACGGTTTGGCTGGAATCATGGCGGATCGTTCCCTTGAAAT<br>GGTGGTCGGGATTTTAGCCATCTTGAAGGCAGGCGGAGCCTATGTCCCTGTAGACCCTGAATATCCAGAGGACCGCA<br>TTCGCTTTATGCTTGAGGATTCGGGAGCCAAGCTACTGCTGACACAAGCGCATCTGGAGCAACGTGTCTCCTTCGCTG<br>GGGACATCGTGAGTCTGGATAAAATGGCTTCCTATAAGGAAGATGTCTCAAACCTGCAGCCTGCAGCCGGACCGGAG<br>CATCTTGCCTACGTCATCTACACATCAGGTACGACAGGCAAGCCAAAGGGAACGCTGATCGAGCATAAAAATGTAGT<br>TCGCTTGCTCTTTAATGATAAAAATATGTTTGACTTTGGTCCTCAGGATACGTGGACACTGTTCCATTCATTCTGTTTT<br>GACTTCTCTGTATGGGAAATGTACGGAGCATTGCTGAACGGAGGACGGTTGGTCATCGTTCCATCGCTTACCGCGAAG<br>AGTCCAGATCGTTTCTTGCAATTGCTTAAGGATCAGAAGGTCACCGTTTTGAACCAGACACCGACGTACTTCTATCAG<br>TTGCTACAGGAAGAGCTCGGTCATCAGGCGGCAGAACTGAGCCTCCGTATGATTATCTTCGGTGGAGAGGCATTAGC<br>CCCGGCCCTGCTCAAGGACTGGAGAACGAAGTATCCGCAAGTGCAGCTCATTAACATGTACGGCATTACCGAAACGA<br>CCGTGCATGTAACATACAAGGAAATTACAGAGTTGGAAATTGAACAGGGCCGCAGCAATATCGGCACCACGATTCCA<br>ACGCTGCGAGCGTACATTTTGGATGAACAACGCCGTCCACAGCCGATTGGCATTCCAGGTGAACTTTATGTGGCGGG<br>CGTAGGTCTGGCGCGAGGCTATCTGAACCGACCGGAATTGACGGAAGAGAAGTTTGTCGCTCATCCGTTTGAAGCGG<br>GCGAGCGCATGTACCGCTCGGGTGACTTGGCACGCTGGTTGCCGGATGGCAGCATGGAGTATTTGGGACGGATTGAC<br>CATCAGGTTAAAATCCGTGGTTACCGTATTGAGCTGGGCGAAGTGGAAGCGAAGCTGCTCCATGCTCCGTCTGTAAG<br>GGAGGCCGTTGTGCTCGCCCGGGAGGATGGAAGTGGACAAAAAGTGCTTGTCGGCTATTTCACTGCCGATCAGATGC<br>TGACGGTAGGCGAGTTGAGAAAAGCCTTGGCTGCCGAACTGCCGACTTATATGATTCCATCTTACTTTATGCAATTGG<br>AACAGATGCCTTTGACGCCAAATGGCAAGCTGGATCGCAAAGCGCTTCCGGCTCCTGAGGCTAATGTGCAGACTGGG<br>GCGGTTTATGAACCGCCAAGGACGAAGGCTGAGGAAGCTTTAGTTTCCGTATGGCAAGGTGTGCTGGGAGCGCAGCA<br>GGTCGGCATCCATGATCATTTCTTCGATCTGGGTGGTGACTCCATCAAGGCGATCCAAGTGTCCTCGAGATTGTTCCA<br>AGCTGGATATAAATTAGAGATGAAGGATCTCTTCAAATATCCGACAATTGCCGAGCTAAGCCCGTATCTTCAGGCAG<br>CTGGACGTATAGCGGAACAGGGTGAAATTAAAGGTGCAGCAGAGTTAATGCCAATTCAGCGTTGGTTCTTTGAACGC<br>CATACAGCGGAGCCGCACCATTATAATCATGCCGTCATGCTCTATCGGAAAGACGGCTTTGATGAGGCTGCACTCCG<br>GTTGACAATGGACCAAATTGCGATCCATCATGACGCGCTGCGCATGGTTTTCCGGCCTACAGAAGCTGGATACGCAG<br>CTTGGAATCGGGGAACGGACGAAGGCGAGCTCTACACATTGGACATTGCCGATATGCAGCAGGCGGAAGACCAGAC<br>AGCTGCGGTTCAAGCCCAAGCCGATGCCATTCAGGCAAGCTTTGACTTGGAAGGTGGCCCACTGTTCAAGCTAGGCC |

TABLE 5-continued

Nucleotide sequences of genes encoding the fusaricidin synthetase (fusA) in *Paenibacillus* sp. strains NRRL B-50374, NRRL B-67721, NRRL B-67723, and NRRL B-67724.

| Strain | SEQ ID NO: | Sequence |
|---|---|---|
| | | TGTTCCATTGTGACGATGGCGATCATTTGTTGATTGTCATTCATCACCTCTTGGTTGACGGCGTATCCTGGCGCATCCT |
| | | GTTTGAGGACATTGCAGCGGGGTACGAGCAGGCATGGAATGGACAAGCAATCGTCCTTCCACAAAAGACCGATTCGT |
| | | ATCTTGTATGGTCTGAGCAAGCGACGAAGTATGCAGCAGGGCCTGCTCTGGACAAGGAGCGTGCATACTGGCAGCTG |
| | | ATTGAGGAGGCGATTTTGGCCCCACTGCCGAAGGATGAGGATCAGAAGCCGGGCACCATTCGGGATACTGAATCGGT |
| | | TACGGTAACGTGGTCTGCGCAGGAAACAGACCTGCTGTTGCGACAAGCGAACCGGGCGTATCATACGGAGACGAAT |
| | | GACTTGCTCTTGACTGCTCTGGGGGCAGCCATTCAGCGCTGGACAGGCATGGAGCAGATTTTGGTCAATCTTGAAGGA |
| | | CATGGACGGGAAATGATCGTACCAGACCTGGATATTACCCGTACCGTGGGTTGGTTCACAACCCAGTATCCAGTTCTG |
| | | CTGAACCTGCAAGGCAGACAGGAAGTATCTGCGCGAATCAAGCGCATCAAGGAGAATTTGCGAGAGGTTCCGCATA |
| | | AAGGAATCGGCTACGGTCTTCTGAAGTATATGGCACCGGAGAAAAGTGTCGGATTCGGCGTGGAGCCGGAAATTTCC |
| | | TTCAATTATCTTGGGCAGTTTGATCAGGATTTGGAGGGTAATGCCCTTAGCTTATCCACACATTCAGTTGGTAAAGCG |
| | | CTCAGCGATCTCACACCACAGCAATATGCTCTGGATGTGAATGGCATGATTGCCGAAGGCCAGCTATCACTGACGATT |
| | | ACGTACAGCAGCAGGCAGTATCGTAAGGAGACGGTGAGTCATTTTGCTGAATTATTACAGTCAAGCCTTAGTGAGGT |
| | | CATCCGTCATTGTGTGGCTCAGGAGCGTTCACAGCTTACACCAAGTGATGTTCTGTTCCAAGGATTAACATTGGAGCA |
| | | GCTTGATCGACTCACGGCGCAGACGGCTCACATCGGAGAGATTGAGGATGTGTACAAGCTGACGCCAATGCAGAAG |
| | | GGAATGCTGTTTCACAGCCTACTGGAGCCGGGCTCCTCTTCATACTTCGAACAGGCAACGTTTGAGCTGCGTGGCAGC |
| | | TTCGATGTAGATACCTTCTTCGAGAGCTTCCAGGCTCTGGTGCAACGACATGCCATACTACGTACCGGCTTTTACAAC |
| | | AACATTGCTGATGTACCGCTGCAAGTTGTCTTTAAGCAACGGTTAATCCCTCTGCACTACGTAGATTTGCGCGACGCA |
| | | TCTATGCAGGAACAAGAAGCCCGAATCAAGGCTTATATTGCTGAAGATATGGTTAAGGGGTTCAGCTTGTCAGAAGA |
| | | TCCGCTGATGCGGGTGACCGTCTTGCAGAAGGATCAAAGCTGTCTTGTATTGTGGAGCTTCCACCATATTGTCATGGA |
| | | TGGCTGGTGTATCCCGATCATTACACAGGAGCTGTTCGATTATTATTCTGCCAAGAAACAGCAAGTACAGCCTGTCCT |
| | | ACCGCCAGCTCAGCCCTATAGCCGTTATATCGAGTGGCTTGATGCACAGGATGATCAAGAAGCTTCAACGTATTGGA |
| | | GCCAATATCTCGAAGATTATGACGGGAATACTGTATTGCCGGAAGGTAAAACGAAATCTCAAGCCAAAGAGGCGGG |
| | | CTATGTTCTGAATGAGCATGTTCTCCATCTGGGTGCATCCTTGACCGGTAAAATGGATGTTGTTGCGAAGCGCAATCA |
| | | CGTAACCGTCAATACACTCATGCAGACAGCTTGGGGACTGATTCTTCAACGTTATAATGCCAGCTCGGATGTCGTTTT |
| | | CGGCGGCGTTGTGTCGGGTAGACCCGCTGAGATTGCAGGGATCGAAAATATGGTGGGTCTGTTCATCAATACAGTAC |
| | | CTATCCGTGTACAGTCATCCAAAGACGAAGCCTTCGTCGAAGTGATGAAACGTACACAGGCACAGTCATTGGCTGGT |
| | | CGTGCCTACGACACCTATCCACTGTATGAGATTCAGGGGAAAACAACCCAAAAGCAGGACCTGATTTCTCATATTAT |
| | | GATCTTTGAAAATTACCCGCTCGACGAGCAGGTGGAGCAATCGGGTAATCAAACGGAGGACAATCTCGAAGTTGCCA |
| | | ACTTCACCATGTTTGAACAAACCAACTATGACTTTAACCTGGTTGTGATTCCAGGCGAAGACATCAAGGTCTGCATTC |
| | | GCTATAATGCTTCGGTTTACGAGCAAGAAAGCATTGCACGTATCGGAGGACACTTGTTGCAGATGCTCGATCAGGTG |
| | | GCTGCTCGTCCGCAGGCGACGATACAGGAACTGGAGATTGTAACATCCGAGGAACGGATGAACCTGCTTGACTGGGG |
| | | CGGCAAGGCCCATACCTATCCAAGTGATCAGGGGCTGCATACCTTGTTTGAAGAACAGGTTGTCCGTACGCCGGATA |
| | | AGATTGCAGCTGTAAATGGGGACACTCAGATCACGTATCGGGAGCTGAACGAGCAGGCGAACAGACTAGCTTCCACC |
| | | TTGATAGACCAAGGACTACGGAGTGAACAAGTGGTAGGTCTGTTGGCAGATCGGTCTGTAGAGCTGCTTGTCGCCAT |
| | | CATGGGTGTGCTCAAAGCGGGTGGAGCCTACGTACCTATTGATCCTGAATATCCGCAGGAGCGGATTCAGTATATTCT |
| | | GAAGGATTCTGGCGCTGAAATTCTGCTCACACAGAGCCACCTGACGGAGTTAGCCTCTTTTGAGGGGACGGTTATGG |
| | | AATTGGATTCCCCGCACATTTACGGAACCGAGGTGGATAATCCCAATATTCCTGTTGGAGGAAACGATCTGGTGTACT |
| | | TAATCTATACCTCGGGTACAACCGGAAATCCGAAGGGAACCATGATTAACCACAAAGGGATCGTGAACTACATCTGG |
| | | TGGGCCAATAAGGTCTATTGTGCTGGAAAACCAACGGATTTCCCGTTGTATTCATCCATTTCCTTTGACTTAACGATG |
| | | ACATCGATCTTTACTCCATTAATTAACGGAGGAGTAGTGCGGATTTATGATGGTATAGATAAAGCGGAGGTTGTACA |
| | | GCATATTTTGCGCGAAAATGCGGTGGACATTCTCAAGCTGACGCCGACTCATCTCAGTCTGATTAAAGATATGACCAT |
| | | CCCGGCAGAAAGTCGCATTCAGCAGCTTATTGTGGGTGGAGAGAATCTGACCACACATTTGTCGAAAACCATCACAG |
| | | ATCTCTTTGGCAGCAACATCAAAATCTACAATGAATATGGACCAACCGAAACGGTCGTCGGCTGCATGATTCACCTGT |
| | | ACAATCCTGCGAAGGATACGCGTGAATCTGTACCGATTGGGTTGCCAGCAGACAATATATACATCCATATTATGGAT |
| | | GATCAGCTTCGTCTCGTACCGTTAGGCGTGGAGGGCGAAATGTACATCGCCGGGGACGGGGTAGCCCGTGGATATCT |
| | | GAACCGTCCTGAGCTTACCGCAGATAAATTCATTAGAAATCCGTTCGCTTCGGAAGGAAATATGTATCGCACTGGGG |
| | | ATTTGGCTCGTCGCCTTCCTAATGGAGACATTGAGTACATTGGGCGTATTGACCATCAAGTTAAAATACGGGGCTATC |
| | | GTATTGAGCTTGGTGAGATTGAGGCCAAGTTGCTGGATATGCCACTTGTCGAGGAAGCTCTCGTTGTTGCGTGGGCAG |
| | | ACGCCAATGGACAGAAGTCTCTGTGTGCTTACTTTGTAGCGGATCGAGAAATGTCTGTCAGCGAGCTGAGAAACGAA |
| | | CTGTCTGCCGGACTGCCTGCATATATGATTCCGTCTTACTTCGTCCAACTGGACGTGATGCCTCTGACACCGAATGGC |
| | | AAGCTGGATCGCAAGGCACTGCCTGAACCGAACTCGGGTATAAAGGCGGGAGCAGACTTTACCGCTCCGCGGACGG |
| | | ATGTGGAGAACATTTTGGCTTCAATCTGGCAAGGTGTACTTGGCGTGCCGCTGGTCGGCATACATGATAATTTCTTTG |
| | | AACTTGGAGGTGACTCGATCAAATCCATTCAAGTATCCTCAAGGCTTCTTCAAGCAGGCTACAAGCTTGAAATGAAG |
| | | GATTTGTTCGGTTATCCGACAATTGCAGAGTTGGCGCAGCGCGTTAGTGTGGTCAGCCGAATTGCGGACCAAAGCGA |
| | | GGTACACGGAGCGGTAAGACTGGGACCTGCTCAGCACAGATTCTTCGATGAACAGTCAATGGATCTGCATCACTTTA |
| | | ATCAGTCGGTCATGTTGTACCGACGGGATGGCTTCAATACCGATGCGCTCGCCGAGGTTGTTCGGAAAATTGCAGAG |
| | | CATCATGATGCTTTACGACTGGTGTTCCGCCAAGGAGAGCAGGGATTTGAGGCCTGGAACCGGAGCATGGGTGAGGG |
| | | TGAGCTCTATAGCCTCCAAATCCACGACCTGCGGGATGAGACAGACCCGGCTTCAGCAATAGAAGCAGGTGCGGAAG |
| | | CCATTCAGCGCAGCATCTCTCTGGAGGATGGACCTCTCTTTAGACTGGGTCTGTTCCGCTGTGCGGAAGGCGAACATC |
| | | TGTTGATCGTTATTCATCATCTGGCTGTGGATGGCGTATCCTGGCGTATTCTTTTTGAGGACCTGCAGGATGGCTACGA |
| | | GCAGGCAGCACGTGGAGAAGCGGTCAAGCTTCCACAGAAGACGGATTCGTACCGTGCATGGGTTGAGGGAATCACA |
| | | CAATTTGCGAATAGTCTGGCGGCTGAACAAGAACGCAGCTATTGGGTAGAGGTAGAGGGAGATGGCTTTGTCCCTCT |
| | | TCCCAAAGACAAGGTAGACGGCGCTCTTCTCATCAAAGACAGTGAGGCTGTCACGGTGAGATGGTCACCAGAAGAG |
| | | ACAGAGCAGTTCCTGAAAGAAGCGAACCGCACTTACAATACGGAGGTCAACGATCTGCTCCTGACGGCTCTGGGTAT |
| | | GGCTGTTCACGAGTGGACAGGAATCGAACGTGTAGGCATCCTTCTGGAGGGACATGGACGGGAGCCTGTTGTGCCGG |
| | | AACTGGATATTACTCGCACAATAGGCTGGTTTACAAGTCAATACCCTGTCGCCCTTGAGATGGGAGGGGAATTGGAG |
| | | ATCGGCGCCAGAATCAAGCACGTCAAGGAAGGCTTGCGTCGTATCCCGAACAAAGGTGTCGGATATGGTATTTTGAA |
| | | ATATTTAAGCGACGGTTCCGACGTCTCCTCCTTCTCGGCTGAACCTGAGATTACCTTCAACTACTTGGGACAGTTCGA |
| | | CCAGGATCTTGCAGGAGGGATGATGGAAGTATCGTCTTATTCAGTAGGACCTGAGGTCAGTGAGCAGATGGTGCAGC |
| | | ATCAGGCATTGAACATTAATGGACTGATTGCCGAAGGACAGCTTCAACTTTCGGTCAGCTATAACCGTCATCAGCTCG |
| | | ACGGGGAGTCCGTGACTAAGTTTGTTGGCATTCTGAAGAACCGTCTCAGCGAAGTCATTGGACATTGCGTAAGTAAG |
| | | GAAAGAACAGAACTTACACCAAGCGATGTACTCCTCAAAGATATCAGCTTAGAAAAGATTGAGGAGCTAGAAGAGC |
| | | AGACACGGCATATCGGCAGTATTGAAAATATGTATAAACTAACACCGATGCAAAAAGGAATGTTGTTCCACAGCTTG |

TABLE 5-continued

Nucleotide sequences of genes encoding the fusaricidin synthetase (fusA) in *Paenibacillus* sp. strains NRRL B-50374, NRRL B-67721, NRRL B-67723, and NRRL B-67724.

| Strain | SEQ ID NO: | Sequence |
|---|---|---|
| | | CTGGAACCTCATTCGGAAGTCTACTTTGAGCAGGCCAAATTTGAAATTCAGGGAGCATTCTATCCTGAGGATTTCAAA<br>CGCAGCTTAAAATATCTGATGAAACGGCATGCCATATTGAGAACGAATTTCCATGCCGGGTGGGGCGATTTCCCTATT<br>CAGATTGTGTTCAAAGAAAGAGCGTGTGACTTCGTATACGAGGATCTGCACGAGCTGGAAGCCGATGAAATTCAAGC<br>GCGTCTTGCAGCTTATACTGCTCAGGACAAAGCAAGAGGCTTTAATCTTGCTGAAGAAGCGTTGCTGCGTGTTGCTAT<br>TCTACGTACAGCAGAAGAGGCCTACCATCTGCTGTGGAGCTCTCATCACATCATTTTGGATGGGTGGTGTATGCCGCT<br>TGTGCTCCAGGAAGTATTTGAGACGTATGGGGTTCTGCGTGAGCAAAGGGAACCAGAGCTTCCTGCAGCTGTATCGT<br>ACAGTCAGTATATTCAATGGTTGGAGAAGCAAGGCGAGGAAGAGGCATCCTCTTACTGGAGAGGGTACCTGGAAGG<br>CTACGAGCAGCAGACGAAGCTGCCACAGGCCATCACACAGCCATCGGCAAAAGCAGAAGCCTACGTGTCGGAGAAG<br>CTGGTATTCACGTTGGATGCGGAATTGACCGATCGCCTGGAACAGGTGGCCAAACAGCATCAGGTGACGATGAATAC<br>ATTGATGCAAGCAGCCTGGGGAATCGTGTTGCAGCGCTACAATAGAAGCCAGGATATCGTCTTCGGAAGTGTAGTAT<br>CGGGGAGACCTGCCGAGATTCCGGGTATCGAAAGTATGATCGGTCTCTTCATTAATACAGTTCCGGTTCGGGTTCAGG<br>CCGAGGGAAGCGATACGTTCTCCCATGTGATGAAAAGACAGCAGGAATTATATTTGGCAGGACATGCTTATGATTCC<br>TATCCGCTCTATGAGATTCAAGCACAGAGCGAACAAAAGCAAGATTTGATTTCTCATATTATGGTGTTCGAAAATTAC<br>CCGGTAGAAGAGCATCTGGAAGAGAAAATTGCCAGTGAAGAGGCTGAATACAGAATTACGGATGTTCAGATGTTTG<br>AACAGACGAATTATGATTTTAACCTCATTGTGCTGCCGGGCCGTAATCTGGAGTTCTTGTACCGTTACAATGCCCGCG<br>TCTATGATCGGGAGAGCGTGGAACGCATTCAAGGACACTTGACGAGAATTCTGACAAGCGTTGCTGTTCAACCTACC<br>ATCCGTATTGATGAGCTGGAGTTGATCACGCCAGAAGAGAAATCGCAGATTATAGAGGTGTGGGGCGATACAGCAGC<br>TCCTTATCCGCGTGAGCAGACCCTTCACGGTATATTTGAGGAAAAAGCAGCGCTCACACCGGATCGTACAGCACTTAT<br>TTACGGTGAAACGGAGCTTACCTATGGAGAACTTCATCAGCAGGCGAACCGCCTTGCACGTACGCTGCGTGCCCAAG<br>GGATCAGACCGGACCAACCAGTCGGCATCATGGTCGAGCGCTCGCTTGAGATGATCATTGGTATTCATGCCATTCTAA<br>AAGCTGGCGGGGCCTATGTACCGATTGATCCGGAGTTCCCAGAAGATCGTATTCGCCACATGCTGGAGGATTCGGGA<br>GCGAAGCTTCTGCTGACGAAGAACCATCTCAAAGATCGTTTTCCGTTCACTGGCACGATCCTGGCACTTGATGATCCG<br>CAGGCGTATCATGCGGATAGCTCGAATCTGGAGCCAATTGCGGGGCCGGAGCATCTGGCGTATATCATTTACACGTC<br>AGGTTCAACCGGCAAGCCGAAAGGGGTAATGATTGAACATCGCGCTGCCGTCCATACGCTGAGTCAGTTGGAAGCTG<br>AATATCCGATGTTGGCAGGCGACCGTTTCCTGCTCAAAACGACATTCACCTTTGACTTCTCCGTGCCGGAGCTGTTCT<br>GCTGGTTCTTTGGACAAGGGACTCTCGTGATCCTGCCACAAGGCGTGGACAAAGACCCGATGGCACTGCTAGAGGCC<br>GTGGATACGAACCGTATCACCCATCTCAATTTGGTGCCGTCGATGCTCAGTGTGCTCGTTCAATACTTGAAAGAAAGC<br>GGCACCCAAGGATTCCTTACTCTGAAATACCTGTTTGCCTGCGGCGAGACGCTGCCTGCCAAACTTGTGGAAGAGTAT<br>TATAAAGTATCTCCTTACGCAGTACTGGAAAACATCTACGGTCCTACGGAAGCAGCCGTATATGCGACTCGGTATACA<br>ACGAGCCTTGAGACTGCGGCTCTAACGCATGTGCCGATCGGCAAACCGTACGCTAACGTCCAAGTATGGATGATGGA<br>CAGCGCTTCTCAGGTATCACCTGTGGGGGTACCGGGAGAACTCTGCATTGCGGGCGAAGGGGTAGCGCGGGGGTATT<br>TCAACCAGCCGGACCTGACGGCAGAGAAGTTCATTCCTCACCCGTACAAACCGGGAGCACGAATTTACCGAACGGGC<br>GATTTGGCCCGATGGCTGCCAGACGGGAATATTGAGTATTTGGGGCGGATCGATCACCAGGTAAAAATCCGCGGTTA<br>CCGCATTGAGCTGGGAGAAGTGGAAGCACAAATTCTGAAGGTGCCATCGGTGCAGGAAGCGGTTGTTCTAGCACTGG<br>CTGACTCCACCGGAAGTACTCAGCTTTGTGCATACTTTGTGGCCGAAGAGGGGCTTGCAGCGGGCGTACTACGCGAG<br>GCACTGGCCAGCGAACTGCCAAGCTACATGATTCCGACTGCTTTCGTACAGTTGGCACAAATGCCGCTGAATCCGAAT<br>GGAAAATTGGATCGCAAAGCGCTACCGGCACCGGAAACACTTCTGCGGAGCACAGCGGAGTATATCGCGCCGCGTA<br>CGCAGACAGAAGTAGAGCTCGCTCAGATTTGGTCCGAGGTGCTCGGCGTACAGGAAATCGGGATCAGGGATCATTTC<br>TTCGAACTTGGGGGCCATTCCCTGAAAGTATTGGGCTTGATCCAAAGGATCTCGTCCGGTATGGGCGTCCAGCTCCCA<br>CTCCAAGTCGTGTTTAATCTGCCGACTGTGGAAGAAATGGCGCATGAAATTTCCAAGCTGCAAGCAACAACTGCTGCT<br>AATGAAGAGGAAATGGAAATTATCCGCTTCCCAGGGAAAGGAACGCTCAAAGTATTTTGCTTCCCTCCACGGGTAGG<br>CCACTCTCTGGGATACTATGAGATGGCGAAGGAGCTGGAAGGGCTTTGCGAGGTGTACGGGATGGAATTTATCGGCG<br>ATCGTTTCCAGGGTCAAGATATGCTGGATCGATACATCGATGCCATCGTGGATATTCAAGCAGAGGGTCCGTATATAT<br>TCCTGGGATACTCACTTGGAGGAAATCTCGCCTTCGAGGTAGCTAAAGCCATGGAAAGCCGAGGTCACCATGTTAGC<br>GACCTTATTATGGTAGATGCTATGAGAAAGATGTCCAAGGATGAATCGACACCGGAGGAGCTTGAAGAGATTGTCGA<br>GATGGTACTGGACAGCATTAGGGACCAGTACAAAGCATTCCTCGCCGATCCAGTGGACAGGGAGCGAGTCATGGAC<br>AAAATGTTGGTGTACTCCACCTACCGCGATGAGCTTATTAACGCAGGTGAAGTTCATGCGAATATCCATGCTCTGATT<br>GCAGAGGATGATAGTATTGGTCCGGATACATCATTAGATAAATTGTTATGGCAACAGGCGACACTTGGTCAATACAA<br>AGAATACGAAGTCATCGGAACGCATGATGTGCTGCTTGATTCCGGTTTTATTGGGGAGAATGCTAAAGTACTGAGAC<br>AGATACTTGGCAAGGTCACAGAGGCTTCATCTAATAACAAGCCCATTTTGTCCTAA |
| NRRL B-67723 | 3 | ATGAATGACATGCAGTTATATGATTTAACAAATGCGCAGAAACGTATATGGTATACCGAATTACTCTATCCAGATACG<br>TCAGTGTCACAGCTTTCCGGTACAGCCAAGATGAAGGGCCGTATCCATATCGCTGCCTTCATGCAGTCCATTAATTTG<br>ATTATCAAACAGTATGATGCGTTCCGCATTCGTATCACCTCAGTGGATGGAGTGCCTCAGCAGTATGTCGTTCCTTAT<br>GAAGAGAGACAGTTGGAGTATCTGGACCTTACCCACTATGAAAGTATCTCTGAGGTGGAAGCCTTACTTGAGCAACA<br>CAAAAGCAAACCCTTGCAACTGCTGGATTCTGAGCTATTCCAGTTTTTGATTGTGAAGATTAGCGAGGATGAGTATTG<br>GATTAATACCAAGATGCACCATATTATTTCTGACGGGATCTCAATGGTGATCTATGGCAATCAATTGACGGAATTTTA<br>CATGCAGATCATTCAAGGAAATGAACCGACGCTGAATGACGATTGCTCCTATATTCAATATATTGCAGAAGAGAACG<br>CATACGAGCTTTCTGACAGATATCAAAAGGACAAGACATACTGGCTCAATAAATTTTCTGATTTACCTGAACTTACGG<br>GTTGGAAGTCATACAATCCGTTATCTCTGAGCACCCACGCCGTTCGGGAGCATTTTACCGTGCCAGAGGTGCTGTATC<br>ACGAGTTGCAGGCATTTTGCCAACAGAACAGGATTTCTCTGTTCCAGTTCTTCATGGGTGTGATGTATATCTACATAC<br>ACAAAGTAACGAATCAGCCGGATGTGGTGATTGGTACTTCGTTCGCTAACCGTGGGAACAAAAAAGAGAAGCAAAA<br>GATCGGTATGTTCGTTAGTACGGCTGCAGCCAGAACATACGTCGAAAAGGACATGGATGTGCTGAGCTTCCTGCAGG<br>AAGTAGCCAGGGATCAAATGTCAATCCTGCGGCATCAGAAGTATCCATATAATCAGTTAATTCAGGATCTTAGAGAA<br>ATGCATGGTAACAGGGATATCCAGCGGCTTTTTGGCGTCTCCATGGAATACCGTCTTATCAATTGGGTTGATTTGGAT<br>GACGTGCGCATTTTGACGGATTATGATTTCTGCGGCGACGAAGTGAACGATTTCGTGCTTCATATCGTGGAGATCCTG<br>GATGAAGGCGAGCTGGTACTGGATGTCGATTACCGGACGAAGTTGTTTGAACGCAGTGAAGTTAAGGACATGGTTTC<br>CCAGTTGCTTACGATCGCCGAGCAGATCATTCATGCACCGCAGCTTTCCATCGCCGAGGTAAACCTATTGGGTGAAGC<br>AGAAGAGCAGTCCATTTTGGCTCTTTCGGAAGGCGTTGCAGTCGATTATCCGCGTGAAAAGACAATCCATGGCTTATT<br>CGAAGAACAAGCCGAGCGCATGCCAGATCACGTAGCCGTTCAGATGGGCGAGCAGAGTATTACATACCTAGCTCTAA<br>ACGAGCAGGCTAACCAGCTTGCGAGATATTTGCGCACCGAAGGCGTTGGTGCAGATGTACTCGTGGGGATTATGGCT<br>GATCGTTCCCTGGAAATGGTCGTCGGCATGCTGGCGGTTTTGAAGGCGGGAGGAGCCTATGTGCCCATTGATCCCGAT<br>TATCCCGAAGAACGTATTCGTTACATGCTAGAGGATTCAGGAGTCCGTCTGTTGCTCACCCAAAGCCATCTATGGGAG |

TABLE 5-continued

Nucleotide sequences of genes encoding the fusaricidin synthetase (fusA) in *Paenibacillus* sp. strains NRRL B-50374, NRRL B-67721, NRRL B-67723, and NRRL B-67724.

| Strain | SEQ ID NO: | Sequence |
|---|---|---|
| | | AGTACCACATTTGACGGAAAGCTTGTGAATCTGGACGAAGTTGCATCGTATAAAGGGGACACTTCAAATCTGGAGAG |
| | | CATGTCGGGGGCGAGCAATCTTGCCTATGTTATCTATACGTCGGGTACAACTGGCAAGCCGAAGGGAACTCTGATCG |
| | | AGCATAAAAATGTAGTTCGACTGCTCTTTAACGATAAAAATTTATTTGATTTCAGCGCTCAGGATACGTGGACGCTAT |
| | | TCCATTCGTTCTGCTTTGACTTCTCCGTTTGGGAGATGTATGGAGCCCTTCTCTACGGAGGAAAATTGGTGATTGTTCC |
| | | GTCTCTTACAGCCAAGAGTCCAGCAGCTTTCCTGAAGTTGTTGAAAGACAACAAAGTCACCATTTTGAACCAGACACC |
| | | AACGTATTTTTATCAGGTGCTACAGGAAGAATTGGTGCACTCTTCGACAGAGCTTAACCTTAGAAAAATCATTTTTGG |
| | | TGGAGAGGCCTTAAGCCCATCTCTTCTGAGAAACTGGCGGGTCAAGTATCCTGATGTGCAACTGATTAATATGTACGG |
| | | AATTACGGAAACAACGGTCCATGTCACCTACAAGGAAATCACGGAACATGAGATTGAAGCGGGGAAAAGCAATATT |
| | | GGTAGAACGATTCCGACACTTAGCGCTTACATTTTTGATGAGCAAAGACGTCTGCAGCCTGTTGGGGTTCCGGGGGA |
| | | GCTATACATCGCGGGCGACGGTCTTGCCCGAGGGTATTTGAACCGTCCAGAGTTGACGGCTGAAAAGTTCGTAGAAC |
| | | ATCCATTTCGGGCGGGAGAGCGGATGTACCGTACTGGGGATCTGGCTCGCTGGTTGCCTGATGGTAATATCGAATATT |
| | | TGGGCCGGATCGACCATCAGGTCAAAATTCGCGGCTACCGAATTGAGCTTGGCGAGGTGGAAGCCCAAATTCTCAAG |
| | | GCTCCGAATGTAAGGGAAACGATTGTCCTCGCACGGGACGACGAACAGGGCCAAAAATTGCTTTGCGCCTACTACGT |
| | | GGCCTCCACCGACCTTTCGCCGGGCGAATTGAGATCTCAGCTGGCAGTGGAACTACCAGCCTACATGATCCCCTCTTA |
| | | TTTTGTCCGGCTGGAGCAAATGCCGCTTACGCCAAATGGTAAGCTGGATCGTCGCGCGCTGCCAGATCCTGAAGGCA |
| | | GTGTACAATCCAGCGAGGTTTATCTGGCTCCGAGAACTGCTGCGGAAGCGCAGATGGTGCTAATCTGGCAAGATATC |
| | | CTGGGAGTTGCCCGCGTCGGTGTCAGAGATAATTTCTTTGAAATTGGTGGTCACTCTTTGCGGGCAACATTGCTCGTTT |
| | | CGCGGATTCACAAAGAGTTGGGATGTAGCATTTCGCTGCGCGAAGTGTTTCAGTCGCCTACGGTTGAGTCTTTGGCGC |
| | | AACTGGTCAAAAAGCACATTCCGACAGTGTATGAATCCATCCCACAGGCGGAGGAAAGCGCATCTTACCCAGTGTCC |
| | | TCAGCGCAAAAGCGGTTATACGTGTTGAGACAAATGGACGGAGGAGAGCTCAGCTACAATATGCCTGGGGCATTCAC |
| | | AGTGGATGGGCCGTTGGATCGCGTACGGCTGGAGTCTGCGTTCCAGGCACTGATCCAGCGTCACGAATCGCTGAGAA |
| | | CGGGCTTCTATATGAAGGATGGAGAGCTTGTTCAGCGTGTGCATAAGGAAGTGCCGTTTGCGTTGGACTGCACAGAA |
| | | GCTTCGGTGGAGGAGACGGATACGCTCATACGCAGCTTTATCCGTGCCTTTGATCTCAGCCAGGCCCCATTACTGCGT |
| | | GTTGGCTTGGTGAAGCTGAAAGAGGAACGTCATCTGTTGCTGTTTGATATGCACCATATCATTTCGGATGGGGTTTCC |
| | | ATTCAAATACTGGTGGAAGAACTCACCTCATTGTATCAGGGAGAACAGCTGCCAGAACTGCACATCCAGTACAAGGA |
| | | TTATGCTGTATGGCAACGGGAGCATTCAGAGAACCAGTGGAAAGAGCTTGAAGCATACTGGCTGCAGGCTTTTGAAG |
| | | GGGAACTGCCTGTACTTGATTTGCCTACGGATTATCAAAGACCTTCTGTTCGCAGCTTCGAGGGTAGCCGAATTGATT |
| | | TTACATTGGATGCATCCGGCAATAAGGCAATACAGGAACTCGCATCCCGTACAGGTACTACGCTGTATATGGTATTGC |
| | | TGGCTGCTTATTCGGTCCTGTTGCACAAATATACGGGGCAGGAGGACATCATCGTAGGTTCTCCGGTGGCCGGAAGA |
| | | CCGCAAACGGAGCTTGAGAGCATCATCGGGATGTTTGTCAATACACTGGCTATGCGCAGCTATCCGGCAGGAGATAA |
| | | GACATTTCAGGATTATCTTCTCGAAATCAAGGAAACGGCGCTCAAGGCGTTCGAGCATCAGGACTATCCTTTGGAAA |
| | | AACTGATTGAGAAGCTGGGTGTAGGACGTGATGTCAGCCGCAATCCACTCTTTGATACTCTGTTGGTATTGCAAAATA |
| | | CGGAGCAGGCAGAGCAGGACATGGGCGGGCTGCGCTTTACTCCTTACCCGCTGGAGACTGTTACAGCCAAATTTGAC |
| | | CTGTCACTCAATGTAGAGGAGCAGGGGGCAGAGCTAGCTTTTGGTTTGGAGTATAGCACGGCTTTATATCAGCGAGA |
| | | GAGTGTAGAGCGACTGGCTATGCACTTGCTTCGGGTTCTGCATGCGGTTGCTGTCAATCCCCAGTTAAAGCTGGCGGA |
| | | GATTGAGATGATCACACCGGAGGAGAAGGTGCAGATCATTGAAGAATTCAATGCGACATCGGCTCCTTATCCAAGTG |
| | | AGAAGACTATTCATGAGCTGTTCGCAGAGCAAGTAAAGCGTACACCGGAGCAGACGGCGCTTGTATTCGGCAACGTC |
| | | CAGCTAACCTACCTCGAATTGGAAGAGAAGGCGGGGCGGCTGGCCCAAACACTGCGTCGCTTGGGAACGTTGAGGG |
| | | AGCAGCCTGTAGCCGTGATGGGCGGACGAAGCATCGAGATGGTCATTGGTATGCTCGCGATACTACAGGCGGGTGGA |
| | | GCCTATGTGCCTATTGATCCCGAATACCCGGAAGACCGGGTTCGTTATATGCTCAATGATTCCGGCGCCAAGCTACTA |
| | | CTGGTGCAAAAGGGTGAGTTTGTAAGTGTAGACTACGGTTTACCGATTGTCGACCTCAGCAGTGAAGAGGCTTATGC |
| | | AGCCGAACCTGCCCAGCTGGAGACTGCCCAGGGGTCACAGGGGCTTGCTTATGTCATTTATACATCGGGAACCACAG |
| | | GTAGGCCGAAGGGCGTTATGGTTGAACACCGGAACGTGGTCCGTCTGGTCAAAGAGACTAACTATGTGGAGTTGAAT |
| | | GAATCCACACGAATTTTGCAGACAGGAGCCGTGGCCTTCGATGCTTCTACTTTCGAGATATGGGGGGCGTTGCTTAAC |
| | | GGCGGACAGCTCTATTTCGTAGAGAATGACGACATTCTGATTGCTGATAGGCTCAAAGCTGCCATCGCCAAGTACAG |
| | | GATTACGACGTTGTGGCTCACTTCACCGCTTTTCAATCAGCTTTCATTGCAGGATGAGTACCTGTTCAGAGGGCTAAA |
| | | AACATTGCTCGTCGGCGGTGACGTACTGTCCATATCTCATATGAACCGTGTGATCGATGCTAATCCTGATCTTGTTCCT |
| | | GTCAATTGCTATGGTCCGACAGAGAATACTACCTTCTCCACCACCTACAAGATTCCGGGTCGATTTGAAGGGGGAGTA |
| | | CCGATTGGTCGCCCGATTAGCAACTCGACCGCTTATGTAGTCAATGGATCGCTTCAATTACAACCCATTGGTGCTTGG |
| | | GGTGAACTGATTGTCGGCGGTGAAGGTGTAGCGCGCGGATATCTCAATCGGCCTGATCTCACGGCAGAAAAATTTGT |
| | | CCCTAGTCCCGTGAAGGACGGAGAATCCTGCTACCGAACTGGTGATCTGGTACGCTGGCTTCCAGATGGCAATCTGG |
| | | AATTTAAAGGAAGAATCGATGAACAGGTTAAAATACGTGGCTACCGCATTGAGCTCCCCGAAATCGAGGCTCAGTTG |
| | | GCCAAGGTGGAGACGGTCATCGACGCCGTAGTAGTCGTTCGCGCGGATGAGCTTGGAGAGAAGCAGCTTTGCGCTTA |
| | | TTATGTGGCGGATCGCATGCTCACCGCAGGAGAAGTGCGTCTTGCTCTATCGCAGGTACTTCCGGGTTATATGATCCC |
| | | GTCCTATTTTGTGCAGCTGGATCGTATGCCATTAACGTCGAACGGAAAAGTGGACCGCAGATCTCTGCCGGCTCCCCA |
| | | AGTGGGTGCGCATACGGGACGGAATTATACGGCTCCTCGTACACCGGCGGAAGAAGCCTTGGCGTCTGTTTGGCAAG |
| | | GGGTGCTGGGTGCCGATCAGGTGGGTATCCATGACAATTTCTTTGAACTGGGAGGAGACTCCATTAAGGCGATTCAG |
| | | GTTTCGTCACGGCTACTACAGGCTGGTTATCGCTTAGAGATGAAGGAGCTGTTCAAATCCCCAACCATTGCGGAGCTA |
| | | GGCGCGGAAATACAAACCGCTGTGCGCATGGCCGAACAGGGAGCTGTGCGTGGAGCGACTTGCTTGACTCCAGTCCA |
| | | ACAGTGGTTCTTTGGACGGAAGCAGGCAGAGCCGCATCACTTCAATCAAGCGGTCATGCTGTACCGTGAACAGGGAT |
| | | TTGAGGAAAAGGCTTTGCACCGTGTGCTAAGAAAACTCGCTAAGCATCATGACGCCCTTCGCATGGTTTTCCGTCAGA |
| | | CAGAGCATGGCTACGAAGCTTGGAATCGTGATCTTGAAGAAGGAGAGCTTTATAACCTGCTTACCGCTGATTTACGG |
| | | AATGAATCCGATCCGGCTGCAGCTATTACAACGCTGTCGGATGACATTCAGCGCAGTATCAATCTGGCAGAAGGTCC |
| | | GCTGCTGAAGTTAGGACTTTTCCATTGTCAGGATGGAGACCATCTCCTGATCGTGATCCACCATTTGGTGGTGGACGG |
| | | AGTATCCTGGCGGATTTTGTTTGAGGATATCGCAGCAGGCTATGAACAGGTGACTCAAGGACAAGCGCTGGTATTCC |
| | | CGCAGAAGACGGACTCCTTCCGTGACTGGGGCGATGCGCTTTCCCGTTATTCCGAAAGCCAGGAAATCGAAATTCAT |
| | | CAGGCGTATTGGAGAGAACTGGAAGGTCAGCAACTTGAGCAGTTGCCGAAGGATGAGGCTGTAGAGAGCCTTCTTTT |
| | | ACGGGATAGCAAAGTGGTAACAGCACAATGGACTATAGAAGAAACCGACCAATTGCTGAGAAAAGCTCACCGTGCT |
| | | TACCAAACGGAGACGAACGATCTGTTATTGACCGCTCTGGGCATGGCCATATCCAAGTGGTCCGGCATTGGAAAGAT |
| | | TGCTGTGAATCTTGAAGGCCATGGTCGTGAACCGATTATACCGAATATCGACATCACCCGTACTGTTGGCTGGTTTAC |
| | | AAGCCAATATCCGGTGATTTTAGACTTGGGCGATAACCTGGAAGTGGCAGCCTTGATCAAGTCTGTGAAAGAAGGAC |
| | | TGCGCCAAATTCCGAACAAGGGTATCGGATACGGGTTGCTCAAAACCATGGCAAGTCAGGTGGATGCAGACAGCTTC |
| | | AGCTTGCAGCCTGAGATTTCTTTTAACTATCTGGGGCAATTTGATCAGGATTTGCAAGGAAGCTCGTTGCAGATTTCG |

TABLE 5-continued

Nucleotide sequences of genes encoding the fusaricidin synthetase (fusA) in *Paenibacillus* sp. strains NRRL B-50374, NRRL B-67721, NRRL B-67723, and NRRL B-67724.

| Strain | SEQ ID NO: | Sequence |
|---|---|---|
| | | CCTTATCCGACCGGAAACGCCCAAAGCTTGTTGGGGGAACCAGCCTACACGCTAGATATCAATGGCATGGTGACGGA |
| | | CGGAGCCCTGACTCTGACGATGACTTATAACGGAAAACAGTATAAGTCATCTACGATGGAACAGCTCGCTGGATATA |
| | | TTGAAGAAAGCTTGCGAATGCTTCTCCATCATTGCGTAGCCCAGGAAAGAACCGTTTTGACACCAAGTGACGTGCTTG |
| | | CGAAGGGTCTAAGCATTGCCGATCTGGAAGAGCTCTCCAAGCAAACCAGCCACATAGGCGATATTGAGAATGTATAC |
| | | AGTCTGACACCGATGCAGAAGGGCATGCTGTTTCATGATATGTTTGAGCCGCATACAGGTGCTTATTTTGAGCAGGCT |
| | | GCCTTTGATTTTAAGGGTAGCTTTGATCCGGCCGTCTTTGGACAAAGTCTCGATGCCTTAGTGGAGCGTCATGCCATC |
| | | CTCCGGACGAACTTTTATAACGGATGGGGCAGCGAGCCTTTACAGGTTGTTTTTCGGCACAGAGGCGCCAAGCTGGT |
| | | GTACGAAGACCTGCGGGAGATGGACGAAACGCAGCGCGAAGCTTATTTGAAGACATTTGCTGCAAAGGACAAGGCA |
| | | CAGGGCTTCAACTTATCTGAGGATGAGCTTCTACGTGTTTCGATTTTGTGTACAGGTGAGGAGAGCTTCCGTCTCTTGT |
| | | GGAGCTTTCACCACATCGTCATGGATGGATGGTGTGTTCCGTTAATTACGCAGGAGGTATTTGAACATTATTTTGCCC |
| | | TCCTGGAAGGAAGAGAGCCTCAGTTGGCAGAGGTTCAGCCGTACAGTCGATATATTGAATGGCTGGAACAGCAGGAT |
| | | GAAGCAGCTGCGTCCAACTATTGGAGTCGATATCTGGCCGGTTACGAGCAGCAGACGCTTTTACCTCAAGTCGGGGA |
| | | AGCAAGTAAAGGAGAAGGGTACGTATCAGAAAAGCAGAATTACATCCTCGGCAGGGAATTAACTGGACGTCTGGAG |
| | | AAGGTAGCCAGAGATGCTCATGTCACGATGAATATATTGCTGCAATCCATATGGGGCATTGCACTTCAACGCTATAAC |
| | | GGTAGCCGGGATGTCGTATACGGAAGTGTAGTATCAGGCAGACCAGCAGAAATTCCGGGCATTGATCGGATGATCGG |
| | | TTTGTTCATCAATACGATTCCAGTCCGTGTGAAGACGGAGGAAAATCTCCCCTTCTCAGTTTTGATGAAGCAGCAGCA |
| | | GGAACAATTTATGGCTTCCCATATGTATGACACCTACCCGCTGTTTGAGATTCAGGCTCAGACCGATCAGAAACAGGA |
| | | CTTAATCTCACATATTATGGTGTTTGAGAACTATCCTGTTGAGGAGGAGGTAGAACGTCTGGGTGGTGGCGAGGCTGA |
| | | CTTTGAGATTGAGGACGCCGAGCTTCTGGAGCAAACGAATTACGATTTTAACTTAATTATCCTGCCTGGCAAAGAGAT |
| | | GAGATTGCTATTCCAGTACAATGCACTTGTGTATGATCAAGTGACGATTGAGCAAATCAAGGGACATCTGGTTCACCT |
| | | CATGGAACAAATTGTGGAGAATCCTGCAATTTCCGTGGATGCTCTGGAATTGGTCACGCCGCAGGAGAGAGAGCTGA |
| | | TTCTGGACGTATGGGGTAACACGAAAGTCAGTTACGAGCACTGTAACACGTTCCACGGGCTGTTGGAGGAACAGGCG |
| | | GGACGAACGCCGGAGGCGACTGCCATTGTGTTCGAGGATGAGATGCTGACCTATGCCGAGCTCAATGCAAAAGCCAA |
| | | CGGACTGGCAAGAAAACTGCGTAATCAGGGAATCCAGACGGGAGATCTGGTGGGGCTGATTGCTGACCGTTCGTCCG |
| | | AAATGATCGTTGGAATCTACGGCATTATGAAAGCCGGAGGTGCCTATGTTCCAATTGATCCAGAGTATCCGAAAGAA |
| | | CGGATCAGTTACATGCTTGAAGATTCCGGAGCAAAGCTGGTCCTTACACAGGCCCGCCTCTTGGAGCATCTTGGATGG |
| | | ACGGAAAATGTTTTGTTGCTGGATGAACCATCGACATATGATGCCGATACCTCGAATTTGAAGGATACTGTTGGCCCG |
| | | GATAATCTGGCTTATGTGATCTATACTTCAGGTACGACGGGTCAGCCTAAGGGCGTATTAGTCGAACATCGGGGACTA |
| | | CAAAATCTTTCGGACGTATACGGGACATACTTCGAAGTTACACCGCAGGACCGAATCGTTCAGTTTGCAAGTCTGTCA |
| | | TTTGATGCATCGGTTTCGGAAGTTTTAACGGCACTAAGCCATGGGGCTGCTCTGTGCATCCCTTCTACACAAGACATT |
| | | TTAGATTATGCCTTGTTCGAACAGTTCATAAACGACAAGGGAATTACGATAGCGACTCTGCCACCAGCTTACGCTATC |
| | | CACCTTGAGCCTGAGCGCCTGCCAGCACTGCGATGTCTGCTTACCGCCGGATCAGCCGCATCTGTCGAGTTGATCGAA |
| | | AAGTGGAGGAAGCATGTACGCTACTCCAATGGCTACGGCCCAACGGAGGACTCTATTTGCACCACAATCTGGTCTGT |
| | | TCCGGATAGCGAGGAAACGCTGGAGACAGTATCCATTGGCCGACCTATTGCTAACCATAGTGTGTACGTGTTGGATG |
| | | AGCATCTCAGATTGCAGCCTGTCGGCGTAGTTGGAGAGCTATGCATTTCAGGTATCGGGTTAGCACGGGGGTATCATA |
| | | ACCGACCTGCATTAATGGACGAGAAGTTCGTCGAAAATCCGTTCACTCCAGGGGAGCGTATGTATCGGACAGGTGAC |
| | | TTGGTTCGCTGGTTACCGAACGGTACCATCGAATACGTGGGCCGAATAGATCATCAAGTCAAAATTCGCGGCTATCG |
| | | GATCGAGCTGGGTGAGGTAGAAGCACAAATGCTCAGAGTGCAGTCCGTTCAGGAAGTCGTGGCCATGGCTGTGGAA |
| | | GGCGATGACGGTCAGAAGGATCTGGTCGCTTATTTCGTAGCCGCCCGGGAGCTGGAGGTATCCGAGCTCCAGACAGT |
| | | TCTGTCGGAGATGTTACCTGGATATATGATCCCTTCCCGCTTCATACAACTGGAGGATATGCCTCTGACGTCGAACGG |
| | | GAAAATCAATCGAAAAGCGTTGCAGGGAGAGCGCGGATGGGCAGTTGCTTCATCTGTAGCTCCGAAGACACCTTTGG |
| | | AAATTCAATTAGCTGAAATTTGGCAAGAAGTGTTGGGTGTAGAGAATGCGGGAGTGAAGGATAATTTCTTCCATTTTG |
| | | GAGGTCACTCCCTGCGTGCAGCTCTGCTAGTCTCACGAATTCGCAAGGAAATGAACCGCGATATTAGTCTGAGAGAA |
| | | GTGTTCGATTCTCCTACAATTGAAGGATTGGCTCGCGCCATTGAGGGCTATACACCGCTCAATTTTGAAGAAATTCCT |
| | | ACGGCGGGAGTGCGTGAGCACTACCCACTGTCCTCAGCCCAAAAACGGCTGTTTATTCTAAGTCAGTTGGAAGGCGG |
| | | AGAGCTGAGCTACAATATGCCGGGAATCCTTACGGTTGAGGGAGCCTTGGATCGGGAACGGCTGGAACAGGCATTCC |
| | | GTCGTCTGATTCATCGCCATGGTTCGCTGCGTACCCGTTTTGTGACTGTTAACGGTGAACCCGTACAGCAGACCCTGC |
| | | CTGATGTGCAGTTTACTGTGGAATATGCGGAGTTGAGCGAGAAGGAGGCAGAAGCTTCCCTTCAGCAATTTGTCCGC |
| | | CCTTTTGATCTTGGCGAGGTTCCATTGCTGCGGGTCGGCCTCATCCGGATTGCGCATGACCGCCATTTACTGTTGTTTG |
| | | ACATGCATCATATTGTCTCGGATGGTGTTTCTATGAATATTCTCATAGAAGAGTTTCTCCGCTTCTACCAAGAGGAGG |
| | | ACTTATTACCTGCACTACAGATCCAGTACACAGACTATGCGGTATGGCAGCAGGAGCAACTCGGAAGCGAACGTCTC |
| | | AAAGCCCAGGAAGCTTACTGGCTGGATGCATTCCGCGGAAGCTTGCCAGTGCTGGATTTGCCGGGAGATGAAGTCCG |
| | | TCCAGCGGTGCGAAGCTTTGCGGGGGATCGGATCGACTTCTGTATTGATTCTTCTCTGAGCGGTTCACTCCAGCAGCT |
| | | GGCTACCCGAACGGGTTCTACGCTATTCATGGTACTGCTGGCAGCCTATACAGCGCTCTTGCACAAGTACACGGGTCA |
| | | GGAAGATGTCATTGTCGGTTCACCTGTGGCTGGGAGATCCCATACGACACTCGAAGGCCTCATCGGTATGTTCGTTGG |
| | | CACACTGGCACTGCGTACTTATCCGGAAGGGGAGAAGTCTTTCGAGACTTATTTGCAGGAAGTGAAGGAAACAGCGC |
| | | TGCGGGCCTATGAAAACCAGGATTATCCGTTCGAGGAGCTGGTAGAAAAGCTGGAGCTTCAGCGTGACCTGAGCCGC |
| | | AACCCGTTATTTGATACCATGTTTGTCCTGCAAAATATCGAGCAGGGAGAACAAGAAATAGAGGGATTGCGTTTCAC |
| | | TCCTTACGATAATGTACATCCTGCTGCCAAGTTCGACCTCACGCTGACCGTAAGTGAAGCGGATGGGGCATTGGATTG |
| | | CACGCTTGAGTACTCGACTGCGATCTACAAGCGAGAGACTGCTGAACGAATGGCAGGCCACTTTGTACAGCTTATTC |
| | | GGGAAGCAACCGCCAATCCGGCAATGCCGTTGTCATCCCTTGATATCGTGACACCTCAGGAAAAATCAAAGCTGATG |
| | | CAGGAGTCGGCCGAAGCCAGAGCAGATTATCCTCGTGACAAGACGATTCATGCGTTGTTCGAGGAACAGGCTGCTCG |
| | | TACTCCGAATGCAATAGCAGTCGTATGTGAAGAGGCAACCCTGTCCTACAGCGAGCTGAACGAACGGGCAAACAGA |
| | | CTTGCCAGAACGCTCCGCGAGCGTGGCCTCCAACCAGATGGTTTGGCTGGAATCATGGCGGATCGTTCCCTCGAAATG |
| | | GTCGTCGGGATTTTGGCCATTTTGAAGGCGGGCGGAGCTTACGTCCCTGTGGACCCTGAATATCCGGAGGACCGCATA |
| | | CGCTTTATGCTTGAGGATTCAGGAGCCAAGCTACTGCTGACACAAGCGCATCTGGAGAAACATGTCTCCTTCGCCGGG |
| | | GACATCGTCAATCTGGACGAGACGGCTTCCTACAAGGAAGATATCTCAAACCTGAAGTCTACAACCGGACCGGAGCA |
| | | TCTTGCCTACGTCATCTACACATCGGGTACGACAGGCAAGCCAAAGGGAACACTGATCGAGCACAAAAATGTAGTTC |
| | | GCTTGCTCTTTAATGATAAAAATATGTTTGATTTCGGTCCTCAGGATACGTGGACGCTGTTCCATTCATTCTGCTTTGA |
| | | CTTCTCCGTATGGGAGATGTATGGGGCATTGCTGAATGGAGGTCGTCTGGTCATCGTTCCATCGCTTACCGCGAAGAG |
| | | TCCAGATCGTTTCTTGCAATTGCTAAAGGACCAGAAGGTCACCGTCTTGAACCAGACGCCGACATACTTCTACCAGTT |
| | | ACTACAGGAAGAGCTTGGTCATCACGCGGCAGAACTGAGTCTCCGTATGATTATCTTCGGTGGCGAGGCATTAAGCC |
| | | CGGCCTTGCTCAAGGACTGGAGAACGAAGTACCCACAAGTGCAGCTCATCAACATGTACGGCATTACCGAAACAACC |

TABLE 5-continued

Nucleotide sequences of genes encoding the fusaricidin synthetase (fusA) in *Paenibacillus* sp. strains NRRL B-50374, NRRL B-67721, NRRL B-67723, and NRRL B-67724.

| Strain | SEQ ID NO: | Sequence |
|---|---|---|
| | | GTGCATGTAACATACAAGGAAATTACAGATCTGGAAATTGAACAGGGCCGCAGCAATATCGGTACCACGATTCCGAC |
| | | GCTGCGTGCATACATTCTGGATGAACAACGTCGTCCACAGCCGATTGGCATTCCAGGTGAACTCTACGTGGCGGGCG |
| | | AAGGACTGGCGCGCGGCTACCTGAACCGACCGGAATTGACGGAAGAGAAGTTTGTCGCTCATCCGTTTGCAGCGGGC |
| | | GAGCGTATGTACCGCTCGGGTGACCTGGCACGCTGGCTGCCTGATGGAAGCATGGAGTATTTGGGACGGATTGACCA |
| | | CCAGGTTAAAATCCGGGGTTACCGCATCGAGCTGGGCGAAGTGGACGCGAAGCTGCTCCATGCTCCGTCTGTAAGGG |
| | | AGGCTGTAGTGCTCGCTCAGGAGGATGGAAGTGGACAAAAGGTGCTTGTCGGCTATTTTACAGCCGATCAGATACTG |
| | | ACGGTAGGCGAATTGAGAAAAGCCTTGGCCGCAGAGCTGCCAGCTTATATGATTCCGTCTTACTTCATGCAATTGGAA |
| | | CAGATGCCATTGACGCCAAATGGCAAGCTGGATCGCAAAGCACTTCCGGCTCCGGAGGCCAATGTGCAGACAGGAG |
| | | CGGTTTATGAACCGCCAAGGACGAAGGCTGAGGAAGCTCTGGCGTCCGTATGGCAAGGGGTGCTGGGAGCACAGAA |
| | | GGTCGGCATCCATGATCATTTCTTCGATCTGGGTGGTGACTCCATCAAGGCGATCCAGGTATCCTCAAGATTGTTCCA |
| | | AGCCGGGTATAAGCTAGAGATGAAGGATCTCTTCAAATATCCGACAATTGCTGAGCTAAGCCCGTATCTTCAAGTAG |
| | | CCGGACGCACAGCAGAACAGGGTGAAATTAAAGGCGCAGCAGAGCTGATGCCAATTCAGCGGTGGTTCTTTGAGCGT |
| | | CATACAGAGGAGCCGCATCATTACAATCATGCCGTCATGCTCTATCGGAAAGACGGCTTTGACGAGGCTGCACTCCG |
| | | GTTGACAATGACCCAAATTGCTACCCACCATGACGCGCTGCGTATGGTCTTCCGGTCTACAGAGGCCGGATATGCAGC |
| | | CTGGAATCGTGGAACGGATGAAGGCGAGCTCTATACATTGGATATAGACGATGTGCGACAGGCAGAAGACCAGGTT |
| | | GCTGCCGTTCAAGCCAAAGCCGATGCCATTCAGGCAAGCTTCCACTTGGAAGACGGCCCGCTGTTCAAGCTAGGCTT |
| | | GTTCCATTGTGAAGATGGGGATCATTTATTAATTGTTATCCATCACCTTCTAGTTGACGGGGTATCCTGGCGCATCCTG |
| | | TTTGAGGACATCGCAACGGGATACGAGCAGGCGTTGAATGGACAAGCGATTGTCCTTCCACAAAAGACAGATTCGTA |
| | | TCTTGTATGGTCTGAACAAGCGGCGAAGTATGCAGCAGGGCCTGCACTGGACAAGGAGCGTGCATACTGGCAGCAGA |
| | | TCGAGGATACAATTCTGGCCCTACTGCCAAAAGATGAAGATCAGGAGCCAGGCACCATTCGGGATACCGAGTCGGTA |
| | | ACGGTAACGTGGTCTGCGCAGGAAACAGACCTGCTGCTGCGACAAGCGAACCGGGCGTATCATACGGAGACGAATG |
| | | ATTTGCTTTTGACTGCTCTGGGAGCAGCAATTCAGCGCTGGACAGGCATGGAGCAGATTTTGGTCAATCTTGAAGGGC |
| | | ATGGACGGGAAATGATCATACCGGAACTGGATATCACCCGTACCGTGGGCTGGTTCACAACCCAGTATCCGGTTCTG |
| | | CTGAACCTTCAAGACGGACAGGAAGTATCTGCACGAATCAAGCGTATCAAGGAGAATTTGCGCCAGATTCCGCACAA |
| | | AGGAATCGGCTACGGCCTTCTGAAGTATATAGCACTGGAGAAAAGTGGCGGGTTCGGCGTAGAGCCGGAGATTTCCT |
| | | TCAACTATCTTGGACAGTTTGATCAGGATTTGGAGGGGAATGCACTCAGCCTATCCACACATTCAGTCGGTAAGGCGC |
| | | TCAGCGACCACACACCACAGCAGTATGCTCTGGATGTGAATGGCATGATTGCCGAAGGCCAGCTATCACTGACGGTT |
| | | ACGTACAGCAGCAGGCAGTATCGCAAGGAGACGGTGAATCATTTTGCCGAATTATTACAGTCCAGCCTTAGCGAGGT |
| | | TATCCGGCATTGCGTGGCGCAGGAGCGCTCACAGCTTACGCCAAGTGATGTTTTGTTCCAGGGATTAGCGCTGGAGCA |
| | | GCTTGATCGACTTACGGAGCAGACGGCCCACATTGGAGAGATTGAAGATGTGTACAAGCTTACGCCAATGCAGAAGG |
| | | GGATGCTGTTTCACAGCCTGCTGGAGCCAGACTCCTCTTCATACTTCGAGCAGGCTACGTTCGAGCTGCGAGGCAGCT |
| | | TCGATGTAGAGACCTTCTTCGAGAGCTTCCAAGCTTTGGTGCAAAGACATGCCATACTGCGTACCAACTTTTACAACA |
| | | ACATTGGTGATTTACCGCTGCAAGTCGTCTTTAAGCAACGGCCAATCCCATTGCACTACGTAGATCTGCGTGCCGCAA |
| | | CTTTGCAAGAGCAAGAAGCCCAGATCAAGGCTTACACTGCTGAGGATATGGCTAAGGGGTTCAGCTTGTCGGAAGAT |
| | | CCGCTGATGCGGGTAAGCGTCTTGCAAACAGAACAAAGCTCTCTGGTATTATGGAGCTTCCATCATATTGTCATGGAT |
| | | GGCTGGTGCATCCCGATCATTACACAGGAGCTATTCGATTATTATTCTGCTCTGCGCCAGCAAGTACAGCCTGTGCTG |
| | | CCGCCAGCTCAGCCCTATAGCCGTTATATTGAGTGGCTTGATGCACAGGATGATGAGGAAGCTTCCACGTATTGGAGC |
| | | CAATACCTCAAGGACTATGATGGGAATACCGTATTGCCGGAAGGCAAAACGAAATCTCAAGCTAAAGAAGCGGGCT |
| | | ATGTTCTGAATGAGCATGTTCTCCATCTGGGTGCATCCTTGACCGGTAAAATGGATACTGTCGCTAAGCGAAACCACG |
| | | TGACCGTCAACACACTCATGCAGACAGCCTGGGGACTGATTCTTCAACGTTACAATGCCAGCTCGGATGTGGTTTTCG |
| | | GCGGCGTTGTATCGGGCAGACCGGCTGAGATTGCAGGGATCGAAAATATGGTGGGTCTGTTCATTAATACAGTACCT |
| | | ATCCGTGTACAGTCCTCCAAAGACGAAGCCTTTGTCGAGGTGATGAAACGTACACAGGCACAGTCATTGGCTAGTCG |
| | | TGCCTACGACACCTATCCACTGTATGAGATTCAGGGGAAAACAACCCAAAAGCAGGACCTGATTTCTCATATTATGAT |
| | | CTTTGAAAATTATCCGCTCGACGAGCAGGTGGAGCAATCGGGTAATCAAAATGAGGACAATCTCGAAGTCGCGAACT |
| | | TCACCATGTTTGAACAAACGAACTATGACTTTAACCTGGTTGTGATTCCAGGCGAGGATATCAAGGTTTGCATTCGTT |
| | | ACAATGCTTTGGTCTACGAACAAGAAAGCATTGCACGAATCGGTGGACACTTGATGCAAATGCTCGATCAGGTAGCT |
| | | ACCCGTCCGCAGGCAGTCATAAAGGAACTGGAGCTTGTAACCTCTGATGAACGAATGCAATTGCTAGACTGGGGCGG |
| | | CAAGGCCTACACCTATCCAAGTGATCAGGGTCTGCATACCTTGTTTGAAGAACAGGTTGTCCGTACGCCAGATAAGAT |
| | | TGCAGCTGTTAACGGCGATATTCAGGTCACGTATCGGGAGCTGAACGAGCAGGCGAACAGATTGGCCTCCACCTTGA |
| | | TCGCCCAGGAACTTCGGAGTGAACAAGTGGTCGGTCTGTTGGCGGATCGGTCTGTGGAACTGCTTGTCGCCATTATGG |
| | | GTGTGCTCAAAGCGGGCGGGTCCTATGTACCTATTGATCCTGAATATCCGCAGGAACGGATTCAGTATATTCTAAAGG |
| | | ATTCCGGCGCTGAGATTTTGCTCACACAGAGCCACTTGACGGAGCTGGCCTCCTTTGAGGGAACGGTTATGGAATTGG |
| | | ATTCCCCGCACATCTACGGAGACGGGGGGATAACCCTAATCTACCTGTGAGAGGAAACGATCTGGTGTATTTAATC |
| | | TATACATCGGGTACAACAGGAAATCCGAAGGGAACCATGATTAACCATAAAGGGATCGTGAACTACATCTGGTGGGC |
| | | CAATAAGGTCTACTGTGCAGGGAAACCAACAGATTTTCCGCTGTACTCGTCCATTTCATTTGACCTGACGCTGACATC |
| | | AATTTTCACTCCATTAATTAACGGAGGATTAGTACGGATTTACGATGGTATAGATAAGGCGGAGGTTGTTCAGCATAT |
| | | TTTGCGCGAAAATGCGGTGGACATTCTCAAGCTGACGCCAACTCATCTCAGTCTGATTAAAGATATGACCATCCCGGC |
| | | GGAAAGTCGCATTCAGCAGCTCATTGTGGGTGGAGAGAATTTGACCACACATTTGTCGCAAACCATCACAGATCTCTT |
| | | TGGCGGCAAGATCAAAATCTACAATGAATACGGTCCTACCGAAACGGTCGTCGGCTGCATGATTCACCTTTATGATCC |
| | | TGTGAAGGATACACGTGAATCCGTACCTATTGGATTGCCGGCAGACAACATATACATCCATATCCTGGATGACCAGCT |
| | | TCGTCTCGTACCATTAGGCGTGGAGGGCGAAATGTACATCGCCGGGGACGGGGTAGCCCGCGGATACCTGAACCGTC |
| | | CTGAGCTTACCGCAGAAAAATTCATTAGAGACCCGTTCGCCTCGGAAGGAAATATGTATCGAACCGGGGATTTGGCC |
| | | CGTCGTCTTCCTAATGGAGACATTGAGTACATTGGACGTATTGACCATCAAGTTAAAATACGGGGCTATCGTATAGAG |
| | | CTTGGTGAGATTGAGGCCAAGCTGCTGGATATTCCACTTATCGAGGAAGCTCTCGTTGTTGCGTGGGCAGATGCCCAT |
| | | GGACAGAAGTCTCTGTGTGCCTACTTCGTAGCTGATCGGGAAATGTCTGTCAGCGAGCTGCGGAACGAACTTTCTGGA |
| | | CTGCCTGCATATATGATCCCGTCCTACTTCGTCCAACTGGACGTGATGCCTTTGACACCGAATGGCAAGCTGGACCGT |
| | | AAGGCACTGCCTGAACCGAACTCGGGTGTGAAGGCGGGCGCGGCCTTTACTGCTCCGCGGACGGATGTGGAGAACAT |
| | | TTTGGCTTCGATCTGGCAGGGTGTGCTAGGTGTTCCGCTTGTCGGCATACATGACAATTTCTTTGAGCTCGGAGGCGA |
| | | CTCGATCAAATCCATTCAAGTCTCATCAAGGCTGCTCCAAGCAGGCTATAAACTTGAGATGAAGGATTTGTTCAGCTA |
| | | TCCGACCATTGCAGAGCTGGCCCAGCGTGTTAGGGCGGTCAGCCGAATTGCGGATCAGAGCGAGGTACACGGAGCG |
| | | GTAAGACTGGGACCTGCCCAGTGCAGATTTTTCGACGAGCAGTCGACGGACCTGCACCACTTTAATCAGTCGGTCATG |
| | | TTGTACCGTCGGGAAGGCTTCGATACCGATGCGCTCGCCAAGGTTGTTCGGAAAATTGCAGAACATCATGATGCGCT |
| | | GCGACTGGTGTTCCGCCAAGGAGAGCGGGGATTTGAAGCCTGGAACCGCAGCTTAGGTGAGGGTGAGCTTTATAGCC |

TABLE 5-continued

Nucleotide sequences of genes encoding the fusaricidin synthetase (fusA) in *Paenibacillus* sp. strains NRRL B-50374, NRRL B-67721, NRRL B-67723, and NRRL B-67724.

| Strain | SEQ ID NO: | Sequence |
|---|---|---|
| | | TCCAGATCCACGATCTGCAGGATGAAACAGACCCGGCTTCGGCAATAGAAGCAGGTGTGGAAGCCATTCAGCGCAGC |
| | | ATCTCTCTCGGTGATGGACCTCTCTTAAGATTGGGCCTGTTCCGCTGCGCGGAAGGCGAACATCTGCTAATCGTTATT |
| | | CATCATCTGGCTGTTGATGGCGTATCCTGGCGCATCCTCTTTGAGGACCTGCAGGAAGGCTACGAGCAGGCAGCACG |
| | | CGGAGAAGCTGTCAAGCTTCCGCAGAAGACGGATTCGTACCGTGCATGGGCCCAGGGAATCACACAATATGCGAAC |
| | | AGTCCGGCGGCTGAACAAGAACGCAGCTATTGGGCAGAGGTAGAAGGGGATGGCTTCGCCCCTCTTCCAAAAGACA |
| | | AGGTAGACGACGCTCTTCTCATCAAAGACAGCGGGACGGTTACGGTGAGATGGTCACCAGAAGAGACAGAGCAGTT |
| | | CCTGAAAGAGGCGAACCGCACTTACAACACGGAAGTTAACGATTTGCTCCTGACGGCCCTCGGCATGGCTGTTCACG |
| | | AGTGGACCGGGATCGAACGTGTAGGCATCCTTCTGGAAGGACATGGACGGGAGCCTGTTGTACCTGAACTGGATATC |
| | | ACTCGCACTATAGGCTGGTTTACAAGTCAATACCCTGTCGCCCTTGAGATGAAAGAGGAACTGGAGATCGGCGCTAG |
| | | AATCAAGCGTGTCAAGGAAGGCTTGCGTCACATTCCTAACAAAGGTGTCGGATATGGTATTTTGAAATATTTGAGCG |
| | | ACGTATCCGATGTCTCCTCCTTCTCTGCTGAACCGGAGATTATCTTCAACTACCTGGGACAGTTCGACCAGGATCTTGC |
| | | AGGGGGGATGATGGAGGTATCGCCTTACTCAGTAGGATCTGAGGTCAGTGAGCAGATGGTACAGCATCAGGCATTGA |
| | | ACATTAATGGACTGATTGCCGAAGGACGACTTCAGCTTTCGGTCAGCTATAACCGTCAGCAGTTCCACACAGAGTCG |
| | | GTAGAGAAGTTTGTCGGCATCCTGAAGAACCGTCTCAGCGAAGTCATTGGACATTGTGTACGCAAGGAAAGAACGGA |
| | | ACTTACACCAAGCGATGTACTCCTCAAAGATATCAGCCTGGAAAAAATCGAGGAGCTGGAAGAGCAGACACGGCAT |
| | | ATCGGCAGTATTGAAAATATTTATAAACTGACACCGATGCAAAAGGGCATGTTGTTCCACAGCTTGCTGGAGCCTCAT |
| | | TCGGAAGTCTACTTTGAGCAGGCTAAATTTGAAATTCACGGAGCATTCTATCCTGAGGATTTCAAACGCAGCATAAAG |
| | | CATCTGATGAAACGGCATGCCATATTGAGAACGAATTTCCATGCCGGATGGGGCGATTTCCCTATACAGATTGTGTTC |
| | | AAAGAAAGAGCGTGTGACTTCGTATACGAGGACCTGCACGAGCTGGAATCCGGTGAAATTGAAGTGCGTCTTTCAGC |
| | | TTATACTGCTCAGGACAAAGCAAGAGGCTTTGATCTTGCTGAAGGAGCATTGCTGCGTGTTGCTATTCTACGGACAGC |
| | | AGATGAGGCTTACCATCTGCTGTGGAGCTCTCATCACATCATTTTGGATGGCTGGTGTATGCCTCTTGTGCTTCAGGA |
| | | AGTGTTTGAAACGTACGGGGTTCTGCGTGAGCAGAGGGAGCCTGAACTTCCTGCTGCTGTATCGTACAGCCAGTATAT |
| | | TCAATGGCTGGAGGAGCAAGGTGAGGAAGAGGCATCCTCTTACTGGAGAGGTTATCTGGAAGGTTACGAACAGCAG |
| | | ACGAAGCTACCGCAAGCGACAACACAGCCATTGGCAAAAGCAGAAGCCTACGTATCAGAGAAGCTTGTATTCACGTT |
| | | GGATGCGGAGCTGACCGAGCGGCTGGAACAAGTGGCCAAGCAGAACCAGGTAACGATGAACACGCTGATGCAAGCA |
| | | GCCTGGGGAATCGTGTTGCAGCGCTACAATAGAAGTCAGGATGTCGTCTTCGGAAGTGTGGTATCGGGAAGACCTGC |
| | | CGAGATTCCCGGTATCGAAAGCATGATCGGTCTCTTCATTAATACGGTTCCGGTTCGGGTACAGGCCGAGGGAAGCG |
| | | ATACGTTCTCCCATGTGATGAAAAGACAGCAGGAATTATATTTGGCAGGACATGCTTATGATTCCTATCCGCTCTATG |
| | | AGATTCAAGCACAGAGCGAACAGAAGCAAGATTTAATTTCTCATATTATGGTATTCGAGAATTATCCGGTAGAGGAG |
| | | CATCTAGAAGAGAAAATTGCCAGTGAAGAGGCTGAATACAAAATTACGGATGTTCAGATGTTTGAACAGACGAATTA |
| | | TGATTTTAACCTCATTGTGCTGCCAGGCCGTAATCTGGAGTTCTTGTACCGTTACAATGCCAGCGTCTATGATCGGGA |
| | | GAGCGTGGAACGGATTCAAGGGCACTTGATGAAAATTCTGGGAAATGTATCTATTCATCCTGCCATTCGTATTGAGGA |
| | | ACTGGAGCTGATCACGCCAGAAGAGAAATCGCAGATTATAGAGGTGTGGGGCGATACAGCAGCTCCTTATCCGCGTG |
| | | AGAAGACCCTTCACGGCATATTTGAGGAAAAAGCGGCGCTCACACCGGATCGTACAGCACTTATCTATGGCGAAACG |
| | | AAGCTTACCTACGGAGAACTTCATCAGCAGGCGAACCGCCTCGCACGTACGTTGCGTGCCCAAGGGGTCAGACCGGA |
| | | CCAGCCGGTCGGCATCATGGTTGAACGTTCGCTTGAGATGATCATCGGCATCCATGCCATTCTAAAAGCGGGCGGGG |
| | | CCTATGTACCGATTGATCCGGAATTCCCGGAAGATCGTATTCGCCACATGCTGGAGGATTCGGGAGCGAAGCTTCTGC |
| | | TGACGAAGAACCATCTCAAAGATCGCTTTCCGTTCACTGGCACGATCCTGGCACTCGATGACCCGCAGGCGTATCATG |
| | | CTGATGACTCGAATCTGGAGCCAATCGCGGGGCCGGAGCATCTGGCGTATATCATTTACACGTCAGGTTCAACTGGC |
| | | AAGCCGAAAGGTGTAATGATTGAGCATCGCTCTGCCGTCCATACGCTGAGCCAGTTGGAAGCTGAATATCCGATGAT |
| | | GGCGGGTGACCGATTCCTGCTCAAAACGACATTCACCTTTGACTTCTCCGTTCCGGAGCTATTCTGCTGGTTCTTTGGG |
| | | CAGGGAACTCTCGTGATCTTGCCGCAGGGCGCGGACAAAGATCCGGTGGCACTGTTGGAGGCCGTGGATACGAGCCG |
| | | TATCACGCATCTCAATCTGGTGCCGTCGATGCTCAGTGTTCTTGTTCAATATTTGAAAGAAGGCGGCAGCCAAGGATT |
| | | CCTTACTTTGAAATACCTGTTTGCCTGCGGCGAGACGCTGCCCGCCAAACTTGTGGAAGAGTACTATAAAGTATCTCC |
| | | ATGCGCAGTGCTGGAGAACATCTATGGTCCTACGGAGGCGGCCGTATATGCGACCCGATATACAACGAGCCTTGAGA |
| | | CTGCTGCGCTAACGCATGTACCTATCGGTAAACCGTACGCTAATGTCCAAGTATGGATGATGGACAGTGCTTCTCAGG |
| | | TATCACCTGTAGGTGTACCGGGAGAACTCTGCATTGCAGGCGAAGGGGTAGCGCGAGGGTACTTCAACCAGCCGGAC |
| | | CTGACGGCAGAGAAGTTCATTCCTCACCCGTACAAACCGGGAGCGCGGATTTACCGGACGGGCGATTTGGCCCGATG |
| | | GCTGCCAGACGGGAATATTGAGTATTTGGGACGGATCGATCACCAGGTAAAAATCCGGGGTTACCGCATTGAGCTGG |
| | | GGGAAGTGGAAGCACAAATTTTGAAAGTGCCATCTGTGCAGGAAACGGTTGTTCTTGCACTGGCTGATTCCACTGGA |
| | | AGTACTCAGCTTTGTGCATACTTTGTGGCCGAAGAGGGGCTTGCAGCGGGCGTACTACGCGAGGCACTGGCCAGCGA |
| | | GCTGCCAAGCTACATGATTCCGACTGCTTTCGTACAGCTGGCACAAATGCCGCTGAATCCAAATGGAAAATTGGATC |
| | | GCAAAGCGCTGCCGGCACCGGAAGCACTTCTGCGGAGCACAGCGGAGTACATCCCGCCGCGTACGCCGACAGAAGT |
| | | AGAGCTAGCGCAGATCTGGTCCGAGGTACTCGGCGTGCAGGAAATCGGGGTCAAAGATCATTTCTTCGAACTTGGGG |
| | | GCCATTCCCTGAAAGTATTGGGATTGATCCAAAAGATCTCAACCGGCATGGGTGTTCAGCTTCCGCTCCAACTCGTGT |
| | | TTAATCTTCCGACTGTTGAGCAAATGGCCCATGAAATATCCAAGCTGCGGGCAACAGCTGCTCCTGATGAAGAAGAA |
| | | ATGGAAATTATCCACTTCCCAGGGAAAGGAACGCTTAAAGTGTTTTGCTTCCCTCCTCGGGTAGGTTACTCTCTGGGG |
| | | TACTATGAGATGGCCAATGAGCTGGAAGGACATTGCGAGGTGTTCGGGCTGGAATTTATCGGCGATCGTTTCCAGGG |
| | | CCAAGACATGCTGGATCGATACATGGATGCCATCGTGGATATTCAAGCTGAGGGCCCATATGTCTTCCTGGGATACTC |
| | | CCTCGGAGGAAATCTGGCCTTCGAGGTGGCCAAAGCCATGGAAAGCCGAGGTCACCATGTCAGCGACCTTATTATGG |
| | | TGGATGCTATGAGAAAGATGTCCAAGGATGAATCGACACCGGAGCAGCTTGAGGAGATTGTCGAGACGGTGCTGGA |
| | | CAGCATTGGGGACCAGTACAAATCATTTCTCGCCGATCCAGCTGACAGAGCGCGAGTCAAAGACAAAATGTTGATCT |
| | | ACTCCATCTACCGCAATGAGCTTATTAACGTAGGTGGGGTTCAGGCGAATATCCATGCCTTGGTTGCAGAGGACGATA |
| | | GTATTGGTCCGGTGACATCATCGGATAAACTGCTATGGCAACAGGCAACGCTTGGTCAATACGAAGAGTATGGAGTC |
| | | ATCGGTACGCACGATGTGCTGCTTGATTCCGGTTATATCGGGGAAAATGCTAAAGTGCTGAGACAGATACTTGGCAA |
| | | GGTCGCAGAGACCTCATCTAAAAACAAGCCCATTTTGTCCTAA |
| NRRL B-67724 | 4 | ATGAATGACATGCAGTTATATGATTTAACAAATGCGCAGAAGCGTATATGGTATACCGAATTACTCTACCCAGATAC |
| | | GTCAGTGTCACAGCTTTCCGGTACAGCTAAGATGAAGGGGCATATCAATATTGCTGCCTTTATGCAGTCCATTAATTT |
| | | GATTATCAAACAGTATGATGCGTTCCGCATCCGTATTACCTCAGTGGATGGAGTGCCTCAGCAGTACGTCGTTCCTTA |
| | | TGAAGAGAGACAGTTGGAGTGCCTGGATCTTAGTCACTATGAAAGTGTATCTGAGGTGGAAGCTTTACTTGAGCAAC |
| | | ACAAAAGAAAACCCTTGCCCCTGCTGGATTCTGAGCTCTTCCAGTTTTTAATTGTGAAGATTAGCGAGGAAGAGTATT |
| | | GGATTAATATCAAGATGCACCATATTATTTCTGACGGGATCTCAATGGTGGTCTATGGCAATCAGCTGACAGCATTTT |

TABLE 5-continued

Nucleotide sequences of genes encoding the fusaricidin synthetase (fusA) in *Paenibacillus* sp. strains NRRL B-50374, NRRL B-67721, NRRL B-67723, and NRRL B-67724.

| Strain | SEQ ID NO: | Sequence |
|---|---|---|
| | | ACATGGAGTTAATTCAAGGAAATGAACCGGAGCTGGGCGACGATTGCTCGTATATTCAATATATTGCAGATGAGAAT |
| | | GCATACGAACTTTCTGACAGATACCAAAGGATAAGGCTTACTGGCTAGATAAATTTTCCGATTTGCCTGAGCTTACG |
| | | GGTTGGAAGTCATATAATCCGTTATCTTTAAGCACCCACGCCGTTCGGGAGCATTTTACCGTACCAGAAGTGCTATAT |
| | | CACGAGCTGCAAGCATTTTGCCAACAGAATAGGATTTCTTTGTTCCAGTTCTTCATGGGTGCGATGTATATCTACATA |
| | | CACAAAATGACGAATCAGCCGGATGTGGTGATTGGCACTTCGTTCGCTAACCGGGGGAACAAAAAAGAGAAGCAAA |
| | | AGATAGGTATGTTCGTCAGCACCGCTGCTGCCAGAACATACGTCAAAAAGGATATAGATGTGTTGAGCTTCCTGCAG |
| | | GATGTAGCCAGAGATCAGATGTCAGTCCTGCGGCATCAGAAATATCCATACAATCAGTTAATTCAGGATCTTAGAGA |
| | | AATGCATGGGAACAAGGATATTCAGCGGCTTTTTGGCGTTTCAATGGAATATCGTCTTATCAATTGGGTTGATTTGGA |
| | | TGATGTGCGTATTTTGACAGATTATGATTTCTGCGGGGACGAAGTGAACGATTTCGTGCTTCATATCGTGGAGATCCT |
| | | GGATGAAGGCGAACTGGTACTGGATGTCGATTATCGGACAGAGCTGTTTGAACGCAGTGAAGTTAAGGACATGGTTT |
| | | CCCAGTTGCTTACGATCGCCGAGCAGATCATTCATTCACCTCAGCTTTCTATCGCAGAGGTAAGCTTATTAGGTGAAC |
| | | CAGAAGAGCAATCCATTTTGGCTCTTTCGGAAGGCGCCGCAGTCGATTATCCACGAGAGAAGACCATTCATGGCTTAT |
| | | TCGAGGAACAAGCCGAGCACACGCCAGATCACGTAGCCGTTCAGATGGACGAGCAGAGCATTACATACCAAGCTCT |
| | | AAACGAGCAGGCTAACCAGCTTGCGAGATATTTGCGCTCCGAGGGAGTAGGGGCAGATACGCTCGTAGGGATTATGG |
| | | CTGACCGTTCCTTGGAGATGGTCATCGGGATGTTGGCCATTTTGAAAGCAGGTGGTGCCTATGTACCAATTGACCCCG |
| | | ATTATCCCGAAGAGCGTATCCACTATATGCTGGAGGATTCAGGTGTAAGTCTGTTGCTCACCCAAAGTCATCTATGGG |
| | | AGAGCACCACTTTTGACGGAAAGCTTGTGAGTCTGGACGAAGCTGCAACGTATACAGGAGATGCTTCCAATCTGGAG |
| | | AGTATTTCGGGACCAAGCCATCTGGCCTATGTTATCTACACGTCGGGTACGACTGGCAAGCCGAAGGGCACGCTGAT |
| | | TGAACACAAAAATGTAGTTCGACTGCTCTTTAACGATAAAAATTTATTTGACTTCAACTCTCAGGATACGTGGACGCT |
| | | GTTCCATTCGTTCTGCTTCGATTTCTCCGTTTGGGAGATGTACGGAGCGCTTCTTTACGGAGGGAAATTGGTGATTGTT |
| | | CCATCTCTCACAGCCAAGAGCCCAGCAGCTTTCCTGGAGTTGTTGAAAGACAACCAAGTCACCATCTTAAATCAGAC |
| | | GCCGACGTATTTTTATCAGGTGCTACAGGAAGAGTTAATGCACTCTTCGACAGAGCTTGGCCTTAGAAAAATCATTTT |
| | | TGGTGGAGAGGCTTTAAGTCCATCTCTTCTGAGAAACTGGCGGGTCAAGTATCCTGATGTGCAGCTGATTAATATGTA |
| | | CGGAATTACGGAAACAACGGTTCATGTCACCTATAAGGAAATCACGGAACATGAGATTGAAGCGGGGAAAAGCAAT |
| | | ATTGGCAGAACGATCCCCACACTTAGCGCTTACATTCTCGATGAGCAAAGACGCCTGCAGCCTGTTGGGGTTCCAGG |
| | | AGAGCTATACATTGCGGGAGACGGTCTTGCCCGTGGGTATTTGAATCGGCCGGATTTGACGTCTGAGAAATTCGTTGA |
| | | GCATCCGTATCGGGTGGGAGAGCGGCTGTACCGAACTGGGGATCTTGCTCGTTGGTTGCCTGATGGCAATATTGAATA |
| | | TTTGGGGCGGATCGACCATCAGGTCAAAATTCGCGGCTACCGAATTGAGCTTGGCGAGGTAGAAGCCCAAATTCTCA |
| | | AGGCTCCAAGCGTACGAGAAACGATTGTCCTCGCACGGGAAGACGAACAGGGCCAAAAATTGCTGTGCGCCTACTAT |
| | | GTAGCCTCCAGTGACCTTTCGCCGGGGGAATTGCGGTCTCAGCTGGCGGCGGAACTCCCCGCTTACATGATTCCTTCT |
| | | TATTTTGTCCGGCTGGAGCAAATGCCGCTTACACCAAATGGCAAACTGGATCGCCGTGCGTTGCCGGCTCCTGAAAGC |
| | | AGCGTACAATCCGGTGAGGCTTATTTGGCTCCGAGAACTGCTGTGGAAGCTCAGATGGTACTCATCTGGCAAGATATC |
| | | TTGGGCGTTGCTCGTGTCGGTGTCAGAGATAATTTCTTTGAAATTGGTGGTCACTCTTTGCGGGCAACAGTGCTCGTTT |
| | | CACGGATTCACAAAGAATTGGGATGTAGCATTTCGCTGCGTGAGGTGTTTCAGTCACCTACGGTCGAATCCTTGGCGC |
| | | AACTTGTGAAAAAACACATTCCGACCATGTACGAATCCATCCCACAGGCAACGGAAAGCGAGGCTTACCCAGTGTCC |
| | | TCAGCGCAAAAGCGGTTATACGTGCTGAGACAGATGGACGGGGGAGAGCTCAGCTACAATATGCCAGGGGTCTTCAC |
| | | AGTGGATGGACCGTTGGATCGCACGCGGCTGGAGTCTGCGTTCCAGGCACTGATCCAGCGTCATGAATCCCTGAGAA |
| | | CCGGCTTTTATATGCAGGATGGAGAGCTTGTTCAGCGTGTGCATAGGAATGTGCCGTTTGCGTTGAACTACACAGAGG |
| | | CTTTGGTGGAGGAGACGGATACGCTCATTCACAACTTTATTCGTGCCTTTGATCTGAGCCAGGCTCCATTACTGCGTG |
| | | TTAGCTTGGTGAAGCTCCAGGAGGAGCGTCATCTGTTGCTGTTTGATATGCATCACATCATTTCAGATGGGGTTTCTAT |
| | | TCAAATATTGATAGAGGAACTTACTCATTTGTATCAAGGAGAACAGCTCCCAGAGCTGCACATCCAGTACAAGGATT |
| | | ATGCCGTATGGCAACGGGAACAGTCAGAGAACCAATGGCAAGATCTTGAGAAATATTGGCTGCAATCCTTTGAAGGA |
| | | GAGTTGCCGGTATTGGATTTGCCTACAGACTTCCAACGACCTTCAGTTCGGAGCTTCGAGGGTAGCCGAATTGATTTT |
| | | ACATTGGATGAGTCTGGCAATAAGGCGATACAAGAGCTTGCATCCCGTACAGGTACTACACTGTATATGGTATTGCTG |
| | | GCCGCCTATTCGGTACTACTGCACAAATATACAGGACAGGAGGACATCGTCGTAGGTTCTCCAGTAGCCGGAAGACC |
| | | GCAGGCTGAGCTTGAGGGCATCATCGGGATGTTTGTCAACACACTGGCCTTGCGCAGCTACCCGGCAGGAGATAAAA |
| | | CCTTTCAGGATTATCTTCTGGAAATCAAGGAAACGGCGCTCAAGGCGTTTGAGCATCAGGATTACCCTTTTGAAAAAT |
| | | TGGTCGAAAAGCTGGGCGTAGGACGTGATGTCAGCCGCAATCCGCTCTTTGACACCCTATTGGTATTACAAAATACCG |
| | | AGCAGGAAGAGCAGGAAATGGACGGAGTGCACTTTACTCCTTACTTGATGGACACCGTCACAGCCAAATTTGACCTG |
| | | TCCCTCAATGTAGAGGAGAAGGGGTCAAAATTAGCCTTTGGCCTCGAGTATAGTACGGCTTTATATCGGCGTGAAAC |
| | | CGTAGAGCGACTTGCAACGCACTTGCTCCGGGTTCTGCATGCAGTCTCGGCCAATCCTCAGTTGCAACTGGCCGAGAT |
| | | AGAAATGATCACACCGGAGGAGAAAGTACAGATCGTTGAAGTATTTAACGCGACATCGGCTCCTTATCCAAGGGACA |
| | | AGACCATTCATGAGCTGTTCGTAGAACAAGTCAATCGTACACCAGAGCAGACGGCGCTTGTATTCGGCGATGTCCAG |
| | | CTAACGTACCTTGAATTGCAAGACAAGGCGAGCCGACTGGCCCAAACACTGCGTCGTTTGGGAACGTTGAGGGAGCA |
| | | GCCTGTGGCCGTGATGGGCGGACGAAGCATTGAGATGGTCATTGGTATGCTCGCGGTGCTTCAAGCGGGTGGAGCCT |
| | | ATGTGCCGATTGATCCTGATTACCCGGAAGATCGGGTTCGTTATATGCTTAATGATTCCGACGCCAAGCTATTATTGG |
| | | TGCAAAAGGGCGAGCTTATAAGTGTAGACTACGGTATACCGATTGTCGATCTTAGCAGTGAAGAGGCCTATGCAGCT |
| | | GAACCTGCCCAGCCGGAGACTGCTCAGGGATCGCAGGGGCTTGCTTATGTCATCTATACATCGGGTACGACGGGTAG |
| | | ACCGAAGGGCGTTATGGTTGAACACCGGAACGTGGTCCGTCTAGTCAAAGAGACCAACTATGTGGAGCTGAATGAAT |
| | | CCACACGAATTTTGCAGACAGGAGCCGTGGCCTTTGATGCTTCTACATTCGAAATATGGGGAGCGTTACTTAACGGTG |
| | | GGCAGCTCTATTTCGTGGAGAACGACGATATCCTGATTGCCGATAGGCTAAAAGCGGCCATTACCAAGTACGGGATT |
| | | ACAACAATGTGGCTTACTTCACCGCTTTTCAATCAGCTTTCCCTGCAGGATGAGTACCTGTTCAGAGGGCTAAAAACA |
| | | TTGCTGGTCGGCGGAGACGTACTGTCCATATCTCATATGAACCGTGTAATCGAGGCTAATCCTGATCTTGTCCCTATC |
| | | AATGGCTATGGTCCGACAGAGAATACGACCTTCTCCACCACCTACAAGATTCTGGGTCGTGCCGAAGGGGTCGTGCC |
| | | GATTGGCCGCCCAATTAGTAATTCTACCGCTTATGTGGTCAATGGATCGCTGCAATTACAGCCTATTGGTGCTTGGGG |
| | | TGAACTCATTGTCGGCGGTGAAGGTGTAGCGCGCGGATATCTCAATCGTCCTGATCTCACAGCAGAGAAATTTGTTCC |
| | | TAGTCCTGTGAAGGACGGAGAACCCTGCTACAGAACTGGGGATTTGGTACGCTGGCTTCCAGATGGGAATTTGGAGT |
| | | TTAAAGGAAGAATTGATGAGCAGGTCAAAATACGTGGTTACCGCATCGAACTCCCTGAAATCGAGGCCCAACTGGCC |
| | | AAGATGGAGTCAGTAATCGACGCCGTAGTGGTCGTTCGCGCGGATGAGCTTGGCGAGAAGCAACTTTGCGCTTATTA |
| | | TGTGGCGGATCGTACGCTCACGGCAGGCGAAGTACGTCTTTCCCTATCGCAGGTACTTCCAGGCTATATGATTCCATC |
| | | CTACTTTATCCAGATGGATCGTATGCCATTAACGTCAAACGGAAAAGTGGACCGGAGGTCTCTGCCGGCTCCTCAAGT |
| | | AGGCGCGCATACAGGACGGAAGTATACAGCTCCTCGTACACCGGCTGAGGAAGCTTTGGCATCTGTCTGGCAAGGGG |
| | | TGCTGGGTGCCGAACAGGTGGGTATCCATGACAATTTCTTTGAATTGGGCGGAGACTCCATAAAAGCTATTCAGGTGT |

TABLE 5-continued

Nucleotide sequences of genes encoding the fusaricidin synthetase (fusA) in *Paenibacillus* sp. strains NRRL B-50374, NRRL B-67721, NRRL B-67723, and NRRL B-67724.

| Strain | SEQ ID NO: | Sequence |
|---|---|---|
| | | CGTCACGGTTACTGCAGGCCGGCTATCGGTTAGAGATGAAGCAGCTGTTCAAATCGCCAACCATTGCCGAGCTAGGC<br>GCGGAAATTCAAACGGCTGTGCATATGGCTGAACAGGGAGTTGTGCGTGGAACGACTCGCTTGACTCCAGTCCAACA<br>GTGGTTCTTTGGACGGAAGCAGGCAGAGCCTCATCACTTCAATCAAGCGGTTATGCTGTATCGTGAACAGGGATTTGA<br>GGAAAAGGCCTTGCATCAGGTGCTAAGAAAACTCGCTGAGCATCATGACGCCCTTCGCATGGTTTTCCGTCAGACAG<br>AGCATGGCTACGAAGCTTGGAATCGTGATCTTGAAGAAGGAGAGTTGTATAGCCTATTCACCGCTGATTTACGGAAT<br>GAATCCGATCCGACTGTAGCCATTACATCGCTGTCGGATGACATTCAGTGCAGTATCAATCTGGCAGAAGGTCCGCTG<br>CTGAAGTTAGGACTTTTCCATTGTCAGGATGGAGACCACCTTCTGATCGTGATCCACCATTTGGTGGTGGACGGAGTA<br>TCCTGGCGGATTTTGTTCGAGGATATTGCAGCAGGTTATGAGCAGGTGATTCAAGGACAAGCGCTGACATTCCCGCA<br>GAAGACGGATTCCTTCCGTGATTGGGGAGACGCCCTTGCTCGTTATTCGGAAGGTCCAGAAATGGAGACTCATCGGG<br>CGTATTGGAGAGAGCTGGAGGATCAGCCACTCGAACAGTTGCCGAAGGATGAGGCTGTGGAAAGCCTTCTTGTACAG<br>GATAGCAAAGTAGTAACAGCACAATGGACTCTAGAAGAAACCGACCAATTATTGAGAAAAGCCCATCGTGCTTATCA<br>AACAGAGACGAATGATCTGCTATTGACTGCTCTGGGCATGGCGGTATCCAAATGGTCTGGCATCGGAAAGGTTGCTG<br>TGAATCTGGAAGGACACGGTCGTGAGCCGATTATACCGAATATCGACATCACCCGTACCGTAGGCTGGTTTACAAGT<br>CAATATCCGGTGATTTTAGACTTGGGGAATAACCCGGAAGTGGCCTCCTTGATCAAGTCTGTGAAAGAAGGGCTGCG<br>CCGAATTCCGAACAAAGGTATTGGCTACGGGTTGCTCAAAACGATGGCAAGTCAGTTGGATGAAGGCAGCTTCAGCT<br>TGCAGCCTGAGATTTCTTTTAACTATCTGGGGCAATTTGATCAGGATTTGCAAGGAAGCTCGTTGCAGATTTCTCCTTA<br>TCCGACCGGAAGCGCGCAAAGCTTGTTGGAGGAACCGGCCTATACGCTAGATATCAATGGCATGGTGACGGACGGA<br>GCCCTGACTCTGACGATTACTTATAACGGAAAACAGTATAAGTCATCTACGATGGAACAGCTCGCTGGATATATTGA<br>AGAAAGCCTGCGGGAACTTCTCCAGCATTGCGTAACCCAAGAAAAAACCGTATTGACACCAAGCGACGTGCTTGCGA<br>AGGGTCTGAGCATTGCCGATCTGGAGGAGCTTTCTAAGCAGACGAGTCACATTGGCGATATTGAGAATGTATATAGT<br>CTGACGCCAATGCAGAAGGGCATGCTGTTCCATGATATGTTTGAGCCGCATACAGGTGCTTATTTTGAGCAGGCCGCT<br>TTTGATTTTAAGGGTAGCTTTGATCCGATCGCCTTCGGGCACAGTCTGGATGCAGTAGTGGAGCGTCATGCTATCCTG<br>CGCACGAACTTTTACAGCGGATGGGGCAGCGAGCCTTTGCAGGTTGTATTTCGGCACAGAGGCGCTAAATTGGTGTA<br>CGAAGACCTGCGGGAGATGAATGCATCGCAGCGCGAAGCTTACCTGAAGACATTTGGTGCTAAGGACAAAGCACTG<br>GGCTTCAACCTAGCTGAAGACGAGCTTCTCCGTGTATCCATTTTACAAACAGATGAAGAGAGCTTCCGTCTCTTATGG<br>AGTTTTCACCACATCGTCATGGATGGGTGGTGTGTTCCGTTAATTACGCAGGAGGTATTTGAACACTATTTTGCCCTCC<br>TGGAAGGTAGAGAGCCGCAGTTGGCAGAGGTTCATCCGTACAGTCGATATATCGAATGGCTCGAACAGCAGGATGA<br>AGCAATTGCGTCCAACTATTGGAGCCGATATCTGGCCGGTTACGAGCAGCAGACGCTTTTACCTCAAGTCGGTGGAG<br>CAAGTAAGGGAGAAGGCTATGTAGCAGAAAAGCTGAATTATCCTCTCAGCAGGGAATTGACTGAGCGCCTTGAAAA<br>GGTGGCCAGGGATGCTCATGTCACGATGAATATATTGCTGCAGTCCCTCTGGGGCATTGCGCTTCAACGCTATAACGG<br>TAGCCGAGATGTCGTGTACGGAAGTGTAGTATCAGGCAGACCAGCAGAAATTCCGGGCATTGATCGGATGATCGGTT<br>TGTTCATCAATACGATTCCCGTTCGTGTGAAGACAGAGGAGAATCTCCCCTTCACAGTTCTGATGAAGCAGCAGCAGG<br>AACAATATATGGCTTCTCATATGTATGACACCTACCCGTTGTTTGAGATTCAGGCTCAGACGGATCAGAAGCAGGATC<br>TAATCTCCCACATTATGGTGTTTGAGAACTATCCTGTGGAGGAGGAGGTAGAGCGTCTGGGTGGTGGCGAGGCTGCC<br>TTTGAGATTGAGGAAGCGGAGCTTCTTGAGCAAACGAATTATGATTTTAATTTAATTGTCCTCCCTGGCGAAGAAATG<br>AGATTGCTGTTCCAGTACAATGCACTTGTTTATGACCCAGTGACAATTGAGCAAATCAAGGGCCATCTGGTTTACCTC<br>ATGGAACAAATTGTAGAGAACCCTGCCATTTCCGTGGATGCACTAGAATTAGTCACGCCGCAGGAGAGAGAACAGAT<br>TCTGAACGTATGGGGAAATACAAAAGGCATTTACGAGCACTGTAACACGTTCCACGGGCTGTTGGAGGAACAGGCGG<br>GACGAACGCCGGATGCGACTGCCCTTTGGTTCGAGGACAAGAGTCTGACCTATGCCGAGCTCAATGCAAAAGCCAAC<br>GGACTGGCGAGAAGGCTCCGTACTCAGGGAATCAAGACGGGAGATCTGGTGGGACTGATTGCTGAACGGTCGCTCG<br>AAATGATCGTTGGGATCTACGGCATTATGAAAGCCGGGGGTGCCTATGTTCCAATCGATCCAGAGTATCCGAAAGAA<br>CGAATCAGTTACATGCTTGAAGATTCCGGGGCGAAGCTGATCCTTACACAGGCCCATCTCTTGGAGCATCTCGGATGG<br>ACGGAAAATGTTTTGCTGCTGGATGAATCATCGACCTATGATGCCGACACCTCGAATTTGGAGGCTACTGCTGGCCCG<br>GATGATCTGGCTTACGTGATCTACACTTCAGGTACGACGGGTCAGCCTAAGGGCGTATTAGTCGAGCATCGGGGACT<br>ACCGAATCTTTCGGACGTATACGGGACACACTTCGAAGTTACACCGCAGGATCGGATCGTTCAGTTTGCAAGTCTGTC<br>GTTTGATGCATCGGTTTCGGAAATTTTAACGGCGCTGAGCCACGGGGCTGCTCTGTGCATCCCTTCTACACAAGATAT<br>TTTAGATCATGCCCTGTTCGAGCAGTTCATGAACGATAAGGGGATTACGGTAGCGACTTTGCCACCCGCTTACGCTAT<br>CCACCTTGATCCAGAGCGTTTGCCAACACTGCGGTGCCTGCTAACCGCTGGATCGGCCGCATCCGTCGAGTTGATCGA<br>TGAGTGGAGGAAGCATGTACGTTACTCTAATGGCTATGGCCCAACAGAGGACTCCGTATGCACCACAATCTGGTCTG<br>TCCCGGACAGTGAGGAAGCAACGGATATTGTATCTATTGGGCGACCTATTGCTAACCACAGTGTGTACATCTTGGATG<br>ACCATTTTAGATTGCAGCCTGTCGGTGTAGCTGGAGAGCTATGCATTTCGAGTATCGGGTTAGCACGGGGGTATCATA<br>ATCGGCCTGAGTTAATGGATGAGAAGTTCGTGGACAATCCGTTTGCTCCAGGAGAGCGCATGTATCGGACGGGTGAC<br>CTGGTTCGCTGGTTACCGAATGGAATCATCGAGTACTTAGGTCGAATAGATCACCAAGTCAAAATCCGCGGTTACCGT<br>ATCGAGCTGGGCGAGGTAGAAGCACAAATGCTCAGAGTGCCGTCCGTTCAGGAAGTCGTAGCCATGGCTGTAGAGG<br>GCGATGACGGCTACAAAGATCTAGTAGCTTACTTCGTAGCCGCTCAGAAACTTGAGGTGTCCGAACTTCGGACTGTTC<br>TGTCGGAGATGATACCTGGATATATGATTCCTTCCCGCTTCATACAACTGGAGGACATGCCTTTGACGTCGAACGGAA<br>AAATCGACCGAAAAGCGCTGCAGGGCGAGCGTGGATGGGCAGTGGCTTCATCTGAGGCTCCAAGGACACCTGTGGA<br>AATTCAATTAGCTGAAATCTGGCAAGAGGTGCTGGGTGTAGAGAGCGCGGGAGTGAAGGATAATTTCTTCCATTTTG<br>GAGGTCATTCACTGCGTGCAGCCCTGCTAGTCTCACGAATTCGCAAGGAAATGAATCGCGAGATTAGTCTGAGAGCA<br>GTGTTCGAGTCTCCTACTATTGAAGGATTGGCTCGTGCCATTGAGGGCTATACACCGCTGAATTTCGAAGAAATTCCT<br>ACAGCGGGAGCGAGAGAGCATTATCCATTGTCCTCGGCCCAAAAACGACTGTTTATTCTAAGTCAGCTGGAAGGTGG<br>AGAGCTGAGCTACAATATGCCGGGGGTCCTTACCGTTGAGGGAGCTTTGGATCGGGAACGGCTAGAGCAGGCATTCC<br>GTCGTCTGATTCATCGTCATGGTTCGCTGCGTACTCGCTTTGTGACCGTGAACGGTGAACCTGTACAGCAGCTCCTGA<br>CAGATGTTCCGTTTACTGTGGAATATGCGGAGTTGAGCGAGGAAGAGGCAGGAGCTACCCTTCAGCAGTTTGTCCGC<br>CCTTTCGATCTAGGTGTAGCTCCATTGCTGCGGGTTGGCCTTATTCGAATTGCACATGAGCGCCATTTACTATTGTTTG<br>ACATGCATCATATTGTCTCAGATGGGGTTTCTATGAATATTCTCATAGAAGAGTTTCTCCGCTTCTACCAAGAGGAGG<br>ACGTATTTCCTGAGCTACAGATCCAGTACACAGACTATGCTGTATGGCAGCAAGAGCAGCTCGAAAGCGAGCGTCTT<br>AAGGCCCAGGAGGCTTACTGGCTGGATGCTTTCCGTGGAAGCTTGCCAGTGCTGGATTTGCCAGGAGATGAAGTTCG<br>TCCTGCGGTGCGAAGCTTTGCGGGCGATCGAATCGACTTCCAAATTGATTCTTCTCTGAGTGCTTCACTTCAGGAGCT<br>GGCTACCCGGACGGGTTCCACTCTGTTCATGGTACTGCTGGCAGCCTATACAGCGCTCTTGCACAAGTACACAGGTCA<br>GGAAGATGTCATTGTCGGTTCACCTGTGGCAGGAAGATCTCATGCGACACTCGAAGGCCTCATCGGTATGTTCGTCGG<br>CACAGTGGCACTTCGTACTTATCCAGAAGGAGAGAAGCCTTTCGAGGCTTATCTGCAGGAAGTGAAGGAAACAGCGC<br>TGCGGGCCTATGAAAACCAGGATTACCCGTTCGAGGAGCTGGTAGAAAAGCTGGAGCTTCAGCGTGATTTGAGCCGT |

TABLE 5-continued

Nucleotide sequences of genes encoding the fusaricidin synthetase (fusA) in *Paenibacillus* sp. strains NRRL B-50374, NRRL B-67721, NRRL B-67723, and NRRL B-67724.

| Strain | SEQ ID NO: | Sequence |
|---|---|---|
| | | AACCCACTATTTGATACCATGTTTGTCCTGCAAAATATCGAGCAGGGAGAACAAGAAATAGAAGGATTGCGCTTCAC |
| | | TCCTTACGATAATGTACATCCGGCTGCCAAGTTCGATCTTACGCTGACCGTGAGTGAAGCAGACGGGGCATTGAATTG |
| | | CACGCTTGAGTATGCGACTGCGATCTACAAGCAAGAGACTGCTGAGCGGATGGCAGGCCACTTTGTACAGCTTATTC |
| | | GGGAAGCCATCGCCAATCCCGCACTGCCGTTGTCATCCCTTGATATCGTGACACCTCAGGAAAAATCAAGGCTGATG |
| | | AAAGCGCCGGACGAAGCCAAGGCAGATTATCCTCGTGACAAGACGATCCATGCGCTGTTCGAGGAGCAGGCCGCAC |
| | | ATACTCCGAATGCAGTGGCAGTCGTATGTGAAGATGCGACCCTGTCCTACAGCGAGCTGAACGAGCGGGCCAATGGA |
| | | CTTGCCCGAACGCTGAGGGAACGTGGTTTGCAACCAGACGGTTTGGCTGGAATTATGGCGGATCGTTCCCTTGAAATG |
| | | GTGGTCGGAATTTTAGCCATCTTGAAGGCAGGCGGGGCCTATGTCCCTGTAGACCCTGAATATCCAGAGGACCGCATT |
| | | CGCTTTATGCTTGAGGATTCGGGAGCCAAGCTACTGCTGACACAAGCGCATCTGGAGCAACGGGTCTCCTTCGCCGG |
| | | GGATATCGTAAGTCTGGACAAAACGGCTTCCTACAAGGAGGATGTCTCAAACCTGCAGCCTGCAGCTGGACCGGAGC |
| | | ATCTTGCCTACGTCATCTACACATCGGGTACGACAGGCAAGCCAAAGGGAACACTGATTGAGCATAAAAATGTAGTT |
| | | CGCTTGCTCTTTAATGATAAAAATATGTTTGACTTTGGTCCTCAGGATACGTGGACACTGTTCCATTCATTCTGTTTTG |
| | | ACTTCTCTGTATGGGAAATGTACGGAGCATTGCTAAACGGAGGACGGTTGGTCATCGTTCCATCGCTTACCGCGAAGA |
| | | GTCCAGATCGTTTCTTGCAATTGCTTAAGGATCAGAAGGTCACCGTTTTGAACCAGACACCGACGTATTTCTACCAGT |
| | | TGCTACAGGAAGAGCTCGGTCATCAAGCGGCAGAACTGAGCCTCCGCATGATTATCTTCGGTGGAGAGGCATTAGCC |
| | | CCGGCCCTGCTCAAGGACTGGAGAACGAAGTATCCGCAAGTGCAGCTCATTAACATGTACGGCATTACCGAAACGAC |
| | | CGTGCATGTAACCTACAAGGAAATTACAGAGTTGGAAATTGAACAGGGCCGTAGCAATATCGGCACCACGATTCCGA |
| | | CGCTGCGAGCGTACATTTTGGATGAACAACGCCGTCCACAGCCGATTGGCATTCCAGGTGAACTCTATGTGGCGGGC |
| | | GTAGGTCTGGCGCGAGGTTATCTGAACCGACCGGAATTGACGGAAGAGAAGTTTGTCGCTCATCCGTTTGAAGCGGG |
| | | CGAGCGCATGTACCGCTCGGGTGACTTGGCACGCTGGTTGCCGGATGGCAGCATGGAGTATTTGGGACGGATTGACC |
| | | ATCAGGTAAAAATCCGTGGTTACCGTATCGAGCTGGGCGAAGTGGAAGCGAAGCTGCTCCATGCTCCGTCTGTAAGG |
| | | GAGGCCGTTGTGCTCGCCCGAGAGGATGGAAGTGGACAAAAAGTGCTTGTCGGCTATTTCACTGCCGATCAGATGCT |
| | | GACGGTAGGCGAGTTGAGAAAAGCCTTGGCTGCCGAACTGCCGACTTATATGATTCCATCTTACTTTATGCAATTGGA |
| | | ACAGATGCCTTTGACGCCAAATGGCAAGCTGGATCGCAAAGCGCTTCCGGCTCCAGAGGCCAATGTGCAGACTGGAG |
| | | CGGTTTATGAACCGCCAAGGACGAAGGCTGAGGAAGCCTTGGCTTCCGTATGGCAAGGTGTGCTGGGAGCGCAGCAG |
| | | GTCGGCATCCATGATCATTTCTTTGATCTGGGTGGTGATTCCATCAAGGCGATCCAAGTGTCCTCGAGATTGTTCCAA |
| | | GCCGGATATAAATTAGAGATGAAGGATCTCTTCAAATATCCGACAATTGCCGAGCTAAGCCCGTATCTTCAGGCAGC |
| | | CGGACGTACAGCGGAACAGGGCGAAATTAAAGGTGCAGCAGAGTTAATGCCAATTCAGCGTTGGTTCTTTGAACGCC |
| | | ATACAGCGGAGCCGCACCATTATAATCATGCCGTCATGCTCTATCGGAAAGACGGCTTTGATGAAGCTGCACTCCGGT |
| | | TGACAATGGACCAAATTGCGATCCATCATGATGCGCTGCGTATGGTTTTCCGGTCTACAGAAGCTGGGTATGTAGCTT |
| | | GGAATCGGGGAACGGACGAAGGCGAGCTCTACACATTGGACATTGCCGATATGCGGCAGGCGGAAGACCAGACAGC |
| | | TGCGGTTCAGGCCCAAGCCGATGCCATTCAGGCAAGTTTTGACTTGGAAGGTGGCCCACTGTTCAAGCTAGGCCTGTT |
| | | CCATTGTGACGATGGCGATCATTTGTTGATTGTCATTCATCACCTCTTGGTTGACGGCGTATCCTGGCGCATCCTGTTT |
| | | GAGGACATTGCAGCGGGGTACGAGCAGGCATTGAATGGACAAGCAATCGTCCTTCCACAAAAGACCGATTCGTATCT |
| | | TGTATGGTCTGAGCAAGCGACGAAGTATGCAGCAGGGCCTGCTCTGGACAAGGAGCGTGCATACTGGCAGCTGATCG |
| | | AAGAGGCGATTTTGGCCCCACTGCCGAAGGATGAGGATCAGAAGCCGGGCACCATCCGGGATACTGAATCGGTTACG |
| | | GTAACGTGGTCTGCGCAGGAAACAGACCTGCTGTTGCGGCAAGCGAACCGGGCGTATCATACGGAGACGAACGACTT |
| | | GCTCTTGACTGCTCTGGGGGCAGCCATTCAGCGCTGGACAGGCATGGAGCAGATTTTGGTCAATCTTGAAGGGCATG |
| | | GACGGGAAATGATCGTACCAGACCTGGATATTACCCGTACCGTCGGTTGGTTCACAACCCAGTATCCAGTTCTGCTGA |
| | | ACCTGCAAGGCGGACAGGAAGTATCTGCGCGCATCAAGCGCATCAAGGAGAATTTGCGAGAGGTTCCGCACAAAGG |
| | | AATCGGCTACGGTCTTCTGAAGTATATGGCACCGGAGAAAAGTGTCGGATTTGGCGTGGAGCCGGAAATTTCCTTCA |
| | | ATTATCTTGGGCAGTTTGATCAGGATCTGGAGGGTAATGCCCTTAGCCTATCCACACATTCAGTTGGTAAGGCGCTCA |
| | | GCGACCTCACACCACAGCAATATGCTCTGGATGTGAATGGCATGATTGCTGAAGGCCGGCTATCACTGACGATTACG |
| | | TACAGCAGCAGGCAGTATCGTAACGAGACGGTGAGTCATTTTGCTGAATTATTACAGTCAAGCCTTAGTGAGGTCATC |
| | | CGTCATTGTGTGGCTCAGGAGCGTTCACAGCTTACACCAAGTGATGTTCTGTTCCAAGGATTAACATTGGAGCAGCTT |
| | | GATCGACTCACGGCGCAGACGGCTCACATCGGAGAGATTGAGGATGTGTACAAGCTGACGCCAATGCAGAAGGGAA |
| | | TGCTGTTTCACAGCCTGCTGGAGCCGGACTCCTCTTCATACTTCGAACAGGCAACGTTTGAGCTGCGTGGTAGCTTCG |
| | | ATGTAGATATCTTCTTCGAGAGCTTCCAGGCTTTGGTGCAACGACATGCCATACTACGTACCGGATTTTACAACAACA |
| | | TTGCTGATGTACCGCTGCAAGTTGTCTTTAAGCAACGGTTAATCCCTCTGCACCACGTAGATTTGCGTGACGCATCTAT |
| | | GCAGGAACAAGAAGCCCGAATCAAGGCTTATATTGCTGAAGATATGGTTAAGGGGTTCAGCTTGTCAGAAGATCCGC |
| | | TGATGCGAGTGACCGTCTTGCAGAAGGATCAAAGCTGTCTTGTATTGTGGAGCTTCCACCATATTGTCATGGATGGCT |
| | | GGTGTATCCCGATCATTACACAGGAGCTGTTCGATTATTATTCTGCCAAGAAACAGCAAGCACAGCCTGTCCTACCGC |
| | | CAGCTCAGCCCTATAGCCGTTATATCGAGTGGCTTGATGCGCAGGATGATCAAGAAGCTTCAACATATTGGAGCCAA |
| | | TATCTTGAAGATTATGACGGGAACACCGTATTACCGGAAGGTAAAACGAAATCTCAAGCAAAAGAAGCGGGCTATGT |
| | | TCTAAAAGAGCATGTTCTCCATCTGGGTGCATCTTTGACAGGTAAAATGGATGTTGTCGCGAAGCGCAATCACGTAAC |
| | | CGTCAATACACTCATGCAGACAGCTTGGGGACTGATTCTTCAACGTTATAATGCCAGCTCGGATGTCGTTTTCGGCGG |
| | | CGTTGTGTCGGGTAGACCCGCTGAGATTGCAGGGATCGAAAATATGGTGGGTCTGTTCATCAATACAGTACCTATCCG |
| | | TGTACAGTCATCCAAAGACGAAGCCTTCGTCGAAGTGATGAAACGTACACAGGCACAGTCATTGGCTGGTCGTGCCT |
| | | ACGACACCTATCCACTGTATGAGATTCAGGGGAAAACAACCCAAAAGCAGGACCTGATTTCTCATATTATGATCTTTG |
| | | AAAATTACCCGCTCGACGAGCAGGTGGAGCAATCGGGTAATCAAACGGAGGACAATCTCGAAGTTTCCAACTTCACC |
| | | ATGTTTGAACAAACCAACTATGACTTTAACCTGGTTGTGATTCCAGGCGAAGACATCAAGGTCTGCATTCGCTATAAT |
| | | GCTTCGGTTTACGAGCAAGAAAGCATTGCACGTATCGGAGGACACTTGTTGCAGATGCTCGATCAGGTGGCTGCTCGT |
| | | CCGCAGGCGACGATACAGGAACTGGAGATTGTAACATCCGAGGAACGGATAAACCTGCTTGACTGGGGCGGCAAGG |
| | | CCCATACCTATCCAAGTGATCAGGGTCTGCATACCTTGTTTGAAGAACAGGTTGTCCGTACGCCGGATAAGATTGCGG |
| | | CTGTAAATGGGGACACTCAGATCACGTATTGGGAGCTGAACGAGCAGGCGAACAGACTAGCTTCCACCTTGATAGAC |
| | | CAAGGACTACAGAGTGAACAAGTGGTAGGTCTGTTGGCAGATCGGTCTGTAGAGCTGCTTGTCGCCATCATGGGTGT |
| | | ACTCAAAGCGGGTGGAGCCTATGTACCTATTGATCCTGAATATCCGCAGGAGCGGATTCAGTATATTTTGAAGGATTC |
| | | TGGCGCTGAAATCCTGCTCACACAGAGCCACCTAACGGAGTTGGCCTCTTTTGAGGGAACGGTTATGGAATTGGATTC |
| | | CCCGTACATCTACGGAACCGAGGTGGATAATCCCAATATTCCTGTTGGAGGAAACGATCTGGTGTACTTAATCTATAC |
| | | CTCGGGTACAACCGGAAATCCGAAGGGAACCATGATTAACCACAAAGGGATCGTGAACTACATCTGGTGGGCCAAT |
| | | AAGGTCTATTGTGCTGGAAAACCAACGGATTTCCCGTTGTATTCATCCATTTCGTTTGACTTGACGATGACATCAATGT |
| | | TTACTCCGTTAATAAACGGAGGAATAGTACGGATTTATGATGGTATAGATAAGGCAGAGGTCGTTCAGCATATTTTGC |
| | | GCGAAAATGCGGTCGATATTCTCAAGCTGACGCCGACGCATCTCAGTCTCATAAAAGACATGACCATTCCAGCAGAA |

TABLE 5-continued

Nucleotide sequences of genes encoding the fusaricidin synthetase (fusA) in *Paenibacillus* sp. strains NRRL B-50374, NRRL B-67721, NRRL B-67723, and NRRL B-67724.

| Strain | SEQ ID NO: | Sequence |
|---|---|---|
| | | AGTCGCATTCAACAGCTCATTGTGGGTGGAGAGAATTTGACCACACATTTGTCCAAAACGATTACCGATCTCTTTGGT<br>GGCAACATCAAAATCTACAATGAATATGGACCAACCGAAACGGTCGTCGGCTGCATGATTCACCTGTACAATCCTGC<br>GAAGGATACGCGTGAATCTGTACCGATTGGGTTGCCAGCAGACAATATATACATCCATATTCTGGATGAACAGCTTC<br>GTCTCGTACCGTTAGGCGTGGAGGGTGAAATGTACATCGCCGGGGACGGGGTAGCCCGTGGATATCTGAACCGTCCT<br>GAGCTTACCGCAGATAAATTCATTAGAAATCCGTTCGCTTCGGAAGGAAATATGTATCGCACTGGGGATTTGGCTCGT<br>CGCCTTCCTAATGGAGACATTGAGTACATTGGACGCATTGACCACCAAGTTAAAATACGGGGCTATCGTATTGAGCTT<br>GGTGAGATTGAGGCCAAGCTGCTGGACATTCCACTTGTCGAGGAAGCTCTCGTTGTTGCGTGGACAGATGCTCATGG<br>GCAGAAATCGCTGTGTGCTTACTTCGTAGCTAATCGCGAAATGTCTGTCAGCGAGCTGAGAGACGAACTGTCTGCCG<br>GACTGCCTGCATATATGATTCCGTCTTACTTCGTCCAACTGGACGTGATGCCTCTGACACCGAATGGTAAGCTGGATC<br>GCAAGGCACTGCCTGAACCGAACTCGGGTATAAAGGCGGGAGCAGACTTTACCGCTCCGCGCACGGATGTGGAGAA<br>CATTTTGGCTTCAATCTGGCAGGGTGTACTCGGCGTGCCGCTTGTCGGCATTCATGATAATTTCTTTGAGCTTGGAGGT<br>GACTCGATCAAATCCATTCAAGTATCCTCAAGGCTTCTCCAAGCAGGCTATAAGCTTGAAATGAAGGATTTGTTCGGT<br>TATCCGACAATTGCAGAGCTGGCACAGCGCGTTAGTGTGGTCAGCCGAATTGCGGACCAAAGCGAGGTACACGGAGC<br>GGTAAGACTGGGACCTGCTCAGCACAGATTCTTCGATGAACAGTCGATGGATCTGCATCACTTTAATCAGTCGGTCAT<br>GTTGTACCGACGGGATGGCTTCAATACCGATGCGCTCGCCGAGGTTGTTCGGAAAATTGCAGAGCATCATGATGCTTT<br>ACGACTGGTGTTCCGCCAAGGAGAGCAGGGATTGGAGGCCTGGAACCGGAGCATGGATGAGGGTGAGCTCTATAGC<br>CTCCAGATCCACGACCTGCGGGATGAGACAGACCCGGCTTCAGCAATAGAAGCAGGTGCGGAAGCCATTCAGCGCA<br>GCATCTCTCTGGAGGATGGACCTCTCTTTAGACTGGGTCTGTTCCGCTGTGCGGAAGGTGAACATCTGTTGATCGTTA<br>TTCATCATCTGGCTGTGGATGGCGTATCCTGGCGTATTCTCTTTGAGGACCTGCAGGATGGCTACGAGCAGGCAGCAC<br>GTGGAGAAGCGGTCAAGCTTCCACAGAAGACGGATTCGTACCGTGCATGGGTTGAGGGAATCACACAATTTGCGAAT<br>AGTCTGGCGGCTGAACAAGAACGCAGCTATTGGGCAGAGGTAGAGGGAGATGGCTTTGTCCCTCTTCCCAAAGACAA<br>GGTAGACGGCGCTCTTCTCATCAAAGACAGTGAGGCTGTCACGGTGAGATGGTCACCAGAAGAGACAGAGCAGTTCC<br>TGAAAGAAGCGAACCGCACTTACAATACGGAGGTCAACGATCTGCTCCTGACGGCTCTGGGTATGGCTGTTCACGAG<br>TGGACGGGAATCGAACGTGTAGGCATCCTTCTGGAGGGACATGGACGGGAGCCTGTTGTGCCGGAACTGGATATTAC<br>TCGCACAATAGGCTGGTTTACAAGTCAATACCCTGTCGCCCTTGAGATGGGAGGGGAATTGGAGATCGGCGCCAGAA<br>TCAAGCACGTCAAGGAAGGCTTGCGTCGTATCCCGAACAAAGGTGTCGGATATGGTATTTTGAAATATTTAAGCGAC<br>GGTTCCGATATCTCCTCCTTCTCGGCTGAACCGGAGATTACCTTCAACTACTTGGGACAGTTCGACCAGGATCTTGCA<br>GGAGGGATGATGGAAGTATCGCCTTACTCAGTAGGACCTGAGGTCAGTGAGCAGATGGTGCAGCATCAGGCATTGAA<br>CATTAATGGACTGATTGCCGAAGGACAGCTTCAACTTTCGGTCAGCTATAACCGTCATCAGCTCGACGGGGAGTCCGT<br>GGCTAAGTTTGTTGGCATTCTGAAGAACCGTCTTAGCGAAGTTATTGGACATTGCGTAAGTAAGGAAAGAACAGAAC<br>TTACACCAAGCGATGTACTCCTCAAAGATATCAGCTTGGAAAAGATTGAGGAGTTAGAAGAGCAGACACGGCATATC<br>GGCAGTATTGAAAATATGTATAAACTGACGCCGATGCAAAAAGGAATGTTGTTCCACAGCTTGCTGGAGCCTCATTC<br>GGAAGTCTACTTTGAGCAGGCCAAATTTGAAATTCAGGGAGCATTCTATCCTGAGGATTTCAAACGCAGCTTAAAAT<br>ATCTGATGAAACGGCATGCCATATTGAGAACGAATTTCCATGCCGGGTGGGGCGATTTCCCTATTCAGATTGTGTTCA<br>AAGAAAGAGCGTGTGACTTCGTATACGAGGATCTGCACGAGCTGGAAACCGATGAAATTCAAGCGCGTCTTGCAGCT<br>TATACTGCTCAGGACAAAGCAAGAGGCTTTAATCTTGCTGAAGAAGCATTGCTGCGTGTTGCTATTCTACGTACAGCA<br>GAAGAGGCTTACCATCTGCTGTGGAGCTCTCATCACATCATTTTGGATGGCTGGTGTATGCCGCTTGTGCTCCAGGAA<br>GTGTTTGAGACGTATGGGGTTCTGCGTGAGCAAAGGGAGCCTGAGCTTCCTGCAGCTGTATCGTACAGCCAGTATATT<br>CAATGGTTGGAGAAGCAAGGCGAGGAAGAGGCATCCTCTTACTGGAGAGGGTACCTGGAAGGCTACGAGCAGCAGA<br>CGAAGCTGCCACAAGCCATCACACAGCCATCAGCAAAAGCAGAAGCCTATGTGTCGGAGAAGCTAGTATTCACGTTG<br>GATGCGGAATTGACCGATCGCCTGGAACAGGTGGCCAAACAGCATCAGGTGACGATGAATACATTGATGCAAGCAG<br>CCTGGGGAATCGTGTTGCAGCGCTACAATAGAAGCCAGGATATCGTCTTCGGAAGTGTAGTATCGGGGAGACCTGCC<br>GAGATTCCGGGTATCGAAAGTATGATCGGTCTCTTTATCAATACAGTTCCGGTTCGGGTTCAGGCCGAGGGAAGTGAT<br>TCGTTCTCCCATGTGATGAAAAGACAGCAGGAATTATATTTGGCAGGACATGCTTATGATTCCTATCCGCTCTATGAG<br>ATTCAAGCACAGAGCGAACAAAAGCAAGATTTGATTTCTCATATTATGGTGTTCGAAAATTACCCGGTAGAAGAGCA<br>TCTGGAAGAGAAAATTGCTAGTGAAGAGGCTGAATACAGAATTACGGATGTTCAGATGTTTGAACAGACGAATTATG<br>ATTTTAACCTCATTGTGCTGCCGGGCCGTAATCTGGAGTTCTTGTACCGTTACAATGCCCGCGTCTATGATCGGGAGA<br>GCGTGGAACGCATTCAAGGACACTTGACGAGAATTCTGACAAGCGTTGCTGTTCAACCTACCATCCGTATTGATGAGC<br>TGGAGTTGATCACCCCAGAAGAGAAATCGCAGATTATAGAGGTGTGGGGCGATACAGCAGCTCCTTATCCGCGTGAG<br>CAGACCCTTCACGGTATATTTGAGGAAAAAGCAGCGCTCACACCGGATCGTACAGCACTTATTTACGGTGAAACGGA<br>GCTTACCTATGGAGAACTCGATCAGCAGGCGAACCGTCTCGCACGTACGCTGCGTGCCCAAGGGGTCAGACCGGACC<br>AACCAGTCGGCATCATGGTCGAGCGCTCGCTTGAGATGATCATTGGTATTCATGCCATTCTAAAAGCTGGCGGGGCCT<br>ATGTACCGATTGATCCGGAGTTCCCAGAAGATCGTATTCGCCACATGCTGGAGGATTCGGGAGCGAAGCTTCTGCTG<br>ACGAAGAACCATCTCCAAGATCGTTTTCCGTTCACTGGTACGATTCTGGCACTTGATGATCCGCAGGCGTATCATGCG<br>GATAGCTCGAAACTGGAGCCAATTGCGGGGCCGGAGCATCTGGCGTATATCATTTACACGTCAGGTTCAACCGGCAA<br>GCCGAAAGGGGTAATGATTGAGCATCGCGCTGCCGTCCATACGCTGAGTCAGTTGGAAGCTGAATATCCGATGTTGG<br>CAGGCGACCGTTTCCTGCTCAAAACGACATTCACCTTTGACTTCTCCGTGCCGGAGCTGTTCTGCTGGTTCTTTGGACA<br>AGGGACTCTCGTGATCCTGCCACAAGGCGTGGACAAAGACCCGATGGCACTGCTAGAGGCCGTGGATACGAACCGTA<br>TCACGCATCTCAATTTGGTGCCGTCGATGCTCAGTGTGCTCGTTCAATACTTGAAAGAAAGCGGCAACCAAGGATTCC<br>TTACTCTGAAATACCTGTTTGCCTGCGGCGAGACGCTGCCTGCCAAACTTGTGGAAGAGTATTATAAAGTATCTCCTT<br>ACGCAGTACTGGAAAACATCTACGGTCCTACGGAAGCAGCCGTATATGCGACTCGGTATACAACGAGCCTTGAGACT<br>GCGGCTCTAACGCATGTGCCGATCGGCAAACCGTACGCTAACGTCCAAGTATGGATGATGGACAGCGCTTCTCAGGT<br>ATCACCTGTGGGGGTACCGGGAGAACTCTGCATTGCGGGCGAAGGGGTAGCGCGGGGGTATTTCAACCAGTCGGACC<br>TGACGGCAGAGAAGTTCATTCCTCACCCGTACAAACCGGGAGCACGAATTTACCGAACGGGCGATTTGGCCCGATGG<br>CTACCAGACGGGAATATTGAGTATTTGGGGCGGATCGATCACCAGGTAAAAATCCGCGGTTACCGCATTGAGCTGGG<br>AGAAGTGGAAGCACAAATTCTGAAGGTGCCATCGGTGCAGGAAGCGGTTGTTCTAGCACTGGCTGACTCCACCGGAA<br>GTACTCAACTTTGTGCATACTTTGTGGCCGAAGAGGGGCTTGCAGCGGGCGTGCTACGCGAAGTACTGGCCAGCGAG<br>CTGCCAAGCTACATGATTCCGACTGCTTTCGTACAGTTGGCACAAATGCCGCTGAATCCGAATGGCAAATTGGATCGC<br>AAAGCGCTACCGGCACCGGAAACACTTCTGCGGAGCACAGCGGAGTATATCGCGCCGCGTACGCAGACAGAAGTAG<br>AGCTCGCTCAGATTTGGTCCGAGGTGCTCGGCGTACAGGAAATCGGGATCAGAGATCATTTCTTCGAACTTGGGGGC<br>CATTCCCTGAAAGTATTGGGCTTGATCCAAAGGATTTCGTCCGGTATGGGCGTCCAGCTACCACTCCAAGTCGTGTTT<br>AATCTGCCGACTGTGGAAGAAATGGCGCATGAAATATCCAAGTTGCAGGCAACAACTGCTGCTAATGAAGAGGAAA<br>TGGAAATTATCCGCTTCCCAGGGAAAGGAACACTCAAAGTGTTTTGCTTCCCTCCACGGGTAGGCCACTCTCTGGGGT |

TABLE 5-continued

Nucleotide sequences of genes encoding the fusaricidin synthetase (fusA) in *Paenibacillus* sp. strains NRRL B-50374, NRRL B-67721, NRRL B-67723, and NRRL B-67724.

| Strain | SEQ ID NO: | Sequence |
|---|---|---|
| | | ACTATGAGATGGCCAAGGAGCTGGAAGGGCTTTGCGAGGTGTACGGGATGGAATTTATCGGCGATCGTTTCCAGGGC<br>CAAGATATGCTGGATCGATACATCGATGCCATCGTGGATATTCAAGCAGAGGGCCCGTATATATTCCTGGGATACTCA<br>CTTGGAGGAAATCTCGCCTTCGAGGTAGCTAAAGCCATGGAAAGCCGAGGTCACCATGTTAGCGACCTTATTATGGT<br>AGATGCTATGAGAAAGATGTCCAAGGATGAATCGACACCGGAGGAGCTTGAAGAGATTGTCGAGATGGTACTGGAC<br>AGCATTAGGGACCAGTACAAAGCATTCCTCGCCGATCCAGTGGACAGGGAGCGAGTCATGGACAAAATGTTGGTGTA<br>CTCCACCTACCGCGATGAGCTTATTAACGCAGGTGAAGTTCATGCGAATATCCATGCTCTGATTGCAGAGGATGATAG<br>TATTGGTCCGGATACATCATTAGATAAATTGTTATGGCAACAGGCGACACTTGGTCAATACAAAGAATACGAAGTCA<br>TCGGAACGCATGATGTGCTGCTTGATTCCGGTTTTATTGGGGAAAATGCTAAAGTACTGAGACAGATACTTGGCAAG<br>GTCACAGAGGCTTCATCTAATAACAAGCCCATTTTGTCCTAA |

TABLE 6

Nucleotide sequences of genes encoding an NRPS (triE) involved in the biosynthesis of tridecaptin in *Paenibacillus* sp. strains NRRL B-50374, NRRL B-67721, NRRL B-67723, and NRRL B-67724.

| Strain | SEQ ID NO: | Sequence |
|---|---|---|
| NRRL B-50374 | 5 | TTGAAAGCCTTATTTGAGAAGGAAAAAAATTACTGGAGTCATAAACTGGAATCTGAGGATCATATCATCTGCCTGCC<br>ATACACCAACCATGTGTCCAGAAGTACAACTGTAACGAGTTTAAATTCCCATACGTACACACTCACATTTCCAACTGA<br>AATTTCCCAAAGAATATCATCTATAACAGGTGGCGCTCCATGGGCCGTGTTTATGGTCCTGCTTGCTGGAGTAGAGAG<br>CTTATTGCATAAATACACAGGTGAGGAACGTGTGCTGCTGGGCATCCCGGTAGCCAAGTCTGGCAACGGTGCTACAA<br>AGCCGATCAACCATCTGCTTTTATTGAAAAATACGCTGGATTCCAGTACAACCTTCAAAGCTTTGCTGTCTCAAATCA<br>AAACCTCTGTCGGCGAAGCTATTGAACATCAAAACATTCCTTTTTGGAACTATTCTGAATTACTTGACATTCAACGTA<br>ATGAGGATGAAAAGCCTCTTATTCACACCACAGTATCCTTGCAAAATATTCATATTTCTGATTTTTTAAATCACGTACA<br>ATCTGAACTGGATTTCCAGTTTCAATGGGAACATGAAGCAGTCTCCCTGAACGTAAAGTATAGTAGCGACCGTTATAG<br>CGAGACGACGATTGAGCACTTTGTTGAGCAGCTTCTGCGGCTGTACACTATTGTTTTGCAGCAGCCAGAGTTGGCGAT<br>TTCCACAGCACAAGTACTGTCAGAGCAAGAAGTAGAGCAGCTGGTCCATACCTTCAACGATACAAATGTGGATTATC<br>CATGTCATGCGTCTATTCATGAATTGTTCGTGAAACAGGCGAAGCAGGCACCACAGCAGGTGGCGGTAGTGTGTGGG<br>CAAGATAGCCTAACCTATGCAGAATTGAATGAAAAGGCCAACCGACTGGCTCATTCTTTACGTAAGCAGGGAATCCG<br>CACCGAGCAGACGGTCGGCATTGTAGCTGAACGCTCGATCGAGATGATTGTCGGTATGCTCGGAATTCTCAAAGCAG<br>GTGGAGCGTATGTACCCATTGATTCTGATTACCCGGATGAGCGTATACGCTATTTGCTGCAGGATTCCGGTGCGGACA<br>TACTGCTCGTGCAGCGAATGGAACATCGGCCCACTGATTTTAAGGGAATGGTGCTTGACCTTAGCGATGCTGCAATTT<br>ATGGAACGGATGATGCTGATCGTTACGATCCAATTTTGCCGAATGATCACGGGACGAATACTGATCCGGGATACGTG<br>GACTGCCTAGATCCGTTCTACTCCATTTTCGCCAGTCCCGAACTTGCTTCTACGACAACCATACAACCAGAAACCATG<br>CAACCAAAAGCTACGCAATCAGAACAAGCAGAACAAATACAGCAGGCTTATGCAGCTGGAGAACAACCGAAGGCGA<br>GCGCAGCTGGTCGTTTGGCCTATATTATGTACACCTCAGGGACTACAGGCCAGCCCAAAGGGGTTATGGTGGAGCAC<br>CGTAATGTCGTGCGTTTGGTGACAAACACAAATTATGCACGCTTGAATGCCGACACGCGCATTTTGCAGACCGGGTCT<br>GTTGTCTTTGACGCGTCCACCTTCGAAATTTGGGGTGCGTTATTGAACGGTGGACAGCTGGTGCTGGTGAGTCAGGAT<br>GTTATTTTGGACGCTCCCAAGCTCAAGGAAGTTGTTCGCAATCACGGCATTACCACGATGTGGCTGACCGCACCACTC<br>TTTAATCAGCTATCCCAGCAGGACTTGGAACTATTTGAGGGGATGCGGGAGCTATTGGTTGGTGGTGATGTGCTGTCC<br>GTACCGCATATTAACCGGGTATTGGAGGCCCATCCGAATCTACATATCATTAACGGCTACGGTCCGACGGAAAATAC<br>GACCTTTTCCACCACACATGCCATTACCGGCGTTCAATCGGCATCTGTGCCCATTGGTAGCCCGATCCATAACTCGAC<br>GGCATATGTCGTGGACCGTTCGATGCAGCTTCAGCCTATTGGAGCGTGGGGGGAGCTGATCGTCGGCGGTGACGGGG<br>TGGCTCGCGGATATCGCAACCGCCCAGACCTGACGACCGAAAAGTTCATCGACAGCCCGTTCCGTGGCGGCGAACGC<br>TGCTATCGTACAGGGGACCTGGTGCGTTGGAATGCGGATGGGACGCTGGAATATAAGGGACGAATCGACGCGCAGGT<br>GAAAATTCGAGGCTACCGGATTGAGCTGGGCGAGGTGGAAGCACAGCTGTTGAAGCTGGAGGCAGTCCGAGAAGCT<br>GTTGTAATTGCACATGAAGATGAGCAGGGGCAAAAGCTGCTCTGCGCATATGTGGTCACCCATGCGGAAGTAGCGAC<br>AAGTGAGCTGCGTAGTGCTTTGAGTCAGGAGCTGCCGGGCTACATGGTACCGTCGTATTTTGTACAGCTGGAGCAATT<br>GCCACTGACGCCCAACGGCAAGGTGGATCGCCGAGCGTTGCCACAGCCAGAGGGAGGTGTAAGCTCAGGCGCAGAA<br>TATGTACCTCCTCAAAATCAATTACAAGCACAACTGGCTAGCATCTGGAAAGATGTGCTGGAGCTTGAGCGCATTGG<br>GATTAAGGATAACTTTTTTGAGGCAGGAGGACATTCCCTGCGGGCGACACATGTCATATCACTCATCTATAAGGAATT<br>GCATAAAAATGTGCAGCTAAAGGATTTGTTCCAGCATCCGACAATTGAACAGCTGGCGCAGGTTATTGAAGCACTGG<br>AGCAAACCACCTATGAATCCATCCCTGTTACGGAGAATAAGCCATTTTATGCGGTCTCTTCGGCTCAAAAACGGATGT<br>ATATCCTCAATCAGCTTGATGGAGCGGGAATTAGCTATAACATACCTGGTGCCCTGACTCTGACCGGTTCACTTGATC<br>ACAAGGCACTGGATAACGCGTTCCGTCAGCTTATTGAACGCCATGAAACATTGCGCACAAGTTTTGAGACCATGAAC<br>GGTGAACCTGTCCAGCGAGTGCATGACGAGGTTCCTTTTCGCATGGAATTGACCTATGCTCACGGAGCTGCCCCAAAG<br>GAAACGGATGAGCTGGTACATAACTTTGTTCAGCCGTTCGATCTGGGGCAAGCTCCGTTATTCCGAGTTGGTTTGATT<br>GAAACAGACCCAGAGCATCATATTTTGCTCATAGATATGCATCATATCATTTCGGACGGTACCTCTATAAATGTACTG<br>ATTCAGGACTTCATTCATTTATATGCAGGCGACACGCTGCCATCGCTGCGCATTCAGTATAAAGACTACGCCGCTTGG<br>CAACAGAAGCAGCAGCAAAGTGAACGCTACCGGGAACAGGAAAACTACTGGCTCAATACCTTCGCAGGAGAGCTAC<br>CTGTGCTTGATCTACCGACTGATTATTCACGCCCAGCGGTGAGAAGCTTTGAAGGAGATGTGCTGGAATTTACGCTTG<br>ACCAACGACAAAGTGAAGGCTTAAAAAGCATTGCGGTGCAGACGGAATCGACATTATATATGGTGCTGTTGGCTGCC<br>TATTCGGCTTTGCTTAGCCACTATAGCGGGCAGGAAGATATTATTGTCGGTTCGCCAATTGCAGGGCGGCCCCATGCA<br>GATCTTGGCAGTCTGATCGGGATGTTCGTGAATACACTGGCAATCCGTAATTATCCAGAAGGCGGGAAAACGTTCCG<br>CGAGTATGTGTTGGAGGTCAAGGATAACGCGTTAACAGCTTTTGAACATCAGGATTATCCGTTTGAAGAGCTGGTGG<br>AGAAGCTGGGCGTGGATCGAGATTTAAGCCGTAATCCGTTATTTGATACCATGTTTGCACTGCAAAACTTAGAGCAAA<br>AAGAGCAGCAGCTGGCGGGGTTGCAATTGGCATCCTATCCAAGTGAACAAACGACGGCCAAATTTGATTTGAGTCTG |

TABLE 6-continued

Nucleotide sequences of genes encoding an NRPS (triE) involved in the biosynthesis of tridecaptin in *Paenibacillus* sp. strains NRRL B-50374, NRRL B-67721, NRRL B-67723, and NRRL B-67724.

| Strain | SEQ ID NO: | Sequence |
|---|---|---|
| | | TTCGCAGTGGAGGATGGAGAACAAATTTCCTGTGCTCTTCAATACGGAACTCGGCTGTACAAACGGGAAACCATTGA<br>ACGACTGACTGAACATTTGCAGCAGCTTATCAATGCGGTTATAGAACAGCCGGATATCGTTCTTTCGGCTATTGAAAT<br>GGTTTCGGCCCAAGAAAAAGAGCTGCTTGTGCAGAGATTCAATGATACGGTAGCAGACTATCCGTATCCACGAGATC<br>AAGCACTGCATGTGCTGTTCGAGGAACAGGTAGTGCAATCACCAGATCGGCTGGCCGTCACCTTTGCGGACACGCAG<br>CTTACCTACCGCGAGCTGAATGAACGTGCCAACCGTCTGGCACGCATACTCGCTTCCCATGGGATACGGCGCGGGTCC<br>GAGCCAGAGACACAGCGAGTAGGGATTATGGCTGAACGCTCCATTGAAATGGTCGTCGGTATGCTGGCGATTTTGAA<br>GGTCGGAGGGGCTTACGTTCCCATTGATCCTGATTATCCTGAGGAGCGTATCCGTTATTTACTGGAGGATTCCAGTGC<br>TGGGCTGTTACTGTTACAGCGACGTGAGCAGATTCCTTTTGAACCCGGCATTCCGATCATCGATTTGAGTGATGAACA<br>GCGATGCAATAGCAAATCTGAATGTGACGCTCAGACGGATGGAACAATTGCGATTACAACAGGGGGATCTTCCTCCG<br>ATCTTGCGTACGTGATCTACACCTCTGGTACGACAGGCAAGCCGAAGGGCGTGATGATTGAGCACCGTAATGTCGTG<br>CGCCTAGTGAAAAACAAAAGCTATGCCATGCTTGATGAAAATACACGTATGCTGCAATTGGGCGCAGTTGTGTTCGA<br>TGCCTCCACATTTGAAATTTGGGGAACGCTGCTGAACGGGGGACAACTGTATGTGGTAAGTCATGACACTATTCTGGA<br>TGCCTCCAAGCTCAAGCAGGCGATTGACAAGTATCGTGTTAACACGATGTTCATGACCACGGCTTTATTCAATCAGTA<br>TTCGCAGCAAGAAATCGGAGTGTTTGCGTCCTTGAAGGAGTTGCTCGTGGGTGGTGATGTATTGTCTGTACCACACGT<br>CAATCGTGTGTTGAAGGAGTACCCGCAGCTTCGCCTGGCCAATATTTATGGGCCGACGGAGAACACCACCTTTTCCAC<br>CATCTATGACATTACAGAACCGCAAACCCAGGCTATTCCCATTGGACGTCCAATTGATCACTCGACCGCTTATGTGGT<br>CAATCGTTCGTTGAAGCTGCAACCTATCGGAGCCTGGGGAGAGCTGATCGTCGGTGGCGACGGCGTTGGGCGAGGAT<br>ATCTGAATCGGCCCGAGCTTACGGCGGAAAAATTTATTGAAAGTCCATTCCGGTCTGGAGAATATTGCTATCGTACAG<br>GGGACTTAGTGCGTTGGCGTGCTGATGGTGTACTGGAGTACAAGGGAAGAATGGATGAACAGGTCAAAATTCGCGGC<br>TACCGCATTGAACTGGGTGAAATTGAAACCCGTTTGTCCACGATTCCAGGTGTGAAGGAATCGGTTGTTACCGTGCGG<br>CAGGATGATCACGGACAAAAACAGCTGTGTGCCTATTTTGCAACAGACAGTGAATTGAGCGCCAGCGACTTACGTAA<br>CATTTTGTCGCAGGATCTGCCTGGCTATATGGTGCCGTCTTACTTTGTGCAGCTCTCCAGACTGCCTTTGACGCTGAAT<br>GGCAAAGTAGACCGCAGGGCACTGCCCGCACCTGAGCACAATCTCGATACAGGTATGGATTATATGGCACCTGAGAC<br>GGATGTCCAACAGGCACTGGCTACGGCTTGGGGAGCCATTCTTGGTATCCCGAAAGTCGGAATACAGGATAACTTTTT<br>CCATTTGGGTGGTGACTCCATCAAGGCCATCCAAGTATCGTCTCGCTTGTTTCAGGCTGGATACAAGCTGGAAATGAA<br>GGACTTGTTCAAATACCCGACAATTGCGGGACTAAGCACATATATTCAGCCTGTTAACCGAATAGCCGAGCAGGGCG<br>AGGTTACAGGAAATGTAGTGCTTACACCGATTCAGCGCTGGTTTTTTGAACAGCCAACGGGAGAACCACACTATTTTA<br>ACCAATCTGTCATGCTCTATCGTCAGGAAGGCTATGACGAACAGGCACTACGGCGGGCGATCCATCAGATTACATCG<br>CACCATGATGCATTGCGTATGGTTTTTAGTTTGTCGGAGAACGGATGTACAGCATGGAACCGCAGTATAGAGGAAGG<br>CGAACCGTACCATCTGGAGTGCTTTGACTATAATGACAGCGATGTAAACAAGCAAGATTTGGCGAAGATAATTGAAG<br>CGAAATGCAATGAAATTCAATCTGGTATTTCCCTAAGCGAAGGTCCGCTGATGAGACTGGGGCTGTTCCGTTGCCCGG<br>ATGGAGATCATCTGCTGGTCGTGATTCATCATTTGGCGGTGGACGGGGTATCCTGGCGCATTTTATTCGAGGATTTGG<br>CGACTGCCTATGATCAAGCCTCCAAGGGTGAACAGGTGATTCAGCTGCCTCATAAAACAGATTCGTTCCAAACGTGG<br>GCCGAGCAGCTGCACGCTTACGCCAACAGTCCAGCTATGGAACGTGAGCGAGCGTATTGGGGGAAACTTGCACAAGC<br>GGAACTGGCTCCTTTGCCGCAGGATTACGGGCATAACGAGCACGAAAAGCCATTGATTGGCGATAGTGAGTCGGTTA<br>CTGCTTTGTGGACACATGCTGAGACAGAGCAGCTGCTCAAGCAGGCCAATCGTGCCTACCGTACAGAAATTAATGAC<br>CTGTTGTTGACGGCGGTAGGAATGGCATTGCAAGCATGGAGCGGACATGAGCGTTTCCTGATTAATCTGGAGGGACA<br>TGGACGTGAAGTCATTTTACCAGAGGTGGACATTACCCGAACGATAGGGTGGTTTACAAGCCAATATCCTGTTTTGCT<br>CGATATGCCGGAAGAACTGGCACTTTCGCAACGGATCAAGGGTGTGAAGGAAGGACTGCGCGGCATCCCGCAAAAA<br>GGGATTGGCTATGGTGTACTGAAATATTTATCCGACCGTCAGACACAGGCACTGGAGGCATCTCCAGCCATATTTACG<br>ACAGATCCCGAAATCAGCTTTAACTATTTGGGACAGTTCGATCAAGATATGAAAGGGAACGACTTGCAATCATCCTC<br>ATATGAGGGTGGGATGCCGCTGAGCCCGACCATGGCTCGAACGTATACACTGGATTTTGGCGGCATCATTTCGGGAG<br>GCCAACTGGGTCTGACGATTAGCTATAGCCGTACCAGCTATAGACCGGAGACGATCGAGCGATTGGCGAAATTATTG<br>GAATCGAGCCTGCGTGAAATTTTGGAGCATTGCATCCATAAAGAACACCCGGAGCTTACCCCAAGTGATATTTCCTAT<br>AAAGGAATGAGTGTGGAGGGCTTGGACAGTCTCTTATCTGAAATGGGTGCTGCGGGTGAGATTGACAATGTATATGC<br>ACTGACCCCGATGCAGAAAGGGATGCTGTTTCACAGCCAGCTAGATAGTCAAGCAGCTGCGAATGACGCGTATTTTG<br>AGCAGGTTTCTTATGATATGCGAGGTCAGATGGACATTCGGGCTTTTGCAGAAAGCCTGAATATTCTGGTTAGGCGAC<br>ATGAGGCGCTACGTACACATTTTTATTTTGGCAGAGATACGGAACCGTTGCAGGTGGTGTATCGAAATCGGGATTGCG<br>GCTTTCAATATGAAGATTTACACCATCTAGATGAGGATGAAATAGATTCCTGGGTGAAAAATTTCAAGCTACAAGAT<br>AAAGCACGGGGCTTTGATCTGCGTCGGGATGTCCTGCTGCGTGTAGCGATTTTACGTACCGGAGAAGACAGCTATCAT<br>TTTGTATGGAGCTTTCATCATATCGTCATGGACGGCTGGTGTCTGTCCCTTATAAACAAAGAAGTGTTTGAAAGCTAT<br>GCAGCACTTCAGGAGGGCAGAGTACCAGAACTGGCACCGGCAGTGCCGTACAGCCGCTTTATTGAATGGCTGGAAGC<br>ACAGGATCGCAAGGCGGCAACCGACTACTGGAGTAGCTATTTATCCGGATATGAGCAGCAAACAGCGTTACCAGCTG<br>TAAAATCCGGTCGCAAGAGTGAAGGCAACACGGCTAGTGATTGGGTGACGGTTTTGGAACGTGAGTTGACCCTCCGG<br>GTGGAGGAGACGGCTAAGCGATATCAAGTGACCATGAATACGTTATTACAAACCGCATGGGGGATTGTGCTGCAAAA<br>ATATAACAACCACAGTGATGTCGTATTTGGCAGTGTCGTCTCAGGCCGTCCATCAGATATTATCGGGGTAGAGGATAT<br>TATCGGCTTGTTCATTAATACCATTCCCGTTCGCATTCTTAGTGAGGCAGGGGAATCTTTTGCAGAAGTTATGAAGAA<br>AACGCAGGAGCAGGCGCTGGCTTCTCATGCATATGATACGTATCCACTGTTTGAGATTCAGGCATTGACCGACCAGA<br>AACAGGATTTAATTAACCATATTATGGTGTTTGAAAATTATCCAGTAGATGAGCAGGTCGAGGAACTGGGAAGTGAC<br>GGGCAGGATACATTCTCGATTTCCAATGTGGTGGCTGCAGAGCAGACTAACTATGATCTGAGCTTAGTCGTTATGCCG<br>GGAGAATGCATCAAGATTCGTTTTATGTATAACGCGTTAAGTTATGATCAAACAGGCATTGAGCGTCTGCATGGACAT<br>TTTGTGAACCTGTTGGAGCAAGTTTTGCTTAACCCGAATGTTTGCGTAGAAGAGCTGGAACTGGTTACAGCGGCGGAA<br>AAACAACAAATTACAGGAGAGTTTAATGACACTGCCTCTGCATATCCAAGCAATCACACGATCCAAAAACTGTTTGA<br>GGAGCAGGCAGAGCGCACGCCGGATCATATTGCCGTAGCTTTGGGTCATCAATCATTGACCTATCGGGAACTCAATG<br>AGACAGCCAACCGTTTAGCGCATACGCTGCGTGATGCAGGGGTGAAATCCGATGAACCTGTGGGCATTTTGACGGAG<br>CGCTCACTGGATATGATTACGGGAACACTCGCTATTTTGAAGGCTGGTGGCGCGTATGTGCCGGTAGACTCTCAATAT<br>CCGGAGGACCGTATCCGTTATATGCTAGAGGACTCGGGAGCCAAGCTGCTGCTGGCCCAGCAGGATTTACTGGATCG<br>TTGCTATTTTGACGGACAGATTGTCAATCTGAATGAGGATACGTCCTACAGTGCAGATGCTTCCAATCTGGGTATAGA<br>TGGAGCGGGTAATCATGCTGCTTATGTCATTTATACCTCAGGTTCAACAGGTAAGCCTAAGGGTGTCGTTGTTGAGCA<br>TCAAAGTGTCGTGCGCCTTGTCCGCAATACGAATTATGTGCCATTTGATGAATCGACCCGAATGCTGCAGACTTGCGC<br>GTTTGTATTTGATGTATCTACGTTTGAAATTTGGGGCGCGCTGCTGAACGGCGGTCAGCTTGTTCTTGTGCATAAGGAT<br>GATCTATTGGACGCGGCCAAGCTTAAAGAGACGATACGGGATCATCGCGTCACCATGATGTGGCTGACCACACCGTT |

TABLE 6-continued

Nucleotide sequences of genes encoding an NRPS (triE) involved in the biosynthesis of tridecaptin in *Paenibacillus* sp. strains NRRL B-50374, NRRL B-67721, NRRL B-67723, and NRRL B-67724.

| Strain | SEQ ID NO: | Sequence |
|---|---|---|
| | | ATTTAATCAGCTTTCACAGCAGGATAGTAAACTTTTCGGCGATGTGAAGTATTTGCTGGTTGGTGGTGATGTTTTGTCT<br>GCACCCCATATTAACCGGGTTCTGCGCGATAATCCGGACATCAACATCATTAACGGCTATGGGCCAACGGAAAATAC<br>AACCTTTTCGACGACGTATCACATTACGGAAGAACAGCTGGATTCTGTGCCGATCGGACGCCCCATCCGCAATTCGAC<br>GGCGTATGTTGTGGATTCGTCATTTAACCTGCAACCGGTCGGAGCTTGGGGTGAGCTGGTTGTCGGCGGAGACGGAGT<br>TGCACGTGGTTATCTAAACCGTCCTGAGCTGACGGCTGAGAGATTTCTTGCTAACCCGTGGGTGGACGGAGATCGCCT<br>GTACTGTACGGGAGACCTTGTTCGCTGGCGTGAAGACGGCATACTGGAATACGCTGGACGGATTGATCAACAGGTTA<br>AAATTCGCGGTTACCGGATTGAGCTGGGCGAGGTGGAGGCGCGGCTGGCAAGTGTACCGTCCGTGCGGGATAGCGTT<br>GTTATCGCTTTGCGGGATGGAGCAGGTCAGCAGCAATTATGTGCTTACTTCACTGCCGATGAACAGCTGACCATCCGT<br>GAGATTCGAGCTGCGATGTCGGCCAGTCTGCCGAGCTATATGATTCCATCCGCATTTGTACAGCTGGATCGGTTTCCG<br>CTGACGACAAACGGCAAAATCGACCGCAAAGCTTTACCTGTGCCGGACAAAGGGCTGCACACGGGTATAGAATATGT<br>CGCACCGCGAACCGATGTGGAACAGTTGCTGGCAGCCATTTGGCAGGAAGTACTTGAAATTCCACAAGTGGGTATCC<br>ACGATGACTTTTTCACGTTAGGTGGACATTCCTTAAAAGTACTGGAGCTTATACGCAAAGTTCACCTTGCTACAGATA<br>TTGAGCTTCCCATCCGTAGTGTTCTGGACTTCCCAACTATAGAAGCGCAGGCGCTCACATTATTGAAAGCCGATCTGG<br>AGTACAAGGCCGATAGTCCAATCATTCGGTTGAATGAACACGGTCCGATCTCCATCTTCTGCTTTCCTCCTATGCTTGG<br>ATACGGGCTGTCGTTCGCGGAGCTTGCGAAACAACTGGATCAGGACGCAGTCGTGTATGGGTTGGAGTTCGTAGATG<br>ATGCTGCGGATGAGCAGGCCATGCTGGCACGTTACGTTGATTTGATCGTCAGCACGCAAGCGCAAGGTCCGTATGTG<br>CTGCTTGGTTATTCCATAGGTGGTAATCTGGCGCATAAGGTTGCTGACACACTGGAACGTCAAGGTCATACTGTATCC<br>GATATTTTTATGCTCGATTCGGTCAAAAGGGCGGAAGCCCTGCCCTTCACAGTTGAAGAAACAGAGCATGAAATTCAT<br>GACATGCTGGAACAAGTTCCCGACTCCTACCGTGAGCTGTTGAATGAAACGTACCAACGTAAAATGATCGCTTACGC<br>GGTATATGGCAACCAGCTTGTGAATACAGAGAGCGTTCAGGCGAATATTCACGGCTTTGTCGCCGTTGGATCAGAAA<br>CGGTCAAGGGTACAGGAGATAATCGACTTTTATGGAAAGACGCTACACAAGGTAGCTATGAAGAGCATAGCTTGATT<br>GGCAATCATTATGAACTGCTGGAACCCGGATTTATCGAGGAAAATGTAAAAAGTATCCGTGCCACAATACAAAAGAT<br>AACTCGGAACACGGACAAAGACATGACACAAGACTTGGCACATCATAAATCTTGA |
| NRRL B-67721 | 6 | TTGAAAGCCTTATTTGAGAAGGAAAAAAATTACTGGAGTCATAAACTGGAATCTGAGGATCATATCATCTGCCTACC<br>ATACACCAACCATGTGTCCAGAAGTACAACTGTAACGAGTTTAAATTCCCATACGTACACACTCACATTTCCAACTGA<br>AATTTCCCAAAGAATATCATCTATAACAGGTGGCGCTCCATGGGCCGTGTTTATGGTCCTGCTTGCTGGAGTAGAGAG<br>CTTATTGCATAAATACACAGGTGAGGAACGTGTGCTGCTGGGCATCCCGGTAGCCAAGTCTGGCAACGGTGCTACAA<br>AGCCGATCAACCATCTGCTTTTATTGAAAAATACGCTGGATTCCAGCACAACCTTCAAAGCTTTGCTGTCTCAAATCA<br>AAACCTCTGTCGGCGAAGCTATTGAACATCAAAACATTCCTTTTTGGAACTATTCTGAATTACTTGACATTCAACGTA<br>ATGAGGATGGAAAGCCTCTTATTCACACCACAGTATCCTTGCAAAATATTCATATATCTGAATTTTTGAATCACGTAC<br>AATCCGAACTACATTTCCAGTTTCAATGGGAACATGAAGCGGTCTCCCTGAACGTAAAGTATAGTAGCGACCGTTATA<br>GCGAGACGACGATTGAGCACTTTGTTGAGCAGCTTCTGCGGCTGTACACTATTGTTTTGCAGCAGCCAGAGTTGGCGA<br>TTTCCACAGCACAAGTACTGTCAGAGCAAGAAGTAGAGCAGCTGGTCCATACCTTCAACGATACAACTGTGGATTAT<br>CCACGTCATGCGTCTATTCATGAATTGTTCGTGAAACAGGCGAAGCAGGCACCACAGCAGGTGGCGGTAGTGTGTGG<br>GCAAGATCGCCTAACCTATGCAGAATTGAATGAAAAGGCCAACCGACTGGCTCATTCTTTACGTAAGCAGGGAATCC<br>GCACTGAGCAGACGGTCGGCATTGTAGCTGAACGCTCGATTGAGATGATTGTCGGTATGCTCGGAATTCTCAAAGCA<br>GGTGGAGCGTATGTACCCATTGATTCTGATTACCCGGATGAGCGTATACGCTATTTGCTGCAGGATTCCGGTGCGGAC<br>ATACTGCTCGTGCAGCGAATGGAACATCGGCCCACTGATTTTAAGGGATTGGTGCTTGACCTTAGCGATGTCGCAATT<br>TACGGAACGGATGATGCTGATCGTTACGATCCAATTTTGCCGAATGATCACGGGACGAATACTGATCCGGGATACGT<br>GGACTGCCTAGATCCGTTCTACTCCATTTTCGCCAGTCCCGAACTTGCTTCTACGACAACCATACAACCAGAAACCAT<br>GCAACCAAAAGCTACGCAATCAGAACAAGCAGAACAAATACAGCAGGCTTATGCAGCTGGAGAACAACCGAAGGCG<br>AGCGCAGCTGGTCGTTTGGCCTATATTATGTACACCTCAGGGACTACAGGCCAGCCCAAAGGGGTTATGGTGGAGCA<br>CCGTAATGTCGTGCGTTTGGTGACAAACACAAATTATGCACGCTTGAATGCCGACACGCGCATTTTGCAGACCGGGTC<br>TGTTGTCTTTGACGCGTCCACCTTCGAAATTTGGGGTGCGTTATTGAACGGTGGACAGCTGGTGCTGGTGAGTCAGGA<br>TGTTATTTTGGACGCGCCCAAGCTCAAGGAAGTTGTTCGCAATCACGGCATTACCACGATGTGGCTGACCGCACCGCT<br>CTTTAATCAGCTATCCCAGCAGGACTTGGAACTATTTGAGGGGATGCGGGAGCTATTGGTTGGTGGTGATGTGCTGTC<br>CGTACCGCATATTAACCGGGTATTGGAGGCCCATCCGAATCTACATATCATTAACGGCTACGGTCCGACGGAAAATA<br>CGACCTTTTCCACCACACATGCCATTACCGGCGTTCAATCGGCATCTGTGCCCATTGGTAGCCCGATCCATAACTCGA<br>CGGCATATGTCGTGAACCGTTCGATGCAGCTCCAGCCTGTTGGAGCGTGGGGAGAACTGATCGTCGGCGGTGACGGG<br>GTGGCTCGCGGATACCGCAACCGCCCAGAACTGACGACCGAAAAGTTCATTGACAGTCCGTTTCGTGGCGGCGAACG<br>CTGCTATCGAACAGGGGACCTGGTGCGTTGGAATGCGGACGGACGCTGGAATATAAGGGACGAATCGACGCACAG<br>GTGAAAATTCGAGGCTACCGGATTGAGCTGGGCGAGGTGGAAGCACTGCTGTTGAAGCTGGAGGCAGTCCGAGAAG<br>CTGTTGTAATTGCACATGAAGATGAGCAGGGGCAAAAGCTGCTCTGCGCATATGTGGTCACCCATGCGGAAGTAGCG<br>ACAAGTGAGCTGCGTAGTGCTTTGAGTCAGGAGCTGCCGGGCTACATGGTACCGTCGTATTTTGTACAGCTGGAGCA<br>ATTGCCACTGACGCCCAACGGCAAGGTGGATCGCCGAGCGTTGCCACAGCCAGAGGGAGGTGTAAGCTCAGGCGCA<br>GAATATGTACCTCCTCAAAATCAATTACAAGCACAACTGGCTAGCATCTGGAAAGATGTGCTGGAGCTTGAGCGCAT<br>TGGGATTAAGGATAACTTTTTTGAGGCAGGAGGACATTCCCTGCGGGCGACACATGTCATATCACTCATTTATAAGGA<br>ATTGCATAAAAATGTGCAGCTAAAGGATTTGTTCCAGCATCCGACAATTGAACAGCTGGCGCAGGTTATTGAAGCAC<br>TGGAGCAAACCACCTATGAATCCATCCCTGTTACGGAGAATAAGCCATTTTATGCGGTCTCTTCGGCTCAAAAACGGA<br>TGTATATCCTCAATCAGCTTGATGGAGAGGGAATTAGCTATAACATACCTGGTGCCCTGACTCTGACCGGTTCACTTG<br>ATCACAAGGCACTGGATAACGCGTTCCGTCAGCTTATTGAACGCCATGAAACATTGCGCACAAGTTTTGAGACCATG<br>AACGGTGAACCTGTCCAGCGAGTGCATGACGAGGTTCCTTTTCGCATGGAATTGACCTATGCTCACGGAGCTGCCCCA<br>AAGGAAACGGATGAGCTGGTACGTAACTTTGTTCAGCCGTTCGATCTGGAGCAGGCTCCGTTATTCCGAGTTGGTTTG<br>ATTGAAACAGACCCAGAGCATCATATTTTGCTCATAGATATGCATCATATCATTTCGGACGGTACCTCTATAAATGTA<br>CTGATTCAGGACTTCATTCATTTATATGCAGGCGACACGCTGCCATCGCTGCGCATTCAGTATAAAGACTACGCCGCT<br>TGGCAACAGAAGCAGCAGCAAAGTGAACGCTACCGAGAACAGGAAAACTACTGGCTCAATACCTTCGCGGGGGAGC<br>TACCAGTGCTTGATCTTCCGACTGATTATCCACGCCCGGCGGTGAGAAGCTTTGAAGGAGATGTGCTGGAATTTACGC<br>TTGACCAACGACAAAGTGAAGGCTTAAAAAGCATTGCGGTGAAGACGGAATCGACATTATATATGGTGCTGTTGGCT<br>GCCTATTCGGCTTTGCTTAGCCACTATAGCGGGCAGGAAGATATTATTGTCGGTTCGCCAATTGCAGGGCGGCCCCAT<br>GCGGATCTTGGCAGTCTGATCGGGATGTTCGTGAATACACTGGCAATCCGTAATTATCCAGAAGGCGGGAAAACGTT<br>CCGCGATTATGTGTTGGAGGTCAAGGAAAATGCGTTAAAGGCTTTTGAACATCAGGATTATCCGTTTGAAGAGCTGGT |

TABLE 6-continued

Nucleotide sequences of genes encoding an NRPS (triE) involved in the biosynthesis of tridecaptin in *Paenibacillus* sp. strains NRRL B-50374, NRRL B-67721, NRRL B-67723, and NRRL B-67724.

| Strain | SEQ ID NO: | Sequence |
|---|---|---|
| | | GGAGAAGCTGGGCGTAGATCGAGATTTAAGCCGTAATCCGTTATTTGATACCATGTTTGCACTACAAAACATAGAGC |
| | | AAAAAGAGCAGCAGCTGGCGGGGCTGCAATTGGCATCTTATCCAAGTGAGCAAACGACGGCCAAATTTGATTTGAGT |
| | | CTGTTCGCAGTGGAGGATGGAGAACAAATTTCCTGTGCTCTTCAATACGGAACTCGGCTGTACAAACGGGAAACCAT |
| | | TGAACGACTGACTGAACATTTGCAGCAGCTTATCAATGCGGTTATAAAACAGCCGGATATCGCTCTTTCGGCTATAGA |
| | | AATGGTTTCGGCCCAAGAAAAAGAGCTGCTTGTGCAGAGATTCAATGATACGGTAGCAGACTATCCGTATCCACGAG |
| | | ATCAAGCACTGCATGTGTTGTTCGAGGAACAGGTAGCGCAATCACCAGATCGGCTGGCCGTCACCTTTGCGGACATG |
| | | CAGCTTACCTACCGCGAGCTGAATGAACGTGCCGACCGTCTGGCACACATACTCGCTTCCCATGGGATACGGCGCGG |
| | | CTCCGAGCCAGAGACACAGCGAGTAGGGATTATGGCTGAACGCTCCATTGAAATGGTCGTCGGTATGCTGGCGATTT |
| | | TAAAGGTCGGAGGGGCTTACGTTCCCATTGATCCCGATTATCCTGAGGAGCGTATCCGTTATTTACTGGAGGATTCCA |
| | | GTGCTGGGCTGTTACTGTTACAGCGACGTGAACAGATGCCTTTTGAACCCGGCATTCCGGTCATCGATTTGAGTGATG |
| | | AACAACGATGGAATAGCAAATCTGAAGGTGACGCTCATACCGATGGAACAATTGCGATTACAACAGGGGGATCTTCC |
| | | TCCGATCTTGCGTACGTGATCTACACCTCTGGTACGACAGGCAAGCCGAAGGGCGTGATGATTGAGCACCGTAATGT |
| | | CGTGCGCCTAGTGAAAAACAAAAGCTATGCCATGCTTGATGAAAATACACGTATGCTGCAATTGGGCGCAGTTGTGT |
| | | TCGATGCCTCCACATTTGAAATTTGGGGAACGCTGCTGAACGGGGGACAACTGTATGTGGTAAGCCATGACACTATTC |
| | | TGGATGCCTCCAAGCTCAAGCAGGCGATTGACAAGTATCGTGTTAACACGATGTTCATGACCACGGCTTTATTCAATC |
| | | AGTATTCGCAGCAAGAAATCGGAGTGTTTGCGTCCTTGAAGGAGTTGCTCGTGGGTGGTGATGTGTTGTCTGTACCAC |
| | | ACGTCAATCGTGTGTTGAAGGAGTACCCGCAGCTTCGCCTGGCCAATATTTATGGTCCGACGGAGAACACCACCTTTT |
| | | CCACCATCTATGACATTACAGAACCGCAAACCCAGGCTATTCCCATTGGACGTCCAATTGATCACTCGACCGCTTATG |
| | | TGGTCAATCGTTCGTTGAAGCTGCAACCTGTCGGAGCCTGGGGAGAGCTGATCGTCGGTGGCGACGGTGTTGGGCGA |
| | | GGATATCTGAATCGGCCCGAGCTTACGGCGGAAAAATTTATTGAAAGTCCATTCCGGTCTGGAGAATATTGCTATCGT |
| | | ACAGGAGACTTAGTGCGTTGGCGTGCTGATGGTGTACTGGAGTACAAGGGAAGAATGGATGAACAGGTCAAAATTC |
| | | GCGGCTACCGCATTGAACTGGGTGAAATTGAAACCCGTTTGTCCACGATTCCAGGTGTGAAGGAATCGGTTGTTACCG |
| | | TGCGGCAGGACGATCACGGACAAAAGCAGCTGTGTGCCTATTTTGCAACAGACAGTGAATTGAGCGCCAGCGACTTA |
| | | CGTAACATTTTGTCGCAGGATCTGCCTAGCTATATGGTGCCGTCCTACTTTGTGCAGCTCTCCAGACTGCCTTTGACGC |
| | | TGAATGGCAAAGTAGACCGCAGGGCACTGCCCGCACCTGAGCAAAATCTCGATACAGGTATGGATTATGTGGCACCC |
| | | GAAACGGATGTTCAACAGGCACTGGCTACGGCTTGGGGATCCATTCTTGGTATCCCGAAAGTTGGAATTCAGGATAA |
| | | CTTTTTCCATTTGGGTGGTGACTCCATCAAGGCCATCCAAGTATCGTCCCGCTTGTTTCAGGCTGGATACAAGCTGGA |
| | | AATGAAGGACTTGTTCAAATACCCGACAATTGCGGGATTAAGCACATATATTCAGCCTGTTAACCGAATAGCCGAGC |
| | | AGGGCGAGGTTACAGGAAATGTAGTGCTTACACCGATTCAGCGCTGGTTTTTTGAACAGCCAACGGAAGAACCACAC |
| | | TATTTTAACCAATCTGTCATGCTCTATCGTCAGGAAGGCTATGACGAACAGGCACTACGGCGGGCGCTCCATCAGATT |
| | | ACTTCGCACCATGATGCATTGCGTATGGTTTTTAGTTTGTCGGAGAACGGATGTACAGCATGGAACCGCAGTGTAGAG |
| | | GAAGGCGAACCGTACCATCTGGAATGCTTTGACTATAATGACAGCGATGTAAACAAGCAAGATTTGGCGAAGATAAT |
| | | TGAAGCGAAATGCAATGAAATTCAATCTGATATTTCCCTAAGCGAAGGTCCGCTGATGAGACTGGGGCTGTTCCGTTG |
| | | CCCGGATGGAGATCATCTGCTGGTCGTGATTCATCATTTGGCGGTGGACGGGGTATCCTGGCGCATTTTATTCGAGGA |
| | | TTTGGCGACTGCTTATGATCAAGCCTCCAAGGGTGAACAGGTGATTCAGCTGCCTCATAAAACAGATTCGTTCCAAAC |
| | | ATGGGCTGAGCAGCTGCACGCTTATGCCAACAGTCCAGCTATGGAACATGAGCGAGCGTATTGGGGGAAACTTGCAC |
| | | AAGCGGAACTGGCTTCTTTGCCGCAGGATTATGGGCATAACGAGCACGAAAAGCCATTGATTGGCGATAGTGAGTCG |
| | | GTTACTGCTTTGTGGACACATGCAGAGACAGAGCAGCTGCTCAAGCAGGCCAATCGTGCCTACCGTACAGAAATTAA |
| | | TGACCTGTTGTTGACGGCGGTAGGAATGGCATTGCAAGCATGGAGTGGAAATGATCGTTTCCTGATAAATCTAGAGG |
| | | GACATGGACGTGAAGCCATTTTACCAGAGGTGGACATTACTCGAACGATAGGGTGGTTTACAAGCCAATATCCTGTTT |
| | | TGCTCGATATGCCGGAAGAACTGGCACTTTCGCAACGGATTAAGCGTGTGAAGGAAGGACTGCGCGGCATTCCGCAA |
| | | AAAGGGATTGGCTACGGTGTACTGAAATATTTATCCGACCGTCAGACACAGACACCGGAGGCATCTCCAGCCATATT |
| | | TACGACAGATCCCGAAATCAGCTTTAACTATTTGGGACAGTTCGATCAGGATATGAAAGGGAACGACTTGCAATCAT |
| | | CCTCATATGAGGGTGGGATGCCGCTGAGCCCGACCATGGCTCGAACGTATACGCTGGATTTTGGCGGCATTATTTCGG |
| | | GAGGCCAACTGGGTCTGACGATTAGCTATAGTCGTACCAGCTATAGACCGGAGACCATCGAGCGATTGGCGAAATTC |
| | | CTGGAATCGAGCCTGCGTGAAATTTTGGCGCATTGCATCCATAAAGAACACCCGGAGCTTACCCCAAGTGATATTTCC |
| | | TATAAAGGAATGAGTGTGGAGGCCTTGGACAGTCTCTTATCTGAAATGGGTGCTGCGGGTGAGATCGACAATGTATA |
| | | TGCACTGACCCCGATGCAGAAAGGGATGCTGTTTCACAGCCAGCTAGATAGTCAAGCAGCTGCGAATGACGCGTATT |
| | | TTGAGCAGGTTTCTTATGATATGCGAGGTCAGATGGACATTCGGGCTTTTGCAGAAAGCCTGAATATTCTGGTTCGGC |
| | | GACATGAGGCGCTGCGTACACATTTGTATTTTGGCAGAGATACGGAACCGTTGCAGGTGGTGTATCGAAATCGGGAT |
| | | TGCGGCTTTCAATATGAAGATTTACACCATCTAGATGAGGATGCAAAAGATACCTGGGTGAAAAATTTCAAGCTACA |
| | | AGATAAAGCACGGGGCTTTGATCTGCGTCGGGATGTCCTGCTGCGTGTAGCGATTTTACGTACCGGAGAAGACAGCT |
| | | ATCATTTTGTATGGAGCTTTCATCATATCGTCATGGACGGCTGGTGTCTGTCCCTTATAAACAAAGAAGTGTTTGAAA |
| | | GCTATGCAGCACTTCAGGAGGGCAGAGTACCAGAACTGGCACCGGCAGTGCCGTACAGCCGCTTTATTGAATGGCTG |
| | | GAAGCACAGGATCGCAAGGCGGCAACCGACTACTGGAGCAGCTATTTATCCGGATATGAGCAGCAAACAGCGTTAC |
| | | CAGCTGTAAAATCCGGTCGCAAGAGTGAAGGCAACACGGCTAGTGATTGGGTGACGGTTTTGGAACGTGAGTTGACC |
| | | CTCCGGGTGGAGGAGACGGCTAAGCGATATCAAGTGACCATGAATACGTTATTACAAACCGCATGGGGGATTGTGCT |
| | | GCAAAAATATAACAACCACAGTGATGTCGTATTTGGCAGTGTCGTCTCAGGCCGTCCATCAGATATTATCGGGGTAG |
| | | AGGATATTATCGGCTTGTTCATTAATACCATTCCCGTTCGCATTCTTAGTGAGGCAGGGGAATCTTTTGCAGAAGTTAT |
| | | GAAGAAAACGCAGGAGCAGGCGCTGGCTTCTCATGCATATGATACGTATCCACTGTTTGAGATTCAGGCATTGACCG |
| | | ACCAGAAACAGGATTTAATTAACCATATTATGGTGTTTGAAAATTATCCAGTAGATGAGCAGGTCGAGGAACTGGGA |
| | | AGTGACGGGCAGGATACATTCTCGATTTCCAATGTGGTGGCTGCAGAGCAGACTAACTATGATCTGAGCTTAGTCGTT |
| | | ATGCCGGGAGAATGCATCAAGATTCGTTTTATGTATAACGCGTTAAGTTATGATCAAACAGGCATTGAGCGTCTGCAT |
| | | GGACATTTTGTGAACCTGTTGGAGCAAGTTTTGCTAAACCCGAATGTTTGCGTAGAAGAGCTGGAACTGGTTACAGCG |
| | | GCGGAAAAACAACAAATTACAGGAGAGTTTAATGACACTGCCTGTGCATATCCAAGCAATCACACGATCCAAAAACT |
| | | GTTTGAGGAGCAGGCAGAGCGCACGCCGGATCATATTGCCGTAGCTTTGGGTCATCAATCATTGACCTATCGGGAAC |
| | | TCAATGAGACAGCCAACCGTTTAGCGCATACGCTGCGTGATGCAGGGGTGAAATCCGATGAACCTGTGGGCATTTTG |
| | | ACGGAGCGCTCACTGGATATGATTACGGGAACACTCGCTATTTTGAAGGCTGGTGGCGCGTATGTGCCGGTAGACCC |
| | | TCAATATCCGGAGGACCGTATCCGTTATATGCTGGAGGACTCGGGAGCCAAGCTGCTGCTGGCTCAGCAGGATTTACT |
| | | GGATCGTTGCTATTTTGATGGACAGATTGTCAATCTGAATGAGGATACGTCCTACAGTGCAGATGCTTCCAATCTGGG |
| | | TATAGATGGAGCGGGTAATCATGCTGCTTATGTCATTTATACCTCAGGTTCAACAGGTAAGCCTAAGGGTGTCGTTGT |
| | | TGAGCATCAAAGTGTCGTGCGCCTTGTCCGCAATACGGATTATGTGCCATTTGATGAATCGACCCGAATGCTGCAGAC |

TABLE 6-continued

Nucleotide sequences of genes encoding an NRPS (triE) involved in the biosynthesis of tridecaptin in *Paenibacillus* sp. strains NRRL B-50374, NRRL B-67721, NRRL B-67723, and NRRL B-67724.

| Strain | SEQ ID NO: | Sequence |
|---|---|---|
| | | TTGCGCGTTTGTATTTGATGTATCTACGTTTGAAATTTGGGGCGCGCTGCTGAACGGCGGTCAGCTTGTTCTTGTGCAT<br>AAGGATGATCTATTGGACGCGGCCAAGCTTAAAGAGACGATACGGGATCATCGCGTCACCATGATGTGGCTGACCAC<br>ACCGTTATTTAATCAGCTTTCACAGCAGGATACTAAACTTTTCGGCGATGTGAAGTATTTGCTCGTTGGTGGTGATGTT<br>TTGTCTGCACCCCATATTAACCGGGTTCTGCGCGATAATCCGGACATCAACATCATTAACGGCTATGGGCCAACGGAA<br>AATACAACCTTTTCGACGACGTATCACATTACGGAAGAACAGCTGGATTCTGTGCCGATCGGACGCCCCATCCGCAAT<br>TCGACGGCGTATGTTGTGGATTCGTCATTTAACCTGCAACCGGTCGGAGCTTGGGGTGAGCTGGTTGTCGGCGGAGAC<br>GGAGTTGCACGTGGTTATCTGAACCGTCCTGAGCTGACGGCTGAGAGATTTCTTGCTAACCCGTGGGTGGACGGAGA<br>TCGCCTGTACTGTACGGGAGACCTTGTTCGCTGGCGTGAAGACGGCATACTGGAATACGCTGGACGGATTGATCAAC<br>AGGTTAAAATTCGCGGTTACCGGATTGAGCTGGGCGAGGTGGAGGCGCGGCTGGCAAGTGTACCGTCCGTGCGGGAT<br>AGCGTGGTTATTGCTTTGCGGGATGGAGCAGGTCAGCAGCAATTATGTGCTTACTTTACTGCTGATGAACAGCTGACC<br>ATCCGTGAGATTCGAGTTGCGATGTCGGCCAGTCTGCCGAGCTATATGATTCCATCCGCATTTGTACAGCTGGATCGG<br>TTTCCGCTGACGACAAACGGCAAAATCGACCGCAAAGCTTTACCTGTGCCGGACAAAGGGCTGCACACGGGTATAGA<br>ATATGTCGCACCGCGAACTGATGTGGAACAGTTGCTGGCAGCCATTTGGCAGGAAGTACTTGAAATTCCACAAGTGG<br>GTATCCACGATGACTTTTTCACGTTGGGTGGACATTCCTTGAAAGTACTGGAGCTTATACGCAAAGTTCACCTTGCTA<br>CAGATATTGAGCTTCCCATCCGTAGTGTTCTGGACTTCCCGACTATAGAAGCGCAGGCGCTCACATTATTGAAAGCCG<br>ATCTGGAATACAAGGCCGATAGTCCAATCATTCGGTTGAATGAAAACGGTCCGATCTCCATCTTCTGCTTTCCTCCTA<br>TGCTTGGATACGGGCTGTCGTTCGCGGAGCTTGCGAAACAACTGGATCAGGACGCAGTCGTGTATGGGTTGGAGTTC<br>GTGGATGATGCTGCGGATGAGCAGGCCATGCTGGCACGTTACGTTGATTTGATCGTCAGCACGCAAGCGCAAGGCCC<br>GTATGTGCTGCTTGGTTATTCCATAGGTGGTAATCTGGCGCATAAGGTTGCTGACACACTGGAACGTCAAGGTCATAC<br>TGTATCCGATATTTTTATGCTCGATTCGGTCAAAAGGGCGGAAGCCCTGCCCTTCACAGTTGAAGAAACAGAGCATGA<br>AATTCATGACATGCTGGAACAGGTTCCCGACTCCTACCGTGAGCTGTTGAATGAAACATACCAACGTAAAATGATCG<br>CTTACGCGGTATATGGCAACCAGCTTGTGAATACAGAGAGCGTTCAGGCGAATATTCACGGCTTTGTCGCCGTTGGAT<br>CAGAAACGGTCAAGGGTACAGGAGATAATCGACTCTTATGGAAAGACGCTACACAAGGTAGCTATGAAGAGCATAG<br>CTTGATTGGCAATCATTATGAACTGCTGGAACCCGGATTTATCGAGGAAAATGTAAAAAGTATCCGTGCCACCATAC<br>AAAAGATAACTCGGAACACGGACAAAGACATGACACAAGACTTGGCACATCATAAATCTTGA |
| NRRL B-67723 | 7 | TTGAAAGCCTTATTTGAGAAGGAAAAAAATTACTGGAGTCATAAGCTGGAATCTGAGGATCATATCATCTGCCTGC<br>CATATACCAACAACGTGTCCAAGGATGCAACTGCAACGAATTTAAATTCCCTTACGTACACGCTCACATTTCCATCT<br>GAAATTTCCGGACGAATATTGTCTATAACAGGTGGCGCTCCATGGGCAGTGTTTATGGTTCTGCTTGCTGGAGTAG<br>AAAGCCTGTTACATAAATACACAGGTGAGGAACGTGTGCTGTTGGGCATTCCGGTAGCCAAGTCTGGCAACGGTGC<br>TACAAAGCCGATCAATCATCTGCTCATACTGAAAAACTCGCTGGATTCTACAACGACCTTCAAAGCCTTGCTGTCTC<br>AAATCAAAACCTCTGTCAGCGAAGCGATTGAGCACCAAAATATACCTTTTTGGAACTATACCGAGGGGCTTGAAAT<br>TCCACGTAACGAGGGTGAACAGCCTCTTATTCACACCACGGCATCCTTGCAAAACATCCATATTTCCGATTTTTCGA<br>ATCATGTACAATCTGAGCTGGATTTTCAATTTCAATGGGACAACACAGCGGTTTCCCTGAATCTGAATTACAGCAG<br>CCACCGCTATAATGAGGCGACAATTGAACGCTTTGTTGAGCAGCTGTTGCGGTTGTACAGCGTTGTTTTGCATCAGC<br>CAGAGCTGGCAATTTCCACAGCACAGGTGTTATCAGAGCAAGAAGTGGAGCAACTGGTTCATATCTTCAACGATAC<br>AACTGCGGATTATCCACGTCATGCGTCCATTCATGAGTTGTTTGAGAAACAGGCGAAGCAGGCACCGGAGCAGGTG<br>GCGGTAGTGTTCGGAAAAGACAGTCTGACCTATGGAGAATTGAATGAAAAAGCCAACCGTCTGGCTCATACATTAC<br>GTAAGCAGGGGATCTGCACCGAGCAGACTGTCGGTATTGTGGCTGAACGCTCGATGGAAATGATCGTCGGTATGCT<br>TGCTATTCTCAAAGCAGGCGGGGCCTATGTGCCGATTGACTCTGATTATCCGGATGAACGCGTGCGCTATTTGCTGG<br>AGGATTCTGGTGCAAACCTACTTCTAGTGCAGCGGATGGAGCATCGGCCCGCTGATTTTCAGGGGATTGTGCTTGA<br>CCTGAGCGATTCAGCAATCTATGGAACGAATGATGCTGATCGTTTCGATCTGGTTTTGCCGAACGATAACGAGACG<br>TATGCTGACAGAGCTGGCATCGGATATGTAGATTGCTTAAACCCGCTCTATTCCATTTCCGCTAGTCCTGAGCTTGC<br>TTCTACTGCAACCACACAACCAGAAATCCTGCAACCAGAAGTTACGCAATCAGAACAAGCGAAGGCAGCCGCTGC<br>TGATCGCTTGGCATACGTTATGTACACCTCAGGGACAACAGGGCAGCCGAAAGGAGTTATGGTGGAGCACCGCAA<br>TGTCGTGCGTCTGGTGAAAAATACAAACTATGCGCAATTGGATGCTGATACGCGCATTTTGCAGACCGGGGCTGTT<br>GTCTTCGACGCGTCCACTTTCGAAATTTGGGGTGCGCTATTGAATGGTGGACAGTTGGTACTGGTGAGTCAGGATG<br>TCATTTTGGACGCGCCGAAGCTCAAGGAAGCTGTTCGCAGCCATGGCATTACCACGATGTGGCTGACAGCGCCGCT<br>CTTTAACCAGCTGTCCCAACAGGACCTGGAACTGTTTGAGGGGATTCGGGAGCTGCTGGTCGGCGGTGATGTGCTG<br>TCCGTCCCGCCTATTAACCGGGTGCTGGAGGCCCATCCTTCCCTGCGGATCATCAACGGCTACGGCCCGACAGAAA<br>ACACGACCTTTTCCACAACACATGCGATAACTGGCGTGCAATCAGAATCGGTGCCGATTGGCAGCCCGATCCATAA<br>CTCGACGGCGTATGTCGTAGACCGTTCGATGCAGCTTCAGCCCGTAGGAGCATGGGGAGAGCTGATTGTCGGCGGT<br>GACGGGGTAGCCCGTGGATACCGCAACCACCCGGACCTGACGGCAGAAAAGTTCATGGACAGTCCGTTCCGCAGT<br>GGAGAACGTTGCTATCGCACAGGCGACCTGGTGCGCTGGAATGCGGACGGGACGCTGAAATACAAGGGACGGATC<br>GACGCCCAGGTGAAAATCCGGGGGTACCGGATCGAGCTGGGCGAGGTGGAAGCACAGCTGTTGAAGCTGGAGGCG<br>GTGCGAGAAGCCGTCGTGATAGCACGAGAGGATGAGCAGGGGCAAAAGCAGCTCTGTGCTTATGTGGTGACTGAT<br>ACGGAGGTGGCGGCAAGCGAGCTGCGCAGCGCTTTGAGCCAGGAGCTGCCGGGCTACATGGTGCCGTCGTATTTTG<br>TACAGCTGGAGCAATTGCCACTCACGCCTAACGGCAAGGTGGATCGCCGGTCATTGCCACAGCCGGAGGGAAGTA<br>TAAGCTCAGGCACAGAATATGTACCTCCTCAAAATCAATTACAAGTACAACTGGCGAGTATCTGGAAAGATGTGCT<br>GGAGCTTGAGCGCATCGGGATTAAGGATAACTTTTTTGAAGCAGGAGGGCACTCCTTGCGGGCGACACATGTCATA<br>TCGCTGATTCATAAGGAACTGCATAAAAATGTGCAGCTAAAGGACCTGTTTCAGCACCCGACGATTGAACAGCTTG<br>CACACGTTATTGAAGCGCTGGATCAAACCGCCTATGAATCCATACCTGTTACCGAGAATAAGCCATATTATGCGGT<br>ATCCTCGGCACAAAAACGGATGTATATCCTCAATCAGCTTGATGGAGCGGGAATTAGCTATAACATCCCTGGTGCT<br>CTGACACTGACAGGTTCACTTGATCATAAGGCACTGGACAATGCGTTCCGCCAGCTTATTGACCGCCATGAAACAT<br>TGCGTACAAGCTTTGAGACCATGAACGGTGAACCTGTCCAGCGAGTACATGACGAGGTTCCTTTTCGCATGGAGTT<br>GATTTATGCCCACGGCGCTGACCCAAAGGAGACGGACGAGCTGGTACGCGACTTTGTCCAGCCATTCGATCTTGGA<br>CAGGCTCCGCTATTCCGAGTCGGTATGATTGAAACAGATCCAGAGCATCATATTTTGCTGCTGGATATGCATCACAT<br>CATTTCGGACGGTACCTCTATAAATGTGCTGATTCAGGACTTCATCTGTTTATATGCAGGTGACACGCTGCCACCAC<br>TGCGCATTCAGTATAAGGACTACGCCGCCTGGCAACAGGATCAGCAGCAAAGTGAACGCTACCGGCAGCAGGAAA<br>GCTACTGGCTGAATACCTTCGCGGGAGAGCTGCCCGTGCTGGATATACCGACCGATTATCCACGTCCGGCGGTGAG<br>AAGCTTTGAAGGAGATGTGCTGGAATTTACGCTCGATCAACGGCAGAGCGAAGGTTTAAAAAGCATTGCGGTACA<br>GACGGAATCGACATTATATATGGTGCTGTTGGCTGCTTATACGGCTTTGCTTAGCCACTACAGCGGGCAAGAGGAT |

TABLE 6-continued

Nucleotide sequences of genes encoding an NRPS (triE) involved in the biosynthesis of tridecaptin in *Paenibacillus* sp. strains NRRL B-50374, NRRL B-67721, NRRL B-67723, and NRRL B-67724.

| Strain | SEQ ID NO: | Sequence |
|---|---|---|
| | | ATTATCGTCGGTTCGCCGATTGCGGGGCGGCCCCATGCTGATCTTGGTAGCCTGATCGGGATGTTTGTGAATACACT |
| | | GGCAATCCGCAATGTTCCGGAAGGCAGTAAGACCTTCCGCGATTATGTATTGGAGGTCAAGGAAAATGCGCTGAA |
| | | GGCATTTGAACATCAGGATTATCCGTTTGAAGAGCTGGTGGACAAGCTGGGCGTGGATCGAGATTTAAGCCGTAAT |
| | | CCGTTATTTGATACCATGTTTGCTCTGCAAAATTTGGAGCAAAAGGAGCAGCAACTGGAAGGCTTGCAATTGACAC |
| | | CCTATCCGAGTGAACAAAATACCGCAAAATTTGATTTGAGTCTGTTCGCGATGGAGGATGGGGAGCAAATTGCCTG |
| | | CGGTCTTCAATACGGAACCCGACTGTACAAACGGGAAACCATCGAACGACTGGCTGTACATTTGCAGCAGCTTATC |
| | | CATGCGGTGATAGAACAGCCGGATATCGCTCTTTCGGCTATTGAAATGGTTTCGTACCAAGAAAAAGAGCAGATTG |
| | | TAATGCAATTCAACGATACAGTAGCAGACTATCCGTATCCACGTGATCAAGTGCTGCATGTGCTGTTCGAGGAACA |
| | | GGCCGCACAATCACCGGATCGGCTGGCTGTCACCTTTGCGGACACACAGCTCACCTACCACGAACTGAAAGAACGC |
| | | TCCGACCGTCTGGCACGTATACTCGCTTCTCATGGGATACGGCGCGGCTCCGAGCCAGAGATACAGCGAGTAGGGA |
| | | TTATGGCGGAGCGCTCCATTGAAATGATCGTGGGTATGCTGGCGATTTTGAAGGCCGGAGGGGCTTACGTTCCCAT |
| | | TGATCCCGAATATCCTGAGGAGCGTATCCGTTATTTACTGGAGGATTCCAGTACTCGGCTGTTACTTTCACAGCGAC |
| | | GTGAGCAGGTTCCTTTTGAACCAGGTATTCCGATCATAGAATTGAGTGATGAACAACGATGGAGTAGCGAATCTGA |
| | | ACTTTACGCTCATGTGGATGAATCTGCTGCTGTTCCAATGGAGGGATCTTCCTCGGATCTTGCGTATGTGATCTACA |
| | | CCTCTGGTACGACAGGCAAGCCGAAGGGCGTGATGATCGATCACCGTAATGTCGTGCGTTTAGTGAAAAACAAAA |
| | | GCTACGCCACGCTTGACGAAAATACGCGTATGCTACAAATGGGTGCCGTGGTGTTCGATGCCTCCACGTTTGAAAT |
| | | CTGGGGAACGCTGCTGAACGGGGGTCAACTGTATCTGGTAAGTCATGACACTATTTTGGACGCCGCCAAGCTCAAA |
| | | CAGGCGATTGACAAGTATCATATTAGCACCATGTTCATGACCACGGCTTTATTCAATCAGCATTCACAGCAAGACA |
| | | TTGGAGTGTTTGCCTCCCTGAAGGAATTGCTCGTGGGTGGTGATGTATTGTCCATACCCCACGTCAACCGCGTGCTG |
| | | AAGGAGTACCCGCAGCTTCATTTGGCCAATATTTATGGGCCGACGGAGAACACCACCTTTTCCACCATCTATGACA |
| | | TTACAGAACCGCAAACCCAAGCTATTCCCATTGGGCGTCCGATTGATCATTCGACCGCGTATGTGGTCAATCGTTCG |
| | | TTGAAGCTGCAGCCGATCGGAGCCTGGGGGGAACTGATCGTCGGTGGTGACGGTGTGGGACGTGGATATCTGAAT |
| | | CGGCCGGAGCTCACGGCGGAAAAGTTTATAGAAAGTCCGTTCCGGCCCGGGGAGCACTGCTATCGTACAGGGGAT |
| | | TTAGTGCGTTGGCGTGCAGATGGCGTGTTGGAGTACAAGGGAAGAATGGATGAGCAGGTCAAAATTCGCGGCTAC |
| | | CGCATTGAGCTGGGTGAAATAGAAACCCGTTTGTCCACGATTGCAGGAGTGAAGGAATCGATTGTTACCGTACGGC |
| | | AGGATGATAACGGGCAAAAACAGTTGTGTGCTTATTTTGTAACAGACAGCGAATTGAGCGCCAGTGACTTACGTAA |
| | | CGTTTTGTCGCAGGATCTGCCTGGCTATATGGTGCCTTCCTATTTTGTGCAACTTTCCAGACTGCCTTTGACGCTGAA |
| | | TGGTAAAGTAGACCGCAGGGCCCTGCCTGCACCGGAGCAAAACGTCGATACAGGCATGGATTATGTAGCACCCGA |
| | | GACGGATGTTCAGCAAGCACTGGCTACCGCCTGGGGGGCAATTCTTGGGATTCAGCGAGTGGGCATACAGGATAA |
| | | CTTTTTCCATCTGGGTGGCGACTCCATCAAGGCCATTCAAGTGTCGTCCCGATTGTTTCAGGCTGGATACAAGCTGG |
| | | AAATGAAGGACTTGTTCAAATACCCGACGATTGCGGGACTAAGCAAATTTATTCAGCCTGTTAACCGAATAGCAGA |
| | | GCAGGGAGAGGTTACAGGATCTGTTTTACTTACACCGATTCAGCGCTGGTTTTTTGAACAGCCAACGGCAGAGCCG |
| | | CACTATTTTAACCAATCTGTCATGCTTTATCGACAAGAAGGCTACGATGAACAGGCACTTCGGCAGGCGCTCAATC |
| | | AGATTACATCGCACCATGATGCATTGCGTATGGTTTTTCGTTCGTCGGAGAACGGGTATACGGCGTGGAATCGTGG |
| | | TATAAAGGAAGGCGAACCATACCATCTGGAAATCTTTGATTATAGGGACAGCGACGTAAATGAGGGCGATTTGGC |
| | | GAAGATGATTGAAGCCAAATGCAATGAAATTCAATCCGGCATTTCCCTAAGCGAAGGGCCGCTCATGAGGCTAGG |
| | | GCTGTTCCGTTGCCCGGATGGAGATCATCTGCTGGTCGTGATTCACCATTTGGCGGTGGACGGGGTATCCTGGCGC |
| | | ATTTTATTCGAGGATTTGGCGACTGCTTATGATCAAGCCTCCAAGGGAGAGCAGGTGATTCAGTTGCCTCATAAAA |
| | | CGGATTCGTTCCAAACGTGGGCCCAGCAGCTGTACGCTTATGCCAATAGCCCAGCCATGGAACGTGAACGCTCGTA |
| | | CTGGGAGGAGCTTGCACAAGCCGAGTTGGCTCCCTTGCCGCAGGATTATGGGCATCATGAGCACGAAAAGCCGTTG |
| | | ATTGGTGACAGTGAGTCGGTTACCGCTGTATGGACAAGTACGGAGACAGAGCAGCTGCTGAAGCAGGCCAATCGT |
| | | GCCTACCACACGGAGGTTAATGATCTGTTGCTGACGGCAGTAGGGATGGCATTGCAAGCGTGGAGCGGATACGAG |
| | | CGTTTCCTGATTCATCTGGAGGGGCATGGACGCGAAGCTATTTTACCTGAGGTAGACATTACCCGAACAATAGGGT |
| | | GGTTTACAAGCCAATATCCTGTTTTGCTTAATATGCCGGAAGAAATTGCTCTTTCGCAACGGATTAAGCATGTGAAG |
| | | GAAGGACTGCGCGGCATCCCGCAAAAAGGGATCGGCTACGGTGTACTGAAATATTTAGCCGACCGCCAGACACAG |
| | | GCACCGGAGGCATCTCCAGCCCTATTTACGACAGATCCCGAAATCAGCTTTAACTATTTGGGACAGTTCGATCAGG |
| | | ATATGAAAGGGAACGACTTGCAATCATCCTCATATGGGGGTGGGATGCCGCTGAGCCCGACCATGGCTCGGACGT |
| | | ATACGCTGGATTTTGGCGGCATCATTTCGGGAGGTCAGCTGGGTCTGACGATTAGCTATAGCCGTACCAGCTATCG |
| | | ACCGGAGACGATAGAGCGATTGGCGAAATTACTGGAATCGAGTCTGCGTGAAATTTTGACGCATTGCATCCATAAA |
| | | GAGCACCCGGAGCTGACCCCAAGTGATATTTCTTATAAAGGAATGAGTGTGGAGGGCTTGGACAGCCTGTTATCTG |
| | | AAATGGGTGCTGCGGGTGAGGTCGACAATGTATATGCACTGACCCCGATGCAAAAAGGGATGCTGTTTCACAGCC |
| | | AGCTGGATAGTCAAGCAGCCGCGAATGACGCGTATTTTGAGCAGGTTTCTTATGATATGCGAGGTCGGATGGACAT |
| | | TCAGGCTTTTGCAGAAAGCCTGAATATTCTGGTTCGGCGACATGAGGCGCTGCGTACACATTTTTATTTTGGCCGGG |
| | | ATACGGAACCGTTGCAGGTGGTGTATCGAAGTCGGGATTGCGGCTTTCAATATGAAGATTTACACAAGCTGGATGC |
| | | GGATACAAGGGATACCTGGGTGAAAAGCTTCGAGTTGGAAGATAGAGCGCGGGGCTTTGATCTGCGTCGGGATGT |
| | | CCTGCTGCGTGTAGCGATTTTACGTACCGGAGAAGACAGCTATCATTTTGTATGGAGCTTCCATCATATCGTCATGG |
| | | ACGGCTGGTGTCTGTCCCTTATAAATAAAGAAGTGTTTGAAAGCTATGCAGCACTTCAGGAGGGCAGAGTGCCAGA |
| | | GTTGGCACCGGCAGTGCCGTACAGCAGCTATATTGAATGGCTGGAAGCACAGGATCGCAAGGCGGCAGCCGACTA |
| | | CTGGAGCAGCTATTTATCCGGGTATGAGCAGCAAACAGCACTACCAGCTGTAAAATCCGGTCGCAAGAGTGAAGG |
| | | CTACAAGGCCAGCGATTGGGCGACGGATTTGGAGCGTGAGCTGACCCTCCGGGTGGAGGAGACGGCTAAGCGGTA |
| | | TCAGGTGACCATGAATACGTTATTACAAACCGCATGGGGGATTGTGCTGCAAAAATATAACAACCACAGTGATGTC |
| | | GTATTTGGCAGTGTTGTCTCAGGTCGTCCATCGGATATTATCGGGGTCGAGGATATTATCGGCTTGTTCATTAATAC |
| | | CATTCCCGTTCGCATCCGCTGCGAGGCAGGGGAATCTTTTGCAGAAGTTATGAAGAAAATGCAAGAGCAGGCGCTG |
| | | GCTTCTCATGCATATGATACGTATCCACTGTTTGAAATTCAGGCATTGACCGACCAGAAGCAGGATTTAATTAACC |
| | | ATATTATGGTGTTTGAAAATTATCCGGTGGAGGAGCAGGTCGAGGAACTGGGAATTGACGGGCAGGATACATTCCC |
| | | GATTTCCAACGTGGTGGCTGCAGAGCAGACCAACTACGAACTGAACCTCGTCGTTATGCCGGGAGAATGCATAAA |
| | | GATTCGTTTTATGTATAACGCGTTAAGCTTTGATCAAACAGACATTGAGCGTCTGCATGGACATTTTGTGAATCTGC |
| | | TGGAGCAAATTTTGCTTAACCCGAATGTTTGCGTAGAAGAGCTGGAACTGGTTACAGCGGCGGAAAAACAACAGA |
| | | TTATAGGAGAGTTTAATGACACTGCCTCTGCATATCCACGGAATCAGACGATCCAAAAACTGTTTGAGGAGCAGGC |
| | | TGAGCGCACGCCGGATCATATTGCCGTAGCTTTGGGTCATCAATCATTGACCTATCGGGAGCTCAATGAGACAGCC |
| | | AACCGATTAGCGCATACGCTGCGGGATGCAGGGGTGAAGCCCGATGAACCGGTTGGCATTCTGACGGAGCGCTCG |
| | | CTGGATATGATTACTGGAACACTCGCTATTTTGAAGGCTGGAGGCGCGTATGTGCCGGTTGACCCTCAATATCCAG |

TABLE 6-continued

Nucleotide sequences of genes encoding an NRPS (triE) involved in the biosynthesis of tridecaptin in *Paenibacillus* sp. strains NRRL B-50374, NRRL B-67721, NRRL B-67723, and NRRL B-67724.

| Strain | SEQ ID NO: | Sequence |
|---|---|---|
| | | AGGACCGTATCCGTTATATGCTGGAGGACTCGGGAGCCAAGCTGCTGCTGGCTCAGCAGGATTTACTGGATCGTTG<br>CTATTTTGACGGACAGATTGTCAATCTGAATGATGATATGTCCTACAGTACGGATCATTCCAATCTGGGGATGGAT<br>GGAGCGGGCCATCATGCTGCTTATGTCATTTATACCTCAGGCTCAACAGGCAAGCCTAAGGGCGTCGTTGTTGAGC<br>ATCAAAGTGTCGTGCGCCTGGTCCGCAATACGGATTATGTCCCATTTGATGAATCGGTCCGAATGCTGCAGACTTG<br>CGCGTTTGTATTCGATGTATCTACGTTTGAAATTTGGGGCGCGCTGCTGAACGGCGGTCAGCTTGTTCTCGTGCATA<br>AGGATGATCTTTTGGACGCGGCCAAGCTCAAGGAGACGATACGGGATCATCGCGTCACCATGATGTGGCTGACCAC<br>ACCGTTATTTAATCAGCTTTCGCAGCAGGACAGTAAGCTTTTCGGCGATGTGAAGTATTTGCTGGTTGGTGGTGATG<br>TTTTGTCTGCGCCCCATATTAACCGGGTCCTGCGTGATAATCCGAACATGAACATCATTAATGGCTATGGGCCAACG<br>GAAAATACAACCTTTTCGACGACGTACCACATTACGGAAGAGCAGTTGGATTCTGTGCCGATCGGACGTTCCATCC<br>GCAATTCGACGGCATATGTTGTGGATTCGTCATTTAACCTGCAGCCGGTCGGAGCCTGGGGTGAGCTGGTTGTCGG<br>CGGAGACGGAGTTGCACGCGGTTATCTGAACCGTCCTGAGCTGACGGCCGAGAGATTTCTTGCTAACCCGTGGATA<br>GATGGAGATCGCCTGTACCGTACGGGAGACCTGGTTCGCTGGCGTGAAGATGGCATGCTGGAATACGCTGGACGG<br>ATTGATCAACAGGTTAAAATTCGCGGTTACCGGATTGAGCTGGGCGAGGTGGAGGCGCGGCTGGCAAGTGTACCG<br>TCCGTACGGGATAGCGTTGTTATCGCTTTGCGGGATGGAGCAGGCCAGCAGCAATTATGTGCTTACTTCACTTCCGA<br>TGAACAGCTGACTGTCCGCGAGATTCGGGCTGTGCTGTCGGGTAGTCTGCCGAGCTATATGATTCCATCCGCATTTG<br>TACAGCTAGATCGGTTTCCGCTGACGACCAACGGCAAAATCGACCGCAAAGCTTTACCTGTGCCGGACAAAGCGTT<br>GCATACGGGTATAGAATATGTCGCACCGCGAACCGATGTGGAGCAGTTGCTGGCAGGCATTTGGCAGGAAGTGCT<br>CGAAATCCCGCAAGTGGGTATCCAGGATGACTTTTTCACGTTGGGGGGACATTCCTTGAAAGTGCTGGAGCTTGTA<br>CGCAAAGTTTACCTTGCCACAGACATCGAGCTTCCAATCCGAAGTGTTCTGGAGTTCCCGACCATAGAAGAGCAGG<br>CGCTCGCATTATTGAAATCGGATTTGCAATCCAAGGCAGATAGTCCAATCATTCAGTTGAATGAACACGGTCCTGT<br>CTCCATCTTCTGCTTTCCGCCTATGCTTGGATACGGGCTGTCGTTCGCGGAGCTTGCGAAACAACTGGATCAGGACG<br>CAGTCGTGTATGGATTGGAGTTCGTAGATGATGCTGCGGATGAGCAGGAAATGTTGGCACGGTATGTTGATTTGAT<br>CGTCAGCACTCAAGCGCAAGGTCCGTATGTGCTGCTTGGTTATTCCATAGGCGGTAATCTGGCGCATAAGGTTGCC<br>GACACGCTGGAGCGTCAAGGTCATGCTGTATCCGACATTTTGATGCTCGATTCGGTCAAAAGGACGGAAGCCCTGT<br>CCTTCACAGTCGAAGAAACAGAGCACGAAATTCATGCCATGCTGGAACAGGTTCCCGAATCCTACCGTGAGCTGTT<br>GAATGAAACGTACCAGCGTAAAATGATCGCTTACGCGGTGTATGGTAACCATCTCCTGAATACAGAGACGGTTCGG<br>GCGAATATTCACGGCTTTGTTGCTGTCGGATCGGAAACAGTTAGGGGAACTGGAGACAATCGACTTTTATGGAAAG<br>ACGCTACACAAGGAAGCTATGAAGAGCATAGCTTGATTGGCAATCATTATGAACTGCTGGAACCCGGATTTATCGA<br>GGAAAATGTAAAAAGTATCCGTGCCGCAATACAAAACATAACCCGGAATATGGACAAAGACATGGCACAAGATTT<br>GGCACATCATAATTCTTGA |
| NRRL B-67724 | 8 | TTGAAAGCCTTATTTGAGAAGGAAAAAAATTACTGGAGCCATAAACTGGAATCTGAGGATCATATCATCTGTCTTCCA<br>TATACTAACAACGTGTCCAAAAGTACAACTGCAACGAGTTTAAATTCCCACACATACACACTCACATTTCCATCTGAA<br>ATTTCCCAAAGAATATCATCTATAACAGGTGGCGCTCCATGGGCCGTGTTTATGGTCCTGCTTGCTGGAGTAGAGAGC<br>TTATTGCATAAATACACATGTGAGGAACGTGTGCTGCTGGGCATTCCGGTAGCCAAGTCTAGCAACGGTGCTACAAA<br>GCCGATCAACCATCTGCTTTTATTGAAAAATACGCTGGATTCCAGCACAACCTTCAAAGCCTTGCTGTCTCAAATCAA<br>AACCTCTGTCGGCGAAGCTATTGAACATCAAAACATTCCTTTTTGGAACTATTCTGAATTACTTGACATTCAACGTAA<br>TGAGGATGGAAAGCCTCTTATTCACACCACAGTATCCTTGCAAAATATTCATATTTCTGATTTTTTGAATCACGTACAA<br>CCTGAACTAGATTTCCAGTTTCAATGGGAACATGAAGCGGTCTCCCTGAACGTAAAGTATAATAGCGACCGTTATAGC<br>GAGACGACGATTGAGCACTTTGTTGAGCAGCTTCTGCGGCTGTACACTATTGTTTTGCAGCAGCCAGAGTTGGCGATT<br>TCCACAGCACAAGTGCTGTCAGAGCAAGAAGTAGAGCAGCTGCTCCATACCTTCAACGATACAAATGTGGATTATCC<br>ACGTCATGCGTCTATTCATGAATTGTTCGAGAAACAGGTGAAGCAGACACCACAGCAGGTGGCGGTAGTGTGTGGGC<br>AAGATAGCCTAACCTATGCAGAATTGAATGAAAAGGCCAACCGACTGGCTCATTCTTTACGTAAGCAGGGAATCCGC<br>ACCGAGCAGACGGTCGGCATTGTAGCTGAACGCTCGATTGAGATGATTGTCGGTATGCTCGGAATTCTCAAAGCAGG<br>TGGAGCGTATGTACCTATTGATTCTGATTACCCGGATGAGCGTGTACGCTATTTACTGAAGGATTCCGGTGCGGACAT<br>ACTGCTCGTGCAGCGAATGGAACATCGGCCCACTGATTTTAAGGGAAGGGTGCTTGACCTTAGCGATGCTGCAATTTA<br>TGGAACGGATGATGCTGATCGTTACGATCCCATTTTGCCGAATGATCACGGAACGAATACTGATCCGGGATACGTGG<br>ACTGCCTAGATCCGTTCTACTCCATTTCCGCCAGTCCCGAACTTGCTTCTACGACAACCATACAACCAGAAAACATGC<br>AACCCAAAGCTACGCAATCAGAACAAGCAAAACAAATACAGCAGACTTATGCAGCTAAAGAACAACCGAAGGCGAG<br>CGCAGCTGATTGCTTGGCCTATATTATGTACACCTCAGGGACTACAGGCCAGCCCAAAGGGGTTATGGTGGAGCACC<br>GTAATGTCGTGCGTTTGGTGACAAATACAAACTATGCACGCTTGAATGCCGACACACGCATTTTGCAGACCGGGTCTG<br>TTGTCTTTGACGCGTCCACCTTCGAAATTTGGGGTGCGCTATTGAACGGTGGACAGCTTGTGCTGGTGAGTCAGGATG<br>TTATTTTGGACGCGCCCAAGCTCAAGGAAGTTGTTCGCAATCACGGCATTACCACGATGTGGCTGACCGCACCACTCT<br>TTAATCAGCTATCCCAGCAGGACTTGGAACTATTTGAGGGAATGCAGGAGCTGTTGGTCGGTGGTGATGTGCTGTCCG<br>TACCGCATATTAACCGGGTATTGGAGGCCCATCCGAATCTACATATTATTAACGGCTACGGTCCGACGGAAAATACG<br>ACCTTTTCCACCACACATGCCATTACCGGCGTTCAATCGGCATCTGTGCCCATTGGTAGCCCGATCCATAACTCGACG<br>GCATATGTTGTGGACGGTTCGATGCAGCTCCAGCCTGTTGGAGCGTGGGGAGAACTGATCGTCGGCGGTGACGGGGT<br>GGCTCGCGGATACCGCAACCGCCCAGAACTGACGACCGAAAAGTTCATTGACAGTCCGTTCCGTGGCGGCGAACGCT<br>GCTATCGAACAGGGGACCTGGTGCGTTGGAATGCGGACGGACGCTGGAATATAAGGGACGAATCGACGCGCAGGT<br>GAAAATTCGAGGCTACCGGATTGAGCTGGGCGAGGTGGAAGCACAGCTGTTGAAGCTGGAGGCAGTCCGAGAAGCT<br>GTTGTAATTGCACATGAAGATGAGCAGGGGCAAAAGCTGCTCTGCGCATATGTGGTCACCCATGCGGAAGTAGCGAC<br>AAGTGAGCTGCGTAGTGCTTTGAGCCAGGAGCTACCGGGCTACATGGTACCGTCGTATTTTGTGCAGCTGGAGCAATT<br>GCCACTGACGCCCAATGGCAAGGTGGATCGCCGAGCGTTGCCACAACCAGAGGGAGGTGTAAGCTCAGGCGCAGAA<br>TATGTACCTCCTCAAAATCAATTACAAGCACAACTGGCTAGCATCTGGAAAGATGTGCTGGAGCTTGAGCGCATTGG<br>GATTAAGGATAACTTTTTTGAGGCAGGAGGACATTCCCTGCGGGCGACACATGTCATATCACTCATCTATAAGGAATT<br>GCATAAAAATGTGCAACTAAAGGATCTGTTCCAGCATCCGACAATTGAACAGCTGGCGCAGGTTATTGAAGCACTGG<br>AGCAAACCACCTATGAATCCATCCCTGTTACGGAGAATAAGCCATTTTATGCGGTTTCTTCAGCTCAAAAACGGATGT<br>ATATCCTCAATCAGCTTGATGGAGCGGGAATTAGCTATAACATACCTGGTGCCCTGACTCTGACCGGTTCACTTGATC<br>ACAAGGCACTGGATAACGCGTTCCGTCAGCTTATTGACCGCCATGAAACATTGCGCACAAGTTTTGAGACCATGAAC<br>GGTGAACCTGTCCAGCGAGTACATGACGAGGTTCCTTTTTGCATGGAATTGACCTATGCTCACGGAGCTGCCCCAAAG<br>GAAACGGATGAGCTGGTACGTAACTTTGTCCAACCATTCGATCTGGGGCAGGCCCCGTTATTCCGAGTTGGTTTGATT<br>GAAACAGACCCAGAGCATCATATTTTGCTCATGGACATGCATCATATCATTTCGGACGGCACCTCTATAAATGTACTA |

TABLE 6-continued

Nucleotide sequences of genes encoding an NRPS (triE) involved in the biosynthesis of tridecaptin in *Paenibacillus* sp. strains NRRL B-50374, NRRL B-67721, NRRL B-67723, and NRRL B-67724.

| Strain | SEQ ID NO: | Sequence |
|---|---|---|
| | | ATTCAGGACTTTATTCATTTATATGCAGGCGACACACTGCCATCGCTACGCATTCAGTATAAAGACTACGCCGCTTGG |
| | | CAACAGAAGCAGCAGCAAAGTGAACGCTACCGGGAACAGGAAAACTACTGGCTCAATACCTTCGCAGGAGAGCTAC |
| | | CTGTGCTTGATCTACCGACTGATTATCCACGCCCAGCGGTGAGAAGCTTTGAAGGAGATGTGCTGGAATTTACGCTTG |
| | | ACCAACGACAAAGCGAAGGCTTAAAAAGCATTGCGGTGCAGACGGAATCGACATTATATATGGTGCTGTTGGCTGCC |
| | | TATTCGGCTTTGCTTAGCCACTATAGCGGGCAGGAGGAAATTATTGTCGGTTCGCCAATTGCAGGGCGGCCCCATGCG |
| | | GATCTTGGCAGTCTGATCGGGATGTTCGTGAATACACTGGCAATCCGTAATTATCCAGAAGGCGGGAAAACGTTCCG |
| | | CGATTATGTGTTGGAGGTCAAGGAAAACGCGTTAAAGGCTTTTGAACATCAGGATTATCCGTTTGAAGAGCTGGTGG |
| | | AGAAGCTGGGCGTGGATCGAGATTTAAGCCGTAATCCGTTATTTGATACCATGTTTGCACTGCAAAACTTAGAGCAA |
| | | AAAGAGCAACAGCTGGCGGGGCTTCAATTGGCATCCTATCCAAGTGAACAAACGACGGCCAAATTTGATTTGAGTCT |
| | | GTTCGCAGTGGAGAATGGAGAACAAATTTCCTGTGCTCTGCAATACGGAACTCGGCTGTACAAACGGGAAACCATTG |
| | | AACGACTGACTGAACATTTGCAGCAGCTTATCAATGCGGTTATAGAACAGCCGGATATCGTTCTTTCGGCTATTGAAA |
| | | TGGTTTCGGCCCAAGAAAAAGAGCTGCTTGTGCAGAGATTCAATGATACGGTAGCAGACTATCCGTATCCACGAGAT |
| | | CAAGCACTGCATGTGCTGTTCGAGGAACAGGTAGCGCAATCACCAGATCGGCTGGCCGTCACCTTTGCGGACATGCA |
| | | GCTTACCTACCGCGAGCTGAATGAACGTGCCAACCGTCTGGCACGCATACTCGCTTCCCATGGGATACGGCGCGGGT |
| | | GCGAGCCAGAGACACAGCGAGTAGGGATTATGGCTGAACGCTCCATTGAAATGGTCGTCGGTATGCTGGCGATTTTG |
| | | AAGGTCGGAGGGGCTTACGTTCCCATTGATCCCGATTATCCTGAGGAGCGTATCCGTTATTTACTGGAGGATTCCAGT |
| | | GCGGGGCTGTTACTGTTACAGCGACGTGAGCAGATGCCTTTTGAACCCGGCATTCCGGTCATTGATTTGAGTGATGAA |
| | | CAACGATGGAATAGCAAATCTGAATGTGACACTCATACCGATGGAACAATTGCGATTACAACAGGGGGATCTTCCTC |
| | | AGATCTTGCGTATGTGATCTACACCTCTGGTACGACAGGCAAACCGAAGGGCGTGATGATTGAGCACCGTAATGTCG |
| | | TGCGGCTAGTGAAAAACAAAAGCTATGCCATGCTTGATGAAAATACACGTATGCTGCAATTGGGCGCAGTTGTGTTC |
| | | GATGCCTCCACATTTGAAATCTGGGGAACGCTGCTGAACGGGGGACAACTGTATGTGGTAAGCCATGACACTATTCT |
| | | GGATGCCTCCAAGCTCAAGCAGGCGATTGACAAGTATCGTGTTAACACGATGTTCATGACCACGGCTTTATTCAATCA |
| | | GTATTCGCAGCAAGAAATCGGAGTGTTTGCGTCCTTGAAGGAGTTGCTCGTGGGTGGTGATGTGTTGTCTGTACCACA |
| | | CGTCAATCGTGTGTTGAAGGAGTACCCGCAGCTTCGCCTGGCCAATATTTATGGGCCGACGGAGAACACCACCTTTTC |
| | | CACCATCTATGACATTACAGAACCGCAAACCCTGGCTATTCCCATTGGACGTCCAATTGATCACTCGACCGCTTATGT |
| | | GGTCAATCGTTCGTTGAAGCTGCAACCTATCGGAGCCTGGGGAGAGTTGATCGTCGGTGGCGACGGTGTTGGGCGAG |
| | | GATATCTGAATCGGCCCGAGCTTACGGCGGAAAAATTTATTGAAAGTCCATTCCGGTCTGGAGAATATTGCTATCGTA |
| | | CAGGAGACTTAGTGCGTTGGCGTGCTGATGGTGTACTGGAGTACAAGGGAAGAATGGATGAACAGGTCAAAATTCGC |
| | | GGCTACCGCATTGAACTGGGTGAAATTGAAACCCGATTGTCCACAATTCCAGGTGTGAAGGAATCGGTTGTTACCGT |
| | | GCGGCAGGATGATCACGGACAAAAACAGCTGTGTGCCTATTTTGCAACAGACAGTGAATTGAGCGCCAGCGACTTAC |
| | | GTAACATTTTGTCGCAGGATCTGCCTGGCTATATGGTGCCGTCCTACTTTGTGCAGCTCTCCAGACTGCCTTTGACGCT |
| | | GAATGGCAAAGTAGACCGTAGGGCACTGCCCGGACCTGAGCACAATCTCGATACAGGTATGGATTATGTGGCACCCG |
| | | AGACGGATGTCCAACAGGCACTGGCTACGGCTTGGGGAGCCATTCTTGGTATCCCGAAAGTCGGAATACAGGATAAC |
| | | TTTTTCCATTTGGGTGGTGACTCCATCAAGGCCATCCAAGTATCGTCCCGCTTGTTTCAGGCTGGATACAAGCTGGAA |
| | | ATGAAGGATTTGTTCAAATACCCGACAATTGCGGGACTAAGCACATATATTCAGCCTGTTAACCGAATAGCCGAGCA |
| | | GGGCGAGGTTACAGGAAATGTAGTGCTTACACCGATTCAGCGCTGGTTTTTTGAACAGCCAACGGAAGAACCACACT |
| | | ATTTTAACCAATCTGTCATGCTCTATCGTCAGGAAGGCTATGACGAACAGGCACTACGGCGGGCGCTCCATCAGATTA |
| | | CTTCGCACCATGATGCATTGCGTATGGTTTTTAGTTTGTCGGAGAACGGATGTACAGCATGGAACCGCAGTGTAGAGG |
| | | AAGGCGAACCGTACCATCTGGAATGCTTTGACTATAATGACAGCGATGTAAACAAGCAAGATTTGGCGAAGATAATT |
| | | GAAGCGAAATGTAATGAAATTCAATCTGGTATTTCCCTAAGCGAAGGTCCGCTGATGAGACTGGGGCTGTTCCGTTGC |
| | | CCGGATGGAGATCATCTGCTGGTCGTGATTCATCATTTGGCGGTGGACGGAGTATCCTGGCGCATATTATTCGAGGAT |
| | | TTGGCGACTGCCTATGATCAAGCCTCCAAGGGTGAACAGGTGATTCAGCTGCCTCATAAAACAGATTCGTTCCAAAC |
| | | ATGGGCCGAGCAGCTGCACGCTTATGCCAACAGTCCAGCTATGGAACGTGAGCGAGCGTATTGGGGGAAACTTGCAC |
| | | AAGCGGATCCGGCTCCTTTGCCGCAGGATTACGGGCATAACGAGCACGAAAAGCCATTGATTGGCGATAGTGAGTCG |
| | | GTTACTGCTTTGTGGACACATGCAGAGACAGAGCAGCTGCTCAAGCAGGCCAATCGTGCCTACCGTACAGAAATTAA |
| | | TGACCTGTTGTTGACGGCGGTAGGAATGGCATTGCAAGCATGGAGTGGAAATGATCGTTTCCTGATAAATCTAGAGG |
| | | GACATGGACGTGAAGCCATTTTACCAGAGGTGGACATTACTCGAACGATAGGGTGGTTTACAAGCCAATATCCTGTTT |
| | | TGCTCGATATGCCGGAAGAACTGGCACTTTCGCAACGGATTAAGCGTGTGAAGGAAGGACTGCGCGGCATTCCGCAA |
| | | AAAGGGATTGGCTACGGTGTACTGAAATATTTATCCGACCGTCAGACACAGGCACCAGAGGCATCTCCAACCATATT |
| | | TACGACAGATCCCGAAATCAGCTTTAACTATTTGGGACAGTTCGATCAGGATATGAAAGGGAACGACTTGCAATCAT |
| | | CCTCATATGAGGGTGGGATGCCGCTGAGCCCGACCATGGCTCGAACGTATACGCTTGATTTTGGCGGCATCATTTCGG |
| | | GAGGCCAACTGGGTCTGACGATTAGCTATAGCCGTACCAGCTATAAACCGGAGACCATCGAGCGATTGGCGAAATTC |
| | | CTGGAATCAAGCCTACGTGAAATTTTGGCGCATTGCATCCATAAAGAACACCCGGAGCTTACCCCAAGTGATATTTCT |
| | | TATAAAGGAATGAGTGTGGAGGGCTTGGACAGCCTCTTATCTGAAATGGGTGCTGCGGGTGAGATCGACAATGTATA |
| | | TGCACTGACCCCCATGCAGAAAGGGATGCTGTTTCACAGCCAGCTAGATAGTCAAGCAGCTGCGAATGACGCATATT |
| | | TTGAGCAGGTTTCTTATGATATGCGAGGTCAGATGGACATTCGGGCTTTTGCAGAAAGCCTGAATATTCTGGTTCGGC |
| | | GACATGAGGCGCTGCGTACACATTTTTATTTTGGCAGAGATACGGAACCGTTGCAGGTGGTGTATCGAAATCGGGATT |
| | | GCGGCTTTCAATATGAAGATTTACACCATCTGGATGAGGATGAAATAGATACCTGGGTGAAAAATTTCAAGCTACAA |
| | | GATAAAGCACGGGGCTTTGATCTGCGCCGGGATGTCCTGCTGCGTGTAGCGATTTTACGTACTGGAGAAGACAGCTA |
| | | TCATTTTGTATGGAGCTTCCATCATATCGTCATGGACGGCTGGTGTCTCTCCCTTATAAATAAAGAAGTGTTTGAAAG |
| | | CTATGCAGCACTTCAGGAGGGCAGAGTACCAGAGCTGGCACCGGCAGTGCCGTACAGCCGCTTTATTGAATGGCTGG |
| | | AAGCACAGGATCGCAAGGCGGCAACCGACTACTGGAGCAGCTATTTATCCGGATATGAGCAGCAAACAGCGTTACC |
| | | AGCTGTAAAATCCGGTCGCAAGAGTGAAGGCAACACGGCTAGTGATTGGGTGACGGTTTTGGAACGTGAGTTGACCC |
| | | TCCGGGTGGAGGAGACGGCTAAGCGATATCAAGTGACCATGAATACGTTATTACAAACCGCATGGGGGATTGTGCTG |
| | | CAAAAATATAACAACCACAGTGATGTCGTATTTGGCAGTGTCGTCTCAGGCCGTCCATCAGATATTATCGGGGTAGA |
| | | GGATATTATCGGCTTGTTCATTAATACCATTCCCGTTCGCATTCTTAGTAAGGCAGGGGAATCTTTTGCAGAAGTTATG |
| | | AAGAAAACGCAGGAGCAGGCGCTGGCTTCTCATGCATATGATACGTATCCACTGTTTGAGATTCAGGCATTGACCGA |
| | | CCAGAAACAGGATTTAATTAACCATATTATGGTGTTTGAAAATTATCCGGTAGATGAGCAGGTCGAAGAACTGGGAA |
| | | GTGCCGGGCAGGATACATTCCCGATTTCCAACGTGGTGGCTGCAGAGCAGACTAACTATGATCTGAGCTTAGTCGTTA |
| | | TGCCGGGAGAATGCATCAAGATTCGTTTTATGTATAATGCGTTAAGTTATGATCAAACAGGCATTGAGCGTCTGCATG |
| | | GGCATTTTGTGAATCTGTTGGAGCAAGTTTTGCTTAACCCGAATGTTTGCGTAGAAGAGCTGGAACTCGTTACAGCGG |
| | | CGGAAAAACAACAAATTACAGGAGAGTTTAATGACACTGCCTCTGCATATCCAAGCCATCACACGATCCAAAAACTG |

TABLE 6-continued

Nucleotide sequences of genes encoding an NRPS (triE) involved in the biosynthesis of tridecaptin in *Paenibacillus* sp. strains NRRL B-50374, NRRL B-67721, NRRL B-67723, and NRRL B-67724.

| Strain | SEQ ID NO: | Sequence |
|---|---|---|
| | | TTTGAGGAGCAGGCAGAGCGCACGCCGGATCATATTGCTGTAGCTTTGGGTCATCAATCATTGACCTATCGGGAACTC |
| | | AATGAGACAGCCAACCGTTTAGCGCATACGCTACGTGATGCAGGGGTGAAATCCGATGAACCTGTGGGCATTTTGAC |
| | | GGAGCGCTCACTGGATATGATTACGGGAACACTCGCTATTTTGAAGGCTGGAGGCGCGTATGTGCCGGTAGACCCTC |
| | | AATATCCGGAGGACCGTATCCGTTATATGCTGGAGGACTCGGGAGCTAAGCTGCTGCTGGCTCAGCAGGATTTACTG |
| | | GATCGTTGCTATTTTGACGGACAGATTGTCAATCTGAATGAGGATACGTCCTACAGTGCAGATGCTTCCAATCTGGGT |
| | | ATAGATGGAGCGGGTAATCATGCTGCTTATGTCATTTATACCTCAGGTTCAACAGGTAAGCCTAAGGGTGTCGTAGTT |
| | | GAGCATCAAAGTGTCGTGCGCCTTGTCCGCAATACGGATTATGTGCCATTTGATGAATCGACCCGAATGCTGCAGACT |
| | | TGCGCGTTTGTATTTGATGTATCTACGTTTGAAATTTGGGGTGCGCTACTGAATGGTGGTCAGCTTGTTCTTGTGCATA |
| | | AGGATGATCTATTGGACGCGGCCAAGCTTAAAGAGACGATACGGGATCATCACGTCACCATGATGTGGCTGACCACA |
| | | CCGTTATTTAATCAGCTTTCACAGCAGGATAGTAAACTTTTCGGCGATGTGAAGTATTTGCTGGTTGGTGGTGATGTTT |
| | | TGTCTGCACCCCATATTAACCGGGTCCTGCGCGATAATCCGGACATGAACATCATTAACGGCTATGGGCCAACGGAA |
| | | AACACAACCTTTTCGACAACGTATCACATTACGGAAGAACAGCTGGATTCTGTGCCGATCGGACGGCCCATCTGCAA |
| | | TTCGACGGCGTATGTTGTAGATTCGTCATTTAACCTGCAACCGGTCGGAGCTTGGGGTGAGCTGGTCGTCGGCGGAGA |
| | | CGGAGTTGCACGTGGTTATCTAAATCGTCCTGAGCTGACGGCTGAGAGATTTCTTGCTAACCCGTGGAGGGACGGAG |
| | | ATCGCCTGTACTGTACGGGAGACCTTGTTCGCTGGCGTGAAGACGGCATACTGGAATACGCTGGACGGATTGATCAA |
| | | CAGGTTAAAATTCGCGGTTACCGGATTGAGCTGGGTGAGGTGGAGGCGAGGCTGGCAAGTGTACCGTCCGTGCGGGA |
| | | TAGCGTGGTTATTGCTTTGCGGGATGGAGCAGGTCAGCAGCAATTATGTGCTTACTTTACTGCCGATGAACAGCTGAC |
| | | CATCCGTGAGATTCGAGCTGCGATGTCGGTCAGTCTGCCGAGCTATATGATTCCATCCGCATTTGTACAGCTGGATCG |
| | | GTTTCCGCTGACGACCAACGGCAAAATCGACCGCAAAGCTTTACCTGTGCCGGACAAAGGGCTGCACACGGGTATAG |
| | | AATATGTCGCACCGCGAACCGATGTGGAGCAGTTGCTGGCATCTATTTGGCAGGAAGTGCTTGAAATTCCACAAGTG |
| | | GGTATCCATGATGACTTTTTCACGTTGGGCGGACATTCCTTGAAAGTACTGGAGCTTATACGCAAAGTTCACCTTGCC |
| | | ACAGACATTGAGCTCCCCATCCGTAGTGTAATGGACTTCCCGACTATAGAAGAGCAGGCGCTCACATTATTGAAAGC |
| | | CGATCTGGAATACAAGGCCGATAGTCCAATCATTCGGTTGAATGAACACGGTCCGATCTCCATCTTCTGCTTTCCTCC |
| | | TATGCTTGGATACGGGCTGTCGTTCGCGGAGCTGGCGAAACAACTGGATCAGGACGCAGTCGTGTATGGATTAGAGT |
| | | TCGTGGATGATGCTGCGGATGAGCAGGCCATGCTGGCACGTTACGTTGATTTGATCGTCAGCACGCAAGCGCAAGGT |
| | | CCGTATGTGCTGCTTGGTTATTCCATAGGTGGTAATCTGGCGCATAAGGTTGCTGACACACTGGAACGTCAGGGCCAT |
| | | GCTGTATCCGATATTTTTATGCTCGATTCGGTCAAAAGGGCGGAAGCCCTGCCCTTCACAGTTGAAGAAACAGAGCAT |
| | | GAAATTCATGACATGCTGGAACAGGTTCCCGAATCCTACCGTGAGCTGTTGAATGAAACGTACCAACGTAAAATGAT |
| | | CGCTTACGCGGTGTATGGCAACCAGCTTGTGAATACAGAGAGCGTTCAGGCGAATATTCACGGCTTTGTCGCCGTTGG |
| | | ATCGGAAACGGTGAGGGGTACAGGAGATAATCGACTTTTATGGAAAGACGCTACACAAGGTAGCTATGAAGAGCAT |
| | | AGCTTGATTGGTAATCATTATGAACTACTGGAACCCGGATTTATCGAGGAAAATGTAAAAAGTATCCGTGCCGCAAT |
| | | ACAAAAGATAACTCGGAACACGGACAAAGACATGACACAAGATTTGGCACATCATAAATCTTGA |

Example 5. Characterization of Fusarcidins in *Paenibacillus* sp. Strains NRRL B-50374, NRRL B-67721, NRRL B-67723, and NRRL B-67724

Whole broth cultures of *Paenibacillus* sp. strains NRRL B-50374, NRRL B-67721, NRRL B-67723, and NRRL B-67724 were prepared by culturing each strain in a soy-based medium as in Examples 1-3. Cell extracts of the whole broth cultures were prepared, and fusaricidin-like compounds were quantified in each cell extract.

A chromatographic method using ultra performance liquid chromatography/mass spectrometry triple time of flight (UPLC/MS Triple TOF) was utilized to fragment and quantify the fusaricidin-like molecules in the cell extracts: Column: YMC-Triart C8, 4.6×50 mm, 12 nm; Water (0.1% Formic Acid) and acetonitrile (0.1% Formic Acid); Gradient (% B): 0-5 min 10-70%; Wash. Mass fragmentation patterns obtained from an AB SCIEX TRIPLE TOF® mass spectrometer were analyzed to confirm the identity of each fusaricidin-like compound. The fusaricidin-like compounds analyzed included Fusaricidin A ("Fus A"), Fusaricidin B ("Fus B"), Fusaricidin C ("Fus C"), Fusaricidin D ("Fus D"), LiF05a, LiF05b, LiF06a, LiF06b, LiF07a, and LiF07b. These compounds are described in WO 2016/154297 where their structures are outlined in FIGS. 3, 4, and 12. The analytical method used to quantify the fusaricidin-like compounds did not distinguish between LiF05a and LiF06a or between LiF05b and LiF06b. Therefore, the signals produced by these two groups of compounds are referred to herein as LiF05/6a and LiF05/6b, respectively.

Quantification was performed using standard curves generated with known concentrations of the fusaricidin-like compounds. Quantification of LiF05/6a, LiF05/6b, LiF07a, and LiF07b was determined from the standard curve generated with Fusaricidin C. The lowest chemical standard used was at a concentration of 0.5 μg/g. When a signal was detected from an analyte in a cell extract but the intensity of the signal was below that produced with the lowest standard, the quantity of the analyte was determined to be Below the Level of Quantification (BLOQ). The results of the quantification of the fusaricidin-like compounds in each *Paenibacillus* sp. strain are presented in Table 7.

TABLE 7

Quantification of fusaricidin-like compounds in *Paenibacillus* sp. Strains NRRL B-50374, NRRL B-67721, NRRL B-67723, and NRRL B-67724.

| | Fusaricidins (μg/g) | | | | | | | | |
|---|---|---|---|---|---|---|---|---|---|
| Strain | Fus A | Fus B | Fus C | Fus D | LiF05/6a | LiF05/6b | LiF07a | LiF07b | Total |
| NRRL B-67724 | 287 | 78 | 127 | 31 | 168 | 32 | 64 | 8 | 795 |
| NRRL B-67721 | 266 | 79 | 66 | 15 | 197 | 45 | 30 | 3 | 703 |
| NRRL B-50374 | 167 | 35 | 53 | 9 | 217 | 32 | 23 | 1 | 536 |
| NRRL B-67723 | 31 | 11 | 8 | 0.3 | 21 | 1 | 13 | BLOQ | 86 |

Example 6. Analysis of Nitrogen Fixation Gene Clusters in *Paenibacillus* sp. Strains NRRL B-50374, NRRL B-67721, and NRRL B-67724

Additional analysis of the genomes of *Paenibacillus* sp. strains NRRL B-50374, NRRL B-67721, and NRRL B-67724 revealed that these strains also possess a nitrogen fixation gene cluster. The presence of a nitrogen fixation gene cluster was previously reported in the laboratory strain, *Paenibacillus* sp. WLY78. Wang L, Zhang L, Liu Z, Zhao D, Liu X, et al. (2013) A Minimal Nitrogen Fixation Gene Cluster from *Paenibacillus* sp. WLY78 Enables Expression of Active Nitrogenase in *Escherichia coli*. *PLoS Genet* 9(10): e1003865. In *Paenibacillus* sp. WLY78, the nitrogen fixation gene cluster contains nifB, nifH, nifD, nifK, nifE, nifN, nifX, hesA, and nifV. A similar gene cluster structure was found in *Paenibacillus* sp. strains NRRL B-50374, NRRL B-67721, and NRRL B-67724.

Without wishing to be bound to any theory, the presence of the nitrogen fixation gene cluster in the genomes of *Paenibacillus* sp. strains NRRL B-50374, NRRL B-67721, and NRRL B-67724 may contribute to the ability of these strains to promote efficient nitrogen uptake in plants and stimulate plant growth.

Comparison of the genome sequences for nifB encoding a nitrogen fixation protein showed that the nifB sequence in each strain shared at least 96.9% sequence identity with that of the other strains (see Table 8). The nucleotide sequences for the nifB sequences from the three strains are presented in Table 9.

TABLE 8

Percent identity matrix created with MAFFT for the nifB genes from *Paenibacillus* sp. strains NRRL B-50374, NRRL B-67721, and NRRL B-67724.

| | Percent Sequence Identity | | |
|---|---|---|---|
| Strain | NRRL B-67724 | NRRL B-50374 | NRRL B-67721 |
| NRRL B-67724 | 100.00 | 97.27 | 96.93 |
| NRRL B-50374 | 97.27 | 100.00 | 99.40 |
| NRRL B-67721 | 96.93 | 99.40 | 100.00 |

TABLE 9

Nucleotide sequences of genes encoding a nitrogen fixing protein (nifB) in *Paenibacillus* sp. strains NRRL B-50374, NRRL B-67721, and NRRL B-67724.

| Strain | SEQ ID NO: | Sequence |
|---|---|---|
| NRRL B-50374 | 9 | ATGGACTCTTTAGCTGATCTCTCGGAAACCCCCTTAGCATTGGAAACCCTCAGACGACATCCCTGTTATAACGAAGAG<br>GCACATCGCTATTTTGCGCGCATTCATCTTCCAGTAGCCCCGGCATGCAATATTCAATGCCATTATTGCAACCGCAAA<br>TTCGATTGCGTCAATGAAAGCCGTCCCGGCGTTGTTAGTGAACTGCTCACGCCGGAGCAGGCGGCGAGCAAGACCTA<br>TGGCGTAGCGGCACAGCTGATGCAGCTGTCCGTTGTCGGCATTGCGGGACCTGGAGATCCGCTGGCCAATGCGGAGG<br>CAACCTTCGATACCTTCCGCCGGGTCCGTGAGACAGTTAAGGATGTCATATTCTGTCTCAGCACGAATGGCCTTACCT<br>TGATCAGGCATATCGACAGGATTGTAGAGCTGGGTATTTCGCATGTCACGATCACGATCAATGCTGTAGATCCAGTGG<br>TGGGGAGCCGCATTTATGGATGGGTCTACGATGAAGGAAAACGCTATGCAGGAGAGGAGGCCGCGCGGCTGTTGATT<br>GACCGCCAGCTGGCAGGCTTGAAGATGCTGGCTTCGAGAGGCGTATTGTGCAAGGTGAACTCGGTGCTGATTCCCGA<br>AGTCAATGATGCCCATCTGCCGGAGGTAGCCAGGGTAGTCAAGGAGCACGGCGCAGTGCTGCACAACATTATGCCGC<br>TCATCATCGCACCTGGTAGCCGGTATGAGCAGGAAGGGATGCGGGCTCCCCGTCCCCGTCTGGTCCGGCAGCTGCAG<br>GAGCAATGTGCTGAAGCGGGGGCTGTCATTATGCGCCATTGCCGTCAGTGCAGGGCGGATGCGATTGGACTGCTGGG<br>CGAGGATCGGAATCAGGATTTTACATGGGAGAACATAGCGGCTGCTCCTCCCATGGATGAAGGGGCAAGGGCACAAT<br>TTCAGAAAGAACTGGATGAGAAGGTGAGAGTGAGAATGGAACGCAAGGAGGGACAATCACACCACAAACAACCGTC<br>AACCGGGGCTGGCTGTAGCTGCCCGTTATCGGGAGATAAGCCTGAAGCGAGCTTCACCTCAAAGCCAGTCCTAATCG<br>CAGTGGCCAGTCGTGGCGGAGGGAAGGTGAATCAGCATTTCGGCCGTGCCAAGGAATTTATGATCTATGAAAGCGAC<br>GGGACCATCGTAAATTTCATAGGCATTCGTAAGGTGCAATCCTACTGCCACGGGAAAGCCGATTGCAATGGGGACAA<br>GGTCGAGACGATGAAGGAGATCCTTTCCATGGTGCATGACTGTGCATTGCTGCTGTCGTCCGGCATAGGCGAAGCCCC<br>CAAAGAGGCATTGCAGGAAGCTGGCGTGCTGCCTATTGTATGCGGCGGGGATATTGAGGAATCGGTTCTGGAATATG<br>TGAAATTTCTGCGTTATATGTATCCTGTGCAGAGCAATAAAGGAAGTAAGCGCAATAAGGGAGTTAAGGGCAATCAT<br>TCGGATTTACCCATTAAACATTTTGGAGGCTGA |
| NRRL B-67721 | 10 | ATGGACTCTTTAGCTGATCTCTCGGAAACCCCCTTAGTATTGGAAACCCTCAGACGACATCCCTGTTATAACGAAGAG<br>GCACATCGCTATTTTGCGCGCATTCATCTTCCAGTAGCCCCGGCATGCAATATTCAATGCCATTATTGCAACCGAAAA<br>TTCGATTGCGTCAATGAAAGCCGTCCCGGCGTTGTTAGTGAACTGCTCACGCCGGAGCAGGCGGCGAGCAAGACCTA<br>TGGCGTAGCGGCACAGCTTATGCAGCTGTCCGTTGTCGGCATTGCGGGACCTGGAGATCCGCTGGCCAATGCGGAGG<br>CAACCTTCGATACCTTCCGCCGGGTCCGTGAGACAGTTAAGGATGTCATATTCTGTCTCAGCACAAATGGCCTTACCT |

TABLE 9-continued

Nucleotide sequences of genes encoding a nitrogen fixing protein (nifB) in *Paenibacillus* sp. strains NRRL B-50374, NRRL B-67721, and NRRL B-67724.

| Strain | SEQ ID NO: | Sequence |
|---|---|---|
| | | TGATCAGGCATATTGACAGGATTGTAGAGCTGGGTATTTCGCATGTCACGATCACGATCAATGCTGTAGATCCAGTGG |
| | | TGGGGAGCCGCATTTATGGATGGGTCTACGATGAAGGAAAACGCTATGCAGGAGAGGAGGCCGCGCGGCTGTTGATT |
| | | GACCGCCAGCTGGCAGGCTTGAAGATGCTGGCTTCGAGAGGCGTATTGTGCAAGGTGAACTCGGTGCTGATTCCCGA |
| | | AGTCAATGATGCCCATCTGCCGGAGGTAGCCAGGGTGGTCAAGGAGCACGGTGCAGTGCTGCACAACATTATGCCGC |
| | | TCATCATCGCACCTGGTAGCCGGTATGAGCAGGAAGGGATGCGGGCTCCCCGTCCCCGTCTGGTCCGGCAGCTGCAG |
| | | GAGCAATGTGCTGAAGCGGGGGCTGTCATTATGCGCCATTGCCGTCAGTGCAGGGCGGATGCGATTGGACTGCTGGG |
| | | CGAGGATCGCAATCAGGATTTTACATGGGAGAACATAGCGGCTGCTCCTCCCATGGATGAAGGGGCAAGGACACAAT |
| | | TTCAGAAAGAACTGGATGAGAAGGTGAGAGTGAGAATGGAACGCAAGGAGGGACAATCACACCACAAACAACCGTC |
| | | AACCGGGGCTGGCTGTAGCTGCCCGTTATCGGGAGATAAGCCTGAAGCGAGCTTCACCTCAAAGCCAGTCCTAATCG |
| | | CAGTGGCCAGTCGTGGCGGAGGGAAGGTGAATCAGCATTTCGGCCGTGCCAAGGAATTTATGATCTATGAAAGCGAC |
| | | GGGACCATCGTAAATTTCATAGGCATTCGTAAGGTGCAATCCTACTGCCACGGGAAAGCCGATTGCAATGGGGACAA |
| | | GGTCGAGACGATGAAGGAGATCCTTTCCATGGTGCATGACTGTGCATTGCTGCTGTCGTCCGGCATAGGCGAAGCCC |
| | | CCAAAGAGGCATTGCAGGAAGCTGGCGTGCTGCCTATTGTATGCGGCGGGGATATTGAGGAATCGGTTCTGGAATAT |
| | | GTGAAATTTCTGCGTTATATGTATCCTGTGCAGAGCAATAAAGGAAGTAAGCGCAATAAGGGAGTTAAGGGCAATCA |
| | | TTCGGATTTACCCATTAAACATTTTGGAGGCTGA |
| NRRL B-67724 | 11 | ATGGACTCTTTAGCTGATCTCTCGGAAACCCCCTTAGCATTGGACACCCTTAGACGACATCCCTGTTATAACGAAGAG |
| | | GCACATCGCTATTTTGCGCGCATTCATCTTCCAGTAGCCCCGGCATGCAATATTCAGTGCCATTATTGCAACCGCAAA |
| | | TTCGATTGCGTCAATGAAAGCCGTCCCGGCGTTGTTAGTGAACTGCTCACGCCGGAGCAGGCGGCGAGCAAGACCTA |
| | | TGGCGTAGCGGCACAGCTGATGCAACTGTCCGTTGTCGGCATTGCGGGACCTGGAGATCCGCTGGCCAATGCGGAGG |
| | | CAACCTTCGATACCTTCCGCCGGGTCCGTGAGACAGTTAAGGATGTCATATTCTGTCTCAGCACGAATGGCCTTACCT |
| | | TGATCAGGCATATCGACAGGATTGTAGAGTTGGGTATTTCGCATGTCACGATCACGATCAATGCTGTAGATCCAGTGG |
| | | TGGGGAGCCGCATTTATGGATGGGTCTACGATGAAGGAAAACGCTATGCAGGAGAGGAGGCCGCGCGGCTGTTGATT |
| | | GACCGCCAGCTGGCAGGCTTGAAGATGCTGGCTTCGAGAGGCGTATTGTGCAAGGTAAACTCGGTGCTGATTCCCGA |
| | | AGTCAATGATGCCCATCTGCCAGAGGTAGCCAGGGTGGTCAAGGAGCACGGCGCGGTACTGCACAACATTATGCCGC |
| | | TCATCATCGCACCCGGCAGTCGGTATGAGCATGAAGGGATGCGGGCCCCCCGTCCCCGTCTGGTCCGGCAGCTGCAG |
| | | GAGCAATGTGCTGAGGCGGGAGCTGTCATTATGCGCCATTGCCGTCAGTGCAGGGCGGATGCGATTGGACTGCTGGG |
| | | CGAGGATCGCAATCAGGATTTTACATGGGAGAACATTGGGGCTGCTCCTCCCATGGATGAAGAGGCAAGGGCACAAT |
| | | TTCAGAAAGAACTGGATGAGAAGGTGAGAGTGAGAATGGAACGCAAGGAGGGACAATCGCACCACAAAAAAACGT |
| | | CAACCGGGGTTGGATGTAGCTGCCCGTTATCGGAGGATAAGCCTGAAGCAAGCTTTACCTCAAAGCCAGTCCTAATC |
| | | GCTGTGGCCAGTCGTGGCGGAGGGAAGGTGAATCAGCATTTCGGTCGTGCCAAGGAATTCATGATCTATGAAAGCGA |
| | | CGGGACTATCGTAAATTTCATAGGCATTCGTAAGGTGCAATCCTACTGCCATGGGAAAGCCGATTGCAATGGAGACA |
| | | AGGTCGAGACGATGAAGGAGATCCTTTCCATGGTGCATGACTGTGCATTGCTGCTGTCGTCCGGCATAGGCGAAGCC |
| | | CCCAAAGAGGCATTGCAGGATGCTGGCGTGCTGCCTATTGTATGCGGCGGGGATATTGAGGAATCCGTTCTGGAATA |
| | | TGTAAAATTTCTGCGTTATATGTATCCTGTGCAGAGCAATAAGGGAAGTAAGCGCAATAAGGGAGTTAAGGGCAATC |
| | | ATTCGGATTTACCCATTGAACATTTTGGAGGCTGA |

Example 7. Plant Growth Promotion Properties of *Paenibacillus* sp. Strains NRRL B-50374, NRRL B-67721, NRRL B-67723, and NRRL B-67724

*Paenibacillus* sp. strain NRRL B-50374, *Paenibacillus* sp. strain NRRL B-67721, *Paenibacillus* sp. strain NRRL B-67723, and *Paenibacillus* sp. strain NRRL B-67724 were cultured in a soy-based medium to produce whole broths that were diluted in water to a concentrations of 20%. The diluted whole broths were applied to tomato plants as a drench at the time of planting. Several days later when the tomato seedlings had developed into young plants the average weights and standard deviations for forty whole tomato plants in each treatment group were measured. An untreated control group ("UTC") and a group treated with the soy-based medium only ("Medium") were included in the analysis for comparison.

Figure 2:
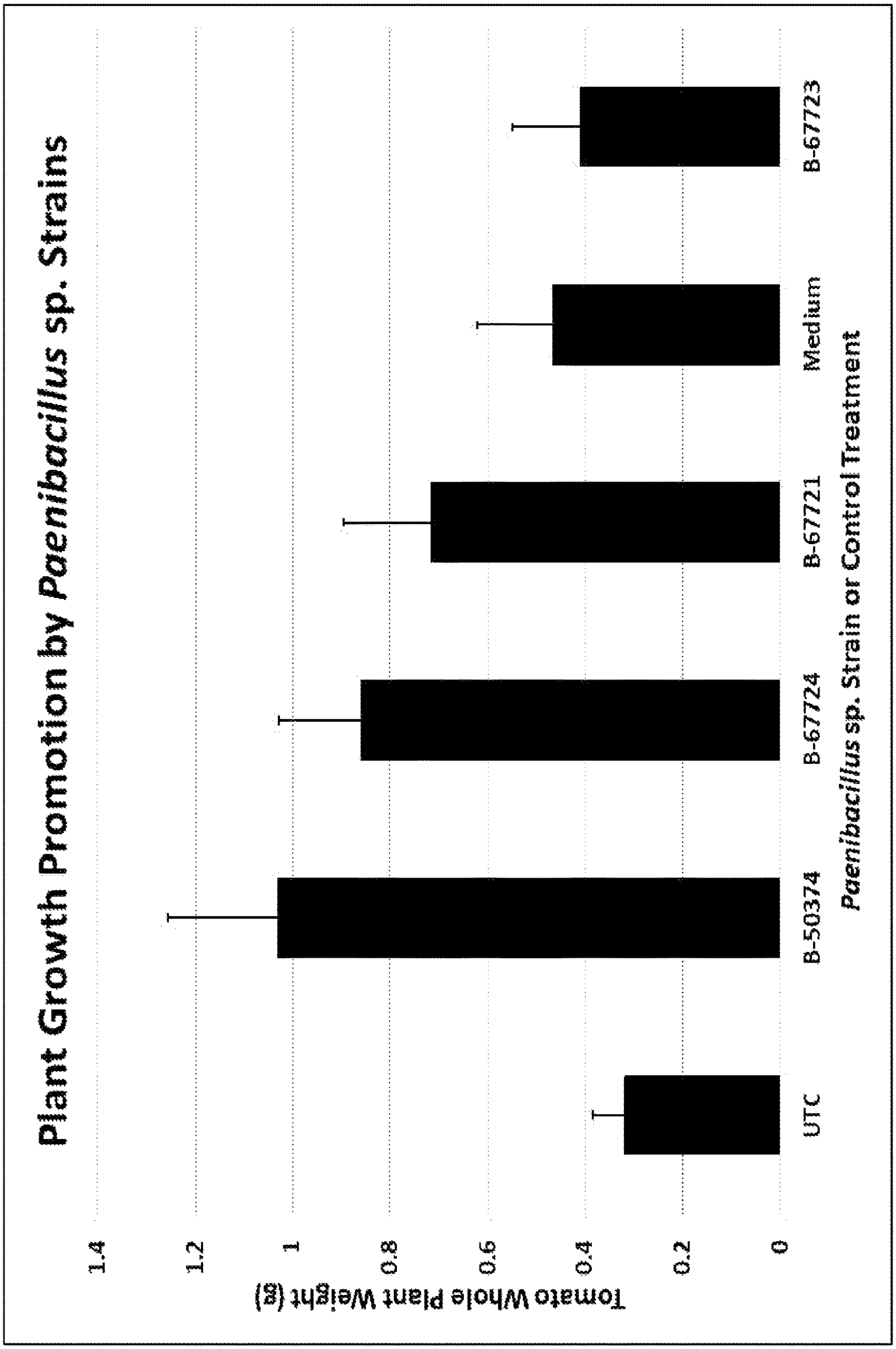
FIG. 2 depicts the plant growth promotion in tomato plants resulting from drench treatments with whole broth cultures of *Paenibacillus* sp. strain NRRL B-50374, *Paenibacillus* sp. strain NRRL B-67721, *Paenibacillus* sp. strain NRRL B-67723, or *Paenibacillus* sp. strain NRRL B-67724.

Interestingly, *Paenibacillus* sp. strain NRRL B-50374, *Paenibacillus* sp. strain NRRL B-67721, and *Paenibacillus* sp. strain NRRL B-67724, each of which possesses a nitrogen fixation gene cluster, produced a significant increase in tomato plant growth compared to the UTC and Medium controls (see FIG. 2). In contrast, *Paenibacillus* sp. strain NRRL B-67723, which does not possess a nitrogen fixation gene cluster, did not increase tomato plant growth compared to the UTC and Medium controls.

Unless defined otherwise, all technical and scientific terms herein have the same meaning as commonly understood by one of ordinary skill in the art to which this invention belongs. All publications, patents, and patent publications cited are incorporated by reference herein in their entirety for all purposes.

It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

We claim:

1. A composition comprising a preservative and a biologically pure culture of a *Paenibacillus* sp. strain or a cell-free preparation thereof comprising a fusaricidin and a tridecaptin;

wherein the *Paenibacillus* sp. strain comprises a fusaricidin synthetase gene of fusA encoded by a DNA sequence exhibiting at least 90.5% sequence identity to SEQ ID NO: 3; and the *Paenibacillus* sp. strain comprises a nonribosomal peptide synthetase (NRPS) gene of triE encoded by a DNA sequence exhibiting at least 90.0% sequence identity to SEQ ID NO: 7, wherein the culture comprises at least $1\times10^4$ colony forming units (CFU) of the strain per mL and wherein the *Paenibacillus* sp. strain is *Paenibacillus* sp. strain NRRL B-50374, *Paenibacillus* sp. strain NRRL B-67721, *Paenibacillus* sp. strain NRRL B-67723, *Paenibacillus* sp. strain NRRL B-67724, or a fungicidal mutant strain thereof.

2. The composition according to claim 1, comprising Fusaricidin A, Fusaricidin B, Fusaricidin C, Fusaricidin D, LiF05a, LiF05b, LiF06a, LiF06b, LiF07a, and/or LiF07b.

3. The composition according to claim 1, wherein the composition effectively controls a plant disease caused by a fungus selected from the group consisting of *Botrytis cinerea, Sphaerotheca fuliginea*, and *Puccinia triticina*.

4. The composition according to claim 1 comprising a fermentation product of *Paenibacillus* sp. strain NRRL B-50374, *Paenibacillus* sp. strain NRRL B-67721, *Paenibacillus* sp. strain NRRL B-67723, *Paenibacillus* sp. strain NRRL B-67724, or a fungicidal mutant strain thereof.

5. The composition according to claim 1, wherein the fungicidal mutant strain has a genomic sequence with greater than about 90% sequence identity to *Paenibacillus* sp. strain NRRL B-50374, *Paenibacillus* sp. strain NRRL B-67721, *Paenibacillus* sp. strain NRRL B-67723, or *Paenibacillus* sp. strain NRRL B-67724 and/or the fungicidal mutant strain has fungicidal activity and/or levels of a fusaricidin that are comparable to or better than that of *Paenibacillus* sp. strain NRRL B-50374, *Paenibacillus* sp. strain NRRL B-67721, *Paenibacillus* sp. strain NRRL B-67723, or *Paenibacillus* sp. strain NRRL B-67724.

6. The composition according to claim 1 wherein the *Paenibacillus* sp. strain is *Paenibacillus* sp. strain NRRL B-50374, *Paenibacillus* sp. strain NRRL B-67721, *Paenibacillus* sp. strain NRRL B-67724, or a fungicidal mutant strain thereof and further comprises a nitrogen fixation gene cluster; and the nitrogen fixation gene cluster comprises a nitrogen fixation gene of nifB encoded by a DNA sequence exhibiting at least 96.9% sequence identity to SEQ ID NO: 10.

7. The composition according to claim 6, wherein expression of the nitrogen fixation gene cluster contributes to enhanced plant growth, plant vigor, and/or crop yield.

8. The composition according to claim 6, wherein the *Paenibacillus* sp. strain comprises a fusaricidin synthetase gene of fusA encoded by a DNA sequence exhibiting at least 97.3% sequence identity to SEQ ID NO: 1 and the *Paenibacillus* sp. strain comprises a NRPS gene of triE encoded by a DNA sequence exhibiting at least 97.5% sequence identity to SEQ ID NO: 5.

9. The composition according to claim 6 comprising a fermentation product of *Paenibacillus* sp. strain NRRL B-50374, *Paenibacillus* sp. strain NRRL B-67721, *Paenibacillus* sp. strain NRRL B-67724, or a fungicidal mutant strain thereof.

10. The composition according to claim 6, wherein the fungicidal mutant strain has a genomic sequence with greater than about 90% sequence identity to *Paenibacillus* sp. strain NRRL B-50374, *Paenibacillus* sp. strain NRRL B-67721, or *Paenibacillus* sp. strain NRRL B-67724 and/or the fungicidal mutant strain has fungicidal activity and/or levels of a fusaricidin that are comparable to or better than that of *Paenibacillus* sp. strain NRRL B-50374, *Paenibacillus* sp. strain NRRL B-67721, or *Paenibacillus* sp. strain NRRL B-67724.

11. A method of treating an agricultural plant to control a disease, wherein the method comprises applying to a part of the plant and/or to a locus of the plant an effective amount of a composition comprising a biologically pure culture of a *Paenibacillus* sp. strain or a cell-free preparation thereof comprising a fusaricidin and a tridecaptin;

wherein the *Paenibacillus* sp. strain comprises a fusaricidin synthetase gene of fusA encoded by a DNA sequence exhibiting at least 90.5% sequence identity to SEQ ID NO: 3; and the *Paenibacillus* sp. strain comprises a nonribosomal peptide synthetase (NRPS) gene of triE encoded by a DNA sequence exhibiting at least 90.0% sequence identity to SEQ ID NO: 7, wherein the culture comprises at least $1\times10^4$ colony forming units (CFU) of the strain per mL and wherein the *Paenibacillus* sp. strain is *Paenibacillus* sp. strain NRRL B-50374, *Paenibacillus* sp. strain NRRL B-67721, *Paenibacillus* sp. strain NRRL B-67723, *Paenibacillus* sp. strain NRRL B-67724, or a fungicidal mutant strain thereof.

12. The method according to claim 11, wherein the method comprises applying the composition to foliar plant parts.

13. The method according to claim 11, wherein the composition is applied at about $1\times10^{10}$ to about $1\times10^{12}$ colony forming units (CFU) of the *Paenibacillus* sp. strain per hectare or at about 0.5 kg to about 5 kg fermentation solids per hectare.

14. The method according to claim 11, wherein the disease is a fungal disease or a bacterial disease.

15. A method for increasing the vigor and/or crop yield of an agricultural plant, wherein the plant, the plant propagule, the seed of the plant and/or a locus where the plant is growing or is intended to grow is treated with an effective amount of a composition comprising a biologically pure culture of a *Paenibacillus* sp. strain or a cell-free preparation thereof comprising a fusaricidin and a tridecaptin;

wherein the *Paenibacillus* sp. strain comprises a fusaricidin synthetase gene of fusA encoded by a DNA sequence exhibiting at least 90.5% sequence identity to SEQ ID NO: 3; and the *Paenibacillus* sp. strain comprises a nonribosomal peptide synthetase (NRPS) gene of triE encoded by a DNA sequence exhibiting at least 90.0% sequence identity to SEQ ID NO: 7, wherein the culture comprises at least $1\times10^4$ colony forming units (CFU) of the strain per mL and wherein the *Paenibacillus* sp. strain is *Paenibacillus* sp. strain NRRL B-50374, *Paenibacillus* sp. strain NRRL B-67721, *Paenibacillus* sp. strain NRRL B-67723, *Paenibacillus* sp. strain NRRL B-67724, or a fungicidal mutant strain thereof.

16. The method according to claim 15, wherein the treatment is carried out as an in-furrow treatment, seed treatment, and/or foliar treatment.

17. The method according to claim 11, wherein the agricultural plant is selected from the group consisting of soybean, corn, wheat, triticale, barley, oat, rye, rape, millet, rice, sunflower, cotton, sugar beet, pome fruit, stone fruit, citrus, banana, strawberry, blueberry, almond, grape, mango, papaya, peanut, potato, tomato, pepper, cucurbit, cucumber, melon, watermelon, garlic, onion, broccoli, carrot, cabbage, bean, dry bean, canola, pea, lentil, alfalfa, trefoil, clover, flax, elephant grass, grass, lettuce, sugarcane, tea, tobacco and coffee; each in its natural or genetically modified form.

18. A seed treated with the composition according to claim 1.

* * * * *

SEQUENCE LISTING

<160> NUMBER OF SEQ ID NOS: 11

<210> SEQ ID NO 1
<211> LENGTH: 23727
<212> TYPE: DNA
<213> ORGANISM: Paenibacillus

<400> SEQUENCE: 1
atgaatgaca tgcagttata tgatttaaca aatgcgcaga agcgtatatg gtataccgaa 60
ttactctacc cagatacgtc agtgtcacag ctttccggta cagctaagat gaaggggcat 120
atcaatattg ctgcctttat gcagtccatt aatttgatta tcaaacagta tgatgcgttc 180
cgcatccgta ttacctcagt ggatggagtg cctcagcagt acgtcgttcc ttatgaagag 240
agacagctgg agtgcctgga tcttagccac tatgaaagtg tatctgaggt ggaagcctta 300
cttgagcaac acaaaagcaa acctttgccc ctgctggatt ctgagctctt ccagttttta 360
attgtgaaga ttagcgagga agagtattgg attaatatca agatgcacca tattatttct 420
gacggaatat caatggtggt ctatggcaat cagctgacaa cattttacat ggagttaatt 480
caaggaaatg aaccgaagct gggcgacgat tgctcgtata ttcaatatat tgcagatgag 540
aatgcatacg aactttctga cagataccaa aaggataagg cttactggct ggataaattt 600
tctgatttgc ctgagcttac gggttggaag tcatataatc cgttatcttt aagcacccac 660
gccgttcggg agcattttac cgtaccagaa gtgctatatc acgagctgca agcattttgc 720
caacagaaca ggatttcttt gttccagttc ttcatgggtg cgatgtatat ctacatacac 780
aaaatgacga atcagccgga tgtggtgatt ggcacttcgt tcgctaaccg gggggaacaaa 840 aaagagaagc aaaagatagg tatgtttgtc agcaccgctg ctgccagaac atacgtcaaa 900
aaggatatgg atgtgttgag cttcctgcag gatgtagcca gagatcagat gtcagtcctg 960
cggcatcaga agtatccgta caatcagtta attcaggatc ttagagaaat gcatggtaac 1020
aaggatattc agcggctttt tggcgtttca atggaatatc gtcttatcaa ttgggttgat 1080
ttggatgatg tgcgcatttt gacggattat gatttctgcg gggacgaagt gaacgatttc 1140
gtgcttcata tcgtggagat cctggatgaa ggcgaactgg tactggatgt cgattatcgg 1200
acggagctgt ttgaacgcag tgaagttaag gacatggttt cccagttgct tacgatcgcc 1260
gagcagatca ttcattcacc tcagctttct atcgcagagg taaacttatt gggtgaacca 1320
gaagagcagt ccattttggc tctttcggaa ggcgctgcag tcgattatcc acgtgagaag 1380
accatccatg gcttattcga ggaacaagcc gagcgcacgc cagatcacgt agccgttcag 1440
atggacgaac agagcattac atacctagct ctaaacgagc aggctaacca gcttgcgaga 1500
tatttgcgct ccgagggagt agttgcagat acgctcgtag ggattatggc tgaccgttcc 1560
ttggagatgg tcattgggat gttggccatt ttgaaagcag gtggtgccta tgtaccgatt 1620
gaccccgatt atcccgagga acgtatccat tatatgctgg aggattcagg ggtccgtctg 1680
ttgctcaccc aaagtcatct atgggagagc accacttttg acggaaagct tgtgagtttg 1740
gacgaagcta caacgtatac aggagatgct tccaatctgg agagtatttc gggaccaagc 1800
catctagcct atgttatcta cacgtcgggt acgaccggca agccgaaggg cacgctgatt 1860
gaacacaaaa atgtggttcg actgctcttt aacgataaaa atctatttga tttcagctct 1920
caggatacgt ggacgctatt ccattcgttc tgcttcgatt tctccgtttg ggagatgtac 1980
ggagcgcttc tttacggagg gaaattggtg attgttccat ctctcacagc caagagccca 2040
gcagctttcc tggagttgtt gaaagacaac caagtcacca ttttaaatca gacgccgacg 2100

-continued

```
tatttttatc aggtgctaca ggaagagtta acgcactctt cgacagagct tggccttaga   2160
aaaatcattt ttggtggaga ggccttaagt ccatctcttc tgagaaactg gcgggtcaag   2220
tatcctgatg tgcagctgat taatatgtac ggaattacgg aaacaacggt ccatgtcacc   2280
tacaaggaaa tcacggaaca tgagattgaa gcggggaaaa gcaatattgg cagaacgatc   2340
cccacactta gcgcttatat tctcgatgag caaagacggc tgcagcctgt tggggttccg   2400
ggagagctat acattgcagg ggacggtctt gcccgtgggt atttgaatcg gccggatttg   2460
acgtctgaga aattcgttga gcatccgtat cgggcgggag agcggctgta ccgaactggg   2520
gatcttgctc gttggttgcc tgatggcaat attgaatatt tgggacggat cgaccatcag   2580
gtcaaaattc gcggctaccg aattgagctt ggcgaggtag aagcccaaat tctcaaggct   2640
ccgaacgtac gagaaacgat tgtcctcgca cgggatgacg aacagggcca aaaattgctg   2700
tgcgcctact atgtagcctc cagtgatctt tcgccggggg aattgcggtc tcagctggca   2760
gcggaactcc ccgcttacat gattccttct tattttgtcc ggctggagca aatgccgctt   2820
acgccaaatg gcaaactgga tcgccgtgcg ttgccggctc ctgaaagcag cgtacaatcc   2880
ggcgaggctt atttggctcc gagaactgct gtggaagctc agatggtact catctggcaa   2940
gatatcttgg gagttgcccg cgtcggtgtc agagataatt tctttgaaat tggtggtcac   3000
tctttgcggg caacagtgct cgtttcacgg attcacaaag aattgggatg tagcatttcg   3060
ctgcgtgagg tgtttcagtc acctacggtc gaatccttgg cgcaacttgt gaaaaaaacac   3120
attccgaccc tgtacgaatc catcccacag gcaacggaaa gcgaagctta cccagtgtcc   3180
tcagcgcaaa agcggttata cgtgctgaga cagatggatg ggggagagct tagctacaat   3240
atgccagggg ccttcacagt ggatggaccg ttggatcgca cgcggctgga gtccgcgttc   3300
cagggactga tccagcgtca tgaatcccta agaaccggct tttatatgca ggatggagag   3360
cttgttcagc gtgtgcatag gaatgtgccg ttcgcgttga actatacaga ggcttcggtg   3420
gaggagacgg atacgctcat tcacaacttt attcgtgcct ttgatctgag ccaggctcca   3480
ttactgcgtg ttagcttggt gaagctccag gaggagcgtc atctgttgct gtttgatatg   3540
catcacatca tttcagatgg ggtttctatt caaatattga tacaggaact tactcatttg   3600
tatcaaggag aacagctacc agaactgcac atccaataca aggattatgc cgtatggcaa   3660
cgagaacagt cagagaacca atggcaagat cttgagaaat attggctgca atcctttgaa   3720
ggagagttgc cggtattgga tttgcctaca gacttccaac gaccttcagt tcggagcttc   3780
gagggtagcc gaattgattt tacattggat gagtctggaa ataaggcgat acaagagctt   3840
gcatcccgta caggtactac actgtatatg gtattgctgg ccgcttattc ggtactactg   3900
cacaaatata caggacagga ggacatcgtc gtaggttctc cagtagccgg aagaccgcag   3960
gctgagcttg agggcatcat cggaatgttt gtcaacacac tggccttgcg cagctacccg   4020
gcaggagata aaacctttca ggattatctt ctggaaatca aggaaacggc gctcaaggcg   4080
tttgagcatc aggattaccc ttttgaaaaa ttggtcgaaa agctgggcgt aggacgtgat   4140
gtcagccgca atccgctctt tgacacctta ttggtattac aaaataccga gcaggaagag   4200
caggatatgg acggagtgca ctttactcct tacttgatgg acaccgtcac agccaaattt   4260
gacctgtccc tcaatgtaga ggagaaggga tcaaaattag cctttggcct cgagtatagt   4320
acggctttat atcggcgtga aagtgtagag cgacttgcaa cgcacttgct ccgggttctg   4380
catgcagtct cggccaatcc tcagttgcaa ctggccgaga ttgaaatgat cacaccggag   4440
```

-continued

```
gagaaagtac agatcgttga agtatttaac gcgacatcgg ccccttatcc aagggacaag   4500
accattcatg atctgttcgc ggaacaagtc aagcgtacac cggagcagac ggcgcttgta   4560
ttcggcgatg tccagctaac gtaccttgaa ttggaagaca aggcgagccg actggcccaa   4620
acactgcgtc gtttgggaac gttgagggag cagcctgtgg ccgtgatggg cggacgaagc   4680
attgagatgg tcattggtat gctcgcggtg cttcaggcag gtggagccta tgtgccgatt   4740
gatcctgatt acccggaaga tcgggttcgt tatatgcttg atgattccga cgccaagcta   4800
ttattggtgc aaaagggcga gcttataagt gtagactacg gtataccgat tgtcgatctt   4860
agcagtgaag aggcttatgc tgctgagcct gcccagccgg agacggctca gggatcgcag   4920
gggcttgctt atgtcatcta tacatcgggt acgacgggta gaccgaaggg cgttatggtt   4980
gaacaccgga acgtggtccg tctggtcaaa gagaccaact atgtggagct gaatgaatcc   5040
acacgaattt tgcaaacagg agccgtggcc tttgatgctt ctacatttga gatatgggga   5100
gcgttgctta acggtgggca gctctatttt gtagagaatg acgacattct gattgctgat   5160
aggctcaaag cggctattgc caagtacggg attacaacat tgtggcttac ttcacccctt   5220
ttcaatcagc tttctctgca ggatgagtac ctgttcagag ggctaaaagc attgttagtc   5280
ggcggtgacg tactgtctct atctcatatg aatcgtgtaa tcgaggctaa tcctgatctt   5340
gtccctatca attgctatgg tccgacagag aatacgacct tctccaccac ctacaagatt   5400
ccaggttgtg ccgaaggggg tgtgccgatt ggtcgcccaa ttagtaattc gaccgcttat   5460
gtggtcaatg gatcgctgca attacagcct attggtgctt ggggtgaact cattgtcggc   5520
ggtgaaggtg tagcacgcgg atatctcaat cgtcctgatc tcacagcaga gaaatttgtt   5580
cctagtcctg tgaaggacgg agaaccctgc taccgaactg gggatttggt acgctggctt   5640
ccagatggga atttggagtt taaaggaaga attgatgagc aggtcaaaat acgtggttac   5700
cgcatcgaac tccctgaaat cgaggcccaa ctggccaagg tggagtcggt aatcgacgcc   5760
gtagtggtcg ttcgcgcgga cgagcttggc gagaagcagc tttgcgctta ttatgtggcg   5820
gatcgtacgc tcacggcagg cgaagtacgt ctttccctat cgcaggtact tccaggctat   5880
atgattccat cctactttat ccagatggat cgtatgccat taacatcaaa cggaaaggtg   5940
gaccgcaggt ctctgccggc tcctcaagta ggcgcgcata caggacggaa gtatacagct   6000
cctcgtacac cggctgagga agctttggca tctgtctggc aaggggtgct gggtgccgaa   6060
caggtgggta tccatgataa tttctttgaa ttgggtggag actccataaa agctatccag   6120
gtgtcgtcac ggttactaca ggccggctat cggttagaga tgaagcagct gttcaaatcg   6180
ccaaccattg ccgagctagg agcggaaata caaacggctg tgcatatggc tgaacaggga   6240
gttgtgcgtg gagcgactcg cttgactcca gtccaacagt ggttctttgg acggaagcag   6300
gcagagcctc atcacttcaa tcaagcggtt atgctgtatc gtgaacaggg atttgaggaa   6360
aaggccttgc atcaggtgct aagaaaactc gctgagcatc atgacgccct tcgcatggtt   6420
ttccgtcaga cagagcatgg ttacgaagct tggaatcgtg atcttgaaga aggagagctt   6480
tatagcctgt tcaccgctga tttacggaat gaatccgatc cggctgcagc cattacatcg   6540
ctgtcggatg acattcagcg cagtatcaat ctggcagaag gcccgctgct gaagttagga   6600
cttttccatt gtcaggatgg agaccacctt ctgatcgtga tccaccattt ggtggtggac   6660
ggagtatcct ggcggatttt gttcgaggat attgcagcag gctatgagca ggtgattcaa   6720
ggacaagcgc tgacattccc gcagaagacg aattccttcc gtgactgggg agacgccctt   6780
gctcgttatt cggaaggtcc tgaaatggag actcatcggg cgtattggag ggagctggag   6840
```

-continued

```
aatcagccac tcgaacagtt gccgaaggat gaggctgtgg aaagccttct tttacaggat   6900
agcaaagtaa taacagcaca atggactata gaagaaaccg accaattgtt gagaaaagcc   6960
catcgtgctt atcaaacaga gacgaatgat ctgctattga ctgctctggg catggcggta   7020
tccaaatggt ctggcatcgg aaaggttgct gtgaatctgg aaggacacgg tcgtgagccg   7080
attataccga atatcgacat cacccgtacc gtcggctggt ttacaagtca atacccggtg   7140
attttagact tgggggatga cccagaagtg gcctccttga tcaagtctgt gaaagaaggg   7200
ctgcgccgaa ttccgaacaa aggtattggc tacgggttgc ttaaaacgat ggcaagtcag   7260
ttggatgaag acagcttcag cttgcagcct gagatttctt ttaactattt ggggcaattt   7320
gatcaggatt tgcaaggcag ctcgttgcag atttctcctt atccgaccgg aagcgcccaa   7380
agcttgttgg aggaaccagc ctatacgcta gatatcaatg gcatggtgac ggacggagcc   7440
ctgactctga cgattactta taacggaaaa cagtataagt tatctacgat ggaacagctc   7500
gctggatata ttgaagaaag cctgcgagag cttctccagc attgcgtaac ccaagaaaaa   7560
accgtattga caccaagcga cgtgcttgcg aagggtctaa gcattgccga tctggaggag   7620
ctttctaagc agatcagcca cataggcgat attgagaatg tatatagtct gacgccgatg   7680
cagaagggca tgctgttcca tgatatgttt gagccgcata caggtgctta ttttgagcag   7740
gctgcctttg actttaaggg tagctttgat ccgactgcat tcggacacag tctggatgcc   7800
gtggtggagc gtcatgccat cctgcgcacg aacttttaca gcggatgggg cagcgagcct   7860
ttgcaggttg tatttcgaca cagaggcgct aaattggtgt acgaagacct gcgtgagatg   7920
aatgcatcgc agcgcgaagc ttacctgaag acatttggtg ctaaggacaa agcacagggc   7980
ttcaacctag ctgaagacga gcttctccgt gtatcaattt tacaaacaga tgaagagagc   8040
ttccgactct tatggagctt tcaccacatc gtcatggatg gctggtgtgt tccgttaatt   8100
acgcaggagg tatttgaaca ctattttgcc ctcctggaag gaagagagcc gcagctggca   8160
gaggtccatc cgtacagtcg atatatcgaa tggctggaac agcaggatga agcagttgcg   8220
tccaactatt ggagccgata tctggccggt tacgagcagc agacgctttt acctcaagtc   8280
ggtggagcaa gtaagggaga aggctatgta gcagaaaagc tgaattatcc tctcagcagg   8340
gaattgactg agcgccttga aaaggtggcc agggatgctc atgtcacgat gaatatattg   8400
ctgcagtccc tctggggcat tgcgcttcaa cgctacaacg gtagccggga tgtcgtgtac   8460
ggaagtgtag tatcaggccg accagcagaa attccgggca ttgaccggat gatcggtttg   8520
ttcatcaata cgattcccgt tcgtgtgaag acagaggaga atctcccctt caccgttctg   8580
atgaagcagc agcaggaaca atatatggct tctcatatgt atgacaccta cccgttgttt   8640
gagattcagg ctcagacgga tcagaagcag gatctaatct cccatattat ggtgtttgag   8700
aactatcctg tggaggagga ggtagagcgt ctgggtggtg gcgaggctgc ctttgagatt   8760
gaggaagcgg agcttcttga gcaaacgaat tatgatttta atttaattgt cctccctggc   8820
gaagagatga gattgctgtt ccagtacaat gcacttgttt atgaccaagt gacaattggg   8880
caaatcaagg gccatctggt tcaccttatg gaacaaattg tagagaaccc tgctatttcc   8940
gtggatgctc tagaattagt cacgccgcag gagagagaac agattctgaa cgtatgggga   9000
aatatgaaag gcatttacga gcactgtaac acgttccacg ggctattgga ggaacaggcg   9060
ggacgaacgc cggatgcgac tgccatttgg ttcgaggacg agagtctgac ctatgccgag   9120
cttaatgcaa aagccaatgg actggccaga aggctccgta ctcagggaat caagacggga   9180
```

gatctggtgg gactgattgc tgaacggtcg ctcgaaatga tcgttgggat ctacggcatt 9240
atgaaagccg gggtgcctta tgttccaatc gacccagagt atccgaaaga acgaatcagt 9300
tatatgcttg aagattccgg agcgaagctg atccttacac aggcccatct cttggaacat 9360
ctcggatgga cggaaaatgt tttgctgctg gatgaatcat cgacctatga tgccgacacc 9420
tcgaatttgg aggatactgc tggcccggat gatctggctt acgtgatcta tacttcaggt 9480
acgaccggtc agcctaaggg cgtattagtc gagcatcggg gactaccaaa tctttcaaac 9540
gtatatgggg cacacttcga agttacaccg caggatcgga tcgttcagtt tgcaagcctg 9600
tcgtttgatg catcggtttc ggaaatttta acggcgctga gccatggggg tgttctgtgc 9660
atcccttcta cagaagatat tttagatcat gccctgttcg agcagttcat gaacgataag 9720
gggattacgg tagcgacttt gccacccgct tacgctatcc accttgatcc agagcgtttg 9780
ccaacactgc ggtgcctgct aaccgctgga tcggccgcat cggtcgagtt gatcgaagag 9840
tggaggaagc atgtacgtta ctctaatggc tatggcccaa cggaggactc cgtatgcacc 9900
acaatctggt ctgtcccgga cagtgaggaa gcaacggata ttgtatctat tggacgacct 9960
attgctaacc atagtgtgta catcttggat gaccatttta gattgcaacc tgtcggtgta 10020
gctggagagc tatgcatttc gagtatcgga ttagcacggg ggtatcataa ccggcctgag 10080
ttaatggatg agaagttcgt ggacaatccg tttgctccag gagagcgtat gtatcggacg 10140
ggtgacctgg ttcgctggtt accgaatgga accatcgagt acttaggccg aatagatcat 10200
caagtcaaaa tccgcggcta ccgtatcgag ctaggcgagg tagaagcaca aatgctcaga 10260
gtgccgtccg ttcaggaagt cgtagccatg gctgtagagg gcgatgacgg ctacaaagat 10320
ctagtcgctt atttcgtagc tgctcagaaa cttgaggtat ccgagcttcg ggccgtcctg 10380
tcggagatat tacctggata tatgatccct tcccgcttca tacaactgga ggatatgcct 10440
ctgacgtcga acggaaaaat cgatcgaaaa gcgctgcagg gcgagcgtgg atgggcagcg 10500
gcttcatctg aggctccaag gacacctgtg gaaattcaat tagccgaaat ctggcaagag 10560
gtgctgggtg tagagagcgc gggagtgaag gataatttct tccattttgg aggtcattca 10620
ctgcgtgcag ccctgctagt ctcacgaatt cgcaaggaaa tgaatcgcga gattagtctg 10680
agagcagtgt tcgagtctcc tactattgaa ggattggctc gtgccattga gggctataca 10740
ccgctgaatt tcgaagaaat tcctacagcg ggagcgagag agcattatcc attgtcctcg 10800
gcccaaaaac gactgtttat tctaagtcag ctggaaggtg gagagctgag ctacaatatg 10860
ccgggtatcc ttaccgttga gggagctttg gatcgggaac ggctagagca ggcattccgt 10920
cgtctaattc atcgtcatgg ttcgctgcgt actcgttttg tgaccgtgaa cggtgaacct 10980
gtacagcagc tcctgacgga tgttccgttt actgtggaat atgcggagtt gagcgaggaa 11040
gaggcaggag ctacccttca gcagtttgtc cgtccttttg atttaggtgt agctccattg 11100
ctgcgggtcg gccttattcg aattgcacat gagcgccatt tactattgtt tgacatgcat 11160
catattgtct cagatggggt ttctatgaat attctcatag aagagtttct ccgcttctac 11220
caagaggagg acgtattccc tgaactacag atccagtaca cagactatgc tgtatggcag 11280
caagagcagc tcggaagcga gcgtcttaag gcccaggaag cttactggct ggatgctttc 11340
cgcggaagct tgccagtgct ggatttgcca ggagatgaag ttcgtcctgc ggtgcgaagc 11400
tttgcgggcg atcgaatcga cttccaaatt gattcttctc tgagtgcttc acttcaggag 11460
ctggctaccc gaacgggttc cactctgttc atggtactgc tggcagccta tacggcgctc 11520
ttacacaagt acacaggtca ggaagatgtc attgtcggtt cacctgtggc aggaagatcc 11580
catgcgacac tcgaaggcct catcggtatg ttcgtcggca cagtggcact tcgtacttat 11640
ccagaagggg aaaagccttt cgaggcttat ctgcaggaag tgaaggaaac agcgctgcgg 11700
gcctatgaaa accaggatta cccgttcgag gagctggtag aaaagctgga gcttcagcgt 11760
gatttgagcc gtaacccgct atttgatacc atgtttgtcc tgcaaaatat cgagcaggga 11820
gaacaagaaa tagaaggatt gcgcttcact ccttacgata atgtacatcc ggctgccaag 11880
ttcgatctca cgctgaccgt gagtgaagca gacggggtat tgaactgcac gcttgagtac 11940
gcgactgcga tctacaagca agagactgcc cagcggatgg caggacactt tgtacagctt 12000
attcgggaag ccgtctccaa tccgggaatg ccgttgtcat cccttgatat cgtgacacct 12060
caggaaaaat caaggctgat gaaagcgccg gacgaagcca aggcagatta tcctcgtgac 12120
aagacgatcc atgcgctgtt cgaggaacag gctgcacgta ctccgaatgc ggtggcagtc 12180
gtatgtgaaa atgcagccct gtcctacagc gagctgaacg agcgggccaa tggacttgcc 12240
agaacgctga gggaacgtgg tttgcaacca gacggtttgg ctggaatcat ggcggatcgg 12300
tcccttgaaa tggtggttgg aattttagcc atcttgaagg caggcggggc ctatgtccct 12360
gtagaccctg aatatccaga ggaccgcatt cgctttatgc ttgaggattc gggagccaag 12420
ctactgctga cacaagcgca tctggagcaa cgtgtctcct tcgctgggga catcgtgagt 12480
ctggataaaa tggcttccta taaggaagat gtctcaaacc tgcagcctgc agccggaccg 12540
gagcatcttg cctacgtcat ctacacatcg ggcacgacag gcaagccaaa gggaacgctg 12600
attgagcata aaaatgtagt tcgcttgctc tttaatgata aaaatatgtt tgactttggt 12660
cctcaggata cgtggacact gttccattca ttctgttttg acttctctgt atgggaaatg 12720
tacggagcat tgctgaacgg aggacggttg gtcatcgttc catcgcttac cgcgaagagt 12780
ccagatcgtt tcttgcaatt gcttaaggat cagaaggtca ccgttttgaa ccagacaccg 12840
acgtacttct atcagttgct acaggaagag cttggtcatc aggcggcaga actgagcctc 12900
cgtttgatta tcttcggtgg agaggcatta gccccggccc tgctcaagga ctggagaacg 12960
aagtatccgc aagtgcagct cattaacatg tacggcatta ccgaaacgac cgtgcatgta 13020
acctacaagg aaattacaga gttggaaatt gaacagggtc gcagcaatat cggcaccacg 13080
attccgacgc tgcgggcgta cattttggat gaacaacgtc gtccacagcc gattggcatt 13140
ccgggtgaac tctatgtggc gggcgtaggc ctggcgcgag gttatctgaa ccgaccggaa 13200
ttgacggaag agaagtttgt cgctcatccg tttgaagcgg gcgagcgtat gtaccgctcg 13260
ggtgacttgg cacgctggtt gccggatgga agcatggagt atttgggacg cattgaccat 13320
caggttaaaa tccgtggtta ccgtatcgag ctgggcgaag tggaagcgaa gctgctccat 13380
gctccgtctg taagggaggc cgttgtgctc gcccgggagg atggaagtgg acaaaaagtg 13440
cttgtcggct atttcactgc cgatcagatg ctgacggtag gcgagttgag aaaagacttg 13500
gctgccgaac tgccgactta tatgattcca tcttacttta tgcaattgga acagatgcct 13560
ttgacgccaa atggcaagct ggatcgcaaa gcgcttccgg ctcctgaggc caatgtgcag 13620
actggggcgg tttatgaacc gccaaggacg aaggctgagg aagctttagt ttccgtatgg 13680
caaggtgtgc tgggagcgca gcaggtcggc atccatgatc atttcttcga tctgggtggt 13740
gactccatca aggcgatcca agtgtcctcg agattgttcc aagctggata taaattagag 13800
atgaaggatc tcttcaaata tccgacaatt gccgagctaa gcccgtatct tcaggcagct 13860
ggacgtatag cggaacaggg tgaaattaaa ggtgcagcag agttaatgcc aattcagcgt 13920

-continued

```
tggttctttg aacgccatac agcggagccg caccattata atcatgccgt catgctctat  13980
cggaaagacg gctttgatga ggctgcactc cggttgacaa tggaccaaat tgcgatccat  14040
catgacgcgc tgcgcatggt tttccggcct acagaagctg gatacgcagc ttggaatcgg  14100
ggaacggacg aaggcgagct ctacacattg gacattgccg atatgcggca ggcggaagac  14160
cagacagctg cggttcaggc ccaagccgat gccattcagg caagctttga cttggaaggt  14220
ggcccactgt tcaagctagg cctgttccat tgtgacgatg gcgatcattt gttgattgtc  14280
attcatcacc tcttggttga cggcgtatcc tggcgcatcc tgtttgagga cattgcagcg  14340
gggtacgagc aggcatggaa tggacaagca atcgtccttc cacaaaagac cgattcgtat  14400
cttgtatggt ctgagcaagc gacgaagtat gcagcagggc ctgctctgga caaggagcgt  14460
gcatactggc agctgatcga ggaggcgatt ttggctccac tgccgaagga tgaggatcag  14520
aagccgggca ccattcggga tactgaatcg gttacggtaa cgtggtctgc gcaggaaact  14580
gacctgctgt tgcgacaagc gaaccgggcg tatcatacgg agacgaatga cttgctcttg  14640
actgctctgg gggcagccat tcagcgctgg acaggcatgg agcagatttt ggtcaatctt  14700
gaaggacatg gacgggaaat aatcgtacca gacctggata ttacccgtac cgtgggttgg  14760
ttcacaaccc agtatccagt tctgctgaac ctgcaaggca gacaggaagt atctgcgcga  14820
atcaagcgca tcaaggagaa tttgcgagag gttccgcata aaggaatcgg ctacggtctt  14880
ctgaagtata tggcaccgga gaaaagtgtc ggactcggcg tggagccgga aatttccttc  14940
aattatcttg ggcagtttga tcaggatttg gagggtaatg cccttagcct atccacacat  15000
tcagttggta aagcgctcag cgatctcaca ccacagcaat atgctctgga tgtgaatggc  15060
atgattgccg aaggccagct atcactgacg attacgtaca gcagcaggca gtatcgtaag  15120
gagacggtga gtcattttgc tgaattatta cagtcaagcc ttagtgaggt catccgtcat  15180
tgtgtggctc aggagcgttc acagcttaca ccaagtgatg ttctgttcca aggattaaca  15240
ttggagcagc ttgatcgact cacggcgcag acggctcaca tcggagagat tgaggatgtg  15300
tacaagctga cgccgatgca gaagggaatg ctgtttcaca gcctactgga gccgggctcc  15360
tcttcatact tcgaacaggc aacgtttgag ctgcgtggca gcttcgatgt agataccttc  15420
ttcgagagct tccaggctct ggtgcaacga catgccatac tacgtaccgg cttttacaac  15480
aacattgctg atgtaccgct gcaagttgtc tttaagcaac ggttaatccc tctgcactac  15540
gtagatttgc gcgacgcatc tacgcaggaa caagaagccc gaatcaaggc ttatattgct  15600
gaagatatgg ttaaggggtt cggcctgtca gaagatccgc tgatgcgggt gaccgtcttg  15660
cagaaggatc aaagctgtct tgtattgtgg agcttccacc atattgtcat ggatggctgg  15720
tgtatcccga tcattacaca ggagctgttc gattattatt ctgccaagaa acagcaagta  15780
cagcctgtcc taccgccagc tcagccctat agtcgttata tcgagtggct tgatgcacag  15840
gatgatcaag aagcttcaac gtattggagc caatatctcg aagattatga cgggaatact  15900
gtattgccgg aaggtaaaac gaaatctcaa gccaaagagg cgggctatgt tctaaaagag  15960
catgttctcc atctgggtgt atctttgaca ggtaaaatgg atgttgtcgc gaagcgcaat  16020
cacgtgaccg tcaacacact catgcagaca gcttggggac tgattcttca acgttataat  16080
gccagctcgg atgtcgtttt cggcggcgtt gtgtcgggta gacccgctga gattgcaggg  16140
atcgaaaata tggtgggtct gttcattaat acagtaccta tccgtgtaca gtcatccaaa  16200
gacgaagcct ttgtcgaagt gatgaaacgt acacaggcac agtcattggc tggtcgtgcc  16260
tacgacacct atccactgta tgagattcag ggaaaacaa cccaaaagca ggacctgatt  16320
```

-continued

```
tctcatatta tgatctttga aaattacccg ctcgacgaac aggtggagca atcgggtaat  16380
caaacggagg acaatctcga agttgccaac ttcaccatgt ttgaacaaac caactatgac  16440
tttaacctgg ttgtaattcc aggcgaagac atcaaggtct gcattcgcta taatgcttcg  16500
gtttacgagc aagaaagcat tgcacgaatc ggaggacact tgttgcagat gctcgaccag  16560
gtggctgctc gtccgcaggc gacgatacag gaactggaga ttgtaacatc tgaggaacgg  16620
atgaacctgc ttgactgggg cggcaaggcc catacctatc caagtgatca ggggctgcac  16680
accttgtttg aggaacaggt ggtccgtacg ccggataaga ttgcggcagt aaacggcgac  16740
atccagatca cgtatcggga gctgaacgag caggcgaaca gactagcttc caccttgata  16800
gaccaaggac tacggagtga acaagtggta ggtctgttgg cagatcggtc tgtagagctg  16860
cttgtcgcca tcatgggtgt actcaaagcg ggtggagcct atgtacctat tgatcctgaa  16920
tatccgcagg agcggattca gtatattctg aaggattctg gcgctgaaat tctgctcaca  16980
cagagccacc tgactaagtt ggcctctttt gagggaacgg ttatggaatt ggattccccg  17040
cacatctacg gaaccgaggt ggataatccc aatattcctg ttggaggaaa cgatctggtg  17100
tacttaatct atacctcggg tacaaccgga aatccgaagg gaaccatgat taaccacaaa  17160
gggatcgtga actacatctg gtgggccaat aaggtctatt gtgctgggaa accaacggat  17220
ttcccgttgt attcatccat ttcgtttgac ttgacgatga catcaatgtt tactccgtta  17280
ataaacggag gaatagtgcg gatttatgat ggtatagata aagcggaggt tgttcagcat  17340
attttgcgcg aaaatgcggt cgatattctc aagctgacgc caacgcatct cagtctgata  17400
aaagacatga ccattccagc ggaaagtcgt attcagcaac tcattgtggg cggagaaaat  17460
ctgaccacac atttgtccaa aacgattacc gacctctttg gtggcaacat caaaatctac  17520
aatgaatacg gtccgaccga aaccgtcgtc ggctgcatga ttcacctgta cgatcctgcg  17580
aaggatacac gggaatccgt accgattggg ttgccgtccg acaacatatt catccatatt  17640
ctggatgatc agcttcgtct cgtaccgtta ggcgtggagg gcgaaatgta catcgccggg  17700
gacggggtag cccgtggata tctgaaccgt cctgagctta ccgcagataa attcattaga  17760
aatccgttcg cttcggaagg aaatatgtat cgcactgggg atttggctcg tcgccttcct  17820
aatggagaca ttgagtacat tggacgcatt gaccatcaag ttaaaatacg gggctatcgt  17880
attgagcttg gtgagattga ggccaagctg ctggacattc cacttgtcga ggaagctctc  17940
gttgttgcgt gggcagatgc tcatgggcag aaatcgctgt gtgcttactt cgtagctgat  18000
cgcgaaatgt ctgtcagcga gctgagagac gaactgtctg ccggactgcc tgcatatatg  18060
attccgtctt acttcgtcca actggacgtg atgcctctga caccgaatgg caagctggat  18120
cgcaaggcac tgcctgaacc gaactcgggt ataaaggcgg gagcagactt taccgctccg  18180
cggacggatg tggagaacat tttggcttca atctggcaag gtgtactcgg cgtgccgctt  18240
gtcggcatac atgataattt ctttgagctt ggaggtgact cgatcaaatc cattcaagta  18300
tcctcaaggc ttctccaagc aggctataag cttgaaatga aggatttgtt cggttatccg  18360
acaattgcag agttggcgca gcgcgttagt gtggtcagcc gaattgcgga tcaaagcgag  18420
gtacacggag cggtaagact ggggcctgcc cagcacagat tcttccatga acagtctatg  18480
gatctgcatc actttaatca gtcggtcatg ttgtaccgac gggatggctt caataccgat  18540
gcgctcgccg aggttgttcg gaaaattgca gagcatcatg atgctttacg actggtgctc  18600
cgccaaggag agcaggggtt ggaggcctgg aaccggagcg tgggtgaggg agaactctat  18660
```

-continued

```
agtctccaaa tccatgacct gcgggatgaa acagaccccg cttcagcgat agaagcaggt  18720
gcggaagcca ttcagcgtag catctctctg gaggatggac ctctctttag actgggtctg  18780
ttccgctgtg tggaaggcga acatctgttg atcgttattc atcatctggc tgtggatggc  18840
gtatcctggc gtattctctt tgaggacctg caggaaggct acgagcaggc agtacgtgga  18900
gaagcggtca agcttccaca gaagacggat tcgtaccgtg catgggttga gggaatcaca  18960
caatttgcaa acagcccggc ggctgaacaa gaactcagct attgggcaga ggtagaggga  19020
gatggctttg cccctcttcc aaaagacaag gtagacggcg ctcttctcat caaagacagt  19080
gaggctgtca cggtgagatg gtcaccagaa gagacagagc agttcctgaa agaagcgaac  19140
cgcacttaca atacggaggt taacgatctg ctcctgacgg ctctgggtat ggctgttcac  19200
gagtggacgg gaatcgaacg tgtaggcatc cttctggagg gacatgggcg ggagcctatt  19260
gtgccggaac tggatattac tcgcacaata ggctggttta caagtcaata ccctgtcgcc  19320
cttgagatgg gaggggaatt ggagatcggc gccagaatca agcacattaa ggaaggcttg  19380
cgtcgtatcc cgaacaaagg tgtcggatat ggtattttga aatatttaag cggcggttct  19440
ggtgtctcct ccttctcggc tgaacctgag attaccttca actacttggg acagttcgac  19500
caggatcttg caggagggac gatggaagta tcgccttact cagtaggacc tgaggtcagt  19560
gagcagatgg tgcagcatca gacattgaac attaatggac tgattgccga aggacagctt  19620
caactttcgg tcagctataa ccgtcatcag ttccacgggg agtctgtggc taagtttgtt  19680
gacattctga agaaccgtct cagcgaagtc attggacatt gcgtaagtaa gaaaagaaca  19740
gaacttacac caagcgatgt actcctcaaa gatatcagct tggaaaaaat cgaggagtta  19800
gaagagcaga cacggcatat cggcagtatt gaaaatatgt ataaactgac gccgatgcaa  19860
aaaggaatgt tgttccacag cttgctggag cctcattcgg aagtctactt tgagcaggcc  19920
aagtttgaaa ttcagggagc attctatcct gaggatttca aacgcagctt aaaatatctg  19980
atgaaacggc atgccatatt gagaaccaat ttccatgccg ggtggggcga tttccctatt  20040
cagattgtgt tcaaagaaag agcatgtgac ttcgtatacg aggatctgca cgagctggaa  20100
gccgatgaaa ttcaagcgcg tcttgcagct tatactgctc aggacaaagc aagaggcttt  20160
aatcttgctg aagaagcatt gctgcgtgtt gctattctac gtacagcaga agaggcttac  20220
catttgctgt ggagctctca tcacatcatt ttggatggct ggtgtatgcc gcttgtgctc  20280
caggaagtgt ttgagacgta tggggttctg cgtgagcaaa gggaacctga gcttcctgca  20340
gctgtatcgt acagccagta tattcaatgg ttggagaagc aaggcgagga agaggcatcc  20400
tcttactgga gagggtacct ggaaggctac gagcagcaga cgaagctgcc acaagccatc  20460
acacagccat cggcaaaagc agaagcctac gtgtcggaga agctggtatt cacgttggat  20520
gcggaactga ccgatcgcct ggaacaggtg gccaaacagc atcaggtgac gatgaatacg  20580
ctgatgcaag cagcctgggg aatcgtgttg cagcgttaca atagaagcca ggatatcgtc  20640
ttcggaagtg tggtatcggg aagacctgcc gagattccgg gtatcgaaag catgatcggt  20700
ctcttcatta atacagttcc ggttcgggta caggccgagg gaagcgattc gttctcccat  20760
gtgatgaaaa gacagcagga attatatttg gcaggacatg cttatgattc ctatccgctc  20820
tatgagattc aagcacagag cgaacaaaag caagatttga tttctcatat tatggtgttc  20880
gaaaattacc cagtagaaga gcatttggaa gagaaaattg ccagtgaaga ggctgaatac  20940
aaaattacgg atgttcagat gtttgaacag acgaattatg attttaacct cattgtgctg  21000
ccgggtcgta atctggagtt cttgtaccgt tacaatgccc gcgtctatga tcgggagagc  21060
```

gtggaacgaa ttcaaggaca cttgacgaga attctgacaa gcgttgctgt tcaacctgct 21120
atccgtattg atgagctgga gctgatcacg ccagaagaga aatcgcagat tatagaggtg 21180
tggggcgata cagcagctcc ttatccgcgt gagcagaccc ttcacggtat atttgaggaa 21240
aaagcagcac tcacaccgga ttgtacagca cttatttacg gtgaaacgga gcttacctat 21300
ggagaacttc atcagcaggc gaaccgcctt gcacgtacgc tgcgtgccca aggggtcaga 21360
ccggaccaac cagtcggcat catggtcgag cgttcgcttg agatgatcat tggcattcat 21420
gccattctaa aagctggcgg ggcctatgta ccgattgatc cggagttccc agaagatcgt 21480
attcgccaca tgctggagga ttcgggagcg aagcttctgc tgacgaagaa ccatctcaaa 21540
gatcgttttc cgttcactgg cacgatcctg gcacttgatg atccgcaggc gtatcatgcg 21600
gatagctcga atctggagcc aattgcgggg ccggagcatc tggcgtatat catttacacg 21660
tcaggttcaa ccggcaagcc gaaaggggta atgattgaac atcgcgctgc cgtccatacg 21720
ctgagtcagt tggaagctga atatccgatg ttggcaggcg accgtttcct gctcaaaacg 21780
acatttacct ttgacttctc cgtgccggag ctgttctgct ggttctttgg agaggggact 21840
ctcgtgatcc tgccacaagg cgtggacaaa gacccgatgg cactgctagg ggccgtggat 21900
acgaaccgta tcacgcatct caatttggtg ccgtcgatgc tcagtgtgct cgttcaatac 21960
ttgaaagaaa gcggcaccca aggattcctt actctgaaat atctgtttgc ctgcggcgag 22020
acgctgcctg ccaaacttgt ggaagagtat tataaagtat ctccttacgc agtactggaa 22080
aacatctacg gtcctacgga agcagccgta tatgcgactc ggtatacaac gagccttgag 22140
actgcggctc taacgcatgt gccaatcggc aaaccgtacg ctaacgtcca agtatggatg 22200
atggacagcg cttctcaggt atcacctgtg gggtaccgg gagaactctg cattgcgggc 22260
gaaggggtag cgcgggggta tttcaaccag ccggacctga cggcagagaa gttcattcct 22320
cacccgtaca aaccgggagc acggatttac cgaacgggcg atttagcccg atggctgccg 22380
gacgggaata ttgagtattt gggacggatc gatcaccagg taaaaatccg gggttaccgc 22440
attgagctgg gagaagtgga agcacaaatt ttgaaagtgc catctgtgca ggaagcggtt 22500
gttcttgcac tggctgattc tactggaagt actcagcttt gtgcatactt tgtggccgaa 22560
gaggggctta cagcgggcat actacgcgag gcactggcca gcgagctgcc aagctacatg 22620
attccgactg ctttcgtaca gttggcacaa atgccgctga atccgaatgg caaattggat 22680
cgcaaagcgc taccggcacc ggaaacactt ctgcggagca cagcggagta tatcgcgccg 22740
cgtacgcaga cagaagtaga gctcgctcag atttggtccg aggtgctcgg cgtacaggaa 22800
atcgggatca gggatcattt ctttgaactt gggggccatt ccctgaaagt attgggcttg 22860
atccaaagga tctcgtccgg tatgggcgtc cagctcccac tccaagtcgt gtttaatctg 22920
ccgactgtgg aagaaatggc gcatgaaatt tccaagctgc aggcaacaac tgctgctaat 22980
gaagaggaaa tggaaattat ccgcttccca gggaaaggaa cgctcaaagt gttttgcttc 23040
cctccacggg tgggccactc tctgggatac tatgagatgg ccaaggagct ggaagggctt 23100
tgcgaggtgt acgggatgga atttatcggc gatcgtttcc agggtcaaga tatgctggat 23160
cgatacatcg atgccatcgt ggatattcaa gcagagggtc cgtatatatt cctgggatac 23220
tcacttggag gaaacctcgc cttcgaggta gctaaagcca tggaaagccg aggtcaccat 23280
gttagcgacc ttattatggt agatgctatg agaaagatgt ccaaggatga atcgacaccg 23340
gaggagcttg aagagattgt cgagatggta ctggacagca ttagggacca gtacaaagcg 23400

-continued

```
ttccttgccg atccagtgga cagggagcga gtcatggaca aaatgttggt ttactccgtc  23460

taccgcgatg agcttattaa ctcaggtgaa gttcatgcga atatccatgc tctaattgca  23520

gaggatgata gtattggtcc ggatacatca ttagataaat tgttatggca acaggcgaca  23580

cttggtcaat acaaagaata cgaagtcatc ggaacgcatg atgtgctgct tgattccggt  23640

tttattgggg aaaatgctaa agtactgaga cagatacttg gcaaggtcac agaggcctca  23700

tctaaaaaca agcccatttt gtcctaa                                      23727
```

<210> SEQ ID NO 2
<211> LENGTH: 23727
<212> TYPE: DNA
<213> ORGANISM: Paenibacillus

<400> SEQUENCE: 2

```
atgaatgaca tgcagttata tgatttaaca aatgcgcaga agcgtatatg gtataccgaa     60

ttactctacc cagatacgtc agtgtcacag ctttccggta cagctaagat gaaggggcac    120

atcaatattg ctgcctttat gcagtccatt aatttgatta tcaaacagta tgatgcgttc    180

cgcatccgta ttacctcagt ggatggagtg cctcagcagt acgtcgtccc ttatgaagag    240

agacagctgg agtgcctgga tcttagccac tatgaaagtg tatctgaggt ggaagcctta    300

cttgagcaac acaaaagcaa gcccttgccc ctgttggatt ctgagctctt ccagtttttta    360

attgtgaaga ttagcgagga agagtattgg attaatatca agatgcacca tattatttct    420

gacggaatat caatggtggt ctatggcaat cagctgacag cattttacat ggagttaatt    480

caaggaaatg aaccgaagct gggcgacgat tgctcgtata ttcaatatat tgctgatgag    540

aatgcatacg aactttctga cagataccaa aaggataagg cttactggct ggataaattt    600

tctgatttgc ctgagcttac gggttggaag tcatataatc cgttatcttt aagcacccac    660

gccgttcggg agcattttac cgtaccagaa gtgctatatc acgagctgca agcattttgc    720

caacagaaca gaatttcttt gttccagttc ttcatgggtg cgatgtatat ctacatacac    780

aaaatgacga atcagccgga tgtggtgatt ggaacttcgt tcgctaaccg gggggaacaaa    840

aaagagaagc aaaagatagg tatgttcgtc agcaccgctg ctgccagaac atacgtcaaa    900

aaggatatag atgtattgag cttcctgcag gatgtagcca gagatcagat gtcagtcctg    960

cggcatcaga aatatccata caatcagtta attcaggatc ttagagaaat gcatgggaac   1020

aaggatattc agcggctttt tggcgtttcc atggaatatc gtcttatcaa ttgggttgat   1080

ttggatgatg tgcgtatttt gacagattat gatttctgcg gggacgaagt gaacgatttc   1140

gtgcttcata tcgtggagat tctggatgaa ggcgaactgg tactggatgt cgattatcgg   1200

acagagctgt ttgaacgcag tgaagttaag gacatggttt cccagttgct tacgatcgcc   1260

gagcagatca ttcattcacc tcagctttct attgcagagg taaacttatt gggtgaacca   1320

gaagagcaat ccattttggc tctttcggaa ggcgccgcag tcgattatcc acgtgagaag   1380

accattcatg gcttattcga ggaacaagcc gagcgcacac cagatcacgt agccgttcag   1440

atggacgagc agagcattac ataccaagct ctaaacgagc aggctaacca gcttgcgaga   1500

tatttgcgct ccgagggagt aggagcagat acgctcgtag ggattatggc tgaccgttcc   1560

ttggagatgg tcatcgggat gttggccatt ttgaaagcag gtggtgccta tgtaccgatt   1620

gaccccgatt atcccgaaga acgtatccat tatatgctgg aggattcagg tgtccgtctg   1680

ttgctcaccc aaagtcatct atgggagagc accacttttg acggaaagct tgtgagtctg   1740

gacgaagcta caacgtatac aggggatgct tccaatctgg agagtatttc gggaccaagc   1800
```

-continued

```
catctggcct atgttatcta cacgtcgggt acgaccggca agccgaaggg cacgctgatt   1860
gaacacaaaa acgtagttcg actgctcttt aacgataaaa atctatttga tttcagctct   1920
caggatacgt ggacgctatt ccattcgttc tgcttcgatt tctccgtttg ggagatgtac   1980
ggagcgcttc tttacggagg gaaattggtg attgttccat ctctcacagc caagagccca   2040
gcagctttcc tggagttgtt gaaagacaac caagtcacca ttttaaatca gacgccgacg   2100
tatttttatc aggtgctaca ggaagagtta acgcactctt cgacagagct tggccttaga   2160
aaaatcattt ttggtggaga ggccttaagt ccatctcttc tgagaaactg gcgggtcaag   2220
tatcctgatg tgcagctgat taatatgtac ggaattacgg aaacaacagt ccatgtcacc   2280
tacaaggaaa tcacggaaca tgagattgaa gcggggaaaa gcaatattgg cagaacgatc   2340
cccacactta gcgcttatat tctcgatgag caaagacggc tgcagcctgt tggggttccg   2400
ggagagctat acattgcagg ggacggtctt gcccgtgggt atttgaatcg gccggatttg   2460
acgtctgaga aattcgttga gcatccgtat cgggcgggag agcggctgta ccgaactggg   2520
gatcttgctc gttggttgcc tgatggcaat attgaatatt tgggacggat cgaccatcag   2580
gtcaaaattc gcggctaccg aattgagctt ggcgaggtag aagcccaaat tctcaaggct   2640
ccgaacgtac gagaaacgat tgtcctcgca cgggatgacg aacagggcca aaaattgctg   2700
tgcgcctact atgtagcctc cagtgatctt tcgccggggg aattgcggtc tcagctggca   2760
gcggaactcc ccgcttacat gattccttct tattttgtcc ggctggagca aatgccgctt   2820
acgccaaatg gcaaactgga tcgccgtgcg ttgccggctc ctgaaagcag cgtacaatcc   2880
ggcgaggctt atttggctcc gagaactgct gtggaagctc agatggtact catctggcaa   2940
gatatcttgg gagttgcccg cgtcggtgtc agagataatt tctttgaaat tggtggtcac   3000
tctttgcggg caacagtgct cgtttcacgg attcacaaag aattgggatg tagcatttcg   3060
ctgcgtgagg tgtttcagtc acctacggtc gaatccttgg cgcaacttgt gaaaaaacac   3120
attccgaccc tgtacgaatc catcccgcgg gcagcggaaa gcgaagctta cccagtgtcc   3180
tcagcgcaaa agcggttata cgtgctgaga cagatggacg ggggagagct tagctacaat   3240
atgccagggg tcttcacagt ggatggacca ttggatcgca cgcggctgga gtccgcgttc   3300
caggcactga tccagcgtca tgaatcccta agaaccggct tttatatgca ggatggagag   3360
cttgttcagc gtgtgcatag gaatgtgccg ttcgcgttga actatacaga ggcttcggtg   3420
gaggagacgg atacgctcat tcacaacttt attcgtgcct ttgatctgag ccaggctcca   3480
ttactgcgtg ttagcttggt gaagctccag gaggagcgtc atctgttgct gtttgatatg   3540
catcacatca tttcagatgg ggtttctatt caaatattga tacaggaact tactcatttg   3600
tatcaaggag aacagctacc agaactgcac atccaataca aggattatgc cgtatggcaa   3660
cgagaacagt cagagaatca atggcaagat cttgagaaat attggctgca atcctttgaa   3720
ggagagttgc cggtattgga tttgcctaca gacttccaac gaccttcggt tcggagcttc   3780
gagggtagcc gaattgattt tacattggat gagtctggaa ataaggcgat acaagagctt   3840
gcatcccgta caggtactac actgtatatg gtattgctgg ccgcttattc ggtactactg   3900
cacaaatata caggacaaga ggacatcgtc gtaggttctc cagtagccgg aagaccgcag   3960
gctgagcttg agggcatcat cggaatgttt gtcaacacac tggccttgcg cagctacccg   4020
acaggagata aaacctttca ggattacctt cttgaaatca aggaaacggc gctcaaggcg   4080
tttgagcatc aggattaccc ttttgaaaaa ttggtagaaa agctgggcgt aggacgtgat   4140
```

-continued

```
gtcagccgca atccgctctt tgacacctta ttggtattac aaaataccga gcaggaagag   4200
caggatatgg acggagtgca ctttactcct tacttgatgg acaccgtcac agccaaattt   4260
gatctgtccc tcaatgtaga ggagaagggg tcaaaattag cctttggcct cgagtatagt   4320
acggctttat atcggcgtga aaccgtagag cgacttgcaa cgcacttgct ccgggttctg   4380
cacgcagtct cggccaatcc tcagttgcaa ctggccgaga tagaaatgat cacaccggag   4440
gagaaagtac agatcgttga agtatttaac gcgacatcgg ctccttatcc aagggacaag   4500
accattcatg agctgttcgt agaacaagtc aagcgtacac cagagcagac ggcgcttgta   4560
ttcggcgatg tccagctaac gtaccttgaa ttgcaagaca aggcgagccg actggcccaa   4620
acactgcgtc gtttgggaac gttgagggag cagcctgtgg ccgtgatggg cggacgaagc   4680
atcgagatgg tcattggtat gctcgcggtg cttcaagcgg gtggagccta tgtgccgatt   4740
gatcctgatt acccggaaga tcgggttcgt tatatgcttg atgattccga cgccaagtta   4800
ttattggtgc aaaagggcga gcttataagt gtagactacg gtataccaat tgtcgatctt   4860
agcagtgaag aggcttatgc tgctgagcct gcccagccgg agacggctca gggatcgcag   4920
gggcttgctt atgtcatcta tacatcgggt acgacgggta gaccgaaggg cgttatggtt   4980
gaacaccgga acgtggtccg tctggtcaaa gagaccaact atgtggagct gaatgaatcc   5040
acacgaattt tgcaaacagg agccgtggcc tttgatgctt ctacatttga gatatgggga   5100
gcgttgctta acggtgggca gctctatttt gtagagaatg acgacattct gattgctgat   5160
aggctcaaag cggctattgc caagtacggg attacaatat tgtggcttac ttcacccctt   5220
ttcaatcagc tttctctgca ggatgagtac ctgttcagag ggctaaaagc attgttagtc   5280
ggcggtgacg tactgtccat atctcatatg aaccgtgtaa tggaggctaa tcctgatctt   5340
gtccctatca atggctatgg tccgacagag aatacgacct tctccaccac ctacaagatt   5400
ctgggtcgtg ccgaaggggt cgtgccgatt ggccgcccaa ttagtaattc taccgcttat   5460
gtggtcaatg gatcgctgca attacagcct attggtgctt ggggtgaact cattgtcggc   5520
ggtgaaggtg tagcgcgcgg atatctcaat cgtcctgatc tcacagcaga gaaatttgtt   5580
cctagtcctg ttaaggacgg agaaccctgc tacagaactg gggatttggt acgctggctt   5640
ccagatggca atttggagtt taaaggaaga attgatgagc aggtcaaaat acgtggttac   5700
cgcatcgaac tccctgaaat cgaggcccaa ctggccaagg tggagtcagt aatcgacgcc   5760
gtagtggtcg ttcgcgcgga tgagcttggc gagaagcagc tttgcgctta ttatgtggcg   5820
gatcgtacgc tcacggcagg cgaagtacgt ctttccctat cgcaggtact tccaggctat   5880
atgattccat cctactttat ccagatggat cgtatgccat taacgtcaaa cggaaaagtg   5940
gaccgcaggt ctctgccggc tcctcaagta ggcgcgcata caggacggaa gtatacagct   6000
cctcgtacac cggctgagga agctttggca tctgtctggc aaggggtgct gggtgccgaa   6060
caggtgggta tccatgacaa tttctttgaa ttgggtggag actccataaa agctattcaa   6120
gtgtcgtcac ggttactgca ggccggctat cggttagaga tgaagcagct gttcaaatcg   6180
ccaaccattg ccgagctagg cgcggaaatt caaacggctg tgcatatggc tgaacaggga   6240
gttgtgcgtg gaacgactcg cttgactcca gtccaacagt ggttctttgg acggaagcag   6300
gcagagcctc atcacttcaa tcaagcggtt atgctgtatc gtgaacaggg atttgaggaa   6360
aaggccttgc atcaggtgct aagaaaactc gctgagcatc atgacgccct tcgcatggtt   6420
ttccgtcaga cagagcatgg ctacgaagct tggaatcgtg atcttgaaga aggagagttg   6480
tatagcctat tcaccgctga tttacggaat gaatccgatc cggctgcagc cattacatcg   6540
```

-continued

```
ctgtcggatg acattcagcg cagtatcaat ctggcagaag gtccgctgct gaagttagga   6600
cttttccatt gtcaggatgg agaccacctt ctaatcgtga tccaccattt ggtggtggac   6660
ggagtatcct ggcggatttt gttcgaggat attgcagcag gctatgagca ggtgattcaa   6720
ggacaagcgc tgacattccc gcagaagacg gattccttcc gtgactgggg agacgccctt   6780
gctcgttatt cggaaggtcc tgaaatggag actcatcggg cgtattggag agagctggag   6840
gatcagccac tcgaacagtt accgaaggat gaggctgtgg aaagccttct tttacaggat   6900
agcaaagtag taacagcaca atggactcta gaagaaaccg accaattgtt gagaaaagcc   6960
catcgtgctt atcaaacaga gacgaatgat ctgctattga ctgctctggg catggcggta   7020
tccaaatggt ctggcatcgg aaaggttgct gtgaatctgg aaggacacgg tcgtgagccg   7080
attataccga atatcgacat cacccgtacc gtaggctggt ttacaagtca atatccggtg   7140
attttagact tgggggataa cccggaagtg gcctccttga tcaagtctgt gaaagaaggg   7200
ctgcgccgaa ttccgaacaa aggtattggc tacgggttgc ttaaaaagat ggcaagtcag   7260
ttggataaag acagcttcag cttgcagcct gagatttctt ttaactattt ggggcaattt   7320
gatcaggatt tgcaaggaag ctcgttgcag atttctcctt atccgaccgg aagcgcccaa   7380
agcttgttgg aggaaccggc ctatacgcta gatatcaatg gcatggtgac ggacggagcc   7440
ctgactctga cgattactta taacggaaaa cagtataagt catctacgat ggaacagctc   7500
gctggatata ttgaaaaaag cctgcgggag cttctccagc attgcgtaac ccaagaaaaa   7560
accgtattga caccaagcga cgtgcttgcg aagggtctaa gcattgccga tctggaggag   7620
ctttctaagc agaccagcca cataggcgat attgagaatg tatatagtct gacgccgatg   7680
cagaagggca tgctgttcca tgatatgttt gagccgcata caggtgctta ttttgagcag   7740
gctgcctttg actttaaggg tagctttgat ccgaccgcct tcggacacag tctggatgca   7800
gtggtggagc gtcatgccat cctgcgcacg aacttttaca gcggatgggg cagcgagcct   7860
ttgcaggttg tatttcggca cagaggcgct aaattggtgt acgaagacct gcgtgagatg   7920
aatgcatcgc agcgcgaagc ttacctgaag acatttggtg ctaaggacaa agcacagggc   7980
ttcaacctag ctgaagacga gcttctccgt gtatcaattt tacaaacaga tgaagagagc   8040
ttccgcctct tatggagctt tcaccacatc gtcatggatg gctggtgtgt tccgttaatt   8100
acgcaggagg tatttgaaca ctattttgcc ctcctggaag gaagagagcc gcagctggca   8160
gaggttcatc cgtacagtcg atatatcgaa tggctggaac agcaggatga agcagttgcg   8220
tccaactatt ggagccgata tctggccggt tacgagcagc agacgctttt acctcaagtc   8280
ggtggagcaa gtaagggaga aggctatgta gcagaaaagc tgaattatcc tctcagcagg   8340
gaattgactg agcgccttga aaaggtggcc agggatgctc atgtcacgat gaatatattg   8400
ctgcagtccc tctggggcat tgcgcttcaa cgctacaacg gtagccggga tgtcgtgtac   8460
ggaagtgtag tatcaggccg accagcagaa attccgggca ttgaccggat gatcggtttg   8520
ttcatcaata cgattcccgt tcgtgtgaag acagaggaga atctcccctt cacagttctg   8580
atgaagcagc agcaggaaca atatatggct tctcatatgt atgacaccta cccgctgttt   8640
gagattcagg ctcagacgga tcagaagcag gatctaatct cccatattat ggtgtttgaa   8700
aactatcctg tggaagagga ggtagagcgt ctgggtggtg gcgaggctgc ctttgagatt   8760
gaggaagcgg agcttcttga gcaaacgaat tatgatttta atttaattgt cctccctggc   8820
gaagaaatga gattgctgtt ccagtacaat gcacttgttt atgacccagt gacaattgag   8880
```

-continued

```
caaatcaagg gccatctggt tcacctcatg gaacaaattg tagagaaccc tgccatttcc   8940
gtggatgcac tagaattagt cacgccgcag gagagagaac agattctgaa cgtatgggga   9000
aatacaaaag gcatttacga gcactgtaac acgttccacg ggctgttgga ggaacaggcg   9060
ggacgaacgc cggatgcgac tgccatttgg ttcgaggacg agagtctgac ctatgccgag   9120
ctcaatgcaa aagccaatgg actggcgaga aggctccgta ctcagggaat caagacggga   9180
gatctggtgg gactgattgc tgaacggtcg ctcgaaatga tcgttgggat ctacggcatt   9240
atgaaagccg gggtgcctat tgttccaatc gatccagagt atccgaaaga acgaatcagt   9300
tacatgcttg aagattccgg ggcgaagcta atccttacac aggcccattt cttggagcat   9360
ctcggatgga cggaaaatgt tttgctgctg gatgaatcat cgacctatga tgccgacacc   9420
tcgaatttgg aggatactgc tggcccggat gatctggctt acgtgatcta tacttcaggt   9480
acgaccggtc agcctaaggg cgtattagtc gagcatcggg gactaccaaa tctttcagac   9540
gtatatgggg cacacttcga agttacaccg caggatcgga tcgttcagtt tgcaagcctg   9600
tcgtttgatg catcggtttc ggaaatttta acggcgctga gccatggggg tgttctgtgc   9660
atcccttcta cagaagatat tttagatcat gccctgttcg agcagttcat gaacgataag   9720
ggggttacgg tagcgacttt gccacccgct tacgctatcc accttgatcc agagcgtttg   9780
ccaacactgc ggtgcctgct aaccgctgga tcggccgcat cggtcgagtt gatcgaagag   9840
tggaggaagc atgtacgtta ctctaatggc tatggcccaa cggaggactc cgtatgcacc   9900
acaatctggt ctgtcccgga cagtgaggaa gcaacggata ttgtatctat tggacgtcct   9960
attgctaacc atagtgtgta catcttggat gaccatttta gattgcaacc tgtcggtgta  10020
gctggagagc tatgcatttc gagtatcgga ttagcacggg ggtatcataa ccagcctgag  10080
ttaatggatg agaaattcgt agacaatccg tttgctccag gagagcgtat gtatcggacg  10140
ggtgacctgg ttcgctggtt accgaatgga accatcgagt acttaggcag aatagatcac  10200
caagtcaaaa tccgcggcta ccgtatcgag ctaggcgagg tagaagcaca aatgctcaga  10260
gtgccgtccg ttcaggaagt cgtagccatg gctgcagagg gcgaagacgg ctacaaagat  10320
ctagtcgctt atttcgtagc tgctcagaaa cttgaggtat ccgagcttcg ggccgtcctg  10380
tcggagatgt tacctggata tatgatccct tcccgcttca tacaactgga ggatatgcct  10440
ctgacgtcga acggaaaaat cgatcgaaaa gcgctgcagg gcgagcgtgg atgggcagcg  10500
gcttcatcgg aggctccaag gacacctgtg gaaatccaat tagccgaaat ctggcaagag  10560
gtgctgggtg tagagagcgc gggagtgaag gatgatttct tccattttgg aggtcattcc  10620
ctgcgtgcag ccctgctagt ctcacgaatt cgcaaggaaa tgaatcgcga gattagtctg  10680
agagcagtgt tcgagtctcc tactattgaa ggattggctc gtgccattga gggctataca  10740
ccgctgaatt tcgaagaaat tcctacagcg ggagcgagag agcattatcc attgtcctcg  10800
gcccaaaaac gactgtttat tctaagtcag ctggaaggtg gagagctgag ctacaatatg  10860
ccgggtatcc ttaccgttga gggagctttg gatcgggaac ggctagagca ggcattccgt  10920
cgtctaattc atcgtcatgg ttcgctgcgt actcgttttg tgaccgtgaa cggtgaacct  10980
gtacagcagc tcctgacgga tgttccgttt actgtggaat atgcggagtt gagcgaggaa  11040
gaggcaggag ctacccttca gcagtttgtc cgtccttttg atttaggtgt agctccattg  11100
ctgcgggtcg gccttattcg aattgcacat gagcgccatt tactattgtt tgacatgcat  11160
catattgtct cagatggggt ttctatgaat attctcatag aagagtttct ccgcttctac  11220
caagaggagg acgtattccc tgaactacag atccagtaca cagactatgc tgtatggcag  11280
```

-continued

```
caagagcagc tcggaagcga gcgtcttaag gcccaggaag cttactggct ggatgctttc  11340
cgcggaagct tgccagtgct ggatttgcca ggagatgaag ttcgtcctgc ggtgcgaagc  11400
tttgcgggcg atcgaatcga cttccaaatt gattcttctc tgagtgcttc acttcaggag  11460
ctggctaccc gaacgggttc cactctgttc atggtactgc tggcagccta tacggcgctc  11520
ttacacaagt acacaggtca ggaagatgtc attgtcggtt cacctgtggc aggaagatcc  11580
catgcgacac tcgaaggcct catcggtatg ttcgtcggca cagtggcact tcgtacttat  11640
ccagaaggag agaagccttt cgaggcttat ctgcaggaag tgaaggaaac agcgctgcgg  11700
gcctatgaaa accaggatta cccgttcgag gagctggtag acaagctgga gcttcagcgt  11760
gatttgagcc gtaacccgct atttgatacc atgtttgtcc tgcaaaatat tgagcaggga  11820
gaacaagaaa tagaaggatt gcgcttcact ccttacgata atgtacatcc ggctgccaag  11880
ttcgatctca cgctgaccgt gagtgaagca gacggggtat tgaactgcac gcttgagtac  11940
gcgactgcga tctacaaaca agagactgcc cagcggatgg caggccactt tgtacagctt  12000
attcgggaag ccgtctccaa tccgggaatg ccgttgtcat cccttgatat cgtgacacct  12060
caggaaaaat caaggctgat gaaagcgccg gacgaagcca aggcagatta tcctcgtgac  12120
aagacgatcc atgcgctgtt cgaggaacag gctgcacgta ctccgaatgc agtggcagtc  12180
gtatgtgaaa atgcagccct gtcctacagc gagctgaacg agcgggccaa tggacttgcc  12240
agaacgctaa gggaacgtgg tttgcaacca gacggtttgg ctggaatcat ggcggatcgt  12300
tcccttgaaa tggtggtcgg gattttagcc atcttgaagg caggcggagc ctatgtccct  12360
gtagaccctg aatatccaga ggaccgcatt cgctttatgc ttgaggattc gggagccaag  12420
ctactgctga cacaagcgca tctggagcaa cgtgtctcct tcgctgggga catcgtgagt  12480
ctggataaaa tggcttccta taaggaagat gtctcaaacc tgcagcctgc agccggaccg  12540
gagcatcttg cctacgtcat ctacacatca ggtacgacag gcaagccaaa gggaacgctg  12600
atcgagcata aaaatgtagt tcgcttgctc tttaatgata aaaatatgtt tgactttggt  12660
cctcaggata cgtggacact gttccattca ttctgttttg acttctctgt atgggaaatg  12720
tacggagcat tgctgaacgg aggacggttg gtcatcgttc catcgcttac cgcgaagagt  12780
ccagatcgtt tcttgcaatt gcttaaggat cagaaggtca ccgttttgaa ccagacaccg  12840
acgtacttct atcagttgct acaggaagag ctcggtcatc aggcggcaga actgagcctc  12900
cgtatgatta tcttcggtgg agaggcatta gccccggccc tgctcaagga ctggagaacg  12960
aagtatccgc aagtgcagct cattaacatg tacggcatta ccgaaacgac cgtgcatgta  13020
acatacaagg aaattacaga gttggaaatt gaacagggcc gcagcaatat cggcaccacg  13080
attccaacgc tgcgagcgta cattttggat gaacaacgcc gtccacagcc gattggcatt  13140
ccaggtgaac tttatgtggc gggcgtaggt ctggcgcgag gctatctgaa ccgaccggaa  13200
ttgacggaag agaagtttgt cgctcatccg tttgaagcgg gcgagcgcat gtaccgctcg  13260
ggtgacttgg cacgctggtt gccggatggc agcatggagt atttgggacg gattgaccat  13320
caggttaaaa tccgtggtta ccgtattgag ctgggcgaag tggaagcgaa gctgctccat  13380
gctccgtctg taagggaggc cgttgtgctc gcccgggagg atggaagtgg acaaaaagtg  13440
cttgtcggct atttcactgc cgatcagatg ctgacggtag gcgagttgag aaaagccttg  13500
gctgccgaac tgccgactta tatgattcca tcttacttta tgcaattgga acagatgcct  13560
ttgacgccaa atggcaagct ggatcgcaaa gcgcttccgg ctcctgaggc taatgtgcag  13620
```

-continued

```
actggggcgg tttatgaacc gccaaggacg aaggctgagg aagctttagt ttccgtatgg  13680
caaggtgtgc tgggagcgca gcaggtcggc atccatgatc atttcttcga tctgggtggt  13740
gactccatca aggcgatcca agtgtcctcg agattgttcc aagctggata taaattagag  13800
atgaaggatc tcttcaaata tccgacaatt gccgagctaa gcccgtatct tcaggcagct  13860
ggacgtatag cggaacaggg tgaaattaaa ggtgcagcag agttaatgcc aattcagcgt  13920
tggttctttg aacgccatac agcggagccg caccattata atcatgccgt catgctctat  13980
cggaaagacg gctttgatga ggctgcactc cggttgacaa tggaccaaat tgcgatccat  14040
catgacgcgc tgcgcatggt tttccggcct acagaagctg gatacgcagc ttggaatcgg  14100
ggaacggacg aaggcgagct ctacacattg gacattgccg atatgcagca ggcggaagac  14160
cagacagctg cggttcaagc ccaagccgat gccattcagg caagctttga cttggaaggt  14220
ggcccactgt tcaagctagg cctgttccat tgtgacgatg gcgatcattt gttgattgtc  14280
attcatcacc tcttggttga cggcgtatcc tggcgcatcc tgtttgagga cattgcagcg  14340
gggtacgagc aggcatggaa tggacaagca atcgtccttc cacaaaagac cgattcgtat  14400
cttgtatggt ctgagcaagc gacgaagtat gcagcagggc ctgctctgga caaggagcgt  14460
gcatactggc agctgattga ggaggcgatt ttggccccac tgccgaagga tgaggatcag  14520
aagccgggca ccattcggga tactgaatcg gttacggtaa cgtggtctgc gcaggaaaca  14580
gacctgctgt tgcgacaagc gaaccgggcg tatcatacgg agacgaatga cttgctcttg  14640
actgctctgg gggcagccat tcagcgctgg acaggcatgg agcagatttt ggtcaatctt  14700
gaaggacatg gacgggaaat gatcgtacca gacctggata ttacccgtac cgtgggttgg  14760
ttcacaaccc agtatccagt tctgctgaac ctgcaaggca gacaggaagt atctgcgcga  14820
atcaagcgca tcaaggagaa tttgcgagag gttccgcata aaggaatcgg ctacggtctt  14880
ctgaagtata tggcaccgga gaaaagtgtc ggattcggcg tggagccgga aatttccttc  14940
aattatcttg ggcagtttga tcaggatttg gagggtaatg cccttagctt atccacacat  15000
tcagttggta aagcgctcag cgatctcaca ccacagcaat atgctctgga tgtgaatggc  15060
atgattgccg aaggccagct atcactgacg attacgtaca gcagcaggca gtatcgtaag  15120
gagacggtga gtcattttgc tgaattatta cagtcaagcc ttagtgaggt catccgtcat  15180
tgtgtggctc aggagcgttc acagcttaca ccaagtgatg ttctgttcca aggattaaca  15240
ttggagcagc ttgatcgact cacggcgcag acggctcaca tcggagagat tgaggatgtg  15300
tacaagctga cgccaatgca gaagggaatg ctgtttcaca gcctactgga gccgggctcc  15360
tcttcatact tcgaacaggc aacgtttgag ctgcgtggca gcttcgatgt agataccttc  15420
ttcgagagct tccaggctct ggtgcaacga catgccatac tacgtaccgg cttttacaac  15480
aacattgctg atgtaccgct gcaagttgtc tttaagcaac ggttaatccc tctgcactac  15540
gtagatttgc gcgacgcatc tatgcaggaa caagaagccc gaatcaaggc ttatattgct  15600
gaagatatgg ttaaggggtt cagcttgtca gaagatccgc tgatgcgggt gaccgtcttg  15660
cagaaggatc aaagctgtct tgtattgtgg agcttccacc atattgtcat ggatggctgg  15720
tgtatcccga tcattacaca ggagctgttc gattattatt ctgccaagaa acagcaagta  15780
cagcctgtcc taccgccagc tcagccctat agccgttata tcgagtggct tgatgcacag  15840
gatgatcaag aagcttcaac gtattggagc caatatctcg aagattatga cgggaatact  15900
gtattgccgg aaggtaaaac gaaatctcaa gccaaagagg cgggctatgt tctgaatgag  15960
catgttctcc atctgggtgc atccttgacc ggtaaaatgg atgttgttgc gaagcgcaat  16020
```

-continued

```
cacgtaaccg tcaatacact catgcagaca gcttggggac tgattcttca acgttataat  16080
gccagctcgg atgtcgtttt cggcggcgtt gtgtcgggta gacccgctga gattgcaggg  16140
atcgaaaata tggtgggtct gttcatcaat acagtaccta tccgtgtaca gtcatccaaa  16200
gacgaagcct tcgtcgaagt gatgaaacgt acacaggcac agtcattggc tggtcgtgcc  16260
tacgacacct atccactgta tgagattcag gggaaaacaa cccaaaagca ggacctgatt  16320
tctcatatta tgatctttga aaattacccg ctcgacgagc aggtggagca atcgggtaat  16380
caaacggagg acaatctcga agttgccaac ttcaccatgt ttgaacaaac caactatgac  16440
tttaacctgg ttgtgattcc aggcgaagac atcaaggtct gcattcgcta taatgcttcg  16500
gtttacgagc aagaaagcat tgcacgtatc ggaggacact tgttgcagat gctcgatcag  16560
gtggctgctc gtccgcaggc gacgatacag gaactggaga ttgtaacatc cgaggaacgg  16620
atgaacctgc ttgactgggg cggcaaggcc catacctatc caagtgatca ggggctgcat  16680
accttgtttg aagaacaggt tgtccgtacg ccggataaga ttgcagctgt aaatggggac  16740
actcagatca cgtatcggga gctgaacgag caggcgaaca gactagcttc caccttgata  16800
gaccaaggac tacggagtga acaagtggta ggtctgttgg cagatcggtc tgtagagctg  16860
cttgtcgcca tcatgggtgt gctcaaagcg ggtggagcct acgtacctat tgatcctgaa  16920
tatccgcagg agcggattca gtatattctg aaggattctg gcgctgaaat tctgctcaca  16980
cagagccacc tgacggagtt agcctctttt gaggggacgg ttatggaatt ggattccccg  17040
cacatttacg gaaccgaggt ggataatccc aatattcctg ttggaggaaa cgatctggtg  17100
tacttaatct atacctcggg tacaaccgga aatccgaagg gaaccatgat taaccacaaa  17160
gggatcgtga actacatctg gtgggccaat aaggtctatt gtgctggaaa accaacggat  17220
ttcccgttgt attcatccat ttcctttgac ttaacgatga catcgatctt tactccatta  17280
attaacggag gagtagtgcg gatttatgat ggtatagata aagcggaggt tgtacagcat  17340
attttgcgcg aaaatgcggt ggacattctc aagctgacgc cgactcatct cagtctgatt  17400
aaagatatga ccatcccggc agaaagtcgc attcagcagc ttattgtggg tggagagaat  17460
ctgaccacac atttgtcgaa aaccatcaca gatctctttg gcagcaacat caaaatctac  17520
aatgaatatg gaccaaccga aacggtcgtc ggctgcatga ttcacctgta caatcctgcg  17580
aaggatacgc gtgaatctgt accgattggg ttgccagcag acaatatata catccatatt  17640
atggatgatc agcttcgtct cgtaccgtta ggcgtggagg gcgaaatgta catcgccggg  17700
gacggggtag cccgtggata tctgaaccgt cctgagctta ccgcagataa attcattaga  17760
aatccgttcg cttcggaagg aaatatgtat cgcactgggg atttggctcg tcgccttcct  17820
aatggagaca ttgagtacat tggcgtatt gaccatcaag ttaaaatacg gggctatcgt  17880
attgagcttg gtgagattga ggccaagttg ctggatatgc cacttgtcga ggaagctctc  17940
gttgttgcgt gggcagacgc caatggacag aagtctctgt gtgcttactt tgtagcggat  18000
cgagaaatgt ctgtcagcga gctgagaaac gaactgtctg ccggactgcc tgcatatatg  18060
attccgtctt acttcgtcca actggacgtg atgcctctga caccgaatgg caagctggat  18120
cgcaaggcac tgcctgaacc gaactcgggt ataaaggcgg gagcagactt taccgctccg  18180
cggacggatg tggagaacat tttggcttca atctggcaag gtgtacttgg cgtgccgctg  18240
gtcggcatac atgataattt ctttgaactt ggaggtgact cgatcaaatc cattcaagta  18300
tcctcaaggc ttcttcaagc aggctacaag cttgaaatga aggatttgtt cggttatccg  18360
```

-continued acaattgcag agttggcgca gcgcgttagt gtggtcagcc gaattgcgga ccaaagcgag 18420
gtacacggag cggtaagact gggacctgct cagcacagat tcttcgatga acagtcaatg 18480
gatctgcatc actttaatca gtcggtcatg ttgtaccgac gggatggctt caataccgat 18540
gcgctcgccg aggttgttcg gaaaattgca gagcatcatg atgctttacg actggtgttc 18600
cgccaaggag agcagggatt tgaggcctgg aaccggagca tgggtgaggg tgagctctat 18660
agcctccaaa tccacgacct gcgggatgag acagacccgg cttcagcaat agaagcaggt 18720
gcggaagcca ttcagcgcag catctctctg gaggatggac ctctctttag actgggtctg 18780
ttccgctgtg cggaaggcga acatctgttg atcgttattc atcatctggc tgtggatggc 18840
gtatcctggc gtattctttt tgaggacctg caggatggct acgagcaggc agcacgtgga 18900
gaagcggtca agcttccaca gaagacggat tcgtaccgtg catgggttga gggaatcaca 18960
caatttgcga atagtctggc ggctgaacaa gaacgcagct attgggtaga ggtagaggga 19020
gatggctttg tccctcttcc caaagacaag gtagacggcg ctcttctcat caaagacagt 19080
gaggctgtca cggtgagatg gtcaccagaa gagacagagc agttcctgaa agaagcgaac 19140
cgcacttaca atacggaggt caacgatctg ctcctgacgg ctctgggtat ggctgttcac 19200
gagtggacag gaatcgaacg tgtaggcatc cttctggagg gacatggacg ggagcctgtt 19260
gtgccggaac tggatattac tcgcacaata ggctggttta caagtcaata ccctgtcgcc 19320
cttgagatgg gaggggaatt ggagatcggc gccagaatca agcacgtcaa ggaaggcttg 19380
cgtcgtatcc cgaacaaagg tgtcggatat ggtattttga aatatttaag cgacggttcc 19440
gacgtctcct ccttctcggc tgaacctgag attaccttca actacttggg acagttcgac 19500
caggatcttg caggagggat gatggaagta tcgtcttatt cagtaggacc tgaggtcagt 19560
gagcagatgg tgcagcatca ggcattgaac attaatggac tgattgccga aggacagctt 19620
caactttcgg tcagctataa ccgtcatcag ctcgacgggg agtccgtgac taagtttgtt 19680
ggcattctga agaaccgtct cagcgaagtc attggacatt gcgtaagtaa ggaaagaaca 19740
gaacttacac caagcgatgt actcctcaaa gatatcagct tagaaaagat tgaggagcta 19800
gaagagcaga cacggcatat cggcagtatt gaaaatatgt ataaactaac accgatgcaa 19860
aaaggaatgt tgttccacag cttgctggaa cctcattcgg aagtctactt tgagcaggcc 19920
aaatttgaaa ttcagggagc attctatcct gaggatttca aacgcagctt aaaatatctg 19980
atgaaacggc atgccatatt gagaacgaat ttccatgccg ggtggggcga tttccctatt 20040
cagattgtgt tcaaagaaag agcgtgtgac ttcgtatacg aggatctgca cgagctggaa 20100
gccgatgaaa ttcaagcgcg tcttgcagct tatactgctc aggacaaagc aagaggcttt 20160
aatcttgctg aagaagcgtt gctgcgtgtt gctattctac gtacagcaga agaggcctac 20220
catctgctgt ggagctctca tcacatcatt ttggatgggt ggtgtatgcc gcttgtgctc 20280
caggaagtat ttgagacgta tggggttctg cgtgagcaaa gggaaccaga gcttcctgca 20340
gctgtatcgt acagtcagta tattcaatgg ttggagaagc aaggcgagga agaggcatcc 20400
tcttactgga gagggtacct ggaaggctac gagcagcaga cgaagctgcc acaggccatc 20460
acacagccat cggcaaaagc agaagcctac gtgtcggaga agctggtatt cacgttggat 20520
gcggaattga ccgatcgcct ggaacaggtg gccaaacagc atcaggtgac gatgaataca 20580
ttgatgcaag cagcctgggg aatcgtgttg cagcgctaca atagaagcca ggatatcgtc 20640
ttcggaagtg tagtatcggg gagacctgcc gagattccgg gtatcgaaag tatgatcggt 20700
ctcttcatta atacagttcc ggttcgggtt caggccgagg gaagcgatac gttctcccat 20760

-continued

```
gtgatgaaaa gacagcagga attatatttg gcaggacatg cttatgattc ctatccgctc  20820
tatgagattc aagcacagag cgaacaaaag caagatttga tttctcatat tatggtgttc  20880
gaaaattacc cggtagaaga gcatctggaa gagaaaattg ccagtgaaga ggctgaatac  20940
agaattacgg atgttcagat gtttgaacag acgaattatg attttaacct cattgtgctg  21000
ccgggccgta atctggagtt cttgtaccgt tacaatgccc gcgtctatga tcgggagagc  21060
gtggaacgca ttcaaggaca cttgacgaga attctgacaa gcgttgctgt tcaacctacc  21120
atccgtattg atgagctgga gttgatcacg ccagaagaga aatcgcagat tatagaggtg  21180
tggggcgata cagcagctcc ttatccgcgt gagcagaccc ttcacggtat atttgaggaa  21240
aaagcagcgc tcacaccgga tcgtacagca cttatttacg gtgaaacgga gcttacctat  21300
ggagaacttc atcagcaggc gaaccgcctt gcacgtacgc tgcgtgccca agggatcaga  21360
ccggaccaac cagtcggcat catggtcgag cgctcgcttg agatgatcat tggtattcat  21420
gccattctaa aagctggcgg ggcctatgta ccgattgatc cggagttccc agaagatcgt  21480
attcgccaca tgctggagga ttcgggagcg aagcttctgc tgacgaagaa ccatctcaaa  21540
gatcgttttc cgttcactgg cacgatcctg gcacttgatg atccgcaggc gtatcatgcg  21600
gatagctcga atctggagcc aattgcgggg ccggagcatc tggcgtatat catttacacg  21660
tcaggttcaa ccggcaagcc gaaaggggta atgattgaac atcgcgctgc cgtccatacg  21720
ctgagtcagt tggaagctga atatccgatg ttggcaggcg accgtttcct gctcaaaacg  21780
acattcacct ttgacttctc cgtgccggag ctgttctgct ggttctttgg acaagggact  21840
ctcgtgatcc tgccacaagg cgtggacaaa gacccgatgg cactgctaga ggccgtggat  21900
acgaaccgta tcacccatct caatttggtg ccgtcgatgc tcagtgtgct cgttcaatac  21960
ttgaaagaaa gcggcaccca aggattcctt actctgaaat acctgtttgc ctgcggcgag  22020
acgctgcctg ccaaacttgt ggaagagtat tataaagtat ctccttacgc agtactggaa  22080
aacatctacg gtcctacgga agcagccgta tatgcgactc ggtatacaac gagccttgag  22140
actgcggctc taacgcatgt gccgatcggc aaaccgtacg ctaacgtcca agtatggatg  22200
atggacagcg cttctcaggt atcacctgtg gggtaccgg  gagaactctg cattgcgggc  22260
gaaggggtag cgcgggggta tttcaaccag ccggacctga cggcagagaa gttcattcct  22320
cacccgtaca aaccgggagc acgaatttac cgaacgggcg atttggcccg atggctgcca  22380
gacgggaata ttgagtattt ggggcggatc gatcaccagg taaaaatccg cggttaccgc  22440
attgagctgg gagaagtgga agcacaaatt ctgaaggtgc catcggtgca ggaagcggtt  22500
gttctagcac tggctgactc caccggaagt actcagcttt gtgcatactt tgtggccgaa  22560
gaggggcttg cagcgggcgt actacgcgag gcactggcca gcgaactgcc aagctacatg  22620
attccgactg ctttcgtaca gttggcacaa atgccgctga atccgaatgg aaaattggat  22680
cgcaaagcgc taccggcacc ggaaacactt ctgcggagca cagcggagta tatcgcgccg  22740
cgtacgcaga cagaagtaga gctcgctcag atttggtccg aggtgctcgg cgtacaggaa  22800
atcgggatca gggatcattt cttcgaactt gggggccatt ccctgaaagt attgggcttg  22860
atccaaagga tctcgtccgg tatgggcgtc cagctcccac tccaagtcgt gtttaatctg  22920
ccgactgtgg aagaaatggc gcatgaaatt tccaagctgc aagcaacaac tgctgctaat  22980
gaagaggaaa tggaaattat ccgcttccca gggaaaggaa cgctcaaagt attttgcttc  23040
cctccacggg taggccactc tctgggatac tatgagatgg cgaaggagct ggaagggctt  23100
```

```
tgcgaggtgt acgggatgga atttatcggc gatcgtttcc agggtcaaga tatgctggat  23160

cgatacatcg atgccatcgt ggatattcaa gcagagggtc cgtatatatt cctgggatac  23220

tcacttggag gaaatctcgc cttcgaggta gctaaagcca tggaaagccg aggtcaccat  23280

gttagcgacc ttattatggt agatgctatg agaaagatgt ccaaggatga atcgacaccg  23340

gaggagcttg aagagattgt cgagatggta ctggacagca ttagggacca gtacaaagca  23400

ttcctcgccg atccagtgga cagggagcga gtcatggaca aaatgttggt gtactccacc  23460

taccgcgatg agcttattaa cgcaggtgaa gttcatgcga atatccatgc tctgattgca  23520

gaggatgata gtattggtcc ggatacatca ttagataaat tgttatggca acaggcgaca  23580

cttggtcaat acaaagaata cgaagtcatc ggaacgcatg atgtgctgct tgattccggt  23640

tttattgggg agaatgctaa agtactgaga cagatacttg gcaaggtcac agaggcttca  23700

tctaataaca agcccatttt gtcctaa                                    23727
```

<210> SEQ ID NO 3
<211> LENGTH: 23724
<212> TYPE: DNA
<213> ORGANISM: Paenibacillus

<400> SEQUENCE: 3

```
atgaatgaca tgcagttata tgatttaaca aatgcgcaga aacgtatatg gtataccgaa     60

ttactctatc cagatacgtc agtgtcacag ctttccggta cagccaagat gaagggccgt    120

atccatatcg ctgccttcat gcagtccatt aatttgatta tcaaacagta tgatgcgttc    180

cgcattcgta tcacctcagt ggatggagtg cctcagcagt atgtcgttcc ttatgaagag    240

agacagttgg agtatctgga ccttacccac tatgaaagta tctctgaggt ggaagcctta    300

cttgagcaac acaaaagcaa acccttgcaa ctgctggatt ctgagctatt ccagtttttg    360

attgtgaaga ttagcgagga tgagtattgg attaatacca agatgcacca tattatttct    420

gacgggatct caatggtgat ctatggcaat caattgacgg aattttacat gcagatcatt    480

caaggaaatg aaccgacgct gaatgacgat tgctcctata ttcaatatat tgcagaagag    540

aacgcatacg agctttctga cagatatcaa aaggacaaga catactggct caataaattt    600

tctgatttac ctgaacttac gggttggaag tcatacaatc cgttatctct gagcacccac    660

gccgttcggg agcattttac cgtgccagag gtgctgtatc acgagttgca ggcattttgc    720

caacagaaca ggatttctct gttccagttc ttcatgggtg tgatgtatat ctacatacac    780

aaagtaacga atcagccgga tgtggtgatt ggtacttcgt tcgctaaccg tgggaacaaa    840

aaagagaagc aaaagatcgg tatgttcgtt agtacggctg cagccagaac atacgtcgaa    900

aaggacatgg atgtgctgag cttcctgcag gaagtagcca gggatcaaat gtcaatcctg    960

cggcatcaga agtatccata taatcagtta attcaggatc ttagagaaat gcatggtaac   1020

agggatatcc agcggctttt tggcgtctcc atggaatacc gtcttatcaa ttgggttgat   1080

ttggatgacg tgcgcatttt gacggattat gatttctgcg gcgacgaagt gaacgatttc   1140

gtgcttcata tcgtggagat cctggatgaa ggcgagctgg tactggatgt cgattaccgg   1200

acgaagttgt ttgaacgcag tgaagttaag gacatggttt cccagttgct tacgatcgcc   1260

gagcagatca ttcatgcacc gcagctttcc atcgccgagg taaacctatt gggtgaagca   1320

gaagagcagt ccattttggc tctttcggaa ggcgttgcag tcgattatcc gcgtgaaaag   1380

acaatccatg gcttattcga agaacaagcc gagcgcatgc cagatcacgt agccgttcag   1440

atgggcgagc agagtattac atacctagct ctaaacgagc aggctaacca gcttgcgaga   1500
```

-continued

```
tatttgcgca ccgaaggcgt tggtgcagat gtactcgtgg ggattatggc tgatcgttcc   1560
ctggaaatgg tcgtcggcat gctggcggtt ttgaaggcgg gaggagccta tgtgcccatt   1620
gatcccgatt atcccgaaga acgtattcgt tacatgctag aggattcagg agtccgtctg   1680
ttgctcaccc aaagccatct atgggagagt accacatttg acggaaagct tgtgaatctg   1740
gacgaagttg catcgtataa aggggacact tcaaatctgg agagcatgtc gggggcgagc   1800
aatcttgcct atgttatcta tacgtcgggt acaactggca agccgaaggg aactctgatc   1860
gagcataaaa atgtagttcg actgctcttt aacgataaaa atttatttga tttcagcgct   1920
caggatacgt ggacgctatt ccattcgttc tgctttgact tctccgtttg ggagatgtat   1980
ggagcccttc tctacggagg aaaattggtg attgttccgt ctcttacagc caagagtcca   2040
gcagctttcc tgaagttgtt gaaagacaac aaagtcacca ttttgaacca gacaccaacg   2100
tatttttatc aggtgctaca ggaagaattg gtgcactctt cgacagagct taaccttaga   2160
aaaatcattt ttggtggaga ggccttaagc ccatctcttc tgagaaactg gcgggtcaag   2220
tatcctgatg tgcaactgat taatatgtac ggaattacgg aaacaacggt ccatgtcacc   2280
tacaaggaaa tcacggaaca tgagattgaa gcggggaaaa gcaatattgg tagaacgatt   2340
ccgacactta gcgcttacat ttttgatgag caaagacgtc tgcagcctgt tggggttccg   2400
ggggagctat acatcgcggg cgacggtctt gcccgagggt atttgaaccg tccagagttg   2460
acggctgaaa agttcgtaga acatccattt cgggcgggag agcggatgta ccgtactggg   2520
gatctggctc gctggttgcc tgatggtaat atcgaatatt tgggccggat cgaccatcag   2580
gtcaaaattc gcggctaccg aattgagctt ggcgaggtgg aagcccaaat tctcaaggct   2640
ccgaatgtaa gggaaacgat tgtcctcgca cgggacgacg aacagggcca aaaattgctt   2700
tgcgcctact acgtggcctc caccgacctt tcgccgggcg aattgagatc tcagctggca   2760
gtggaactac cagcctacat gatcccctct tattttgtcc ggctggagca aatgccgctt   2820
acgccaaatg gtaagctgga tcgtcgcgcg ctgccagatc ctgaaggcag tgtacaatcc   2880
agcgaggttt atctggctcc gagaactgct gcggaagcgc agatggtgct aatctggcaa   2940
gatatcctgg gagttgcccg cgtcggtgtc agagataatt tctttgaaat tggtggtcac   3000
tctttgcggg caacattgct cgtttcgcgg attcacaaag agttgggatg tagcatttcg   3060
ctgcgcgaag tgtttcagtc gcctacggtt gagtctttgg cgcaactggt caaaaagcac   3120
attccgacag tgtatgaatc catcccacag gcggaggaaa gcgcatctta cccagtgtcc   3180
tcagcgcaaa agcggttata cgtgttgaga caaatggacg gaggagagct cagctacaat   3240
atgcctgggg cattcacagt ggatgggccg ttggatcgcg tacggctgga gtctgcgttc   3300
caggcactga tccagcgtca cgaatcgctg agaacgggct tctatatgaa ggatggagag   3360
cttgttcagc gtgtgcataa ggaagtgccg tttgcgttgg actgcacaga agcttcggtg   3420
gaggagacgg atacgctcat acgcagcttt atccgtgcct ttgatctcag ccaggcccca   3480
ttactgcgtg ttggcttggt gaagctgaaa gaggaacgtc atctgttgct gtttgatatg   3540
caccatatca tttcggatgg ggtttccatt caaatactgg tggaagaact cacctcattg   3600
tatcagggag aacagctgcc agaactgcac atccagtaca aggattatgc tgtatggcaa   3660
cgggagcatt cagagaacca gtggaaagag cttgaagcat actggctgca ggcttttgaa   3720
ggggaactgc ctgtacttga tttgcctacg gattatcaaa gaccttctgt tcgcagcttc   3780
gagggtagcc gaattgattt tacattggat gcatccggca ataaggcaat acaggaactc   3840
```

-continued

```
gcatcccgta caggtactac gctgtatatg gtattgctgg ctgcttattc ggtcctgttg   3900
cacaaatata cggggcagga ggacatcatc gtaggttctc cggtggccgg aagaccgcaa   3960
acggagcttg agagcatcat cgggatgttt gtcaatacac tggctatgcg cagctatccg   4020
gcaggagata agacatttca ggattatctt ctcgaaatca aggaaacggc gctcaaggcg   4080
ttcgagcatc aggactatcc tttggaaaaa ctgattgaga agctgggtgt aggacgtgat   4140
gtcagccgca atccactctt tgatactctg ttggtattgc aaaatacgga gcaggcagag   4200
caggacatgg gcgggctgcg ctttactcct tacccgctgg agactgttac agccaaattt   4260
gacctgtcac tcaatgtaga ggagcagggg gcagagctag cttttggttt ggagtatagc   4320
acggctttat atcagcgaga gagtgtagag cgactggcta tgcacttgct tcgggttctg   4380
catgcggttg ctgtcaatcc ccagttaaag ctggcggaga ttgagatgat cacaccggag   4440
gagaaggtgc agatcattga agaattcaat gcgacatcgg ctccttatcc aagtgagaag   4500
actattcatg agctgttcgc agagcaagta aagcgtacac cggagcagac ggcgcttgta   4560
ttcggcaacg tccagctaac ctacctcgaa ttggaagaga aggcggggcg gctggcccaa   4620
acactgcgtc gcttgggaac gttgagggag cagcctgtag ccgtgatggg cggacgaagc   4680
atcgagatgg tcattggtat gctcgcgata ctacaggcgg gtggagccta tgtgcctatt   4740
gatcccgaat acccggaaga ccgggttcgt tatatgctca atgattccgg cgccaagcta   4800
ctactggtgc aaaagggtga gtttgtaagt gtagactacg gtttaccgat tgtcgacctc   4860
agcagtgaag aggcttatgc agccgaacct gcccagctgg agactgccca ggggtcacag   4920
gggcttgctt atgtcattta tacatcggga accacaggta ggccgaaggg cgttatggtt   4980
gaacaccgga acgtggtccg tctggtcaaa gagactaact atgtggagtt gaatgaatcc   5040
acacgaattt tgcagacagg agccgtggcc ttcgatgctt ctactttcga gatatggggg   5100
gcgttgctta acggcggaca gctctatttc gtagagaatg acgacattct gattgctgat   5160
aggctcaaag ctgccatcgc caagtacagg attacgacgt tgtggctcac ttcaccgctt   5220
ttcaatcagc tttcattgca ggatgagtac ctgttcagag ggctaaaaac attgctcgtc   5280
ggcggtgacg tactgtccat atctcatatg aaccgtgtga tcgatgctaa tcctgatctt   5340
gttcctgtca attgctatgg tccgacagag aatactacct tctccaccac ctacaagatt   5400
ccgggtcgat ttgaaggggg agtaccgatt ggtcgcccga ttagcaactc gaccgcttat   5460
gtagtcaatg gatcgcttca attacaaccc attggtgctt ggggtgaact gattgtcggc   5520
ggtgaaggtg tagcgcgcgg atatctcaat cggcctgatc tcacggcaga aaaatttgtc   5580
cctagtcccg tgaaggacgg agaatcctgc taccgaactg gtgatctggt acgctggctt   5640
ccagatggca atctggaatt taaaggaaga atcgatgaac aggttaaaat acgtggctac   5700
cgcattgagc tccccgaaat cgaggctcag ttggccaagg tggagacggt catcgacgcc   5760
gtagtagtcg ttcgcgcgga tgagcttgga gagaagcagc tttgcgctta ttatgtggcg   5820
gatcgcatgc tcaccgcagg agaagtgcgt cttgctctat cgcaggtact tccgggttat   5880
atgatcccgt cctattttgt gcagctggat cgtatgccat taacgtcgaa cggaaaagtg   5940
gaccgcagat ctctgccggc tccccaagtg ggtgcgcata cgggacggaa ttatacggct   6000
cctcgtacac cggcggaaga agccttggcg tctgtttggc aaggggtgct gggtgccgat   6060
caggtgggta tccatgacaa tttctttgaa ctgggaggag actccattaa ggcgattcag   6120
gtttcgtcac ggctactaca ggctggttat cgcttagaga tgaaggagct gttcaaatcc   6180
ccaaccattg cggagctagg cgcggaaata caaaccgctg tgcgcatggc cgaacaggga   6240
```

-continued

```
gctgtgcgtg gagcgacttg cttgactcca gtccaacagt ggttctttgg acggaagcag   6300
gcagagccgc atcacttcaa tcaagcggtc atgctgtacc gtgaacaggg atttgaggaa   6360
aaggctttgc accgtgtgct aagaaaactc gctaagcatc atgacgccct tcgcatggtt   6420
ttccgtcaga cagagcatgg ctacgaagct tggaatcgtg atcttgaaga aggagagctt   6480
tataacctgc ttaccgctga tttacggaat gaatccgatc cggctgcagc tattacaacg   6540
ctgtcggatg acattcagcg cagtatcaat ctggcagaag gtccgctgct gaagttagga   6600
cttttccatt gtcaggatgg agaccatctc ctgatcgtga tccaccattt ggtggtggac   6660
ggagtatcct ggcggatttt gtttgaggat atcgcagcag gctatgaaca ggtgactcaa   6720
ggacaagcgc tggtattccc gcagaagacg gactccttcc gtgactgggg cgatgcgctt   6780
tcccgttatt ccgaaagcca ggaaatcgaa attcatcagg cgtattggag agaactggaa   6840
ggtcagcaac ttgagcagtt gccgaaggat gaggctgtag agagccttct tttacgggat   6900
agcaaagtgg taacagcaca atggactata gaagaaaccg accaattgct gagaaaagct   6960
caccgtgctt accaaacgga gacgaacgat ctgttattga ccgctctggg catggccata   7020
tccaagtggt ccggcattgg aaagattgct gtgaatcttg aaggccatgg tcgtgaaccg   7080
attataccga atatcgacat cacccgtact gttggctggt ttacaagcca atatccggtg   7140
attttagact tgggcgataa cctggaagtg gcagccttga tcaagtctgt gaaagaagga   7200
ctgcgccaaa ttccgaacaa gggtatcgga tacgggttgc tcaaaaccat ggcaagtcag   7260
gtggatgcag acagcttcag cttgcagcct gagatttctt ttaactatct ggggcaattt   7320
gatcaggatt tgcaaggaag ctcgttgcag atttcgcctt atccgaccgg aaacgcccaa   7380
agcttgttgg gggaaccagc ctacacgcta gatatcaatg gcatggtgac ggacggagcc   7440
ctgactctga cgatgactta taacggaaaa cagtataagt catctacgat ggaacagctc   7500
gctggatata ttgaagaaag cttgcgaatg cttctccatc attgcgtagc ccaggaaaga   7560
accgttttga caccaagtga cgtgcttgcg aagggtctaa gcattgccga tctggaagag   7620
ctctccaagc aaaccagcca cataggcgat attgagaatg tatacagtct gacaccgatg   7680
cagaagggca tgctgtttca tgatatgttt gagccgcata caggtgctta ttttgagcag   7740
gctgcctttg attttaaggg tagctttgat ccggccgtct ttggacaaag tctcgatgcc   7800
ttagtggagc gtcatgccat cctccggacg aacttttata acggatgggg cagcgagcct   7860
ttacaggttg tttttcggca cagaggcgcc aagctggtgt acgaagacct gcgggagatg   7920
gacgaaacgc agcgcgaagc ttatttgaag acatttgctg caaaggacaa ggcacagggc   7980
ttcaacttat ctgaggatga gcttctacgt gtttcgattt tgtgtacagg tgaggagagc   8040
ttccgtctct tgtggagctt tcaccacatc gtcatggatg gatggtgtgt tccgttaatt   8100
acgcaggagg tatttgaaca ttattttgcc ctcctggaag gaagagagcc tcagttggca   8160
gaggttcagc cgtacagtcg atatattgaa tggctggaac agcaggatga agcagctgcg   8220
tccaactatt ggagtcgata tctggccggt tacgagcagc agacgctttt acctcaagtc   8280
ggggaagcaa gtaaaggaga agggtacgta tcagaaaagc agaattacat cctcggcagg   8340
gaattaactg gacgtctgga gaaggtagcc agagatgctc atgtcacgat gaatatattg   8400
ctgcaatcca tatggggcat tgcacttcaa cgctataacg gtagccggga tgtcgtatac   8460
ggaagtgtag tatcaggcag accagcagaa attccgggca ttgatcggat gatcggtttg   8520
ttcatcaata cgattccagt ccgtgtgaag acggaggaaa atctcccctt ctcagttttg   8580
```

-continued

```
atgaagcagc agcaggaaca atttatggct tcccatatgt atgacaccta cccgctgttt   8640
gagattcagg ctcagaccga tcagaaacag gacttaatct cacatattat ggtgtttgag   8700
aactatcctg ttgaggagga ggtagaacgt ctgggtggtg gcgaggctga ctttgagatt   8760
gaggacgccg agcttctgga gcaaacgaat tacgatttta acttaattat cctgcctggc   8820
aaagagatga gattgctatt ccagtacaat gcacttgtgt atgatcaagt gacgattgag   8880
caaatcaagg gacatctggt tcacctcatg gaacaaattg tggagaatcc tgcaatttcc   8940
gtggatgctc tggaattggt cacgccgcag gagagagagc tgattctgga cgtatggggt   9000
aacacgaaag tcagttacga gcactgtaac acgttccacg ggctgttgga ggaacaggcg   9060
ggacgaacgc cggaggcgac tgccattgtg ttcgaggatg agatgctgac ctatgccgag   9120
ctcaatgcaa aagccaacgg actggcaaga aaactgcgta atcagggaat ccagacggga   9180
gatctggtgg ggctgattgc tgaccgttcg tccgaaatga tcgttggaat ctacggcatt   9240
atgaaagccg gaggtgccta tgttccaatt gatccagagt atccgaaaga acggatcagt   9300
tacatgcttg aagattccgg agcaaagctg gtccttacac aggcccgcct cttggagcat   9360
cttggatgga cggaaaatgt tttgttgctg gatgaaccat cgacatatga tgccgatacc   9420
tcgaatttga aggatactgt tggcccggat aatctggctt atgtgatcta tacttcaggt   9480
acgacgggtc agcctaaggg cgtattagtc gaacatcggg gactacaaaa tctttcggac   9540
gtatacggga catacttcga agttacaccg caggaccgaa tcgttcagtt tgcaagtctg   9600
tcatttgatg catcggtttc ggaagtttta acggcactaa gccatggggc tgctctgtgc   9660
atcccttcta cacaagacat tttagattat gccttgttcg aacagttcat aaacgacaag   9720
ggaattacga tagcgactct gccaccagct tacgctatcc accttgagcc tgagcgcctg   9780
ccagcactgc gatgtctgct taccgccgga tcagccgcat ctgtcgagtt gatcgaaaag   9840
tggaggaagc atgtacgcta ctccaatggc tacggcccaa cggaggactc tatttgcacc   9900
acaatctggt ctgttccgga tagcgaggaa acgctggaga cagtatccat tggccgacct   9960
attgctaacc atagtgtgta cgtgttggat gagcatctca gattgcagcc tgtcggcgta  10020
gttggagagc tatgcatttc aggtatcggg ttagcacggg ggtatcataa ccgacctgca  10080
ttaatggacg agaagttcgt cgaaaatccg ttcactccag ggagcgtat gtatcggaca  10140
ggtgacttgg ttcgctggtt accgaacggt accatcgaat acgtgggccg aatagatcat  10200
caagtcaaaa ttcgcggcta tcggatcgag ctgggtgagg tagaagcaca aatgctcaga  10260
gtgcagtccg ttcaggaagt cgtggccatg gctgtggaag gcgatgacgg tcagaaggat  10320
ctggtcgctt atttcgtagc cgcccgggag ctggaggtat ccgagctcca gacagttctg  10380
tcggagatgt tacctggata tatgatccct tcccgcttca tacaactgga ggatatgcct  10440
ctgacgtcga acgggaaaat caatcgaaaa gcgttgcagg gagagcgcgg atgggcagtt  10500
gcttcatctg tagctccgaa gacacctttg gaaattcaat tagctgaaat ttggcaagaa  10560
gtgttgggtg tagagaatgc gggagtgaag gataatttct tccattttgg aggtcactcc  10620
ctgcgtgcag ctctgctagt ctcacgaatt cgcaaggaaa tgaaccgcga tattagtctg  10680
agagaagtgt tcgattctcc tacaattgaa ggattggctc gcgccattga gggctataca  10740
ccgctcaatt ttgaagaaat tcctacggcg ggagtgcgtg agcactaccc actgtcctca  10800
gcccaaaaac ggctgtttat tctaagtcag ttggaaggcg gagagctgag ctacaatatg  10860
ccgggaatcc ttacggttga gggagccttg gatcgggaac ggctggaaca ggcattccgt  10920
cgtctgattc atcgccatgg ttcgctgcgt acccgttttg tgactgttaa cggtgaaccc  10980
```

gtacagcaga ccctgcctga tgtgcagttt actgtggaat atgcggagtt gagcgagaag 11040
gaggcagaag cttcccttca gcaatttgtc cgccctttttg atcttggcga ggttccattg 11100
ctgcgggtcg gcctcatccg gattgcgcat gaccgccatt tactgttgtt tgacatgcat 11160
catattgtct cggatggtgt ttctatgaat attctcatag aagagtttct ccgcttctac 11220
caagaggagg acttattacc tgcactacag atccagtaca cagactatgc ggtatggcag 11280
caggagcaac tcggaagcga acgtctcaaa gcccaggaag cttactggct ggatgcattc 11340
cgcggaagct tgccagtgct ggatttgccg ggagatgaag tccgtccagc ggtgcgaagc 11400
tttgcggggg atcggatcga cttctgtatt gattcttctc tgagcggttc actccagcag 11460
ctggctaccc gaacgggttc tacgctattc atggtactgc tggcagccta tacagcgctc 11520
ttgcacaagt acacgggtca ggaagatgtc attgtcggtt cacctgtggc tgggagatcc 11580
catacgacac tcgaaggcct catcggtatg ttcgttggca cactggcact gcgtacttat 11640
ccggaagggg agaagtcttt cgagacttat ttgcaggaag tgaaggaaac agcgctgcgg 11700
gcctatgaaa accaggatta tccgttcgag gagctggtag aaaagctgga gcttcagcgt 11760
gacctgagcc gcaacccgtt atttgatacc atgtttgtcc tgcaaaatat cgagcaggga 11820
gaacaagaaa tagagggatt gcgtttcact ccttacgata atgtacatcc tgctgccaag 11880
ttcgacctca cgctgaccgt aagtgaagcg gatggggcat tggattgcac gcttgagtac 11940
tcgactgcga tctacaagcg agagactgct gaacgaatgg caggccactt tgtacagctt 12000
attcgggaag caaccgccaa tccggcaatg ccgttgtcat cccttgatat cgtgacacct 12060
caggaaaaat caaagctgat gcaggagtcg gccgaagcca gagcagatta tcctcgtgac 12120
aagacgattc atgcgttgtt cgaggaacag gctgctcgta ctccgaatgc aatagcagtc 12180
gtatgtgaag aggcaaccct gtcctacagc gagctgaacg aacgggcaaa cagacttgcc 12240
agaacgctcc gcgagcgtgg cctccaacca gatggtttgg ctggaatcat ggcggatcgt 12300
tccctcgaaa tggtcgtcgg gattttggcc attttgaagg cgggcggagc ttacgtccct 12360
gtggaccctg aatatccgga ggaccgcata cgctttatgc ttgaggattc aggagccaag 12420
ctactgctga cacaagcgca tctggagaaa catgtctcct tcgccgggga catcgtcaat 12480
ctggacgaga cggcttccta caaggaagat atctcaaacc tgaagtctac aaccggaccg 12540
gagcatcttg cctacgtcat ctacacatcg ggtacgacag gcaagccaaa gggaacactg 12600
atcgagcaca aaaatgtagt tcgcttgctc tttaatgata aaaatatgtt tgatttcggt 12660
cctcaggata cgtggacgct gttccattca ttctgctttg acttctccgt atgggagatg 12720
tatggggcat tgctgaatgg aggtcgtctg gtcatcgttc catcgcttac cgcgaagagt 12780
ccagatcgtt tcttgcaatt gctaaaggac cagaaggtca ccgtcttgaa ccagacgccg 12840
acatacttct accagttact acaggaagag cttggtcatc acgcggcaga actgagtctc 12900
cgtatgatta tcttcggtgg cgaggcatta agcccggcct tgctcaagga ctggagaacg 12960
aagtacccac aagtgcagct catcaacatg tacggcatta ccgaaacaac cgtgcatgta 13020
acatacaagg aaattacaga tctggaaatt gaacagggcc gcagcaatat cggtaccacg 13080
attccgacgc tgcgtgcata cattctggat gaacaacgtc gtccacagcc gattggcatt 13140
ccaggtgaac tctacgtggc gggcgaagga ctggcgcgcg gctacctgaa ccgaccggaa 13200
ttgacggaag agaagtttgt cgctcatccg tttgcagcgg gcgagcgtat gtaccgctcg 13260
ggtgacctgg cacgctggct gcctgatgga agcatggagt atttgggacg gattgaccac 13320

-continued

```
caggttaaaa tccggggtta ccgcatcgag ctgggcgaag tggacgcgaa gctgctccat  13380
gctccgtctg taagggaggc tgtagtgctc gctcaggagg atggaagtgg acaaaaggtg  13440
cttgtcggct attttacagc cgatcagata ctgacggtag gcgaattgag aaaagccttg  13500
gccgcagagc tgccagctta tatgattccg tcttacttca tgcaattgga acagatgcca  13560
ttgacgccaa atggcaagct ggatcgcaaa gcacttccgg ctccggaggc caatgtgcag  13620
acaggagcgg tttatgaacc gccaaggacg aaggctgagg aagctctggc gtccgtatgg  13680
caaggggtgc tgggagcaca gaaggtcggc atccatgatc atttcttcga tctgggtggt  13740
gactccatca aggcgatcca ggtatcctca agattgttcc aagccgggta taagctagag  13800
atgaaggatc tcttcaaata tccgacaatt gctgagctaa gcccgtatct tcaagtagcc  13860
ggacgcacag cagaacaggg tgaaattaaa ggcgcagcag agctgatgcc aattcagcgg  13920
tggttctttg agcgtcatac agaggagccg catcattaca atcatgccgt catgctctat  13980
cggaaagacg gctttgacga ggctgcactc cggttgacaa tgacccaaat tgctacccac  14040
catgacgcgc tgcgtatggt cttccggtct acagaggccg gatatgcagc ctggaatcgt  14100
ggaacggatg aaggcgagct ctatacattg gatatagacg atgtgcgaca ggcagaagac  14160
caggttgctg ccgttcaagc caaagccgat gccattcagg caagcttcca cttggaagac  14220
ggcccgctgt tcaagctagg cttgttccat tgtgaagatg gggatcattt attaattgtt  14280
atccatcacc ttctagttga cggggtatcc tggcgcatcc tgtttgagga catcgcaacg  14340
ggatacgagc aggcgttgaa tggacaagcg attgtccttc cacaaaagac agattcgtat  14400
cttgtatggt ctgaacaagc ggcgaagtat gcagcagggc ctgcactgga caaggagcgt  14460
gcatactggc agcagatcga ggatacaatt ctggccctac tgccaaaaga tgaagatcag  14520
gagccaggca ccattcggga taccgagtcg gtaacggtaa cgtggtctgc gcaggaaaca  14580
gacctgctgc tgcgacaagc gaaccgggcg tatcatacgg agacgaatga tttgcttttg  14640
actgctctgg gagcagcaat tcagcgctgg acaggcatgg agcagatttt ggtcaatctt  14700
gaagggcatg gacgggaaat gatcataccg gaactggata tcacccgtac cgtgggctgg  14760
ttcacaaccc agtatccggt tctgctgaac cttcaagacg gacaggaagt atctgcacga  14820
atcaagcgta tcaaggagaa tttgcgccag attccgcaca aaggaatcgg ctacggcctt  14880
ctgaagtata tagcactgga gaaaagtggc gggttcggcg tagagccgga gatttccttc  14940
aactatcttg gacagtttga tcaggatttg gaggggaatg cactcagcct atccacacat  15000
tcagtcggta aggcgctcag cgaccacaca ccacagcagt atgctctgga tgtgaatggc  15060
atgattgccg aaggccagct atcactgacg gttacgtaca gcagcaggca gtatcgcaag  15120
gagacggtga atcattttgc cgaattatta cagtccagcc ttagcgaggt tatccggcat  15180
tgcgtggcgc aggagcgctc acagcttacg ccaagtgatg ttttgttcca gggattagcg  15240
ctggagcagc ttgatcgact tacggagcag acggcccaca ttggagagat tgaagatgtg  15300
tacaagctta cgccaatgca gaaggggatg ctgtttcaca gcctgctgga gccagactcc  15360
tcttcatact tcgagcaggc tacgttcgag ctgcgaggca gcttcgatgt agagaccttc  15420
ttcgagagct tccaagcttt ggtgcaaaga catgccatac tgcgtaccaa cttttacaac  15480
aacattggtg atttaccgct gcaagtcgtc tttaagcaac ggccaatccc attgcactac  15540
gtagatctgc gtgccgcaac tttgcaagag caagaagccc agatcaaggc ttacactgct  15600
gaggatatgg ctaaggggtt cagcttgtcg gaagatccgc tgatgcgggt aagcgtcttg  15660
caaacagaac aaagctctct ggtattatgg agcttccatc atattgtcat ggatggctgg  15720
```

-continued

```
tgcatcccga tcattacaca ggagctattc gattattatt ctgctctgcg ccagcaagta  15780
cagcctgtgc tgccgccagc tcagccctat agccgttata ttgagtggct tgatgcacag  15840
gatgatgagg aagcttccac gtattggagc caatacctca aggactatga tgggaatacc  15900
gtattgccgg aaggcaaaac gaaatctcaa gctaaagaag cgggctatgt tctgaatgag  15960
catgttctcc atctgggtgc atccttgacc ggtaaaatgg atactgtcgc taagcgaaac  16020
cacgtgaccg tcaacacact catgcagaca gcctggggac tgattcttca acgttacaat  16080
gccagctcgg atgtggtttt cggcggcgtt gtatcgggca gaccggctga gattgcaggg  16140
atcgaaaata tggtgggtct gttcattaat acagtaccta tccgtgtaca gtcctccaaa  16200
gacgaagcct ttgtcgaggt gatgaaacgt acacaggcac agtcattggc tagtcgtgcc  16260
tacgacacct atccactgta tgagattcag gggaaaacaa cccaaaagca ggacctgatt  16320
tctcatatta tgatctttga aaattatccg ctcgacgagc aggtggagca atcgggtaat  16380
caaaatgagg acaatctcga agtcgcgaac ttcaccatgt ttgaacaaac gaactatgac  16440
tttaacctgg ttgtgattcc aggcgaggat atcaaggttt gcattcgtta caatgctttg  16500
gtctacgaac aagaaagcat tgcacgaatc ggtggacact tgatgcaaat gctcgatcag  16560
gtagctaccc gtccgcaggc agtcataaag gaactggagc ttgtaacctc tgatgaacga  16620
atgcaattgc tagactgggg cggcaaggcc tacacctatc caagtgatca gggtctgcat  16680
accttgtttg aagaacaggt tgtccgtacg ccagataaga ttgcagctgt taacggcgat  16740
attcaggtca cgtatcggga gctgaacgag caggcgaaca gattggcctc caccttgatc  16800
gcccaggaac ttcggagtga acaagtggtc ggtctgttgg cggatcggtc tgtggaactg  16860
cttgtcgcca ttatgggtgt gctcaaagcg ggcgggtcct atgtacctat tgatcctgaa  16920
tatccgcagg aacggattca gtatattcta aaggattccg gcgctgagat tttgctcaca  16980
cagagccact tgacggagct ggcctccttt gagggaacgg ttatggaatt ggattccccg  17040
cacatctacg gagacggggg ggataaccct aatctacctg tgagaggaaa cgatctggtg  17100
tatttaatct atacatcggg tacaacagga aatccgaagg gaaccatgat taaccataaa  17160
gggatcgtga actacatctg gtgggccaat aaggtctact gtgcagggaa accaacagat  17220
tttccgctgt actcgtccat ttcatttgac ctgacgctga catcaatttt cactccatta  17280
attaacggag gattagtacg gatttacgat ggtatagata aggcggaggt tgttcagcat  17340
attttgcgcg aaaatgcggt ggacattctc aagctgacgc caactcatct cagtctgatt  17400
aaagatatga ccatcccggc ggaaagtcgc attcagcagc tcattgtggg tggagagaat  17460
ttgaccacac atttgtcgca aaccatcaca gatctctttg gcggcaagat caaaatctac  17520
aatgaatacg gtcctaccga aacggtcgtc ggctgcatga ttcaccttta tgatcctgtg  17580
aaggatacac gtgaatccgt acctattgga ttgccggcag acaacatata catccatatc  17640
ctggatgacc agcttcgtct cgtaccatta ggcgtggagg gcgaaatgta catcgccggg  17700
gacggggtag cccgcggata cctgaaccgt cctgagctta ccgcagaaaa attcattaga  17760
gacccgttcg cctcggaagg aaatatgtat cgaaccgggg atttggcccg tcgtcttcct  17820
aatggagaca ttgagtacat tggacgtatt gaccatcaag ttaaaatacg gggctatcgt  17880
atagagcttg gtgagattga ggccaagctg ctggatattc cacttatcga ggaagctctc  17940
gttgttgcgt gggcagatgc ccatggacag aagtctctgt gtgcctactt cgtagctgat  18000
cgggaaatgt ctgtcagcga gctgcggaac gaactttctg gactgcctgc atatatgatc  18060
```

-continued

```
ccgtcctact tcgtccaact ggacgtgatg cctttgacac cgaatggcaa gctggaccgt  18120
aaggcactgc ctgaaccgaa ctcgggtgtg aaggcgggcg cggcctttac tgctccgcgg  18180
acggatgtgg agaacatttt ggcttcgatc tggcagggtg tgctaggtgt tccgcttgtc  18240
ggcatacatg acaatttctt tgagctcgga ggcgactcga tcaaatccat tcaagtctca  18300
tcaaggctgc tccaagcagg ctataaactt gagatgaagg atttgttcag ctatccgacc  18360
attgcagagc tggcccagcg tgttagggcg gtcagccgaa ttgcggatca gagcgaggta  18420
cacggagcgg taagactggg acctgcccag tgcagatttt tcgacgagca gtcgacggac  18480
ctgcaccact ttaatcagtc ggtcatgttg taccgtcggg aaggcttcga taccgatgcg  18540
ctcgccaagg ttgttcggaa aattgcagaa catcatgatg cgctgcgact ggtgttccgc  18600
caaggagagc ggggatttga agcctggaac cgcagcttag gtgagggtga gctttatagc  18660
ctccagatcc acgatctgca ggatgaaaca gacccggctt cggcaataga agcaggtgtg  18720
gaagccattc agcgcagcat ctctctcggt gatggacctc tcttaagatt gggcctgttc  18780
cgctgcgcgg aaggcgaaca tctgctaatc gttattcatc atctggctgt tgatggcgta  18840
tcctggcgca tcctctttga ggacctgcag gaaggctacg agcaggcagc acgcggagaa  18900
gctgtcaagc ttccgcagaa gacggattcg taccgtgcat gggcccaggg aatcacacaa  18960
tatgcgaaca gtccggcggc tgaacaagaa cgcagctatt gggcagaggt agaaggggat  19020
ggcttcgccc ctcttccaaa agacaaggta gacgacgctc ttctcatcaa agacagcggg  19080
acggttacgg tgagatggtc accagaagag acagagcagt tcctgaaaga ggcgaaccgc  19140
acttacaaca cggaagttaa cgatttgctc ctgacggccc tcggcatggc tgttcacgag  19200
tggaccggga tcgaacgtgt aggcatcctt ctggaaggac atggacggga gcctgttgta  19260
cctgaactgg atatcactcg cactataggc tggtttacaa gtcaataccc tgtcgccctt  19320
gagatgaaag aggaactgga gatcggcgct agaatcaagc gtgtcaagga aggcttgcgt  19380
cacattccta acaaaggtgt cggatatggt attttgaaat atttgagcga cgtatccgat  19440
gtctcctcct tctctgctga accggagatt atcttcaact acctgggaca gttcgaccag  19500
gatcttgcag gggggatgat ggaggtatcg ccttactcag taggatctga ggtcagtgag  19560
cagatggtac agcatcaggc attgaacatt aatggactga ttgccgaagg acgacttcag  19620
ctttcggtca gctataaccg tcagcagttc cacacagagt cggtagagaa gtttgtcggc  19680
atcctgaaga accgtctcag cgaagtcatt ggacattgtg tacgcaagga aagaacggaa  19740
cttacaccaa gcgatgtact cctcaaagat atcagcctgg aaaaaatcga ggagctggaa  19800
gagcagacac ggcatatcgg cagtattgaa aatatttata aactgacacc gatgcaaaag  19860
ggcatgttgt tccacagctt gctggagcct cattcggaag tctactttga gcaggctaaa  19920
tttgaaattc acggagcatt ctatcctgag gatttcaaac gcagcataaa gcatctgatg  19980
aaacggcatg ccatattgag aacgaatttc catgccggat ggggcgattt ccctatacag  20040
attgtgttca aagaaagagc gtgtgacttc gtatacgagg acctgcacga gctggaatcc  20100
ggtgaaattg aagtgcgtct ttcagcttat actgctcagg acaaagcaag aggctttgat  20160
cttgctgaag gagcattgct gcgtgttgct attctacgga cagcagatga ggcttaccat  20220
ctgctgtgga gctctcatca catcattttg gatggctggt gtatgcctct tgtgcttcag  20280
gaagtgtttg aaacgtacgg ggttctgcgt gagcagaggg agcctgaact tcctgctgct  20340
gtatcgtaca gccagtatat tcaatggctg gaggagcaag gtgaggaaga ggcatcctct  20400
tactggagag gttatctgga aggttacgaa cagcagacga agctaccgca agcgacaaca  20460
```

-continued

```
cagccattgg caaaagcaga agcctacgta tcagagaagc ttgtattcac gttggatgcg  20520
gagctgaccg agcggctgga acaagtggcc aagcagaacc aggtaacgat gaacacgctg  20580
atgcaagcag cctggggaat cgtgttgcag cgctacaata gaagtcagga tgtcgtcttc  20640
ggaagtgtgg tatcgggaag acctgccgag attcccggta tcgaaagcat gatcggtctc  20700
ttcattaata cggttccggt tcgggtacag gccgagggaa gcgatacgtt ctcccatgtg  20760
atgaaaagac agcaggaatt atatttggca ggacatgctt atgattccta tccgctctat  20820
gagattcaag cacagagcga acagaagcaa gatttaattt ctcatattat ggtattcgag  20880
aattatccgg tagaggagca tctagaagag aaaattgcca gtgaagaggc tgaatacaaa  20940
attacggatg ttcagatgtt tgaacagacg aattatgatt ttaacctcat tgtgctgcca  21000
ggccgtaatc tggagttctt gtaccgttac aatgccagcg tctatgatcg ggagagcgtg  21060
gaacggattc aagggcactt gatgaaaatt ctgggaaatg tatctattca tcctgccatt  21120
cgtattgagg aactggagct gatcacgcca gaagagaaat cgcagattat agaggtgtgg  21180
ggcgatacag cagctcctta tccgcgtgag aagacccttc acggcatatt tgaggaaaaa  21240
gcggcgctca caccggatcg tacagcactt atctatggcg aaacgaagct tacctacgga  21300
gaacttcatc agcaggcgaa ccgcctcgca cgtacgttgc gtgcccaagg ggtcagaccg  21360
gaccagccgg tcggcatcat ggttgaacgt tcgcttgaga tgatcatcgg catccatgcc  21420
attctaaaag cgggcggggc ctatgtaccg attgatccgg aattcccgga agatcgtatt  21480
cgccacatgc tggaggattc gggagcgaag cttctgctga cgaagaacca tctcaaagat  21540
cgctttccgt tcactggcac gatcctggca ctcgatgacc cgcaggcgta tcatgctgat  21600
gactcgaatc tggagccaat cgcggggccg gagcatctgg cgtatatcat ttacacgtca  21660
ggttcaactg gcaagccgaa aggtgtaatg attgagcatc gctctgccgt ccatacgctg  21720
agccagttgg aagctgaata tccgatgatg gcgggtgacc gattcctgct caaaacgaca  21780
ttcacctttg acttctccgt tccggagcta ttctgctggt tctttgggca gggaactctc  21840
gtgatcttgc cgcagggcgc ggacaaagat ccggtggcac tgttggaggc cgtggatacg  21900
agccgtatca cgcatctcaa tctggtgccg tcgatgctca gtgttcttgt tcaatatttg  21960
aaagaaggcg gcagccaagg attccttact ttgaaatacc tgtttgcctg cggcgagacg  22020
ctgcccgcca aacttgtgga agagtactat aaagtatctc catgcgcagt gctggagaac  22080
atctatggtc ctacggaggc ggccgtatat gcgacccgat atacaacgag ccttgagact  22140
gctgcgctaa cgcatgtacc tatcggtaaa ccgtacgcta atgtccaagt atggatgatg  22200
gacagtgctt ctcaggtatc acctgtaggt gtaccgggag aactctgcat tgcaggcgaa  22260
ggggtagcgc gagggtactt caaccagccg gacctgacgg cagagaagtt cattcctcac  22320
ccgtacaaac cgggagcgcg gatttaccgg acgggcgatt tggcccgatg gctgccagac  22380
gggaatattg agtatttggg acggatcgat caccaggtaa aaatccgggg ttaccgcatt  22440
gagctggggg aagtggaagc acaaattttg aaagtgccat ctgtgcagga aacggttgtt  22500
cttgcactgg ctgattccac tggaagtact cagctttgtg catactttgt ggccgaagag  22560
gggcttgcag cgggcgtact acgcgaggca ctggccagcg agctgccaag ctacatgatt  22620
ccgactgctt tcgtacagct ggcacaaatg ccgctgaatc caaatggaaa attggatcgc  22680
aaagcgctgc cggcaccgga agcacttctg cggagcacag cggagtacat cccgccgcgt  22740
acgccgacag aagtagagct agcgcagatc tggtccgagg tactcggcgt gcaggaaatc  22800
```

ggggtcaaag atcatttctt cgaacttggg ggccattccc tgaaagtatt gggattgatc 22860
caaaagatct caaccggcat gggtgttcag cttccgctcc aactcgtgtt taatcttccg 22920
actgttgagc aaatggccca tgaaatatcc aagctgcggg caacagctgc tcctgatgaa 22980
gaagaaatgg aaattatcca cttcccaggg aaaggaacgc ttaaagtgtt ttgcttccct 23040
cctcgggtag gttactctct ggggtactat gagatggcca atgagctgga aggacattgc 23100
gaggtgttcg ggctggaatt tatcggcgat cgtttccagg gccaagacat gctggatcga 23160
tacatggatg ccatcgtgga tattcaagct gagggcccat atgtcttcct gggatactcc 23220
ctcggaggaa atctggcctt cgaggtggcc aaagccatgg aaagccgagg tcaccatgtc 23280
agcgacctta ttatggtgga tgctatgaga aagatgtcca aggatgaatc gacaccggag 23340
cagcttgagg agattgtcga gacggtgctg gacagcattg gggaccagta caaatcattt 23400
ctcgccgatc cagctgacag agcgcgagtc aaagacaaaa tgttgatcta ctccatctac 23460
cgcaatgagc ttattaacgt aggtggggtt caggcgaata tccatgcctt ggttgcagag 23520
gacgatagta ttggtccggt gacatcatcg gataaactgc tatggcaaca ggcaacgctt 23580
ggtcaatacg aagagtatgg agtcatcggt acgcacgatg tgctgcttga ttccggttat 23640
atcggggaaa atgctaaagt gctgagacag atacttggca aggtcgcaga gacctcatct 23700
aaaaacaagc ccattttgtc ctaa 23724

<210> SEQ ID NO 4
<211> LENGTH: 23727
<212> TYPE: DNA
<213> ORGANISM: Paenibacillus

<400> SEQUENCE: 4
atgaatgaca tgcagttata tgatttaaca aatgcgcaga agcgtatatg gtataccgaa 60
ttactctacc cagatacgtc agtgtcacag ctttccggta cagctaagat gaaggggcat 120
atcaatattg ctgcctttat gcagtccatt aatttgatta tcaaacagta tgatgcgttc 180
cgcatccgta ttacctcagt ggatggagtg cctcagcagt acgtcgttcc ttatgaagag 240
agacagttgg agtgcctgga tcttagtcac tatgaaagtg tatctgaggt ggaagcttta 300
cttgagcaac acaaaagaaa acccttgccc ctgctggatt ctgagctctt ccagttttta 360
attgtgaaga ttagcgagga agagtattgg attaatatca agatgcacca tattatttct 420
gacgggatct caatggtggt ctatggcaat cagctgacag cattttacat ggagttaatt 480
caaggaaatg aaccggagct gggcgacgat tgctcgtata ttcaatatat tgcagatgag 540
aatgcatacg aactttctga cagataccaa aaggataagg cttactggct agataaattt 600
tccgatttgc ctgagcttac gggttggaag tcatataatc cgttatcttt aagcacccac 660
gccgttcggg agcattttac cgtaccagaa gtgctatatc acgagctgca agcattttgc 720
caacagaata ggatttcttt gttccagttc ttcatgggtg cgatgtatat ctacatacac 780
aaaatgacga atcagccgga tgtggtgatt ggcacttcgt tcgctaaccg gggggaacaaa 840 aaagagaagc aaaagatagg tatgttcgtc agcaccgctg ctgccagaac atacgtcaaa 900
aaggatatag atgtgttgag cttcctgcag gatgtagcca gagatcagat gtcagtcctg 960
cggcatcaga aatatccata caatcagtta attcaggatc ttagagaaat gcatgggaac 1020
aaggatattc agcggctttt tggcgtttca atggaatatc gtcttatcaa ttgggttgat 1080
ttggatgatg tgcgtatttt gacagattat gatttctgcg gggacgaagt gaacgatttc 1140
gtgcttcata tcgtggagat cctggatgaa ggcgaactgg tactggatgt cgattatcgg 1200

-continued

```
acagagctgt ttgaacgcag tgaagttaag gacatggttt cccagttgct tacgatcgcc   1260
gagcagatca ttcattcacc tcagctttct atcgcagagg taagcttatt aggtgaacca   1320
gaagagcaat ccattttggc tctttcggaa ggcgccgcag tcgattatcc acgagagaag   1380
accattcatg gcttattcga ggaacaagcc gagcacacgc cagatcacgt agccgttcag   1440
atggacgagc agagcattac ataccaagct ctaaacgagc aggctaacca gcttgcgaga   1500
tatttgcgct ccgagggagt aggggcagat acgctcgtag ggattatggc tgaccgttcc   1560
ttggagatgg tcatcgggat gttggccatt ttgaaagcag gtggtgccta tgtaccaatt   1620
gaccccgatt atcccgaaga gcgtatccac tatatgctgg aggattcagg tgtaagtctg   1680
ttgctcaccc aaagtcatct atgggagagc accacttttg acggaaagct tgtgagtctg   1740
gacgaagctg caacgtatac aggagatgct tccaatctgg agagtatttc gggaccaagc   1800
catctggcct atgttatcta cacgtcgggt acgactggca agccgaaggg cacgctgatt   1860
gaacacaaaa atgtagttcg actgctcttt aacgataaaa atttatttga cttcaactct   1920
caggatacgt ggacgctgtt ccattcgttc tgcttcgatt tctccgtttg ggagatgtac   1980
ggagcgcttc tttacggagg gaaattggtg attgttccat ctctcacagc caagagccca   2040
gcagctttcc tggagttgtt gaaagacaac caagtcacca tcttaaatca gacgccgacg   2100
tatttttatc aggtgctaca ggaagagtta atgcactctt cgacagagct tggccttaga   2160
aaaatcattt ttggtggaga ggctttaagt ccatctcttc tgagaaactg gcgggtcaag   2220
tatcctgatg tgcagctgat taatatgtac ggaattacgg aaacaacggt tcatgtcacc   2280
tataaggaaa tcacggaaca tgagattgaa gcggggaaaa gcaatattgg cagaacgatc   2340
cccacactta gcgcttacat tctcgatgag caaagacgcc tgcagcctgt tggggttcca   2400
ggagagctat acattgcggg agacggtctt gcccgtgggt atttgaatcg gccggatttg   2460
acgtctgaga aattcgttga gcatccgtat cgggtgggag agcggctgta ccgaactggg   2520
gatcttgctc gttggttgcc tgatggcaat attgaatatt tggggcggat cgaccatcag   2580
gtcaaaattc gcggctaccg aattgagctt ggcgaggtag aagcccaaat tctcaaggct   2640
ccaagcgtac gagaaacgat tgtcctcgca cgggaagacg aacagggcca aaaattgctg   2700
tgcgcctact atgtagcctc cagtgacctt tcgccggggg aattgcggtc tcagctggcg   2760
gcggaactcc ccgcttacat gattccttct tattttgtcc ggctggagca aatgccgctt   2820
acaccaaatg gcaaactgga tcgccgtgcg ttgccggctc ctgaaagcag cgtacaatcc   2880
ggtgaggctt atttggctcc gagaactgct gtggaagctc agatggtact catctggcaa   2940
gatatcttgg gcgttgctcg tgtcggtgtc agagataatt tctttgaaat tggtggtcac   3000
tctttgcggg caacagtgct cgtttcacgg attcacaaag aattgggatg tagcatttcg   3060
ctgcgtgagg tgtttcagtc acctacggtc gaatccttgg cgcaacttgt gaaaaaacac   3120
attccgacca tgtacgaatc catcccacag gcaacggaaa gcgaggctta cccagtgtcc   3180
tcagcgcaaa agcggttata cgtgctgaga cagatggacg ggggagagct cagctacaat   3240
atgccagggg tcttcacagt ggatggaccg ttggatcgca cgcggctgga gtctgcgttc   3300
caggcactga tccagcgtca tgaatccctg agaaccggct tttatatgca ggatggagag   3360
cttgttcagc gtgtgcatag gaatgtgccg tttgcgttga actacacaga ggctttggtg   3420
gaggagacgg atacgctcat tcacaacttt attcgtgcct ttgatctgag ccaggctcca   3480
ttactgcgtg ttagcttggt gaagctccag gaggagcgtc atctgttgct gtttgatatg   3540
```

-continued

```
catcacatca tttcagatgg ggtttctatt caaatattga tagaggaact tactcatttg   3600
tatcaaggag aacagctccc agagctgcac atccagtaca aggattatgc cgtatggcaa   3660
cgggaacagt cagagaacca atggcaagat cttgagaaat attggctgca atcctttgaa   3720
ggagagttgc cggtattgga tttgcctaca gacttccaac gaccttcagt tcggagcttc   3780
gagggtagcc gaattgattt tacattggat gagtctggca ataaggcgat acaagagctt   3840
gcatcccgta caggtactac actgtatatg gtattgctgg ccgcctattc ggtactactg   3900
cacaaatata caggacagga ggacatcgtc gtaggttctc cagtagccgg aagaccgcag   3960
gctgagcttg agggcatcat cgggatgttt gtcaacacac tggccttgcg cagctacccg   4020
gcaggagata aaacctttca ggattatctt ctggaaatca aggaaacggc gctcaaggcg   4080
tttgagcatc aggattaccc ttttgaaaaa ttggtcgaaa agctgggcgt aggacgtgat   4140
gtcagccgca atccgctctt tgacacccta ttggtattac aaaataccga gcaggaagag   4200
caggaaatgg acggagtgca ctttactcct tacttgatgg acaccgtcac agccaaattt   4260
gacctgtccc tcaatgtaga ggagaagggg tcaaaattag cctttggcct cgagtatagt   4320
acggctttat atcggcgtga aaccgtagag cgacttgcaa cgcacttgct ccgggttctg   4380
catgcagtct cggccaatcc tcagttgcaa ctggccgaga tagaaatgat cacaccggag   4440
gagaaagtac agatcgttga agtatttaac gcgacatcgg ctccttatcc aagggacaag   4500
accattcatg agctgttcgt agaacaagtc aatcgtacac cagagcagac ggcgcttgta   4560
ttcggcgatg tccagctaac gtaccttgaa ttgcaagaca aggcgagccg actggcccaa   4620
acactgcgtc gtttgggaac gttgagggag cagcctgtgg ccgtgatggg cggacgaagc   4680
attgagatgg tcattggtat gctcgcggtg cttcaagcgg gtggagccta tgtgccgatt   4740
gatcctgatt acccggaaga tcgggttcgt tatatgctta atgattccga cgccaagcta   4800
ttattggtgc aaaagggcga gcttataagt gtagactacg gtataccgat tgtcgatctt   4860
agcagtgaag aggcctatgc agctgaacct gcccagccgg agactgctca gggatcgcag   4920
gggcttgctt atgtcatcta tacatcgggt acgacgggta gaccgaaggg cgttatggtt   4980
gaacaccgga acgtggtccg tctagtcaaa gagaccaact atgtggagct gaatgaatcc   5040
acacgaattt tgcagacagg agccgtggcc tttgatgctt ctacattcga aatatgggga   5100
gcgttactta acggtgggca gctctatttc gtggagaacg acgatatcct gattgccgat   5160
aggctaaaag cggccattac caagtacggg attacaacaa tgtggcttac ttcaccgctt   5220
ttcaatcagc tttccctgca ggatgagtac ctgttcagag ggctaaaaac attgctggtc   5280
ggcggagacg tactgtccat atctcatatg aaccgtgtaa tcgaggctaa tcctgatctt   5340
gtccctatca atggctatgg tccgacagag aatacgacct tctccaccac ctacaagatt   5400
ctgggtcgtg ccgaaggggt cgtgccgatt ggccgcccaa ttagtaattc taccgcttat   5460
gtggtcaatg gatcgctgca attacagcct attggtgctt ggggtgaact cattgtcggc   5520
ggtgaaggtg tagcgcgcgg atatctcaat cgtcctgatc tcacagcaga gaaatttgtt   5580
cctagtcctg tgaaggacgg agaaccctgc tacagaactg gggatttggt acgctggctt   5640
ccagatggga atttggagtt taaaggaaga attgatgagc aggtcaaaat acgtggttac   5700
cgcatcgaac tccctgaaat cgaggcccaa ctggccaaga tggagtcagt aatcgacgcc   5760
gtagtggtcg ttcgcgcgga tgagcttggc gagaagcaac tttgcgctta ttatgtggcg   5820
gatcgtacgc tcacggcagg cgaagtacgt ctttccctat cgcaggtact tccaggctat   5880
atgattccat cctactttat ccagatggat cgtatgccat taacgtcaaa cggaaaagtg   5940
```

-continued

```
gaccggaggt ctctgccggc tcctcaagta ggcgcgcata caggacggaa gtatacagct   6000
cctcgtacac cggctgagga agctttggca tctgtctggc aaggggtgct gggtgccgaa   6060
caggtgggta tccatgacaa tttctttgaa ttgggcggag actccataaa agctattcag   6120
gtgtcgtcac ggttactgca ggccggctat cggttagaga tgaagcagct gttcaaatcg   6180
ccaaccattg ccgagctagg cgcggaaatt caaacggctg tgcatatggc tgaacaggga   6240
gttgtgcgtg gaacgactcg cttgactcca gtccaacagt ggttctttgg acggaagcag   6300
gcagagcctc atcacttcaa tcaagcggtt atgctgtatc gtgaacaggg atttgaggaa   6360
aaggccttgc atcaggtgct aagaaaactc gctgagcatc atgacgccct tcgcatggtt   6420
ttccgtcaga cagagcatgg ctacgaagct tggaatcgtg atcttgaaga aggagagttg   6480
tatagcctat tcaccgctga tttacggaat gaatccgatc cgactgtagc cattacatcg   6540
ctgtcggatg acattcagtg cagtatcaat ctggcagaag gtccgctgct gaagttagga   6600
cttttccatt gtcaggatgg agaccacctt ctgatcgtga tccaccattt ggtggtggac   6660
ggagtatcct ggcggatttt gttcgaggat attgcagcag gttatgagca ggtgattcaa   6720
ggacaagcgc tgacattccc gcagaagacg gattccttcc gtgattgggg agacgccctt   6780
gctcgttatt cggaaggtcc agaaatggag actcatcggg cgtattggag agagctggag   6840
gatcagccac tcgaacagtt gccgaaggat gaggctgtgg aaagccttct tgtacaggat   6900
agcaaagtag taacagcaca atggactcta gaagaaaccg accaattatt gagaaaagcc   6960
catcgtgctt atcaaacaga gacgaatgat ctgctattga ctgctctggg catggcggta   7020
tccaaatggt ctggcatcgg aaaggttgct gtgaatctgg aaggacacgg tcgtgagccg   7080
attataccga atatcgacat cacccgtacc gtaggctggt ttacaagtca atatccggtg   7140
attttagact tggggaataa cccggaagtg gcctccttga tcaagtctgt gaaagaaggg   7200
ctgcgccgaa ttccgaacaa aggtattggc tacgggttgc tcaaaacgat ggcaagtcag   7260
ttggatgaag gcagcttcag cttgcagcct gagatttctt ttaactatct ggggcaattt   7320
gatcaggatt tgcaaggaag ctcgttgcag atttctcctt atccgaccgg aagcgcgcaa   7380
agcttgttgg aggaaccggc ctatacgcta gatatcaatg gcatggtgac ggacggagcc   7440
ctgactctga cgattactta taacggaaaa cagtataagt catctacgat ggaacagctc   7500
gctggatata ttgaagaaag cctgcgggaa cttctccagc attgcgtaac ccaagaaaaa   7560
accgtattga caccaagcga cgtgcttgcg aagggtctga gcattgccga tctggaggag   7620
ctttctaagc agacgagtca cattggcgat attgagaatg tatatagtct gacgccaatg   7680
cagaagggca tgctgttcca tgatatgttt gagccgcata caggtgctta ttttgagcag   7740
gccgcttttg attttaaggg tagctttgat ccgatcgcct tcgggcacag tctggatgca   7800
gtagtggagc gtcatgctat cctgcgcacg aacttttaca gcggatgggg cagcgagcct   7860
ttgcaggttg tatttcggca cagaggcgct aaattggtgt acgaagacct gcgggagatg   7920
aatgcatcgc agcgcgaagc ttacctgaag acatttggtg ctaaggacaa agcactgggc   7980
ttcaacctag ctgaagacga gcttctccgt gtatccattt tacaaacaga tgaagagagc   8040
ttccgtctct tatggagttt tcaccacatc gtcatggatg ggtggtgtgt tccgttaatt   8100
acgcaggagg tatttgaaca ctattttgcc ctcctggaag gtagagagcc gcagttggca   8160
gaggttcatc cgtacagtcg atatatcgaa tggctcgaac agcaggatga agcaattgcg   8220
tccaactatt ggagccgata tctggccggt tacgagcagc agacgctttt acctcaagtc   8280
```

-continued

```
ggtggagcaa gtaagggaga aggctatgta gcagaaaagc tgaattatcc tctcagcagg   8340
gaattgactg agcgccttga aaaggtggcc agggatgctc atgtcacgat gaatatattg   8400
ctgcagtccc tctggggcat tgcgcttcaa cgctataacg gtagccgaga tgtcgtgtac   8460
ggaagtgtag tatcaggcag accagcagaa attccgggca ttgatcggat gatcggtttg   8520
ttcatcaata cgattcccgt tcgtgtgaag acagaggaga atctcccctt cacagttctg   8580
atgaagcagc agcaggaaca atatatggct tctcatatgt atgacaccta cccgttgttt   8640
gagattcagg ctcagacgga tcagaagcag gatctaatct cccacattat ggtgtttgag   8700
aactatcctg tggaggagga ggtagagcgt ctgggtggtg gcgaggctgc ctttgagatt   8760
gaggaagcgg agcttcttga gcaaacgaat tatgatttta atttaattgt cctccctggc   8820
gaagaaatga gattgctgtt ccagtacaat gcacttgttt atgacccagt gacaattgag   8880
caaatcaagg gccatctggt ttacctcatg gaacaaattg tagagaaccc tgccatttcc   8940
gtggatgcac tagaattagt cacgccgcag gagagagaac agattctgaa cgtatgggga   9000
aatacaaaag gcatttacga gcactgtaac acgttccacg ggctgttgga ggaacaggcg   9060
ggacgaacgc cggatgcgac tgccctttgg ttcgaggaca agagtctgac ctatgccgag   9120
ctcaatgcaa aagccaacgg actggcgaga aggctccgta ctcagggaat caagacggga   9180
gatctggtgg gactgattgc tgaacggtcg ctcgaaatga tcgttgggat ctacggcatt   9240
atgaaagccg gggtgcctta tgttccaatc gatccagagt atccgaaaga acgaatcagt   9300
tacatgcttg aagattccgg ggcgaagctg atccttacac aggcccatct cttggagcat   9360
ctcggatgga cggaaaatgt tttgctgctg gatgaatcat cgacctatga tgccgacacc   9420
tcgaatttgg aggctactgc tggcccggat gatctggctt acgtgatcta cacttcaggt   9480
acgacgggtc agcctaaggg cgtattagtc gagcatcggg gactaccgaa tctttcggac   9540
gtatacggga cacacttcga agttacaccg caggatcgga tcgttcagtt tgcaagtctg   9600
tcgtttgatg catcggtttc ggaaatttta acggcgctga gccacggggc tgctctgtgc   9660
atcccttcta cacaagatat tttagatcat gccctgttcg agcagttcat gaacgataag   9720
gggattacgg tagcgacttt gccacccgct tacgctatcc accttgatcc agagcgtttg   9780
ccaacactgc ggtgcctgct aaccgctgga tcggccgcat ccgtcgagtt gatcgatgag   9840
tggaggaagc atgtacgtta ctctaatggc tatggcccaa cagaggactc cgtatgcacc   9900
acaatctggt ctgtcccgga cagtgaggaa gcaacggata ttgtatctat tgggcgacct   9960
attgctaacc acagtgtgta catcttggat gaccatttta gattgcagcc tgtcggtgta  10020
gctggagagc tatgcatttc gagtatcggg ttagcacggg ggtatcataa tcggcctgag  10080
ttaatggatg agaagttcgt ggacaatccg tttgctccag gagagcgcat gtatcggacg  10140
ggtgacctgg ttcgctggtt accgaatgga atcatcgagt acttaggtcg aatagatcac  10200
caagtcaaaa tccgcggtta ccgtatcgag ctgggcgagg tagaagcaca aatgctcaga  10260
gtgccgtccg ttcaggaagt cgtagccatg gctgtagagg gcgatgacgg ctacaaagat  10320
ctagtagctt acttcgtagc cgctcagaaa cttgaggtgt ccgaacttcg gactgttctg  10380
tcggagatga tacctggata tatgattcct tcccgcttca tacaactgga ggacatgcct  10440
ttgacgtcga acggaaaaat cgaccgaaaa gcgctgcagg gcgagcgtgg atgggcagtg  10500
gcttcatctg aggctccaag gacacctgtg gaaattcaat tagctgaaat ctggcaagag  10560
gtgctgggtg tagagagcgc gggagtgaag gataatttct tccattttgg aggtcattca  10620
ctgcgtgcag ccctgctagt ctcacgaatt cgcaaggaaa tgaatcgcga gattagtctg  10680
```

```
agagcagtgt tcgagtctcc tactattgaa ggattggctc gtgccattga gggctataca  10740
ccgctgaatt tcgaagaaat tcctacagcg ggagcgagag agcattatcc attgtcctcg  10800
gcccaaaaac gactgtttat tctaagtcag ctggaaggtg gagagctgag ctacaatatg  10860
ccgggggtcc ttaccgttga gggagctttg gatcgggaac ggctagagca ggcattccgt  10920
cgtctgattc atcgtcatgg ttcgctgcgt actcgctttg tgaccgtgaa cggtgaacct  10980
gtacagcagc tcctgacaga tgttccgttt actgtggaat atgcggagtt gagcgaggaa  11040
gaggcaggag ctacccttca gcagtttgtc cgccctttcg atctaggtgt agctccattg  11100
ctgcgggttg gccttattcg aattgcacat gagcgccatt tactattgtt tgacatgcat  11160
catattgtct cagatggggt ttctatgaat attctcatag aagagtttct ccgcttctac  11220
caagaggagg acgtatttcc tgagctacag atccagtaca cagactatgc tgtatggcag  11280
caagagcagc tcgaaagcga gcgtcttaag gcccaggagg cttactggct ggatgctttc  11340
cgtggaagct tgccagtgct ggatttgcca ggagatgaag ttcgtcctgc ggtgcgaagc  11400
tttgcgggcg atcgaatcga cttccaaatt gattcttctc tgagtgcttc acttcaggag  11460
ctggctaccc ggacgggttc cactctgttc atggtactgc tggcagccta tacagcgctc  11520
ttgcacaagt acacaggtca ggaagatgtc attgtcggtt cacctgtggc aggaagatct  11580
catgcgacac tcgaaggcct catcggtatg ttcgtcggca cagtggcact tcgtacttat  11640
ccagaaggag agaagccttt cgaggcttat ctgcaggaag tgaaggaaac agcgctgcgg  11700
gcctatgaaa accaggatta cccgttcgag gagctggtag aaaagctgga gcttcagcgt  11760
gatttgagcc gtaacccact atttgatacc atgtttgtcc tgcaaaatat cgagcaggga  11820
gaacaagaaa tagaaggatt gcgcttcact ccttacgata atgtacatcc ggctgccaag  11880
ttcgatctta cgctgaccgt gagtgaagca gacggggcat tgaattgcac gcttgagtat  11940
gcgactgcga tctacaagca agagactgct gagcggatgg caggccactt tgtacagctt  12000
attcgggaag ccatcgccaa tcccgcactg ccgttgtcat cccttgatat cgtgacacct  12060
caggaaaaat caaggctgat gaaagcgccg gacgaagcca aggcagatta tcctcgtgac  12120
aagacgatcc atgcgctgtt cgaggagcag gccgcacata ctccgaatgc agtggcagtc  12180
gtatgtgaag atgcgaccct gtcctacagc gagctgaacg agcgggccaa tggacttgcc  12240
cgaacgctga gggaacgtgg tttgcaacca gacggtttgg ctggaattat ggcggatcgt  12300
tcccttgaaa tggtggtcgg aattttagcc atcttgaagg caggcggggc ctatgtccct  12360
gtagaccctg aatatccaga ggaccgcatt cgctttatgc ttgaggattc gggagccaag  12420
ctactgctga cacaagcgca tctggagcaa cgggtctcct tcgccgggga tatcgtaagt  12480
ctggacaaaa cggcttccta caaggaggat gtctcaaacc tgcagcctgc agctggaccg  12540
gagcatcttg cctacgtcat ctacacatcg ggtacgacag gcaagccaaa gggaacactg  12600
attgagcata aaaatgtagt tcgcttgctc tttaatgata aaaatatgtt tgactttggt  12660
cctcaggata cgtggacact gttccattca ttctgttttg acttctctgt atgggaaatg  12720
tacggagcat tgctaaacgg aggacggttg gtcatcgttc catcgcttac cgcgaagagt  12780
ccagatcgtt tcttgcaatt gcttaaggat cagaaggtca ccgttttgaa ccagacaccg  12840
acgtatttct accagttgct acaggaagag ctcggtcatc aagcggcaga actgagcctc  12900
cgcatgatta tcttcggtgg agaggcatta gccccggccc tgctcaagga ctggagaacg  12960
aagtatccgc aagtgcagct cattaacatg tacggcatta ccgaaacgac cgtgcatgta  13020
```

-continued

```
acctacaagg aaattacaga gttggaaatt gaacagggcc gtagcaatat cggcaccacg  13080
attccgacgc tgcgagcgta cattttggat gaacaacgcc gtccacagcc gattggcatt  13140
ccaggtgaac tctatgtggc gggcgtaggt ctggcgcgag gttatctgaa ccgaccggaa  13200
ttgacggaag agaagtttgt cgctcatccg tttgaagcgg gcgagcgcat gtaccgctcg  13260
ggtgacttgg cacgctggtt gccggatggc agcatggagt atttgggacg gattgaccat  13320
caggtaaaaa tccgtggtta ccgtatcgag ctgggcgaag tggaagcgaa gctgctccat  13380
gctccgtctg taagggaggc cgttgtgctc gcccgagagg atggaagtgg acaaaaagtg  13440
cttgtcggct atttcactgc cgatcagatg ctgacggtag gcgagttgag aaaagccttg  13500
gctgccgaac tgccgactta tatgattcca tcttacttta tgcaattgga acagatgcct  13560
ttgacgccaa atggcaagct ggatcgcaaa gcgcttccgg ctccagaggc caatgtgcag  13620
actggagcgg tttatgaacc gccaaggacg aaggctgagg aagccttggc ttccgtatgg  13680
caaggtgtgc tgggagcgca gcaggtcggc atccatgatc atttctttga tctgggtggt  13740
gattccatca aggcgatcca agtgtcctcg agattgttcc aagccggata taaattagag  13800
atgaaggatc tcttcaaata tccgacaatt gccgagctaa gcccgtatct tcaggcagcc  13860
ggacgtacag cggaacaggg cgaaattaaa ggtgcagcag agttaatgcc aattcagcgt  13920
tggttctttg aacgccatac agcggagccg caccattata atcatgccgt catgctctat  13980
cggaaagacg gctttgatga agctgcactc cggttgacaa tggaccaaat tgcgatccat  14040
catgatgcgc tgcgtatggt tttccggtct acagaagctg ggtatgtagc ttggaatcgg  14100
ggaacggacg aaggcgagct ctacacattg gacattgccg atatgcggca ggcggaagac  14160
cagacagctg cggttcaggc ccaagccgat gccattcagg caagttttga cttggaaggt  14220
ggcccactgt tcaagctagg cctgttccat tgtgacgatg gcgatcattt gttgattgtc  14280
attcatcacc tcttggttga cggcgtatcc tggcgcatcc tgtttgagga cattgcagcg  14340
gggtacgagc aggcattgaa tggacaagca atcgtccttc cacaaaagac cgattcgtat  14400
cttgtatggt ctgagcaagc gacgaagtat gcagcagggc ctgctctgga caaggagcgt  14460
gcatactggc agctgatcga agaggcgatt ttggccccac tgccgaagga tgaggatcag  14520
aagccgggca ccatccggga tactgaatcg gttacggtaa cgtggtctgc gcaggaaaca  14580
gacctgctgt tgcggcaagc gaaccgggcg tatcatacgg agacgaacga cttgctcttg  14640
actgctctgg gggcagccat tcagcgctgg acaggcatgg agcagatttt ggtcaatctt  14700
gaagggcatg gacgggaaat gatcgtacca gacctggata ttacccgtac cgtcggttgg  14760
ttcacaaccc agtatccagt tctgctgaac ctgcaaggcg gacaggaagt atctgcgcgc  14820
atcaagcgca tcaaggagaa tttgcgagag gttccgcaca aaggaatcgg ctacggtctt  14880
ctgaagtata tggcaccgga gaaaagtgtc ggatttggcg tggagccgga aatttccttc  14940
aattatcttg ggcagtttga tcaggatctg gagggtaatg cccttagcct atccacacat  15000
tcagttggta aggcgctcag cgacctcaca ccacagcaat atgctctgga tgtgaatggc  15060
atgattgctg aaggccggct atcactgacg attacgtaca gcagcaggca gtatcgtaac  15120
gagacggtga gtcattttgc tgaattatta cagtcaagcc ttagtgaggt catccgtcat  15180
tgtgtggctc aggagcgttc acagcttaca ccaagtgatg ttctgttcca aggattaaca  15240
ttggagcagc ttgatcgact cacggcgcag acggctcaca tcggagagat tgaggatgtg  15300
tacaagctga cgccaatgca gaagggaatg ctgtttcaca gcctgctgga gccggactcc  15360
tcttcatact tcgaacaggc aacgtttgag ctgcgtggta gcttcgatgt agatatcttc  15420
```

```
ttcgagagct tccaggcttt ggtgcaacga catgccatac tacgtaccgg attttacaac  15480
aacattgctg atgtaccgct gcaagttgtc tttaagcaac ggttaatccc tctgcaccac  15540
gtagatttgc gtgacgcatc tatgcaggaa caagaagccc gaatcaaggc ttatattgct  15600
gaagatatgg ttaaggggtt cagcttgtca gaagatccgc tgatgcgagt gaccgtcttg  15660
cagaaggatc aaagctgtct tgtattgtgg agcttccacc atattgtcat ggatggctgg  15720
tgtatcccga tcattacaca ggagctgttc gattattatt ctgccaagaa acagcaagca  15780
cagcctgtcc taccgccagc tcagccctat agccgttata tcgagtggct tgatgcgcag  15840
gatgatcaag aagcttcaac atattggagc caatatcttg aagattatga cgggaacacc  15900
gtattaccgg aaggtaaaac gaaatctcaa gcaaaagaag cgggctatgt tctaaaagag  15960
catgttctcc atctgggtgc atctttgaca ggtaaaatgg atgttgtcgc gaagcgcaat  16020
cacgtaaccg tcaatacact catgcagaca gcttggggac tgattcttca acgttataat  16080
gccagctcgg atgtcgtttt cggcggcgtt gtgtcgggta gacccgctga gattgcaggg  16140
atcgaaaata tggtgggtct gttcatcaat acagtaccta tccgtgtaca gtcatccaaa  16200
gacgaagcct tcgtcgaagt gatgaaacgt acacaggcac agtcattggc tggtcgtgcc  16260
tacgacacct atccactgta tgagattcag gggaaaacaa cccaaaagca ggacctgatt  16320
tctcatatta tgatctttga aaattacccg ctcgacgagc aggtggagca atcgggtaat  16380
caaacggagg acaatctcga agtttccaac ttcaccatgt ttgaacaaac caactatgac  16440
tttaacctgg ttgtgattcc aggcgaagac atcaaggtct gcattcgcta taatgcttcg  16500
gtttacgagc aagaaagcat tgcacgtatc ggaggacact tgttgcagat gctcgatcag  16560
gtggctgctc gtccgcaggc gacgatacag gaactggaga ttgtaacatc cgaggaacgg  16620
ataaacctgc ttgactgggg cggcaaggcc catacctatc caagtgatca gggtctgcat  16680
accttgtttg aagaacaggt tgtccgtacg ccggataaga ttgcggctgt aaatggggac  16740
actcagatca cgtattggga gctgaacgag caggcgaaca gactagcttc caccttgata  16800
gaccaaggac tacagagtga acaagtggta ggtctgttgg cagatcggtc tgtagagctg  16860
cttgtcgcca tcatgggtgt actcaaagcg ggtggagcct atgtacctat tgatcctgaa  16920
tatccgcagg agcggattca gtatattttg aaggattctg gcgctgaaat cctgctcaca  16980
cagagccacc taacggagtt ggcctctttt gagggaacgg ttatggaatt ggattccccg  17040
tacatctacg gaaccgaggt ggataatccc aatattcctg ttggaggaaa cgatctggtg  17100
tacttaatct atacctcggg tacaaccgga aatccgaagg gaaccatgat taaccacaaa  17160
gggatcgtga actacatctg gtgggccaat aaggtctatt gtgctggaaa accaacggat  17220
ttcccgttgt attcatccat ttcgtttgac ttgacgatga catcaatgtt tactccgtta  17280
ataaacggag gaatagtacg gatttatgat ggtatagata aggcagaggt cgttcagcat  17340
attttgcgcg aaaatgcggt cgatattctc aagctgacgc cgacgcatct cagtctcata  17400
aaagacatga ccattccagc agaaagtcgc attcaacagc tcattgtggg tggagagaat  17460
ttgaccacac atttgtccaa aacgattacc gatctctttg gtggcaacat caaaatctac  17520
aatgaatatg gaccaaccga aacggtcgtc ggctgcatga ttcacctgta caatcctgcg  17580
aaggatacgc gtgaatctgt accgattggg ttgccagcag acaatatata catccatatt  17640
ctggatgaac agcttcgtct cgtaccgtta ggcgtggagg gtgaaatgta catcgccggg  17700
gacggggtag cccgtggata tctgaaccgt cctgagctta ccgcagataa attcattaga  17760
```

-continued aatccgttcg cttcggaagg aaatatgtat cgcactgggg atttggctcg tcgccttcct 17820
aatggagaca ttgagtacat tggacgcatt gaccaccaag ttaaaatacg gggctatcgt 17880
attgagcttg gtgagattga ggccaagctg ctggacattc cacttgtcga ggaagctctc 17940
gttgttgcgt ggacagatgc tcatgggcag aaatcgctgt gtgcttactt cgtagctaat 18000
cgcgaaatgt ctgtcagcga gctgagagac gaactgtctg ccggactgcc tgcatatatg 18060
attccgtctt acttcgtcca actggacgtg atgcctctga caccgaatgg taagctggat 18120
cgcaaggcac tgcctgaacc gaactcgggt ataaaggcgg gagcagactt taccgctccg 18180
cgcacggatg tggagaacat tttggcttca atctggcagg gtgtactcgg cgtgccgctt 18240
gtcggcattc atgataattt ctttgagctt ggaggtgact cgatcaaatc cattcaagta 18300
tcctcaaggc ttctccaagc aggctataag cttgaaatga aggatttgtt cggttatccg 18360
acaattgcag agctggcaca gcgcgttagt gtggtcagcc gaattgcgga ccaaagcgag 18420
gtacacggag cggtaagact gggacctgct cagcacagat tcttcgatga acagtcgatg 18480
gatctgcatc actttaatca gtcggtcatg ttgtaccgac gggatggctt caataccgat 18540
gcgctcgccg aggttgttcg gaaaattgca gagcatcatg atgctttacg actggtgttc 18600
cgccaaggag agcagggatt ggaggcctgg aaccggagca tggatgaggg tgagctctat 18660
agcctccaga tccacgacct gcgggatgag acagacccgg cttcagcaat agaagcaggt 18720
gcggaagcca ttcagcgcag catctctctg gaggatggac ctctctttag actgggtctg 18780
ttccgctgtg cggaaggtga acatctgttg atcgttattc atcatctggc tgtggatggc 18840
gtatcctggc gtattctctt tgaggacctg caggatggct acgagcaggc agcacgtgga 18900
gaagcggtca agcttccaca gaagacggat tcgtaccgtg catgggttga gggaatcaca 18960
caatttgcga atagtctggc ggctgaacaa gaacgcagct attgggcaga ggtagaggga 19020
gatggctttg tccctcttcc caaagacaag gtagacggcg ctcttctcat caaagacagt 19080
gaggctgtca cggtgagatg gtcaccagaa gagacagagc agttcctgaa agaagcgaac 19140
cgcacttaca atacggaggt caacgatctg ctcctgacgg ctctgggtat ggctgttcac 19200
gagtggacgg gaatcgaacg tgtaggcatc cttctggagg gacatggacg ggagcctgtt 19260
gtgccggaac tggatattac tcgcacaata ggctggttta caagtcaata ccctgtcgcc 19320
cttgagatgg gaggggaatt ggagatcggc gccagaatca agcacgtcaa ggaaggcttg 19380
cgtcgtatcc cgaacaaagg tgtcggatat ggtattttga aatatttaag cgacggttcc 19440
gatatctcct ccttctcggc tgaaccggag attaccttca actacttggg acagttcgac 19500
caggatcttg caggagggat gatggaagta tcgccttact cagtaggacc tgaggtcagt 19560
gagcagatgg tgcagcatca ggcattgaac attaatggac tgattgccga aggacagctt 19620
caactttcgg tcagctataa ccgtcatcag ctcgacgggg agtccgtggc taagtttgtt 19680
ggcattctga agaaccgtct tagcgaagtt attggacatt gcgtaagtaa ggaaagaaca 19740
gaacttacac caagcgatgt actcctcaaa gatatcagct tggaaaagat tgaggagtta 19800
gaagagcaga cacggcatat cggcagtatt gaaaatatgt ataaactgac gccgatgcaa 19860
aaaggaatgt tgttccacag cttgctggag cctcattcgg aagtctactt tgagcaggcc 19920
aaatttgaaa ttcagggagc attctatcct gaggatttca aacgcagctt aaaatatctg 19980
atgaaacggc atgccatatt gagaacgaat ttccatgccg ggtggggcga tttccctatt 20040
cagattgtgt tcaaagaaag agcgtgtgac ttcgtatacg aggatctgca cgagctggaa 20100
accgatgaaa ttcaagcgcg tcttgcagct tatactgctc aggacaaagc aagaggcttt 20160

```
aatcttgctg aagaagcatt gctgcgtgtt gctattctac gtacagcaga agaggcttac  20220
catctgctgt ggagctctca tcacatcatt ttggatggct ggtgtatgcc gcttgtgctc  20280
caggaagtgt ttgagacgta tggggttctg cgtgagcaaa gggagcctga gcttcctgca  20340
gctgtatcgt acagccagta tattcaatgg ttggagaagc aaggcgagga agaggcatcc  20400
tcttactgga gagggtacct ggaaggctac gagcagcaga cgaagctgcc acaagccatc  20460
acacagccat cagcaaaagc agaagcctat gtgtcggaga agctagtatt cacgttggat  20520
gcggaattga ccgatcgcct ggaacaggtg gccaaacagc atcaggtgac gatgaataca  20580
ttgatgcaag cagcctgggg aatcgtgttg cagcgctaca atagaagcca ggatatcgtc  20640
ttcggaagtg tagtatcggg gagacctgcc gagattccgg gtatcgaaag tatgatcggt  20700
ctctttatca atacagttcc ggttcgggtt caggccgagg gaagtgattc gttctcccat  20760
gtgatgaaaa gacagcagga attatatttg gcaggacatg cttatgattc ctatccgctc  20820
tatgagattc aagcacagag cgaacaaaag caagatttga tttctcatat tatggtgttc  20880
gaaaattacc cggtagaaga gcatctggaa gagaaaattg ctagtgaaga ggctgaatac  20940
agaattacgg atgttcagat gtttgaacag acgaattatg attttaacct cattgtgctg  21000
ccgggccgta atctggagtt cttgtaccgt tacaatgccc gcgtctatga tcgggagagc  21060
gtggaacgca ttcaaggaca cttgacgaga attctgacaa gcgttgctgt tcaacctacc  21120
atccgtattg atgagctgga gttgatcacc ccagaagaga aatcgcagat tatagaggtg  21180
tggggcgata cagcagctcc ttatccgcgt gagcagaccc ttcacggtat atttgaggaa  21240
aaagcagcgc tcacaccgga tcgtacagca cttatttacg gtgaaacgga gcttacctat  21300
ggagaactcg atcagcaggc gaaccgtctc gcacgtacgc tgcgtgccca aggggtcaga  21360
ccggaccaac cagtcggcat catggtcgag cgctcgcttg agatgatcat tggtattcat  21420
gccattctaa aagctggcgg ggcctatgta ccgattgatc cggagttccc agaagatcgt  21480
attcgccaca tgctggagga ttcgggagcg aagcttctgc tgacgaagaa ccatctccaa  21540
gatcgttttc cgttcactgg tacgattctg gcacttgatg atccgcaggc gtatcatgcg  21600
gatagctcga aactggagcc aattgcgggg ccggagcatc tggcgtatat catttacacg  21660
tcaggttcaa ccggcaagcc gaaaggggta atgattgagc atcgcgctgc cgtccatacg  21720
ctgagtcagt tggaagctga atatccgatg ttggcaggcg accgtttcct gctcaaaacg  21780
acattcacct ttgacttctc cgtgccggag ctgttctgct ggttctttgg acaagggact  21840
ctcgtgatcc tgccacaagg cgtggacaaa gacccgatgg cactgctaga ggccgtggat  21900
acgaaccgta tcacgcatct caatttggtg ccgtcgatgc tcagtgtgct cgttcaatac  21960
ttgaaagaaa gcggcaacca aggattcctt actctgaaat acctgtttgc ctgcggcgag  22020
acgctgcctg ccaaacttgt ggaagagtat tataaagtat ctccttacgc agtactggaa  22080
aacatctacg gtcctacgga agcagccgta tatgcgactc ggtatacaac gagccttgag  22140
actgcggctc taacgcatgt gccgatcggc aaaccgtacg ctaacgtcca agtatggatg  22200
atggacagcg cttctcaggt atcacctgtg ggggtaccgg gagaactctg cattgcgggc  22260
gaaggggtag cgcgggggta tttcaaccag tcggacctga cggcagagaa gttcattcct  22320
cacccgtaca aaccgggagc acgaatttac cgaacgggcg atttggcccg atggctacca  22380
gacgggaata ttgagtattt ggggcggatc gatcaccagg taaaaatccg cggttaccgc  22440
attgagctgg gagaagtgga agcacaaatt ctgaaggtgc catcggtgca ggaagcggtt  22500
```

-continued

```
gttctagcac tggctgactc caccggaagt actcaacttt gtgcatactt tgtggccgaa  22560

gaggggcttg cagcgggcgt gctacgcgaa gtactggcca gcgagctgcc aagctacatg  22620

attccgactg ctttcgtaca gttggcacaa atgccgctga atccgaatgg caaattggat  22680

cgcaaagcgc taccggcacc ggaaacactt ctgcggagca cagcggagta tatcgcgccg  22740

cgtacgcaga cagaagtaga gctcgctcag atttggtccg aggtgctcgg cgtacaggaa  22800

atcgggatca gagatcattt cttcgaactt gggggccatt ccctgaaagt attgggcttg  22860

atccaaagga tttcgtccgg tatgggcgtc cagctaccac tccaagtcgt gtttaatctg  22920

ccgactgtgg aagaaatggc gcatgaaata tccaagttgc aggcaacaac tgctgctaat  22980

gaagaggaaa tggaaattat ccgcttccca gggaaaggaa cactcaaagt gttttgcttc  23040

cctccacggg taggccactc tctggggtac tatgagatgg ccaaggagct ggaagggctt  23100

tgcgaggtgt acgggatgga atttatcggc gatcgtttcc agggccaaga tatgctggat  23160

cgatacatcg atgccatcgt ggatattcaa gcagagggcc cgtatatatt cctgggatac  23220

tcacttggag gaaatctcgc cttcgaggta gctaaagcca tggaaagccg aggtcaccat  23280

gttagcgacc ttattatggt agatgctatg agaaagatgt ccaaggatga atcgacaccg  23340

gaggagcttg aagagattgt cgagatggta ctggacagca ttagggacca gtacaaagca  23400

ttcctcgccg atccagtgga cagggagcga gtcatggaca aaatgttggt gtactccacc  23460

taccgcgatg agcttattaa cgcaggtgaa gttcatgcga atatccatgc tctgattgca  23520

gaggatgata gtattggtcc ggatacatca ttagataaat tgttatggca acaggcgaca  23580

cttggtcaat acaaagaata cgaagtcatc ggaacgcatg atgtgctgct tgattccggt  23640

tttattgggg aaaatgctaa agtactgaga cagatacttg gcaaggtcac agaggcttca  23700

tctaataaca agcccatttt gtcctaa                                      23727
```

<210> SEQ ID NO 5
<211> LENGTH: 11214
<212> TYPE: DNA
<213> ORGANISM: Paenibacillus

<400> SEQUENCE: 5

```
ttgaaagcct tatttgagaa ggaaaaaaat tactggagtc ataaactgga atctgaggat     60

catatcatct gcctgccata caccaaccat gtgtccagaa gtacaactgt aacgagttta    120

aattcccata cgtacacact cacatttcca actgaaattt cccaaagaat atcatctata    180

acaggtggcg ctccatgggc cgtgtttatg gtcctgcttg ctggagtaga gagcttattg    240

cataaataca caggtgagga acgtgtgctg ctgggcatcc cggtagccaa gtctggcaac    300

ggtgctacaa agccgatcaa ccatctgctt ttattgaaaa atacgctgga ttccagtaca    360

accttcaaag ctttgctgtc tcaaatcaaa acctctgtcg gcgaagctat tgaacatcaa    420

aacattcctt tttggaacta ttctgaatta cttgacattc aacgtaatga ggatgaaaag    480

cctcttattc acaccacagt atccttgcaa aatattcata tttctgattt tttaaatcac    540

gtacaatctg aactggattt ccagtttcaa tgggaacatg aagcagtctc cctgaacgta    600

aagtatagta gcgaccgtta tagcgagacg acgattgagc actttgttga gcagcttctg    660

cggctgtaca ctattgtttt gcagcagcca gagttggcga tttccacagc acaagtactg    720

tcagagcaag aagtagagca gctggtccat accttcaacg atacaaatgt ggattatcca    780

tgtcatgcgt ctattcatga attgttcgtg aaacaggcga agcaggcacc acagcaggtg    840

gcggtagtgt gtgggcaaga tagcctaacc tatgcagaat tgaatgaaaa ggccaaccga    900
```

-continued

```
ctggctcatt ctttacgtaa gcagggaatc cgcaccgagc agacggtcgg cattgtagct    960
gaacgctcga tcgagatgat tgtcggtatg ctcggaattc tcaaagcagg tggagcgtat   1020
gtacccattg attctgatta cccggatgag cgtatacgct atttgctgca ggattccggt   1080
gcggacatac tgctcgtgca gcgaatggaa catcggccca ctgattttaa gggaatggtg   1140
cttgacctta gcgatgctgc aatttatgga acggatgatg ctgatcgtta cgatccaatt   1200
ttgccgaatg atcacgggac gaatactgat ccgggatacg tggactgcct agatccgttc   1260
tactccattt tcgccagtcc cgaacttgct tctacgacaa ccatacaacc agaaaccatg   1320
caaccaaaag ctacgcaatc agaacaagca gaacaaatac agcaggctta tgcagctgga   1380
gaacaaccga aggcgagcgc agctggtcgt ttggcctata ttatgtacac ctcagggact   1440
acaggccagc ccaaaggggt tatggtggag caccgtaatg tcgtgcgttt ggtgacaaac   1500
acaaattatg cacgcttgaa tgccgacacg cgcattttgc agaccgggtc tgttgtcttt   1560
gacgcgtcca ccttcgaaat ttggggtgcg ttattgaacg gtggacagct ggtgctggtg   1620
agtcaggatg ttattttgga cgctcccaag ctcaaggaag ttgttcgcaa tcacggcatt   1680
accacgatgt ggctgaccgc accactcttt aatcagctat cccagcagga cttggaacta   1740
tttgagggga tgcgggagct attggttggt ggtgatgtgc tgtccgtacc gcatattaac   1800
cgggtattgg aggcccatcc gaatctacat atcattaacg gctacggtcc gacggaaaat   1860
acgacctttt ccaccacaca tgccattacc ggcgttcaat cggcatctgt gcccattggt   1920
agcccgatcc ataactcgac ggcatatgtc gtggaccgtt cgatgcagct tcagcctatt   1980
ggagcgtggg gggagctgat cgtcggcggt gacggggtgg ctcgcggata tcgcaaccgc   2040
ccagacctga cgaccgaaaa gttcatcgac agcccgttcc gtggcggcga acgctgctat   2100
cgtacagggg acctggtgcg ttggaatgcg gatgggacgc tggaatataa gggacgaatc   2160
gacgcgcagg tgaaaattcg aggctaccgg attgagctgg gcgaggtgga agcacagctg   2220
ttgaagctgg aggcagtccg agaagctgtt gtaattgcac atgaagatga gcaggggcaa   2280
aagctgctct gcgcatatgt ggtcacccat gcggaagtag cgacaagtga gctgcgtagt   2340
gctttgagtc aggagctgcc gggctacatg gtaccgtcgt attttgtaca gctggagcaa   2400
ttgccactga cgcccaacgg caaggtggat cgccgagcgt tgccacagcc agagggaggt   2460
gtaagctcag gcgcagaata tgtacctcct caaaatcaat tacaagcaca actggctagc   2520
atctggaaag atgtgctgga gcttgagcgc attgggatta aggataactt ttttgaggca   2580
ggaggacatt ccctgcgggc gacacatgtc atatcactca tctataagga attgcataaa   2640
aatgtgcagc taaaggattt gttccagcat ccgacaattg aacagctggc gcaggttatt   2700
gaagcactgg agcaaaccac ctatgaatcc atccctgtta cggagaataa gccattttat   2760
gcggtctctt cggctcaaaa acggatgtat atcctcaatc agcttgatgg agcgggaatt   2820
agctataaca tacctggtgc cctgactctg accggttcac ttgatcacaa ggcactggat   2880
aacgcgttcc gtcagcttat tgaacgccat gaaacattgc gcacaagttt tgagaccatg   2940
aacggtgaac ctgtccagcg agtgcatgac gaggttcctt ttcgcatgga attgacctat   3000
gctcacggag ctgccccaaa ggaaacggat gagctggtac ataactttgt tcagccgttc   3060
gatctggggc aagctccgtt attccgagtt ggtttgattg aaacagaccc agagcatcat   3120
attttgctca tagatatgca tcatatcatt tcggacggta cctctataaa tgtactgatt   3180
caggacttca ttcatttata tgcaggcgac acgctgccat cgctgcgcat tcagtataaa   3240
```

-continued

```
gactacgccg cttggcaaca gaagcagcag caaagtgaac gctaccggga acaggaaaac   3300
tactggctca ataccttcgc aggagagcta cctgtgcttg atctaccgac tgattattca   3360
cgcccagcgg tgagaagctt tgaaggagat gtgctggaat ttacgcttga ccaacgacaa   3420
agtgaaggct taaaaagcat tgcggtgcag acggaatcga cattatatat ggtgctgttg   3480
gctgcctatt cggctttgct tagccactat agcgggcagg aagatattat tgtcggttcg   3540
ccaattgcag ggcggcccca tgcagatctt ggcagtctga tcgggatgtt cgtgaataca   3600
ctggcaatcc gtaattatcc agaaggcggg aaaacgttcc gcgagtatgt gttggaggtc   3660
aaggataacg cgttaacagc ttttgaacat caggattatc cgtttgaaga gctggtggag   3720
aagctgggcg tggatcgaga tttaagccgt aatccgttat ttgataccat gtttgcactg   3780
caaaacttag agcaaaaaga gcagcagctg gcggggttgc aattggcatc ctatccaagt   3840
gaacaaacga cggccaaatt tgatttgagt ctgttcgcag tggaggatgg agaacaaatt   3900
tcctgtgctc ttcaatacgg aactcggctg tacaaacggg aaaccattga acgactgact   3960
gaacatttgc agcagcttat caatgcggtt atagaacagc cggatatcgt tctttcggct   4020
attgaaatgg tttcggccca agaaaaagag ctgcttgtgc agagattcaa tgatacggta   4080
gcagactatc cgtatccacg agatcaagca ctgcatgtgc tgttcgagga acaggtagtg   4140
caatcaccag atcggctggc cgtcaccttt gcggacacgc agcttaccta ccgcgagctg   4200
aatgaacgtg ccaaccgtct ggcacgcata ctcgcttccc atgggatacg gcgcgggtcc   4260
gagccagaga cacagcgagt agggattatg gctgaacgct ccattgaaat ggtcgtcggt   4320
atgctggcga ttttgaaggt cggaggggct tacgttccca ttgatcctga ttatcctgag   4380
gagcgtatcc gttatttact ggaggattcc agtgctgggc tgttactgtt acagcgacgt   4440
gagcagattc cttttgaacc cggcattccg atcatcgatt tgagtgatga acagcgatgc   4500
aatagcaaat ctgaatgtga cgctcagacg gatggaacaa ttgcgattac aacaggggga   4560
tcttcctccg atcttgcgta cgtgatctac acctctggta cgacaggcaa gccgaagggc   4620
gtgatgattg agcaccgtaa tgtcgtgcgc ctagtgaaaa acaaaagcta tgccatgctt   4680
gatgaaaata cacgtatgct gcaattgggc gcagttgtgt tcgatgcctc cacatttgaa   4740
atttggggaa cgctgctgaa cgggggacaa ctgtatgtgg taagtcatga cactattctg   4800
gatgcctcca agctcaagca ggcgattgac aagtatcgtg ttaacacgat gttcatgacc   4860
acggctttat tcaatcagta ttcgcagcaa gaaatcggag tgtttgcgtc cttgaaggag   4920
ttgctcgtgg gtggtgatgt attgtctgta ccacacgtca atcgtgtgtt gaaggagtac   4980
ccgcagcttc gcctggccaa tatttatggg ccgacggaga acaccacctt ttccaccatc   5040
tatgacatta cagaaccgca aacccaggct attcccattg gacgtccaat tgatcactcg   5100
accgcttatg tggtcaatcg ttcgttgaag ctgcaaccta tcggagcctg gggagagctg   5160
atcgtcggtg gcgacggcgt tgggcgagga tatctgaatc ggcccgagct tacggcggaa   5220
aaatttattg aaagtccatt ccggtctgga gaatattgct atcgtacagg ggacttagtg   5280
cgttggcgtg ctgatggtgt actggagtac aagggaagaa tggatgaaca ggtcaaaatt   5340
cgcggctacc gcattgaact gggtgaaatt gaaacccgtt tgtccacgat tccaggtgtg   5400
aaggaatcgg ttgttaccgt gcggcaggat gatcacggac aaaaacagct gtgtgcctat   5460
tttgcaacag acagtgaatt gagcgccagc gacttacgta acattttgtc gcaggatctg   5520
cctggctata tggtgccgtc ttactttgtg cagctctcca gactgccttt gacgctgaat   5580
ggcaaagtag accgcagggc actgcccgca cctgagcaca atctcgatac aggtatggat   5640
```

-continued

```
tatatggcac ctgagacgga tgtccaacag gcactggcta cggcttgggg agccattctt   5700
ggtatcccga aagtcggaat acaggataac tttttccatt tgggtggtga ctccatcaag   5760
gccatccaag tatcgtctcg cttgtttcag gctggataca agctggaaat gaaggacttg   5820
ttcaaatacc cgacaattgc gggactaagc acatatattc agcctgttaa ccgaatagcc   5880
gagcagggcg aggttacagg aaatgtagtg cttacaccga ttcagcgctg gtttttttgaa  5940
cagccaacgg gagaaccaca ctattttaac caatctgtca tgctctatcg tcaggaaggc   6000
tatgacgaac aggcactacg gcgggcgatc catcagatta catcgcacca tgatgcattg   6060
cgtatggttt ttagtttgtc ggagaacgga tgtacagcat ggaaccgcag tatagaggaa   6120
ggcgaaccgt accatctgga gtgctttgac tataatgaca gcgatgtaaa caagcaagat   6180
ttggcgaaga taattgaagc gaaatgcaat gaaattcaat ctggtatttc cctaagcgaa   6240
ggtccgctga tgagactggg gctgttccgt tgcccggatg gagatcatct gctggtcgtg   6300
attcatcatt tggcggtgga cggggtatcc tggcgcattt tattcgagga tttggcgact   6360
gcctatgatc aagcctccaa gggtgaacag gtgattcagc tgcctcataa aacagattcg   6420
ttccaaacgt gggccgagca gctgcacgct tacgccaaca gtccagctat ggaacgtgag   6480
cgagcgtatt gggggaaact tgcacaagcg gaactggctc ctttgccgca ggattacggg   6540
cataacgagc acgaaaagcc attgattggc gatagtgagt cggttactgc tttgtggaca   6600
catgctgaga cagagcagct gctcaagcag gccaatcgtg cctaccgtac agaaattaat   6660
gacctgttgt tgacggcggt aggaatggca ttgcaagcat ggagcggaca tgagcgtttc   6720
ctgattaatc tggagggaca tggacgtgaa gtcattttac cagaggtgga cattacccga   6780
acgatagggt ggtttacaag ccaatatcct gttttgctcg atatgccgga agaactggca   6840
ctttcgcaac ggatcaaggg tgtgaaggaa ggactgcgcg gcatcccgca aaaagggatt   6900
ggctatggtg tactgaaata tttatccgac cgtcagacac aggcactgga ggcatctcca   6960
gccatattta cgacagatcc cgaaatcagc tttaactatt tgggacagtt cgatcaagat   7020
atgaaaggga acgacttgca atcatcctca tatgagggtg ggatgccgct gagcccgacc   7080
atggctcgaa cgtatacact ggattttggc ggcatcattt cgggaggcca actgggtctg   7140
acgattagct atagccgtac cagctataga ccggagacga tcgagcgatt ggcgaaatta   7200
ttggaatcga gcctgcgtga aattttggag cattgcatcc ataaagaaca cccggagctt   7260
accccaagtg atatttccta taaaggaatg agtgtggagg gcttggacag tctcttatct   7320
gaaatgggtg ctgcgggtga gattgacaat gtatatgcac tgaccccgat gcagaaaggg   7380
atgctgtttc acagccagct agatagtcaa gcagctgcga atgacgcgta ttttgagcag   7440
gtttcttatg atatgcgagg tcagatggac attcgggctt ttgcagaaag cctgaatatt   7500
ctggttaggc gacatgaggc gctacgtaca cattttttatt ttggcagaga tacggaaccg  7560
ttgcaggtgg tgtatcgaaa tcgggattgc ggctttcaat atgaagattt acaccatcta   7620
gatgaggatg aaatagattc ctgggtgaaa aatttcaagc tacaagataa agcacggggc   7680
tttgatctgc gtcgggatgt cctgctgcgt gtagcgattt tacgtaccgg agaagacagc   7740
tatcattttg tatggagctt tcatcatatc gtcatggacg gctggtgtct gtcccttata   7800
aacaaagaag tgtttgaaag ctatgcagca cttcaggagg gcagagtacc agaactggca   7860
ccggcagtgc cgtacagccg ctttattgaa tggctggaag cacaggatcg caaggcggca   7920
accgactact ggagtagcta tttatccgga tatgagcagc aaacagcgtt accagctgta   7980
```

-continued

```
aaatccggtc gcaagagtga aggcaacacg gctagtgatt gggtgacggt tttggaacgt   8040
gagttgaccc tccgggtgga ggagacggct aagcgatatc aagtgaccat gaatacgtta   8100
ttacaaaccg catgggggat tgtgctgcaa aaatataaca accacagtga tgtcgtattt   8160
ggcagtgtcg tctcaggccg tccatcagat attatcgggg tagaggatat tatcggcttg   8220
ttcattaata ccattcccgt tcgcattctt agtgaggcag gggaatcttt tgcagaagtt   8280
atgaagaaaa cgcaggagca ggcgctggct tctcatgcat atgatacgta tccactgttt   8340
gagattcagg cattgaccga ccagaaacag gatttaatta accatattat ggtgtttgaa   8400
aattatccag tagatgagca ggtcgaggaa ctgggaagtg acgggcagga tacattctcg   8460
atttccaatg tggtggctgc agagcagact aactatgatc tgagcttagt cgttatgccg   8520
ggagaatgca tcaagattcg ttttatgtat aacgcgttaa gttatgatca aacaggcatt   8580
gagcgtctgc atggacattt tgtgaacctg ttggagcaag ttttgcttaa cccgaatgtt   8640
tgcgtagaag agctggaact ggttacagcg gcggaaaaac aacaaattac aggagagttt   8700
aatgacactg cctctgcata tccaagcaat cacacgatcc aaaaactgtt tgaggagcag   8760
gcagagcgca cgccggatca tattgccgta gctttgggtc atcaatcatt gacctatcgg   8820
gaactcaatg agacagccaa ccgtttagcg catacgctgc gtgatgcagg ggtgaaatcc   8880
gatgaacctg tgggcatttt gacggagcgc tcactggata tgattacggg aacactcgct   8940
attttgaagg ctggtggcgc gtatgtgccg gtagactctc aatatccgga ggaccgtatc   9000
cgttatatgc tagaggactc gggagccaag ctgctgctgg cccagcagga tttactggat   9060
cgttgctatt ttgacggaca gattgtcaat ctgaatgagg atacgtccta cagtgcagat   9120
gcttccaatc tgggtataga tggagcgggt aatcatgctg cttatgtcat ttatacctca   9180
ggttcaacag gtaagcctaa gggtgtcgtt gttgagcatc aaagtgtcgt gcgccttgtc   9240
cgcaatacga attatgtgcc atttgatgaa tcgacccgaa tgctgcagac ttgcgcgttt   9300
gtatttgatg tatctacgtt tgaaatttgg ggcgcgctgc tgaacggcgg tcagcttgtt   9360
cttgtgcata aggatgatct attggacgcg gccaagctta aagagacgat acgggatcat   9420
cgcgtcacca tgatgtggct gaccacaccg ttatttaatc agctttcaca gcaggatagt   9480
aaacttttcg gcgatgtgaa gtatttgctg gttggtggtg atgttttgtc tgcaccccat   9540
attaaccggg ttctgcgcga taatccggac atcaacatca ttaacggcta tgggccaacg   9600
gaaaatacaa ccttttcgac gacgtatcac attacggaag aacagctgga ttctgtgccg   9660
atcggacgcc ccatccgcaa ttcgacggcg tatgttgtgg attcgtcatt taacctgcaa   9720
ccggtcggag cttggggtga gctggttgtc ggcggagacg gagttgcacg tggttatcta   9780
aaccgtcctg agctgacggc tgagagattt cttgctaacc cgtgggtgga cggagatcgc   9840
ctgtactgta cgggagacct tgttcgctgg cgtgaagacg gcatactgga atacgctgga   9900
cggattgatc aacaggttaa aattcgcggt taccggattg agctgggcga ggtggaggcg   9960
cggctggcaa gtgtaccgtc cgtgcgggat agcgttgtta tcgctttgcg ggatggagca  10020
ggtcagcagc aattatgtgc ttacttcact gccgatgaac agctgaccat ccgtgagatt  10080
cgagctgcga tgtcggccag tctgccgagc tatatgattc catccgcatt tgtacagctg  10140
gatcggtttc cgctgacgac aaacggcaaa atcgaccgca aagctttacc tgtgccggac  10200
aaagggctgc acacgggtat agaatatgtc gcaccgcgaa ccgatgtgga acagttgctg  10260
gcagccattt ggcaggaagt acttgaaatt ccacaagtgg gtatccacga tgactttttc  10320
acgttaggtg gacattcctt aaaagtactg gagcttatac gcaaagttca ccttgctaca  10380
```

-continued

```
gatattgagc ttcccatccg tagtgttctg gacttcccaa ctatagaagc gcaggcgctc  10440

acattattga aagccgatct ggagtacaag gccgatagtc caatcattcg gttgaatgaa  10500

cacggtccga tctccatctt ctgctttcct cctatgcttg gatacgggct gtcgttcgcg  10560

gagcttgcga aacaactgga tcaggacgca gtcgtgtatg ggttggagtt cgtagatgat  10620

gctgcggatg agcaggccat gctggcacgt tacgttgatt tgatcgtcag cacgcaagcg  10680

caaggtccgt atgtgctgct tggttattcc ataggtggta atctggcgca taaggttgct  10740

gacacactgg aacgtcaagg tcatactgta tccgatattt ttatgctcga ttcggtcaaa  10800

agggcggaag ccctgccctt cacagttgaa gaaacagagc atgaaattca tgacatgctg  10860

gaacaagttc ccgactccta ccgtgagctg ttgaatgaaa cgtaccaacg taaaatgatc  10920

gcttacgcgg tatatggcaa ccagcttgtg aatacagaga gcgttcaggc gaatattcac  10980

ggctttgtcg ccgttggatc agaaacggtc aagggtacag gagataatcg acttttatgg  11040

aaagacgcta cacaaggtag ctatgaagag catagcttga ttggcaatca ttatgaactg  11100

ctggaacccg gatttatcga ggaaaatgta aaaagtatcc gtgccacaat acaaaagata  11160

actcggaaca cggacaaaga catgacacaa gacttggcac atcataaatc ttga        11214
```

<210> SEQ ID NO 6
<211> LENGTH: 11214
<212> TYPE: DNA
<213> ORGANISM: Paenibacillus

<400> SEQUENCE: 6

```
ttgaaagcct tatttgagaa ggaaaaaaat tactggagtc ataaactgga atctgaggat     60

catatcatct gcctaccata caccaaccat gtgtccagaa gtacaactgt aacgagttta    120

aattcccata cgtacacact cacatttcca actgaaattt cccaaagaat atcatctata    180

acaggtggcg ctccatgggc cgtgtttatg gtcctgcttg ctggagtaga gagcttattg    240

cataaataca caggtgagga acgtgtgctg ctgggcatcc cggtagccaa gtctggcaac    300

ggtgctacaa agccgatcaa ccatctgctt ttattgaaaa atacgctgga ttccagcaca    360

accttcaaag ctttgctgtc tcaaatcaaa acctctgtcg gcgaagctat tgaacatcaa    420

aacattcctt tttggaacta ttctgaatta cttgacattc aacgtaatga ggatggaaag    480

cctcttattc acaccacagt atccttgcaa aatattcata tatctgaatt tttgaatcac    540

gtacaatccg aactacattt ccagtttcaa tgggaacatg aagcggtctc cctgaacgta    600

aagtatagta gcgaccgtta tagcgagacg acgattgagc actttgttga gcagcttctg    660

cggctgtaca ctattgtttt gcagcagcca gagttggcga tttccacagc acaagtactg    720

tcagagcaag aagtagagca gctggtccat accttcaacg atacaactgt ggattatcca    780

cgtcatgcgt ctattcatga attgttcgtg aaacaggcga agcaggcacc acagcaggtg    840

gcggtagtgt gtgggcaaga tcgcctaacc tatgcagaat tgaatgaaaa ggccaaccga    900

ctggctcatt ctttacgtaa gcagggaatc cgcactgagc agacggtcgg cattgtagct    960

gaacgctcga ttgagatgat tgtcggtatg ctcggaattc tcaaagcagg tggagcgtat   1020

gtacccattg attctgatta cccggatgag cgtatacgct atttgctgca ggattccggt   1080

gcggacatac tgctcgtgca gcgaatggaa catcggccca ctgattttaa gggattggtg   1140

cttgacctta gcgatgtcgc aatttacgga acggatgatg ctgatcgtta cgatccaatt   1200

ttgccgaatg atcacgggac gaatactgat ccgggatacg tggactgcct agatccgttc   1260
```

-continued

```
tactccattt tcgccagtcc cgaacttgct tctacgacaa ccatacaacc agaaaccatg   1320
caaccaaaag ctacgcaatc agaacaagca gaacaaatac agcaggctta tgcagctgga   1380
gaacaaccga aggcgagcgc agctggtcgt ttggcctata ttatgtacac ctcagggact   1440
acaggccagc ccaaaggggt tatggtggag caccgtaatg tcgtgcgttt ggtgacaaac   1500
acaaattatg cacgcttgaa tgccgacacg cgcattttgc agaccgggtc tgttgtcttt   1560
gacgcgtcca ccttcgaaat ttggggtgcg ttattgaacg gtggacagct ggtgctggtg   1620
agtcaggatg ttattttgga cgcgcccaag ctcaaggaag ttgttcgcaa tcacggcatt   1680
accacgatgt ggctgaccgc accgctcttt aatcagctat cccagcagga cttggaacta   1740
tttgagggga tgcgggagct attggttggt ggtgatgtgc tgtccgtacc gcatattaac   1800
cgggtattgg aggcccatcc gaatctacat atcattaacg gctacggtcc gacggaaaat   1860
acgacctttt ccaccacaca tgccattacc ggcgttcaat cggcatctgt gcccattggt   1920
agcccgatcc ataactcgac ggcatatgtc gtgaaccgtt cgatgcagct ccagcctgtt   1980
ggagcgtggg gagaactgat cgtcggcggt gacggggtgg ctcgcggata ccgcaaccgc   2040
ccagaactga cgaccgaaaa gttcattgac agtccgtttc gtggcggcga acgctgctat   2100
cgaacagggg acctggtgcg ttggaatgcg gacgggacgc tggaatataa gggacgaatc   2160
gacgcacagg tgaaaattcg aggctaccgg attgagctgg gcgaggtgga agcactgctg   2220
ttgaagctgg aggcagtccg agaagctgtt gtaattgcac atgaagatga gcaggggcaa   2280
aagctgctct gcgcatatgt ggtcacccat gcggaagtag cgacaagtga gctgcgtagt   2340
gctttgagtc aggagctgcc gggctacatg gtaccgtcgt attttgtaca gctggagcaa   2400
ttgccactga cgcccaacgg caaggtggat cgccgagcgt tgccacagcc agagggaggt   2460
gtaagctcag gcgcagaata tgtacctcct caaaatcaat tacaagcaca actggctagc   2520
atctggaaag atgtgctgga gcttgagcgc attgggatta aggataactt ttttgaggca   2580
ggaggacatt ccctgcgggc gacacatgtc atatcactca tttataagga attgcataaa   2640
aatgtgcagc taaaggattt gttccagcat ccgacaattg aacagctggc gcaggttatt   2700
gaagcactgg agcaaaccac ctatgaatcc atccctgtta cggagaataa gccattttat   2760
gcggtctctt cggctcaaaa acggatgtat atcctcaatc agcttgatgg agagggaatt   2820
agctataaca tacctggtgc cctgactctg accggttcac ttgatcacaa ggcactggat   2880
aacgcgttcc gtcagcttat tgaacgccat gaaacattgc gcacaagttt tgagaccatg   2940
aacggtgaac ctgtccagcg agtgcatgac gaggttcctt ttcgcatgga attgacctat   3000
gctcacggag ctgccccaaa ggaaacggat gagctggtac gtaactttgt tcagccgttc   3060
gatctggagc aggctccgtt attccgagtt ggtttgattg aaacagaccc agagcatcat   3120
attttgctca tagatatgca tcatatcatt tcggacggta cctctataaa tgtactgatt   3180
caggacttca ttcatttata tgcaggcgac acgctgccat cgctgcgcat tcagtataaa   3240
gactacgccg cttggcaaca gaagcagcag caaagtgaac gctaccgaga acaggaaaac   3300
tactggctca ataccttcgc gggggagcta ccagtgcttg atcttccgac tgattatcca   3360
cgcccggcgg tgagaagctt tgaaggagat gtgctggaat ttacgcttga ccaacgacaa   3420
agtgaaggct taaaaagcat tgcggtgaag acggaatcga cattatatat ggtgctgttg   3480
gctgcctatt cggctttgct tagccactat agcgggcagg aagatattat tgtcggttcg   3540
ccaattgcag ggcggcccca tgcggatctt ggcagtctga tcgggatgtt cgtgaataca   3600
ctggcaatcc gtaattatcc agaaggcggg aaaacgttcc gcgattatgt gttggaggtc   3660
```

-continued aaggaaaatg cgttaaaggc ttttgaacat caggattatc cgtttgaaga gctggtggag 3720
aagctgggcg tagatcgaga tttaagccgt aatccgttat ttgataccat gtttgcacta 3780
caaaacatag agcaaaaaga gcagcagctg gcggggctgc aattggcatc ttatccaagt 3840
gagcaaacga cggccaaatt tgatttgagt ctgttcgcag tggaggatgg agaacaaatt 3900
tcctgtgctc ttcaatacgg aactcggctg tacaaacggg aaaccattga acgactgact 3960
gaacatttgc agcagcttat caatgcggtt ataaaacagc cggatatcgc tctttcggct 4020
atagaaatgg tttcggccca agaaaaagag ctgcttgtgc agagattcaa tgatacggta 4080
gcagactatc cgtatccacg agatcaagca ctgcatgtgt tgttcgagga acaggtagcg 4140
caatcaccag atcggctggc cgtcaccttt gcggacatgc agcttaccta ccgcgagctg 4200
aatgaacgtg ccgaccgtct ggcacacata ctcgcttccc atgggatacg gcgcggctcc 4260
gagccagaga cacagcgagt agggattatg gctgaacgct ccattgaaat ggtcgtcggt 4320
atgctggcga ttttaaaggt cggaggggct tacgttccca ttgatcccga ttatcctgag 4380
gagcgtatcc gttatttact ggaggattcc agtgctgggc tgttactgtt acagcgacgt 4440
gaacagatgc cttttgaacc cggcattccg gtcatcgatt tgagtgatga acaacgatgg 4500
aatagcaaat ctgaaggtga cgctcatacc gatggaacaa ttgcgattac aacaggggga 4560
tcttcctccg atcttgcgta cgtgatctac acctctggta cgacaggcaa gccgaagggc 4620
gtgatgattg agcaccgtaa tgtcgtgcgc ctagtgaaaa acaaaagcta tgccatgctt 4680
gatgaaaata cacgtatgct gcaattgggc gcagttgtgt tcgatgcctc cacatttgaa 4740
atttggggaa cgctgctgaa cgggggacaa ctgtatgtgg taagccatga cactattctg 4800
gatgcctcca agctcaagca ggcgattgac aagtatcgtg ttaacacgat gttcatgacc 4860
acggctttat tcaatcagta ttcgcagcaa gaaatcggag tgtttgcgtc cttgaaggag 4920
ttgctcgtgg gtggtgatgt gttgtctgta ccacacgtca atcgtgtgtt gaaggagtac 4980
ccgcagcttc gcctggccaa tatttatggt ccgacggaga acaccacctt ttccaccatc 5040
tatgacatta cagaaccgca aacccaggct attcccattg gacgtccaat tgatcactcg 5100
accgcttatg tggtcaatcg ttcgttgaag ctgcaacctg tcggagcctg gggagagctg 5160
atcgtcggtg gcgacggtgt tgggcgagga tatctgaatc ggcccgagct tacggcggaa 5220
aaatttattg aaagtccatt ccggtctgga gaatattgct atcgtacagg agacttagtg 5280
cgttggcgtg ctgatggtgt actggagtac aagggaagaa tggatgaaca ggtcaaaatt 5340
cgcggctacc gcattgaact gggtgaaatt gaaacccgtt tgtccacgat tccaggtgtg 5400
aaggaatcgg ttgttaccgt gcggcaggac gatcacggac aaaagcagct gtgtgcctat 5460
tttgcaacag acagtgaatt gagcgccagc gacttacgta acattttgtc gcaggatctg 5520
cctagctata tggtgccgtc ctactttgtg cagctctcca gactgccttt gacgctgaat 5580
ggcaaagtag accgcagggc actgcccgca cctgagcaaa atctcgatac aggtatggat 5640
tatgtggcac ccgaaacgga tgttcaacag gcactggcta cggcttgggg atccattctt 5700
ggtatcccga aagttggaat tcaggataac tttttccatt tgggtggtga ctccatcaag 5760
gccatccaag tatcgtcccg cttgtttcag gctggataca agctggaaat gaaggacttg 5820
ttcaaatacc cgacaattgc gggattaagc acatatattc agcctgttaa ccgaatagcc 5880
gagcagggcg aggttacagg aaatgtagtg cttacaccga ttcagcgctg gtttttttgaa 5940 cagccaacgg aagaaccaca ctattttaac caatctgtca tgctctatcg tcaggaaggc 6000

-continued

```
tatgacgaac aggcactacg gcgggcgctc catcagatta cttcgcacca tgatgcattg   6060
cgtatggttt ttagtttgtc ggagaacgga tgtacagcat ggaaccgcag tgtagaggaa   6120
ggcgaaccgt accatctgga atgctttgac tataatgaca gcgatgtaaa caagcaagat   6180
ttggcgaaga taattgaagc gaaatgcaat gaaattcaat ctgatatttc cctaagcgaa   6240
ggtccgctga tgagactggg gctgttccgt tgcccggatg gagatcatct gctggtcgtg   6300
attcatcatt tggcggtgga cggggtatcc tggcgcattt tattcgagga tttggcgact   6360
gcttatgatc aagcctccaa gggtgaacag gtgattcagc tgcctcataa aacagattcg   6420
ttccaaacat gggctgagca gctgcacgct tatgccaaca gtccagctat ggaacatgag   6480
cgagcgtatt gggggaaact tgcacaagcg gaactggctt ctttgccgca ggattatggg   6540
cataacgagc acgaaaagcc attgattggc gatagtgagt cggttactgc tttgtggaca   6600
catgcagaga cagagcagct gctcaagcag gccaatcgtg cctaccgtac agaaattaat   6660
gacctgttgt tgacggcggt aggaatggca ttgcaagcat ggagtggaaa tgatcgtttc   6720
ctgataaatc tagagggaca tggacgtgaa gccattttac cagaggtgga cattactcga   6780
acgatagggt ggtttacaag ccaatatcct gttttgctcg atatgccgga agaactggca   6840
ctttcgcaac ggattaagcg tgtgaaggaa ggactgcgcg gcattccgca aaaagggatt   6900
ggctacggtg tactgaaata tttatccgac cgtcagacac agacaccgga ggcatctcca   6960
gccatattta cgacagatcc cgaaatcagc tttaactatt tgggacagtt cgatcaggat   7020
atgaaaggga acgacttgca atcatcctca tatgagggtg ggatgccgct gagcccgacc   7080
atggctcgaa cgtatacgct ggattttggc ggcattattt cgggaggcca actgggtctg   7140
acgattagct atagtcgtac cagctataga ccggagacca tcgagcgatt ggcgaaattc   7200
ctggaatcga gcctgcgtga aattttggcg cattgcatcc ataaagaaca cccggagctt   7260
accccaagtg atatttccta taaaggaatg agtgtggagg ccttggacag tctcttatct   7320
gaaatgggtg ctgcgggtga gatcgacaat gtatatgcac tgaccccgat gcagaaaggg   7380
atgctgtttc acagccagct agatagtcaa gcagctgcga atgacgcgta ttttgagcag   7440
gtttcttatg atatgcgagg tcagatggac attcgggctt ttgcagaaag cctgaatatt   7500
ctggttcggc gacatgaggc gctgcgtaca catttgtatt ttggcagaga tacggaaccg   7560
ttgcaggtgg tgtatcgaaa tcgggattgc ggctttcaat atgaagattt acaccatcta   7620
gatgaggatg caaaagatac ctgggtgaaa aatttcaagc tacaagataa agcacggggc   7680
tttgatctgc gtcgggatgt cctgctgcgt gtagcgattt tacgtaccgg agaagacagc   7740
tatcattttg tatggagctt tcatcatatc gtcatggacg gctggtgtct gtcccttata   7800
aacaaagaag tgtttgaaag ctatgcagca cttcaggagg gcagagtacc agaactggca   7860
ccggcagtgc cgtacagccg ctttattgaa tggctggaag cacaggatcg caaggcggca   7920
accgactact ggagcagcta tttatccgga tatgagcagc aaacagcgtt accagctgta   7980
aaatccggtc gcaagagtga aggcaacacg gctagtgatt gggtgacggt tttggaacgt   8040
gagttgaccc tccgggtgga ggagacggct aagcgatatc aagtgaccat gaatacgtta   8100
ttacaaaccg catgggggat tgtgctgcaa aaatataaca accacagtga tgtcgtattt   8160
ggcagtgtcg tctcaggccg tccatcagat attatcgggg tagaggatat tatcggcttg   8220
ttcattaata ccattcccgt tcgcattctt agtgaggcag gggaatcttt tgcagaagtt   8280
atgaagaaaa cgcaggagca ggcgctggct tctcatgcat atgatacgta tccactgttt   8340
gagattcagg cattgaccga ccagaaacag gatttaatta accatattat ggtgtttgaa   8400
```

-continued

```
aattatccag tagatgagca ggtcgaggaa ctgggaagtg acgggcagga tacattctcg   8460
atttccaatg tggtggctgc agagcagact aactatgatc tgagcttagt cgttatgccg   8520
ggagaatgca tcaagattcg ttttatgtat aacgcgttaa gttatgatca aacaggcatt   8580
gagcgtctgc atggacattt tgtgaacctg ttggagcaag ttttgctaaa cccgaatgtt   8640
tgcgtagaag agctggaact ggttacagcg gcggaaaaac aacaaattac aggagagttt   8700
aatgacactg cctgtgcata tccaagcaat cacacgatcc aaaaactgtt tgaggagcag   8760
gcagagcgca cgccggatca tattgccgta gctttgggtc atcaatcatt gacctatcgg   8820
gaactcaatg agacagccaa ccgtttagcg catacgctgc gtgatgcagg ggtgaaatcc   8880
gatgaacctg tgggcatttt gacggagcgc tcactggata tgattacggg aacactcgct   8940
attttgaagg ctggtggcgc gtatgtgccg gtagaccctc aatatccgga ggaccgtatc   9000
cgttatatgc tggaggactc gggagccaag ctgctgctgg ctcagcagga tttactggat   9060
cgttgctatt ttgatggaca gattgtcaat ctgaatgagg atacgtccta cagtgcagat   9120
gcttccaatc tgggtataga tggagcgggt aatcatgctg cttatgtcat ttatacctca   9180
ggttcaacag gtaagcctaa gggtgtcgtt gttgagcatc aaagtgtcgt gcgccttgtc   9240
cgcaatacgg attatgtgcc atttgatgaa tcgacccgaa tgctgcagac ttgcgcgttt   9300
gtatttgatg tatctacgtt tgaaatttgg ggcgcgctgc tgaacggcgg tcagcttgtt   9360
cttgtgcata aggatgatct attggacgcg gccaagctta aagagacgat acgggatcat   9420
cgcgtcacca tgatgtggct gaccacaccg ttatttaatc agctttcaca gcaggatact   9480
aaacttttcg gcgatgtgaa gtatttgctc gttggtggtg atgttttgtc tgcaccccat   9540
attaaccggg ttctgcgcga taatccggac atcaacatca ttaacggcta tgggccaacg   9600
gaaaatacaa ccttttcgac gacgtatcac attacggaag aacagctgga ttctgtgccg   9660
atcggacgcc ccatccgcaa ttcgacggcg tatgttgtgg attcgtcatt taacctgcaa   9720
ccggtcggag cttggggtga gctggttgtc ggcggagacg gagttgcacg tggttatctg   9780
aaccgtcctg agctgacggc tgagagattt cttgctaacc cgtgggtgga cggagatcgc   9840
ctgtactgta cgggagacct tgttcgctgg cgtgaagacg gcatactgga atacgctgga   9900
cggattgatc aacaggttaa aattcgcggt taccggattg agctgggcga ggtggaggcg   9960
cggctggcaa gtgtaccgtc cgtgcgggat agcgtggtta ttgctttgcg ggatggagca  10020
ggtcagcagc aattatgtgc ttactttact gctgatgaac agctgaccat ccgtgagatt  10080
cgagttgcga tgtcggccag tctgccgagc tatatgattc catccgcatt tgtacagctg  10140
gatcggtttc cgctgacgac aaacggcaaa atcgaccgca aagctttacc tgtgccggac  10200
aaagggctgc acacgggtat agaatatgtc gcaccgcgaa ctgatgtgga acagttgctg  10260
gcagccattt ggcaggaagt acttgaaatt ccacaagtgg gtatccacga tgactttttc  10320
acgttgggtg gacattcctt gaaagtactg gagcttatac gcaaagttca ccttgctaca  10380
gatattgagc ttcccatccg tagtgttctg gacttcccga ctatagaagc gcaggcgctc  10440
acattattga aagccgatct ggaatacaag gccgatagtc caatcattcg gttgaatgaa  10500
aacggtccga tctccatctt ctgctttcct cctatgcttg gatacgggct gtcgttcgcg  10560
gagcttgcga aacaactgga tcaggacgca gtcgtgtatg ggttggagtt cgtggatgat  10620
gctgcggatg agcaggccat gctggcacgt tacgttgatt tgatcgtcag cacgcaagcg  10680
caaggcccgt atgtgctgct tggttattcc ataggtggta atctggcgca taaggttgct  10740
```

gacacactgg aacgtcaagg tcatactgta tccgatattt ttatgctcga ttcggtcaaa 10800
agggcggaag ccctgccctt cacagttgaa gaaacagagc atgaaattca tgacatgctg 10860
gaacaggttc ccgactccta ccgtgagctg ttgaatgaaa cataccaacg taaaatgatc 10920
gcttacgcgg tatatggcaa ccagcttgtg aatacagaga gcgttcaggc gaatattcac 10980
ggctttgtcg ccgttggatc agaaacggtc aagggtacag gagataatcg actcttatgg 11040
aaagacgcta cacaaggtag ctatgaagag catagcttga ttggcaatca ttatgaactg 11100
ctggaacccg gatttatcga ggaaaatgta aaaagtatcc gtgccaccat acaaaagata 11160
actcggaaca cggacaaaga catgacacaa gacttggcac atcataaatc ttga 11214

<210> SEQ ID NO 7
<211> LENGTH: 11184
<212> TYPE: DNA
<213> ORGANISM: Paenibacillus

<400> SEQUENCE: 7
ttgaaagcct tatttgagaa ggaaaaaaat tactggagtc ataagctgga atctgaggat 60
catatcatct gcctgccata taccaacaac gtgtccaagg atgcaactgc aacgaattta 120
aattccctta cgtacacgct cacatttcca tctgaaattt ccggacgaat attgtctata 180
acaggtggcg ctccatgggc agtgtttatg gttctgcttg ctggagtaga aagcctgtta 240
cataaataca caggtgagga acgtgtgctg ttgggcattc cggtagccaa gtctggcaac 300
ggtgctacaa agccgatcaa tcatctgctc atactgaaaa actcgctgga ttctacaacg 360
accttcaaag ccttgctgtc tcaaatcaaa acctctgtca gcgaagcgat tgagcaccaa 420
aatatacctt tttggaacta taccgagggg cttgaaattc cacgtaacga gggtgaacag 480
cctcttattc acaccacggc atccttgcaa aacatccata tttccgattt ttcgaatcat 540
gtacaatctg agctggattt tcaatttcaa tgggacaaca cagcggtttc cctgaatctg 600
aattacagca gccaccgcta taatgaggcg acaattgaac gctttgttga gcagctgttg 660
cggttgtaca gcgttgtttt gcatcagcca gagctggcaa tttccacagc acaggtgtta 720
tcagagcaag aagtggagca actggttcat atcttcaacg atacaactgc ggattatcca 780
cgtcatgcgt ccattcatga gttgtttgag aaacaggcga agcaggcacc ggagcaggtg 840
gcggtagtgt tcggaaaaga cagtctgacc tatggagaat tgaatgaaaa agccaaccgt 900
ctggctcata cattacgtaa gcaggggatc tgcaccgagc agactgtcgg tattgtggct 960
gaacgctcga tggaaatgat cgtcggtatg cttgctattc tcaaagcagg cggggcctat 1020
gtgccgattg actctgatta tccggatgaa cgcgtgcgct atttgctgga ggattctggt 1080
gcaaacctac ttctagtgca gcggatggag catcggcccg ctgattttca ggggattgtg 1140
cttgacctga gcgattcagc aatctatgga acgaatgatg ctgatcgttt cgatctggtt 1200
ttgccgaacg ataacgagac gtatgctgac agagctggca tcggatatgt agattgctta 1260
aacccgctct attccatttc cgctagtcct gagcttgctt ctactgcaac cacacaacca 1320
gaaatcctgc aaccagaagt tacgcaatca gaacaagcga aggcagccgc tgctgatcgc 1380
ttggcatacg ttatgtacac ctcagggaca acagggcagc cgaaaggagt tatggtggag 1440
caccgcaatg tcgtgcgtct ggtgaaaaat acaaactatg cgcaattgga tgctgatacg 1500
cgcattttgc agaccggggc tgttgtcttc gacgcgtcca ctttcgaaat ttggggtgcg 1560
ctattgaatg gtggacagtt ggtactggtg agtcaggatg tcattttgga cgcgccgaag 1620
ctcaaggaag ctgttcgcag ccatggcatt accacgatgt ggctgacagc gccgctcttt 1680
aaccagctgt cccaacagga cctggaactg tttgagggga ttcgggagct gctggtcggc 1740
ggtgatgtgc tgtccgtccc gcctattaac cgggtgctgg aggcccatcc ttccctgcgg 1800
atcatcaacg gctacggccc gacagaaaac acgacctttt ccacaacaca tgcgataact 1860
ggcgtgcaat cagaatcggt gccgattggc agcccgatcc ataactcgac ggcgtatgtc 1920
gtagaccgtt cgatgcagct tcagcccgta ggagcatggg gagagctgat tgtcggcggt 1980
gacggggtag cccgtggata ccgcaaccac ccggacctga cggcagaaaa gttcatggac 2040
agtccgttcc gcagtggaga acgttgctat cgcacaggcg acctggtgcg ctggaatgcg 2100
gacgggacgc tgaaatacaa gggacggatc gacgcccagg tgaaaatccg ggggtaccgg 2160
atcgagctgg gcgaggtgga agcacagctg ttgaagctgg aggcggtgcg agaagccgtc 2220
gtgatagcac gagaggatga gcaggggcaa aagcagctct gtgcttatgt ggtgactgat 2280
acggaggtgg cggcaagcga gctgcgcagc gctttgagcc aggagctgcc gggctacatg 2340
gtgccgtcgt attttgtaca gctggagcaa ttgccactca cgcctaacgg caaggtggat 2400
cgccggtcat tgccacagcc ggagggaagt ataagctcag gcacagaata tgtacctcct 2460
caaaatcaat tacaagtaca actggcgagt atctggaaag atgtgctgga gcttgagcgc 2520
atcgggatta aggataactt ttttgaagca ggagggcact ccttgcgggc gacacatgtc 2580
atatcgctga ttcataagga actgcataaa aatgtgcagc taaaggacct gtttcagcac 2640
ccgacgattg aacagcttgc acacgttatt gaagcgctgg atcaaaccgc ctatgaatcc 2700
atacctgtta ccgagaataa gccatattat gcggtatcct cggcacaaaa acggatgtat 2760
atcctcaatc agcttgatgg agcgggaatt agctataaca tccctggtgc tctgacactg 2820
acaggttcac ttgatcataa ggcactggac aatgcgttcc gccagcttat tgaccgccat 2880
gaaacattgc gtacaagctt tgagaccatg aacggtgaac ctgtccagcg agtacatgac 2940
gaggttcctt ttcgcatgga gttgatttat gcccacggcg ctgacccaaa ggagacggac 3000
gagctggtac gcgactttgt ccagccattc gatcttggac aggctccgct attccgagtc 3060
ggtatgattg aaacagatcc agagcatcat attttgctgc tggatatgca tcacatcatt 3120
tcggacggta cctctataaa tgtgctgatt caggacttca tctgtttata tgcaggtgac 3180
acgctgccac cactgcgcat tcagtataag gactacgccg cctggcaaca ggatcagcag 3240
caaagtgaac gctaccggca gcaggaaagc tactggctga ataccttcgc gggagagctg 3300
cccgtgctgg atataccgac cgattatcca cgtccggcgg tgagaagctt tgaaggagat 3360
gtgctggaat ttacgctcga tcaacggcag agcgaaggtt taaaaagcat tgcggtacag 3420
acggaatcga cattatatat ggtgctgttg gctgcttata cggctttgct tagccactac 3480
agcgggcaag aggatattat cgtcggttcg ccgattgcgg ggcggcccca tgctgatctt 3540
ggtagcctga tcgggatgtt tgtgaataca ctggcaatcc gcaatgttcc ggaaggcagt 3600
aagaccttcc gcgattatgt attggaggtc aaggaaaatg cgctgaaggc atttgaacat 3660
caggattatc cgtttgaaga gctggtggac aagctgggcg tggatcgaga tttaagccgt 3720
aatccgttat ttgataccat gtttgctctg caaaatttgg agcaaaagga gcagcaactg 3780
gaaggcttgc aattgacacc ctatccgagt gaacaaaata ccgcaaaatt tgatttgagt 3840
ctgttcgcga tggaggatgg ggagcaaatt gcctgcggtc ttcaatacgg aacccgactg 3900
tacaaacggg aaaccatcga acgactggct gtacatttgc agcagcttat ccatgcggtg 3960
atagaacagc cggatatcgc tctttcggct attgaaatgg tttcgtacca agaaaaagag 4020

-continued cagattgtaa tgcaattcaa cgatacagta gcagactatc cgtatccacg tgatcaagtg 4080
ctgcatgtgc tgttcgagga acaggccgca caatcaccgg atcggctggc tgtcaccttt 4140
gcggacacac agctcaccta ccacgaactg aaagaacgct ccgaccgtct ggcacgtata 4200
ctcgcttctc atgggatacg gcgcggctcc gagccagaga tacagcgagt agggattatg 4260
gcggagcgct ccattgaaat gatcgtgggt atgctggcga ttttgaaggc cggaggggct 4320
tacgttccca ttgatcccga atatcctgag gagcgtatcc gttatttact ggaggattcc 4380
agtactcggc tgttactttc acagcgacgt gagcaggttc cttttgaacc aggtattccg 4440
atcatagaat tgagtgatga acaacgatgg agtagcgaat ctgaacttta cgctcatgtg 4500
gatgaatctg ctgctgttcc aatggaggga tcttcctcgg atcttgcgta tgtgatctac 4560
acctctggta cgacaggcaa gccgaagggc gtgatgatcg atcaccgtaa tgtcgtgcgt 4620
ttagtgaaaa acaaaagcta cgccacgctt gacgaaaata cgcgtatgct acaaatgggt 4680
gccgtggtgt tcgatgcctc cacgtttgaa atctggggaa cgctgctgaa cgggggtcaa 4740
ctgtatctgg taagtcatga cactattttg gacgccgcca agctcaaaca ggcgattgac 4800
aagtatcata ttagcaccat gttcatgacc acggctttat tcaatcagca ttcacagcaa 4860
gacattggag tgtttgcctc cctgaaggaa ttgctcgtgg gtggtgatgt attgtccata 4920
ccccacgtca accgcgtgct gaaggagtac ccgcagcttc atttggccaa tatttatggg 4980
ccgacggaga acaccacctt ttccaccatc tatgacatta cagaaccgca aacccaagct 5040
attcccattg ggcgtccgat tgatcattcg accgcgtatg tggtcaatcg ttcgttgaag 5100
ctgcagccga tcggagcctg gggggaactg atcgtcggtg gtgacggtgt gggacgtgga 5160
tatctgaatc ggccggagct cacggcggaa aagtttatag aaagtccgtt ccggcccggg 5220
gagcactgct atcgtacagg ggatttagtg cgttggcgtg cagatggcgt gttggagtac 5280
aagggaagaa tggatgagca ggtcaaaatt cgcggctacc gcattgagct gggtgaaata 5340
gaaacccgtt tgtccacgat tgcaggagtg aaggaatcga ttgttaccgt acggcaggat 5400
gataacgggc aaaaacagtt gtgtgcttat tttgtaacag acagcgaatt gagcgccagt 5460
gacttacgta acgttttgtc gcaggatctg cctggctata tggtgccttc ctattttgtg 5520
caactttcca gactgccttt gacgctgaat ggtaaagtag accgcagggc cctgcctgca 5580
ccggagcaaa acgtcgatac aggcatggat tatgtagcac ccgagacgga tgttcagcaa 5640
gcactggcta ccgcctgggg ggcaattctt gggattcagc gagtgggcat acaggataac 5700
tttttccatc tgggtggcga ctccatcaag gccattcaag tgtcgtcccg attgtttcag 5760
gctggataca agctggaaat gaaggacttg ttcaaatacc cgacgattgc gggactaagc 5820
aaatttattc agcctgttaa ccgaatagca gagcagggag aggttacagg atctgtttta 5880
cttacaccga ttcagcgctg gtttttgaa cagccaacgg cagagccgca ctattttaac 5940
caatctgtca tgctttatcg acaagaaggc tacgatgaac aggcacttcg gcaggcgctc 6000
aatcagatta catcgcacca tgatgcattg cgtatggttt ttcgttcgtc ggagaacggg 6060
tatacggcgt ggaatcgtgg tataaaggaa ggcgaaccat accatctgga aatctttgat 6120
tatagggaca gcgacgtaaa tgagggcgat ttggcgaaga tgattgaagc caaatgcaat 6180
gaaattcaat ccggcatttc cctaagcgaa gggccgctca tgaggctagg gctgttccgt 6240
tgcccggatg gagatcatct gctggtcgtg attcaccatt tggcggtgga cggggtatcc 6300
tggcgcattt tattcgagga tttggcgact gcttatgatc aagcctccaa gggagagcag 6360
gtgattcagt tgcctcataa aacggattcg ttccaaacgt gggcccagca gctgtacgct 6420

-continued

```
tatgccaata gcccagccat ggaacgtgaa cgctcgtact gggaggagct tgcacaagcc   6480
gagttggctc ccttgccgca ggattatggg catcatgagc acgaaaagcc gttgattggt   6540
gacagtgagt cggttaccgc tgtatggaca agtacggaga cagagcagct gctgaagcag   6600
gccaatcgtg cctaccacac ggaggttaat gatctgttgc tgacggcagt agggatggca   6660
ttgcaagcgt ggagcggata cgagcgtttc ctgattcatc tggaggggca tggacgcgaa   6720
gctattttac ctgaggtaga cattacccga acaatagggt ggtttacaag ccaatatcct   6780
gttttgctta atatgccgga agaaattgct ctttcgcaac ggattaagca tgtgaaggaa   6840
ggactgcgcg gcatcccgca aaaagggatc ggctacggtg tactgaaata tttagccgac   6900
cgccagacac aggcaccgga ggcatctcca gccctattta cgacagatcc cgaaatcagc   6960
tttaactatt tgggacagtt cgatcaggat atgaaaggga acgacttgca atcatcctca   7020
tatgggggtg ggatgccgct gagcccgacc atggctcgga cgtatacgct ggattttggc   7080
ggcatcattt cgggaggtca gctgggtctg acgattagct atagccgtac cagctatcga   7140
ccggagacga tagagcgatt ggcgaaatta ctggaatcga gtctgcgtga aattttgacg   7200
cattgcatcc ataaagagca cccggagctg accccaagtg atatttctta taaaggaatg   7260
agtgtggagg gcttggacag cctgttatct gaaatgggtg ctgcgggtga ggtcgacaat   7320
gtatatgcac tgaccccgat gcaaaaaggg atgctgtttc acagccagct ggatagtcaa   7380
gcagccgcga atgacgcgta ttttgagcag gtttcttatg atatgcgagg tcggatggac   7440
attcaggctt ttgcagaaag cctgaatatt ctggttcggc gacatgaggc gctgcgtaca   7500
catttttatt ttggccggga tacggaaccg ttgcaggtgg tgtatcgaag tcgggattgc   7560
ggctttcaat atgaagattt acacaagctg gatgcggata caagggatac ctgggtgaaa   7620
agcttcgagt tggaagatag agcgcggggc tttgatctgc gtcgggatgt cctgctgcgt   7680
gtagcgattt tacgtaccgg agaagacagc tatcattttg tatggagctt ccatcatatc   7740
gtcatggacg gctggtgtct gtcccttata aataaagaag tgtttgaaag ctatgcagca   7800
cttcaggagg gcagagtgcc agagttggca ccggcagtgc cgtacagcag ctatattgaa   7860
tggctggaag cacaggatcg caaggcggca gccgactact ggagcagcta tttatccggg   7920
tatgagcagc aaacagcact accagctgta aaatccggtc gcaagagtga aggctacaag   7980
gccagcgatt gggcgacgga tttggagcgt gagctgaccc tccgggtgga ggagacggct   8040
aagcggtatc aggtgaccat gaatacgtta ttacaaaccg catgggggat tgtgctgcaa   8100
aaatataaca accacagtga tgtcgtattt ggcagtgttg tctcaggtcg tccatcggat   8160
attatcgggg tcgaggatat tatcggcttg ttcattaata ccattcccgt tcgcatccgc   8220
tgcgaggcag gggaatcttt tgcagaagtt atgaagaaaa tgcaagagca ggcgctggct   8280
tctcatgcat atgatacgta tccactgttt gaaattcagg cattgaccga ccagaagcag   8340
gatttaatta accatattat ggtgtttgaa aattatccgg tggaggagca ggtcgaggaa   8400
ctgggaattg acgggcagga tacattcccg atttccaacg tggtggctgc agagcagacc   8460
aactacgaac tgaacctcgt cgttatgccg ggagaatgca taaagattcg ttttatgtat   8520
aacgcgttaa gctttgatca aacagacatt gagcgtctgc atggacattt tgtgaatctg   8580
ctggagcaaa ttttgcttaa cccgaatgtt tgcgtagaag agctggaact ggttacagcg   8640
gcggaaaaac aacagattat aggagagttt aatgacactg cctctgcata tccacggaat   8700
cagacgatcc aaaaactgtt tgaggagcag gctgagcgca cgccggatca tattgccgta   8760
```

-continued gctttgggtc atcaatcatt gacctatcgg gagctcaatg agacagccaa ccgattagcg 8820
catacgctgc gggatgcagg ggtgaagccc gatgaaccgg ttggcattct gacggagcgc 8880
tcgctggata tgattactgg aacactcgct attttgaagg ctggaggcgc gtatgtgccg 8940
gttgaccctc aatatccaga ggaccgtatc cgttatatgc tggaggactc gggagccaag 9000
ctgctgctgg ctcagcagga tttactggat cgttgctatt ttgacggaca gattgtcaat 9060
ctgaatgatg atatgtccta cagtacggat cattccaatc tggggatgga tggagcgggc 9120
catcatgctg cttatgtcat ttatacctca ggctcaacag gcaagcctaa gggcgtcgtt 9180
gttgagcatc aaagtgtcgt gcgcctggtc cgcaatacgg attatgtccc atttgatgaa 9240
tcggtccgaa tgctgcagac ttgcgcgttt gtattcgatg tatctacgtt tgaaatttgg 9300
ggcgcgctgc tgaacggcgg tcagcttgtt ctcgtgcata aggatgatct tttggacgcg 9360
gccaagctca aggagacgat acgggatcat cgcgtcacca tgatgtggct gaccacaccg 9420
ttatttaatc agctttcgca gcaggacagt aagcttttcg gcgatgtgaa gtatttgctg 9480
gttggtggtg atgttttgtc tgcgccccat attaaccggg tcctgcgtga taatccgaac 9540
atgaacatca ttaatggcta tgggccaacg gaaaatacaa ccttttcgac gacgtaccac 9600
attacggaag agcagttgga ttctgtgccg atcggacgtt ccatccgcaa ttcgacggca 9660
tatgttgtgg attcgtcatt taacctgcag ccggtcggag cctggggtga gctggttgtc 9720
ggcggagacg gagttgcacg cggttatctg aaccgtcctg agctgacggc cgagagattt 9780
cttgctaacc cgtggataga tggagatcgc ctgtaccgta cgggagacct ggttcgctgg 9840
cgtgaagatg gcatgctgga atacgctgga cggattgatc aacaggttaa aattcgcggt 9900
taccggattg agctgggcga ggtggaggcg cggctggcaa gtgtaccgtc cgtacgggat 9960
agcgttgtta tcgctttgcg ggatggagca ggccagcagc aattatgtgc ttacttcact 10020
tccgatgaac agctgactgt ccgcgagatt cgggctgtgc tgtcgggtag tctgccgagc 10080
tatatgattc catccgcatt tgtacagcta gatcggtttc cgctgacgac caacggcaaa 10140
atcgaccgca aagctttacc tgtgccggac aaagcgttgc atacgggtat agaatatgtc 10200
gcaccgcgaa ccgatgtgga gcagttgctg gcaggcattt ggcaggaagt gctcgaaatc 10260
ccgcaagtgg gtatccagga tgactttttc acgttggggg gacattcctt gaaagtgctg 10320
gagcttgtac gcaaagttta ccttgccaca gacatcgagc ttccaatccg aagtgttctg 10380
gagttcccga ccatagaaga gcaggcgctc gcattattga aatcggattt gcaatccaag 10440
gcagatagtc caatcattca gttgaatgaa cacggtcctg tctccatctt ctgctttccg 10500
cctatgcttg gatacgggct gtcgttcgcg gagcttgcga aacaactgga tcaggacgca 10560
gtcgtgtatg gattggagtt cgtagatgat gctgcggatg agcaggaaat gttggcacgg 10620
tatgttgatt tgatcgtcag cactcaagcg caaggtccgt atgtgctgct tggttattcc 10680
ataggcggta atctggcgca taaggttgcc gacacgctgg agcgtcaagg tcatgctgta 10740
tccgacattt tgatgctcga ttcggtcaaa aggacggaag ccctgtcctt cacagtcgaa 10800
gaaacagagc acgaaattca tgccatgctg gaacaggttc ccgaatccta ccgtgagctg 10860
ttgaatgaaa cgtaccagcg taaaatgatc gcttacgcgg tgtatggtaa ccatctcctg 10920
aatacagaga cggttcgggc gaatattcac ggctttgttg ctgtcggatc ggaaacagtt 10980
aggggaactg gagacaatcg acttttatgg aaagacgcta cacaaggaag ctatgaagag 11040
catagcttga ttggcaatca ttatgaactg ctggaacccg gatttatcga ggaaaatgta 11100
aaaagtatcc gtgccgcaat acaaaacata acccggaata tggacaaaga catggcacaa 11160
gatttggcac atcataattc ttga 11184

<210> SEQ ID NO 8
<211> LENGTH: 11214
<212> TYPE: DNA
<213> ORGANISM: Paenibacillus

<400> SEQUENCE: 8
ttgaaagcct tatttgagaa ggaaaaaaat tactggagcc ataaactgga atctgaggat 60
catatcatct gtcttccata tactaacaac gtgtccaaaa gtacaactgc aacgagttta 120
aattcccaca catacacact cacatttcca tctgaaattt cccaaagaat atcatctata 180
acaggtggcg ctccatgggc cgtgtttatg gtcctgcttg ctggagtaga gagcttattg 240
cataaataca catgtgagga acgtgtgctg ctgggcattc cggtagccaa gtctagcaac 300
ggtgctacaa agccgatcaa ccatctgctt ttattgaaaa atacgctgga ttccagcaca 360
accttcaaag ccttgctgtc tcaaatcaaa acctctgtcg gcgaagctat tgaacatcaa 420
aacattcctt tttggaacta ttctgaatta cttgacattc aacgtaatga ggatggaaag 480
cctcttattc acaccacagt atccttgcaa aatattcata tttctgattt tttgaatcac 540
gtacaacctg aactagattt ccagtttcaa tgggaacatg aagcggtctc cctgaacgta 600
aagtataata gcgaccgtta tagcgagacg acgattgagc actttgttga gcagcttctg 660
cggctgtaca ctattgtttt gcagcagcca gagttggcga tttccacagc acaagtgctg 720
tcagagcaag aagtagagca gctgctccat accttcaacg atacaaatgt ggattatcca 780
cgtcatgcgt ctattcatga attgttcgag aaacaggtga agcagacacc acagcaggtg 840
gcggtagtgt gtgggcaaga tagcctaacc tatgcagaat tgaatgaaaa ggccaaccga 900
ctggctcatt ctttacgtaa gcagggaatc cgcaccgagc agacggtcgg cattgtagct 960
gaacgctcga ttgagatgat tgtcggtatg ctcggaattc tcaaagcagg tggagcgtat 1020
gtacctattg attctgatta cccggatgag cgtgtacgct atttactgaa ggattccggt 1080
gcggacatac tgctcgtgca gcgaatggaa catcggccca ctgattttaa gggaagggtg 1140
cttgacctta gcgatgctgc aatttatgga acggatgatg ctgatcgtta cgatcccatt 1200
ttgccgaatg atcacggaac gaatactgat ccgggatacg tggactgcct agatccgttc 1260
tactccattt ccgccagtcc cgaacttgct tctacgacaa ccatacaacc agaaaacatg 1320
caacccaaag ctacgcaatc agaacaagca aaacaaatac agcagactta tgcagctaaa 1380
gaacaaccga aggcgagcgc agctgattgc ttggcctata ttatgtacac ctcagggact 1440
acaggccagc ccaaaggggt tatggtggag caccgtaatg tcgtgcgttt ggtgacaaat 1500
acaaactatg cacgcttgaa tgccgacaca cgcattttgc agaccgggtc tgttgtcttt 1560
gacgcgtcca ccttcgaaat ttggggtgcg ctattgaacg gtggacagct tgtgctggtg 1620
agtcaggatg ttattttgga cgcgcccaag ctcaaggaag ttgttcgcaa tcacggcatt 1680
accacgatgt ggctgaccgc accactcttt aatcagctat cccagcagga cttggaacta 1740
tttgagggaa tgcaggagct gttggtcggt ggtgatgtgc tgtccgtacc gcatattaac 1800
cgggtattgg aggcccatcc gaatctacat attattaacg gctacggtcc gacggaaaat 1860
acgacctttt ccaccacaca tgccattacc ggcgttcaat cggcatctgt gcccattggt 1920
agcccgatcc ataactcgac ggcatatgtt gtggacggtt cgatgcagct ccagcctgtt 1980
ggagcgtggg gagaactgat cgtcggcggt gacggggtgg ctcgcggata ccgcaaccgc 2040

-continued

```
ccagaactga cgaccgaaaa gttcattgac agtccgttcc gtggcggcga acgctgctat   2100
cgaacagggg acctggtgcg ttggaatgcg gacgggacgc tggaatataa gggacgaatc   2160
gacgcgcagg tgaaaattcg aggctaccgg attgagctgg gcgaggtgga agcacagctg   2220
ttgaagctgg aggcagtccg agaagctgtt gtaattgcac atgaagatga gcaggggcaa   2280
aagctgctct gcgcatatgt ggtcacccat gcggaagtag cgacaagtga gctgcgtagt   2340
gctttgagcc aggagctacc gggctacatg gtaccgtcgt attttgtgca gctggagcaa   2400
ttgccactga cgcccaatgg caaggtggat cgccgagcgt tgccacaacc agagggaggt   2460
gtaagctcag gcgcagaata tgtacctcct caaaatcaat tacaagcaca actggctagc   2520
atctggaaag atgtgctgga gcttgagcgc attgggatta aggataactt ttttgaggca   2580
ggaggacatt ccctgcgggc gacacatgtc atatcactca tctataagga attgcataaa   2640
aatgtgcaac taaaggatct gttccagcat ccgacaattg aacagctggc gcaggttatt   2700
gaagcactgg agcaaaccac ctatgaatcc atccctgtta cggagaataa gccattttat   2760
gcggtttctt cagctcaaaa acggatgtat atcctcaatc agcttgatgg agcgggaatt   2820
agctataaca tacctggtgc cctgactctg accggttcac ttgatcacaa ggcactggat   2880
aacgcgttcc gtcagcttat tgaccgccat gaaacattgc gcacaagttt tgagaccatg   2940
aacggtgaac ctgtccagcg agtacatgac gaggttcctt tttgcatgga attgacctat   3000
gctcacggag ctgccccaaa ggaaacggat gagctggtac gtaactttgt ccaaccattc   3060
gatctggggc aggccccgtt attccgagtt ggtttgattg aaacagaccc agagcatcat   3120
attttgctca tggacatgca tcatatcatt tcggacggca cctctataaa tgtactaatt   3180
caggacttta ttcatttata tgcaggcgac acactgccat cgctacgcat tcagtataaa   3240
gactacgccg cttggcaaca gaagcagcag caaagtgaac gctaccggga acaggaaaac   3300
tactggctca ataccttcgc aggagagcta cctgtgcttg atctaccgac tgattatcca   3360
cgcccagcgg tgagaagctt tgaaggagat gtgctggaat ttacgcttga ccaacgacaa   3420
agcgaaggct taaaaagcat tgcggtgcag acggaatcga cattatatat ggtgctgttg   3480
gctgcctatt cggctttgct tagccactat agcgggcagg aggaaattat tgtcggttcg   3540
ccaattgcag ggcggcccca tgcggatctt ggcagtctga tcgggatgtt cgtgaataca   3600
ctggcaatcc gtaattatcc agaaggcggg aaaacgttcc gcgattatgt gttggaggtc   3660
aaggaaaacg cgttaaaggc ttttgaacat caggattatc cgtttgaaga gctggtggag   3720
aagctgggcg tggatcgaga tttaagccgt aatccgttat ttgataccat gtttgcactg   3780
caaaacttag agcaaaaaga gcaacagctg gcggggcttc aattggcatc ctatccaagt   3840
gaacaaacga cggccaaatt tgatttgagt ctgttcgcag tggagaatgg agaacaaatt   3900
tcctgtgctc tgcaatacgg aactcggctg tacaaacggg aaaccattga acgactgact   3960
gaacatttgc agcagcttat caatgcggtt atagaacagc cggatatcgt tctttcggct   4020
attgaaatgg tttcggccca agaaaaagag ctgcttgtgc agagattcaa tgatacggta   4080
gcagactatc cgtatccacg agatcaagca ctgcatgtgc tgttcgagga acaggtagcg   4140
caatcaccag atcggctggc cgtcaccttt gcggacatgc agcttaccta ccgcgagctg   4200
aatgaacgtg ccaaccgtct ggcacgcata ctcgcttccc atgggatacg gcgcgggtgc   4260
gagccagaga cacagcgagt agggattatg gctgaacgct ccattgaaat ggtcgtcggt   4320
atgctggcga ttttgaaggt cggaggggct tacgttccca ttgatcccga ttatcctgag   4380
gagcgtatcc gttatttact ggaggattcc agtgcggggc tgttactgtt acagcgacgt   4440
```

-continued

```
gagcagatgc cttttgaacc cggcattccg gtcattgatt tgagtgatga acaacgatgg   4500
aatagcaaat ctgaatgtga cactcatacc gatggaacaa ttgcgattac aacaggggga   4560
tcttcctcag atcttgcgta tgtgatctac acctctggta cgacaggcaa accgaagggc   4620
gtgatgattg agcaccgtaa tgtcgtgcgg ctagtgaaaa acaaaagcta tgccatgctt   4680
gatgaaaata cacgtatgct gcaattgggc gcagttgtgt tcgatgcctc cacatttgaa   4740
atctggggaa cgctgctgaa cgggggacaa ctgtatgtgg taagccatga cactattctg   4800
gatgcctcca agctcaagca ggcgattgac aagtatcgtg ttaacacgat gttcatgacc   4860
acggctttat tcaatcagta ttcgcagcaa gaaatcggag tgtttgcgtc cttgaaggag   4920
ttgctcgtgg gtggtgatgt gttgtctgta ccacacgtca atcgtgtgtt gaaggagtac   4980
ccgcagcttc gcctggccaa tatttatggg ccgacggaga acaccacctt ttccaccatc   5040
tatgacatta cagaaccgca aaccctggct attcccattg gacgtccaat tgatcactcg   5100
accgcttatg tggtcaatcg ttcgttgaag ctgcaaccta tcggagcctg ggagagttg    5160
atcgtcggtg gcgacggtgt tgggcgagga tatctgaatc ggcccgagct tacggcggaa   5220
aaatttattg aaagtccatt ccggtctgga gaatattgct atcgtacagg agacttagtg   5280
cgttggcgtg ctgatggtgt actggagtac aagggaagaa tggatgaaca ggtcaaaatt   5340
cgcggctacc gcattgaact gggtgaaatt gaaacccgat tgtccacaat tccaggtgtg   5400
aaggaatcgg ttgttaccgt gcggcaggat gatcacggac aaaaacagct gtgtgcctat   5460
tttgcaacag acagtgaatt gagcgccagc gacttacgta acattttgtc gcaggatctg   5520
cctggctata tggtgccgtc ctactttgtg cagctctcca gactgccttt gacgctgaat   5580
ggcaaagtag accgtagggc actgcccgga cctgagcaca atctcgatac aggtatggat   5640
tatgtggcac ccgagacgga tgtccaacag gcactggcta cggcttgggg agccattctt   5700
ggtatcccga aagtcggaat acaggataac tttttccatt tgggtggtga ctccatcaag   5760
gccatccaag tatcgtcccg cttgtttcag gctggataca agctggaaat gaaggatttg   5820
ttcaaatacc cgacaattgc gggactaagc acatatattc agcctgttaa ccgaatagcc   5880
gagcagggcg aggttacagg aaatgtagtg cttacaccga ttcagcgctg gtttttttgaa  5940
cagccaacgg aagaaccaca ctattttaac caatctgtca tgctctatcg tcaggaaggc   6000
tatgacgaac aggcactacg gcgggcgctc catcagatta cttcgcacca tgatgcattg   6060
cgtatggttt ttagtttgtc ggagaacgga tgtacagcat ggaaccgcag tgtagaggaa   6120
ggcgaaccgt accatctgga atgctttgac tataatgaca gcgatgtaaa caagcaagat   6180
ttggcgaaga taattgaagc gaaatgtaat gaaattcaat ctggtatttc cctaagcgaa   6240
ggtccgctga tgagactggg gctgttccgt tgcccggatg gagatcatct gctggtcgtg   6300
attcatcatt tggcggtgga cggagtatcc tggcgcatat tattcgagga tttggcgact   6360
gcctatgatc aagcctccaa gggtgaacag gtgattcagc tgcctcataa aacagattcg   6420
ttccaaacat gggccgagca gctgcacgct tatgccaaca gtccagctat ggaacgtgag   6480
cgagcgtatt gggggaaact tgcacaagcg gatccggctc ctttgccgca ggattacggg   6540
cataacgagc acgaaaagcc attgattggc gatagtgagt cggttactgc tttgtggaca   6600
catgcagaga cagagcagct gctcaagcag gccaatcgtg cctaccgtac agaaattaat   6660
gacctgttgt tgacggcggt aggaatggca ttgcaagcat ggagtggaaa tgatcgtttc   6720
ctgataaatc tagagggaca tggacgtgaa gccattttac cagaggtgga cattactcga   6780
```

acgatagggt ggtttacaag ccaatatcct gttttgctcg atatgccgga agaactggca 6840
ctttcgcaac ggattaagcg tgtgaaggaa ggactgcgcg gcattccgca aaaagggatt 6900
ggctacggtg tactgaaata tttatccgac cgtcagacac aggcaccaga ggcatctcca 6960
accatattta cgacagatcc cgaaatcagc tttaactatt tgggacagtt cgatcaggat 7020
atgaaaggga acgacttgca atcatcctca tatgagggtg ggatgccgct gagcccgacc 7080
atggctcgaa cgtatacgct tgattttggc ggcatcattt cgggaggcca actgggtctg 7140
acgattagct atagccgtac cagctataaa ccggagacca tcgagcgatt ggcgaaattc 7200
ctggaatcaa gcctacgtga aattttggcg cattgcatcc ataaagaaca cccggagctt 7260
accccaagtg atatttctta taaaggaatg agtgtggagg gcttggacag cctcttatct 7320
gaaatgggtg ctgcgggtga gatcgacaat gtatatgcac tgaccccccat gcagaaaggg 7380
atgctgtttc acagccagct agatagtcaa gcagctgcga atgacgcata ttttgagcag 7440
gtttcttatg atatgcgagg tcagatggac attcgggctt ttgcagaaag cctgaatatt 7500
ctggttcggc gacatgaggc gctgcgtaca catttttatt ttggcagaga tacggaaccg 7560
ttgcaggtgg tgtatcgaaa tcgggattgc ggctttcaat atgaagattt acaccatctg 7620
gatgaggatg aaatagatac ctgggtgaaa aatttcaagc tacaagataa agcacggggc 7680
tttgatctgc gccgggatgt cctgctgcgt gtagcgattt tacgtactgg agaagacagc 7740
tatcattttg tatggagctt ccatcatatc gtcatggacg gctggtgtct ctcccttata 7800
aataaagaag tgtttgaaag ctatgcagca cttcaggagg gcagagtacc agagctggca 7860
ccggcagtgc cgtacagccg ctttattgaa tggctggaag cacaggatcg caaggcggca 7920
accgactact ggagcagcta tttatccgga tatgagcagc aaacagcgtt accagctgta 7980
aaatccggtc gcaagagtga aggcaacacg gctagtgatt gggtgacggt tttggaacgt 8040
gagttgaccc tccgggtgga ggagacggct aagcgatatc aagtgaccat gaatacgtta 8100
ttacaaaccg catgggggat tgtgctgcaa aaatataaca accacagtga tgtcgtattt 8160
ggcagtgtcg tctcaggccg tccatcagat attatcgggg tagaggatat tatcggcttg 8220
ttcattaata ccattcccgt tcgcattctt agtaaggcag gggaatcttt tgcagaagtt 8280
atgaagaaaa cgcaggagca ggcgctggct tctcatgcat atgatacgta tccactgttt 8340
gagattcagg cattgaccga ccagaaacag gatttaatta accatattat ggtgtttgaa 8400
aattatccgg tagatgagca ggtcgaagaa ctgggaagtg ccgggcagga tacattcccg 8460
atttccaacg tggtggctgc agagcagact aactatgatc tgagcttagt cgttatgccg 8520
ggagaatgca tcaagattcg ttttatgtat aatgcgttaa gttatgatca aacaggcatt 8580
gagcgtctgc atgggcattt tgtgaatctg ttggagcaag ttttgcttaa cccgaatgtt 8640
tgcgtagaag agctggaact cgttacagcg gcggaaaaac aacaaattac aggagagttt 8700
aatgacactg cctctgcata tccaagccat cacacgatcc aaaaactgtt tgaggagcag 8760
gcagagcgca cgccggatca tattgctgta gctttgggtc atcaatcatt gacctatcgg 8820
gaactcaatg agacagccaa ccgtttagcg catacgctac gtgatgcagg ggtgaaatcc 8880
gatgaacctg tgggcatttt gacggagcgc tcactggata tgattacggg aacactcgct 8940
attttgaagg ctggaggcgc gtatgtgccg gtagaccctc aatatccgga ggaccgtatc 9000
cgttatatgc tggaggactc gggagctaag ctgctgctgg ctcagcagga tttactggat 9060
cgttgctatt ttgacggaca gattgtcaat ctgaatgagg atacgtccta cagtgcagat 9120
gcttccaatc tgggtataga tggagcgggt aatcatgctg cttatgtcat ttatacctca 9180

```
ggttcaacag gtaagcctaa gggtgtcgta gttgagcatc aaagtgtcgt gcgccttgtc   9240
cgcaatacgg attatgtgcc atttgatgaa tcgacccgaa tgctgcagac ttgcgcgttt   9300
gtatttgatg tatctacgtt tgaaatttgg ggtgcgctac tgaatggtgg tcagcttgtt   9360
cttgtgcata aggatgatct attggacgcg gccaagctta aagagacgat acgggatcat   9420
cacgtcacca tgatgtggct gaccacaccg ttatttaatc agctttcaca gcaggatagt   9480
aaacttttcg gcgatgtgaa gtatttgctg gttggtggtg atgttttgtc tgcaccccat   9540
attaaccggg tcctgcgcga taatccggac atgaacatca ttaacggcta tgggccaacg   9600
gaaaacacaa ccttttcgac aacgtatcac attacggaag aacagctgga ttctgtgccg   9660
atcggacggc ccatctgcaa ttcgacggcg tatgttgtag attcgtcatt taacctgcaa   9720
ccggtcggag cttggggtga gctggtcgtc ggcggagacg gagttgcacg tggttatcta   9780
aatcgtcctg agctgacggc tgagagattt cttgctaacc cgtggaggga cggagatcgc   9840
ctgtactgta cgggagacct tgttcgctgg cgtgaagacg gcatactgga atacgctgga   9900
cggattgatc aacaggttaa aattcgcggt taccggattg agctgggtga ggtggaggcg   9960
aggctggcaa gtgtaccgtc cgtgcgggat agcgtggtta ttgctttgcg ggatggagca  10020
ggtcagcagc aattatgtgc ttactttact gccgatgaac agctgaccat ccgtgagatt  10080
cgagctgcga tgtcggtcag tctgccgagc tatatgattc catccgcatt tgtacagctg  10140
gatcggtttc cgctgacgac caacggcaaa atcgaccgca aagctttacc tgtgccggac  10200
aaagggctgc acacgggtat agaatatgtc gcaccgcgaa ccgatgtgga gcagttgctg  10260
gcatctattt ggcaggaagt gcttgaaatt ccacaagtgg gtatccatga tgactttttc  10320
acgttgggcg gacattcctt gaaagtactg gagcttatac gcaaagttca ccttgccaca  10380
gacattgagc tccccatccg tagtgtaatg gacttcccga ctatagaaga gcaggcgctc  10440
acattattga aagccgatct ggaatacaag gccgatagtc caatcattcg gttgaatgaa  10500
cacggtccga tctccatctt ctgctttcct cctatgcttg gatacgggct gtcgttcgcg  10560
gagctggcga aacaactgga tcaggacgca gtcgtgtatg gattagagtt cgtggatgat  10620
gctgcggatg agcaggccat gctggcacgt tacgttgatt tgatcgtcag cacgcaagcg  10680
caaggtccgt atgtgctgct tggttattcc ataggtggta atctggcgca taaggttgct  10740
gacacactgg aacgtcaggg ccatgctgta tccgatattt ttatgctcga ttcggtcaaa  10800
agggcggaag ccctgccctt cacagttgaa gaaacagagc atgaaattca tgacatgctg  10860
gaacaggttc ccgaatccta ccgtgagctg ttgaatgaaa cgtaccaacg taaaatgatc  10920
gcttacgcgg tgtatggcaa ccagcttgtg aatacagaga gcgttcaggc gaatattcac  10980
ggctttgtcg ccgttggatc ggaaacggtg aggggtacag gagataatcg acttttatgg  11040
aaagacgcta cacaaggtag ctatgaagag catagcttga ttggtaatca ttatgaacta  11100
ctggaacccg gatttatcga ggaaaatgta aaaagtatcc gtgccgcaat acaaaagata  11160
actcggaaca cggacaaaga catgacacaa gatttggcac atcataaatc ttga        11214
```

<210> SEQ ID NO 9
<211> LENGTH: 1500
<212> TYPE: DNA
<213> ORGANISM: Paenibacillus

<400> SEQUENCE: 9

```
atggactctt tagctgatct ctcggaaacc ccctagcat tggaaaccct cagacgacat     60
```

-continued

```
ccctgttata acgaagaggc acatcgctat tttgcgcgca ttcatcttcc agtagccccg    120
gcatgcaata ttcaatgcca ttattgcaac cgcaaattcg attgcgtcaa tgaaagccgt    180
cccggcgttg ttagtgaact gctcacgccg gagcaggcgg cgagcaagac ctatggcgta    240
gcggcacagc tgatgcagct gtccgttgtc ggcattgcgg gacctggaga tccgctggcc    300
aatgcggagg caaccttcga taccttccgc cgggtccgtg agacagttaa ggatgtcata    360
ttctgtctca gcacgaatgg ccttaccttg atcaggcata tcgacaggat tgtagagctg    420
ggtatttcgc atgtcacgat cacgatcaat gctgtagatc cagtggtggg gagccgcatt    480
tatggatggg tctacgatga aggaaaacgc tatgcaggag aggaggccgc gcggctgttg    540
attgaccgcc agctggcagg cttgaagatg ctggcttcga gaggcgtatt gtgcaaggtg    600
aactcggtgc tgattcccga agtcaatgat gcccatctgc cggaggtagc cagggtagtc    660
aaggagcacg gcgcagtgct gcacaacatt atgccgctca tcatcgcacc tggtagccgg    720
tatgagcagg aagggatgcg ggctccccgt ccccgtctgg tccggcagct gcaggagcaa    780
tgtgctgaag cgggggctgt cattatgcgc cattgccgtc agtgcagggc ggatgcgatt    840
ggactgctgg gcgaggatcg gaatcaggat tttacatggg agaacatagc ggctgctcct    900
cccatggatg aaggggcaag ggcacaattt cagaaagaac tggatgagaa ggtgagagtg    960
agaatggaac gcaaggaggg acaatcacac cacaaacaac cgtcaaccgg ggctggctgt   1020
agctgcccgt tatcgggaga taagcctgaa gcgagcttca cctcaaagcc agtcctaatc   1080
gcagtggcca gtcgtggcgg agggaaggtg aatcagcatt tcggccgtgc caaggaattt   1140
atgatctatg aaagcgacgg gaccatcgta aatttcatag gcattcgtaa ggtgcaatcc   1200
tactgccacg ggaaagccga ttgcaatggg gacaaggtcg agacgatgaa ggagatcctt   1260
tccatggtgc atgactgtgc attgctgctg tcgtccggca taggcgaagc cccccaaagag   1320
gcattgcagg aagctggcgt gctgcctatt gtatgcggcg gggatattga ggaatcggtt   1380
ctggaatatg tgaaatttct gcgttatatg tatcctgtgc agagcaataa aggaagtaag   1440
cgcaataagg gagttaaggg caatcattcg gatttaccca ttaaacattt tggaggctga   1500
```

<210> SEQ ID NO 10
<211> LENGTH: 1500
<212> TYPE: DNA
<213> ORGANISM: Paenibacillus

<400> SEQUENCE: 10

```
atggactctt tagctgatct ctcggaaacc cccttagtat tggaaaccct cagacgacat     60
ccctgttata acgaagaggc acatcgctat tttgcgcgca ttcatcttcc agtagccccg    120
gcatgcaata ttcaatgcca ttattgcaac cgaaaattcg attgcgtcaa tgaaagccgt    180
cccggcgttg ttagtgaact gctcacgccg gagcaggcgg cgagcaagac ctatggcgta    240
gcggcacagc ttatgcagct gtccgttgtc ggcattgcgg gacctggaga tccgctggcc    300
aatgcggagg caaccttcga taccttccgc cgggtccgtg agacagttaa ggatgtcata    360
ttctgtctca gcacaaatgg ccttaccttg atcaggcata ttgacaggat tgtagagctg    420
ggtatttcgc atgtcacgat cacgatcaat gctgtagatc cagtggtggg gagccgcatt    480
tatggatggg tctacgatga aggaaaacgc tatgcaggag aggaggccgc gcggctgttg    540
attgaccgcc agctggcagg cttgaagatg ctggcttcga gaggcgtatt gtgcaaggtg    600
aactcggtgc tgattcccga agtcaatgat gcccatctgc cggaggtagc cagggtggtc    660
aaggagcacg gtgcagtgct gcacaacatt atgccgctca tcatcgcacc tggtagccgg    720
```

-continued tatgagcagg aagggatgcg ggctccccgt ccccgtctgg tccggcagct gcaggagcaa 780
tgtgctgaag cgggggctgt cattatgcgc cattgccgtc agtgcagggc ggatgcgatt 840
ggactgctgg gcgaggatcg caatcaggat tttacatggg agaacatagc ggctgctcct 900
cccatggatg aaggggcaag gacacaattt cagaaagaac tggatgagaa ggtgagagtg 960
agaatggaac gcaaggaggg acaatcacac cacaaacaac cgtcaaccgg ggctggctgt 1020
agctgcccgt tatcgggaga taagcctgaa gcgagcttca cctcaaagcc agtcctaatc 1080
gcagtggcca gtcgtggcgg agggaaggtg aatcagcatt tcggccgtgc caaggaattt 1140
atgatctatg aaagcgacgg gaccatcgta aatttcatag gcattcgtaa ggtgcaatcc 1200
tactgccacg ggaaagccga ttgcaatggg gacaaggtcg agacgatgaa ggagatcctt 1260
tccatggtgc atgactgtgc attgctgctg tcgtccggca taggcgaagc cccaaaagag 1320
gcattgcagg aagctggcgt gctgcctatt gtatgcggcg gggatattga ggaatcggtt 1380
ctggaatatg tgaaatttct gcgttatatg tatcctgtgc agagcaataa aggaagtaag 1440
cgcaataagg gagttaaggg caatcattcg gatttaccca ttaaacattt tggaggctga 1500

<210> SEQ ID NO 11
<211> LENGTH: 1500
<212> TYPE: DNA
<213> ORGANISM: Paenibacillus

<400> SEQUENCE: 11
atggactctt tagctgatct ctcggaaacc cccttagcat tggacaccct tagacgacat 60
ccctgttata acgaagaggc acatcgctat tttgcgcgca ttcatcttcc agtagccccg 120
gcatgcaata ttcagtgcca ttattgcaac cgcaaattcg attgcgtcaa tgaaagccgt 180
cccggcgttg ttagtgaact gctcacgccg gagcaggcgg cgagcaagac ctatggcgta 240
gcggcacagc tgatgcaact gtccgttgtc ggcattgcgg gacctggaga tccgctggcc 300
aatgcggagg caaccttcga taccttccgc cgggtccgtg agacagttaa ggatgtcata 360
ttctgtctca gcacgaatgg ccttaccttg atcaggcata tcgacaggat tgtagagttg 420
ggtatttcgc atgtcacgat cacgatcaat gctgtagatc cagtggtggg gagccgcatt 480
tatggatggg tctacgatga aggaaaacgc tatgcaggag aggaggccgc gcggctgttg 540
attgaccgcc agctggcagg cttgaagatg ctggcttcga gaggcgtatt gtgcaaggta 600
aactcggtgc tgattcccga agtcaatgat gcccatctgc cagaggtagc cagggtggtc 660
aaggagcacg gcgcggtact gcacaacatt atgccgctca tcatcgcacc cggcagtcgg 720
tatgagcatg aagggatgcg ggccccccgt ccccgtctgg tccggcagct gcaggagcaa 780
tgtgctgagg cgggagctgt cattatgcgc cattgccgtc agtgcagggc ggatgcgatt 840
ggactgctgg gcgaggatcg caatcaggat tttacatggg agaacattgg ggctgctcct 900
cccatggatg aagaggcaag ggcacaattt cagaaagaac tggatgagaa ggtgagagtg 960
agaatggaac gcaaggaggg acaatcgcac cacaaaaaaa cgtcaaccgg ggttggatgt 1020
agctgcccgt tatcggagga taagcctgaa gcaagcttta cctcaaagcc agtcctaatc 1080
gctgtggcca gtcgtggcgg agggaaggtg aatcagcatt tcggtcgtgc caaggaattc 1140
atgatctatg aaagcgacgg gactatcgta aatttcatag gcattcgtaa ggtgcaatcc 1200
tactgccatg ggaaagccga ttgcaatgga gacaaggtcg agacgatgaa ggagatcctt 1260
tccatggtgc atgactgtgc attgctgctg tcgtccggca taggcgaagc cccaaaagag 1320

-continued

```
gcattgcagg atgctggcgt gctgcctatt gtatgcggcg gggatattga ggaatccgtt   1380

ctggaatatg taaaatttct gcgttatatg tatcctgtgc agagcaataa gggaagtaag   1440

cgcaataagg gagttaaggg caatcattcg gatttaccca ttgaacattt tggaggctga   1500
```